US012496059B2

(12) United States Patent
Stone et al.

(10) Patent No.: US 12,496,059 B2
(45) Date of Patent: *Dec. 16, 2025

(54) METHOD AND APPARATUS FOR SOFT TISSUE FIXATION

(71) Applicant: Biomet Sports Medicine, LLC, Warsaw, IN (US)

(72) Inventors: Kevin T. Stone, Winona Lake, IN (US); Gregory J. Denham, Warsaw, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 190 days.

This patent is subject to a terminal disclaimer.

(21) Appl. No.: 18/497,342

(22) Filed: Oct. 30, 2023

(65) Prior Publication Data

US 2024/0057992 A1 Feb. 22, 2024

Related U.S. Application Data

(60) Continuation of application No. 18/134,897, filed on Apr. 14, 2023, now Pat. No. 12,336,701, which is a (Continued)

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/0406* (2013.01); (Continued)

(58) Field of Classification Search
CPC .......... A61B 17/06166; A61B 17/0401; A61B 2017/0417; A61B 2017/0406; A61B 2017/06185
See application file for complete search history.

(56) References Cited

U.S. PATENT DOCUMENTS 26,501 A 12/1859 Kendrick et al.
64,499 A 5/1867 Daubert
(Continued)

FOREIGN PATENT DOCUMENTS

AU 4957264 A 3/1966
AU 440266 A1 10/1967
(Continued)

OTHER PUBLICATIONS

US 6,238,418 B1, 05/2001, Schwartz (withdrawn)
(Continued)

*Primary Examiner* — Dianne Dornbusch
(74) *Attorney, Agent, or Firm* — SCHWEGMAN LUNDBERG & WOESSNER, P.A.

(57) ABSTRACT

A surgical method can include passing at least two adjustable loops of a flexible construct through at least the first tissue to extend from an outer surface of the first tissue opposite a tissue engaging surface facing the second tissue, and attaching the two adjustable loops to a first selected area of the second tissue. The method can further include positioning an elongated locking member within the two adjustable loops such that the locking member extends between the two adjustable loops adjacent the outer surface, engaging the locking member with the outer surface by drawing the two adjustable loops towards the outer surface, and compressing the first tissue between the locking member and the second tissue by tensioning the two adjustable loops. Related tissue fixation devices are also provided.

28 Claims, 6 Drawing Sheets

Related U.S. Application Data continuation of application No. 18/093,114, filed on Jan. 4, 2023, now Pat. No. 12,329,373, which is a continuation of application No. 16/895,246, filed on Jun. 8, 2020, now Pat. No. 11,723,648, which is a continuation of application No. 15/682,187, filed on Aug. 21, 2017, now Pat. No. 10,729,421, which is a continuation of application No. 14/182,038, filed on Feb. 17, 2014, now Pat. No. 9,763,656, which is a division of application No. 13/098,927, filed on May 2, 2011, now Pat. No. 8,652,171.

(52) U.S. Cl.
CPC ................ *A61B 2017/0417* (2013.01); *A61B 2017/06185* (2013.01)

(56) References Cited

U.S. PATENT DOCUMENTS

| | | | |
|---|---|---|---|
| 65,499 | A | 6/1867 | Miller |
| 126,366 | A | 4/1872 | Wills |
| 233,475 | A | 10/1880 | Cook et al. |
| 261,501 | A | 7/1882 | Vandermark |
| 268,407 | A | 12/1882 | Hughes |
| 330,087 | A | 11/1885 | Binns |
| 394,739 | A | 12/1888 | Toulmin |
| 401,677 | A | 4/1889 | Autenrieth |
| 417,805 | A | 12/1889 | Beaman |
| 445,875 | A | 2/1891 | Brickell |
| 487,304 | A | 12/1892 | Todd |
| 687,221 | A | 11/1901 | Gaff et al. |
| 762,710 | A | 6/1904 | Hall |
| 837,767 | A | 12/1906 | Aims |
| 838,203 | A | 12/1906 | Neil |
| 1,059,631 | A | 4/1913 | Popovics |
| 1,131,155 | A | 3/1915 | Murphy |
| 1,153,450 | A | 9/1915 | Schaff |
| 1,346,940 | A | 7/1920 | Collins |
| 1,505,470 | A | 8/1924 | Kelm |
| 1,635,066 | A | 7/1927 | Wells |
| 1,950,799 | A | 3/1934 | Jones |
| 2,042,403 | A | 5/1936 | Andrew |
| 2,065,659 | A | 12/1936 | Cullen |
| 2,108,206 | A | 2/1938 | Meeker |
| 2,121,193 | A | 6/1938 | Erich |
| 2,242,003 | A | 5/1941 | Lorenzo |
| 2,267,925 | A | 12/1941 | Johnston |
| 2,302,986 | A | 11/1942 | Vollrath |
| 2,329,398 | A | 9/1943 | Duffy |
| 2,379,629 | A | 7/1945 | Eweson |
| 2,397,216 | A | 3/1946 | Stellin |
| RE22,857 | E | 3/1947 | Ogburn |
| 2,526,959 | A | 10/1950 | Lorenzo |
| 2,528,456 | A | 10/1950 | Thomas |
| 2,549,382 | A | 4/1951 | Mitterway |
| 2,562,419 | A | 7/1951 | Ferris |
| 2,581,564 | A | 1/1952 | Jaime |
| 2,600,395 | A | 6/1952 | Joseph et al. |
| 2,610,631 | A | 9/1952 | Calicchio |
| 2,665,597 | A | 1/1954 | Hill |
| 2,669,774 | A | 2/1954 | Mitchell |
| 2,698,986 | A | 1/1955 | Brown |
| 2,760,488 | A | 8/1956 | Pierce |
| 2,833,284 | A | 5/1958 | Springer |
| 2,846,712 | A | 8/1958 | Moe |
| 2,860,393 | A | 11/1958 | Brock |
| 2,880,728 | A | 4/1959 | Rights |
| 2,881,762 | A | 4/1959 | Lowrie |
| 2,883,096 | A | 4/1959 | Horace |
| 2,913,042 | A | 11/1959 | John |
| 2,947,504 | A | 8/1960 | Ruhlman |
| 3,000,009 | A | 9/1961 | Selstad |
| 3,003,155 | A | 10/1961 | Mielzynski |
| 3,013,559 | A | 12/1961 | Thomas |
| 3,037,619 | A | 6/1962 | Ernest |
| 3,039,460 | A | 6/1962 | Chandler |
| 3,081,781 | A | 3/1963 | Stermer |
| 3,090,386 | A | 5/1963 | William |
| 3,103,666 | A | 9/1963 | Bone |
| 3,123,077 | A | 3/1964 | Alcamo |
| 3,125,095 | A | 3/1964 | Kaufman et al. |
| 3,209,422 | A | 10/1965 | Arthur |
| 3,223,083 | A | 12/1965 | Cobey |
| 3,234,938 | A | 2/1966 | Robinson |
| 3,240,379 | A | 3/1966 | Bremer et al. |
| 3,250,271 | A | 5/1966 | Jack |
| 3,399,432 | A | 9/1968 | Merser |
| 3,409,014 | A | 11/1968 | Grant |
| RE26,501 | E | 12/1968 | Himmelstein et al. |
| 3,435,475 | A | 4/1969 | Bisk |
| 3,467,089 | A | 9/1969 | Hasson |
| 3,470,834 | A | 10/1969 | Bone |
| 3,470,875 | A | 10/1969 | Johnson |
| 3,500,820 | A | 3/1970 | Almen |
| 3,507,274 | A | 4/1970 | Soichet |
| 3,513,484 | A | 5/1970 | Hausner |
| 3,515,132 | A | 6/1970 | Mcknight |
| 3,522,803 | A | 8/1970 | Majzlin |
| 3,527,223 | A | 9/1970 | Shein |
| 3,533,406 | A | 10/1970 | Tatum |
| 3,541,591 | A | 11/1970 | Hoegerman |
| 3,545,008 | A | 12/1970 | Bader, Jr. |
| 3,547,389 | A | 12/1970 | Mitchell |
| 3,579,831 | A | 5/1971 | Stevens et al. |
| 3,590,616 | A | 7/1971 | Schussler |
| 3,608,095 | A | 9/1971 | Barry |
| 3,618,447 | A | 11/1971 | Goins |
| 3,628,530 | A | 12/1971 | Schwartz |
| 3,643,649 | A | 2/1972 | Amato |
| 3,648,705 | A | 3/1972 | Lary |
| 3,650,274 | A | 3/1972 | Edwards et al. |
| 3,656,483 | A | 4/1972 | Rudel |
| 3,659,597 | A | 5/1972 | Wolfers |
| 3,664,345 | A | 5/1972 | Dabbs et al. |
| 3,665,560 | A | 5/1972 | Bennett et al. |
| 3,675,639 | A | 7/1972 | Cimber |
| 3,683,422 | A | 8/1972 | Stemmer et al. |
| 3,692,022 | A | 9/1972 | Ewing |
| 3,695,271 | A | 10/1972 | Chodorow |
| 3,699,969 | A | 10/1972 | Allen |
| 3,716,058 | A | 2/1973 | Tanner |
| 3,744,488 | A | 7/1973 | Cox |
| 3,752,516 | A | 8/1973 | Mumma |
| 3,757,629 | A | 9/1973 | Schneider |
| 3,763,856 | A | 10/1973 | Blomberg |
| 3,771,520 | A | 11/1973 | Lerner |
| 3,777,748 | A | 12/1973 | Abramson |
| 3,786,801 | A | 1/1974 | Sartorius |
| 3,802,438 | A | 4/1974 | Wolvek |
| 3,807,407 | A | 4/1974 | Schweizer |
| 3,810,456 | A | 5/1974 | Karman |
| 3,825,010 | A | 7/1974 | Mc Donald |
| 3,840,017 | A | 10/1974 | Violante |
| 3,842,824 | A | 10/1974 | Neufeld |
| 3,842,840 | A | 10/1974 | Schweizer |
| 3,845,772 | A | 11/1974 | Smith |
| 3,867,933 | A | 2/1975 | Kitrilakis |
| 3,867,944 | A | 2/1975 | Samuels |
| 3,871,368 | A | 3/1975 | Johnson et al. |
| 3,871,379 | A | 3/1975 | Clarke |
| 3,874,388 | A | 4/1975 | King et al. |
| 3,875,648 | A | 4/1975 | Bone |
| 3,877,570 | A | 4/1975 | Barry |
| 3,880,156 | A | 4/1975 | Hoff |
| 3,881,475 | A | 5/1975 | Gordon et al. |
| 3,889,666 | A | 6/1975 | Lerner |
| 3,892,240 | A | 7/1975 | Park |
| 3,896,500 | A | 7/1975 | Rambert et al. |
| 3,896,810 | A | 7/1975 | Akiyama |
| 3,907,442 | A | 9/1975 | Reid |
| 3,910,281 | A | 10/1975 | Kletschka |
| 3,918,444 | A | 11/1975 | Hoff et al. |
| 3,918,455 | A | 11/1975 | Coplan |

(56) References Cited

U.S. PATENT DOCUMENTS 3,927,666 A 12/1975 Hoff
3,931,667 A 1/1976 Merser et al.
3,933,153 A 1/1976 Csatary et al.
3,937,217 A 2/1976 Kosonen
3,943,932 A 3/1976 Woo
3,946,446 A 3/1976 Schofield
3,946,728 A 3/1976 Bettex
3,946,740 A 3/1976 Bassett
3,949,755 A 4/1976 Vauquois
3,953,896 A 5/1976 Treace
3,954,103 A 5/1976 Garcia-roel et al.
3,961,632 A 6/1976 Moossun
3,973,560 A 8/1976 Emmett
3,976,079 A 8/1976 Samuels et al.
3,977,050 A 8/1976 Perez
3,979,799 A 9/1976 Merser et al.
3,985,138 A 10/1976 Jarvik
3,990,619 A 11/1976 Russell
4,005,707 A 2/1977 Moulding, Jr.
4,006,747 A 2/1977 Kronenthal et al.
4,007,743 A 2/1977 Blake
4,013,071 A 3/1977 Rosenberg
4,026,281 A 5/1977 Mayberry et al.
4,036,101 A 7/1977 Burnett
4,050,100 A 9/1977 Barry
4,054,954 A 10/1977 Nakayama et al.
4,084,478 A 4/1978 Simmons
4,085,466 A 4/1978 Goodfellow et al.
4,094,313 A 6/1978 Komamura et al.
4,099,750 A 7/1978 Mcgrew
4,103,690 A 8/1978 Harris
RE29,819 E 10/1978 Bone
4,121,487 A 10/1978 Bone
4,143,656 A 3/1979 Holmes
4,144,876 A 3/1979 Deleo
4,146,022 A 3/1979 Johnson et al.
4,149,277 A 4/1979 Bokros
4,157,714 A 6/1979 Foltz et al.
4,158,250 A 6/1979 Ringwald
4,160,453 A 7/1979 Miller
4,164,225 A 8/1979 Johnson et al.
4,172,458 A 10/1979 Pereyra
4,175,555 A 11/1979 Herbert
4,185,636 A 1/1980 Gabbay et al.
4,196,883 A 4/1980 Einhorn et al.
4,207,627 A 6/1980 Cloutier
4,210,148 A 7/1980 Stivala
4,235,161 A 11/1980 Kunreuther
4,235,238 A 11/1980 Ogiu et al.
4,237,779 A 12/1980 Kunreuther
4,243,037 A 1/1981 Smith
4,249,525 A 2/1981 Krzeminski
4,263,913 A 4/1981 Malmin
4,265,246 A 5/1981 Barry
4,273,117 A 6/1981 Neuhauser
4,275,490 A 6/1981 Bivins
4,275,717 A 6/1981 Bolesky
4,287,807 A 9/1981 Pacharis et al.
4,291,698 A 9/1981 Fuchs et al.
4,301,551 A 11/1981 Dore et al.
4,302,397 A 11/1981 Frainier et al.
4,307,723 A 12/1981 Finney
4,312,337 A 1/1982 Donohue
4,316,469 A 2/1982 Kapitanov
4,319,428 A 3/1982 Fox
4,326,531 A 4/1982 Shimonaka
4,344,193 A 8/1982 Kenny
4,345,601 A 8/1982 Fukuda
4,349,027 A 9/1982 Difrancesco
4,388,921 A 6/1983 Sutter et al.
4,400,833 A 8/1983 Kurland
4,402,445 A 9/1983 Green
4,409,974 A 10/1983 Freedland et al.
4,438,769 A 3/1984 Pratt et al.
4,441,489 A 4/1984 Evans et al.
4,454,875 A 6/1984 Pratt et al.
4,462,395 A 7/1984 Johnson
4,463,753 A 8/1984 Gustilo
4,473,102 A 9/1984 Ohman et al.
4,484,570 A 11/1984 Sutter et al.
4,489,446 A 12/1984 Reed
4,489,464 A 12/1984 Massari et al.
4,493,323 A 1/1985 Albright et al.
4,496,468 A 1/1985 House et al.
4,505,274 A 3/1985 Speelman
4,509,516 A 4/1985 Richmond
4,531,522 A 7/1985 Bedi et al.
4,532,926 A 8/1985 O'holla
4,534,350 A 8/1985 Golden et al.
4,535,764 A 8/1985 Ebert
4,537,185 A 8/1985 Stednitz
4,549,545 A 10/1985 Levy
4,549,652 A 10/1985 Free
4,561,432 A 12/1985 Mazor
4,564,007 A 1/1986 Coombs
4,570,623 A 2/1986 Ellison et al.
4,573,844 A 3/1986 Smith
4,576,608 A 3/1986 Homsy
4,584,722 A 4/1986 Levy et al.
4,587,963 A 5/1986 Leibinger et al.
4,590,928 A 5/1986 Hunt et al.
4,595,007 A 6/1986 Mericle
4,596,249 A 6/1986 Freda et al.
4,597,766 A 7/1986 Hilal et al.
4,602,635 A 7/1986 Mulhollan et al.
4,602,636 A 7/1986 Noiles
4,604,997 A 8/1986 De Bastiani et al.
4,605,414 A 8/1986 Czajka
4,616,650 A 10/1986 Green et al.
4,621,640 A 11/1986 Mulhollan et al.
4,624,254 A 11/1986 Mcgarry et al.
4,632,100 A 12/1986 Somers et al.
4,635,637 A 1/1987 Schreiber
4,636,121 A 1/1987 Miller
4,640,271 A 2/1987 Lower
4,641,652 A 2/1987 Hutterer et al.
4,649,916 A 3/1987 Frimberger
4,649,952 A 3/1987 Jobe
4,653,486 A 3/1987 Coker
4,653,487 A 3/1987 Maale
4,653,489 A 3/1987 Tronzo
4,655,771 A 4/1987 Wallsten
4,655,777 A 4/1987 Dunn
4,662,068 A 5/1987 Polonsky
4,667,662 A 5/1987 Titone et al.
4,667,675 A 5/1987 Davis
4,669,473 A 6/1987 Richards et al.
4,683,895 A 8/1987 Pohndorf
4,688,561 A 8/1987 Reese
4,690,169 A 9/1987 Jobe
4,696,300 A 9/1987 Anderson
4,705,040 A 11/1987 Mueller et al.
4,708,132 A 11/1987 Silvestrini
4,711,639 A 12/1987 Grundei
4,714,474 A 12/1987 Brooks, Jr. et al.
4,714,475 A 12/1987 Grundei et al.
4,716,893 A 1/1988 Fischer et al.
4,719,671 A 1/1988 Ito et al.
4,719,917 A 1/1988 Barrows et al.
4,723,540 A 2/1988 Gilmer, Jr.
4,724,839 A 2/1988 Bedi et al.
4,728,329 A 3/1988 Mansat
4,728,332 A 3/1988 Albrektsson
4,730,615 A 3/1988 Sutherland et al.
4,736,746 A 4/1988 Anderson
4,738,255 A 4/1988 Goble et al.
4,739,751 A 4/1988 Sapega et al.
4,741,330 A 5/1988 Hayhurst
4,741,336 A 5/1988 Failla et al.
4,744,353 A 5/1988 Mcfarland
4,744,793 A 5/1988 Parr et al.
4,750,492 A 6/1988 Jacobs
4,751,922 A 6/1988 Dipietropolo
4,754,685 A 7/1988 Kite et al.

(56) References Cited

U.S. PATENT DOCUMENTS 4,760,843 A 8/1988 Fischer et al.
4,760,844 A 8/1988 Kyle
4,760,848 A 8/1988 Hasson
4,770,663 A 9/1988 Hanslik et al.
4,772,261 A 9/1988 Von Hoff et al.
4,772,286 A 9/1988 Goble et al.
4,773,910 A 9/1988 Chen et al.
4,775,380 A 10/1988 Seedhom et al.
4,776,328 A 10/1988 Frey et al.
4,779,372 A 10/1988 Pozo Obeso
4,781,190 A 11/1988 Lee
4,784,126 A 11/1988 Hourahane
4,787,882 A 11/1988 Claren
4,790,297 A 12/1988 Luque
4,790,850 A 12/1988 Dunn et al.
4,793,363 A 12/1988 Ausherman et al.
4,795,468 A 1/1989 Hodorek et al.
4,809,695 A 3/1989 Gwathmey et al.
4,813,406 A 3/1989 Ogle, II
4,813,416 A 3/1989 Pollak et al.
4,823,780 A 4/1989 Odensten et al.
4,823,794 A 4/1989 Pierce
4,828,562 A 5/1989 Kenna
4,832,026 A 5/1989 Jones
4,834,098 A 5/1989 Jones
4,836,080 A 6/1989 Kite, III et al.
4,838,282 A 6/1989 Strasser et al.
4,841,960 A 6/1989 Garner
4,846,835 A 7/1989 Grande
4,851,005 A 7/1989 Hunt et al.
4,858,601 A 8/1989 Glisson
4,858,603 A 8/1989 Clemow et al.
4,858,608 A 8/1989 Mcquilkin
4,860,513 A 8/1989 Whitman
4,863,383 A 9/1989 Grafelmann
4,863,471 A 9/1989 Mansat
4,870,957 A 10/1989 Goble et al.
4,872,450 A 10/1989 Austad
4,873,976 A 10/1989 Schreiber
4,884,572 A 12/1989 Bays et al.
4,887,601 A 12/1989 Richards
4,889,110 A 12/1989 Galline et al.
4,890,615 A 1/1990 Caspari et al.
4,893,619 A 1/1990 Dale et al.
4,893,974 A 1/1990 Fischer et al.
4,895,148 A 1/1990 Bays et al.
4,896,668 A 1/1990 Popoff et al.
4,898,156 A 2/1990 Gatturna et al.
4,899,743 A 2/1990 Nicholson et al.
4,901,721 A 2/1990 Hakki
4,917,700 A 4/1990 Aikins
4,919,667 A 4/1990 Richmond
4,922,897 A 5/1990 Sapega et al.
4,923,461 A 5/1990 Caspari et al.
4,927,421 A 5/1990 Goble et al.
4,946,377 A 8/1990 Kovach
4,946,467 A 8/1990 Ohi et al.
4,946,468 A 8/1990 Li
4,950,270 A 8/1990 Bowman et al.
4,950,285 A 8/1990 Wilk
4,959,069 A 9/1990 Brennan et al.
4,960,381 A 10/1990 Niznick
4,961,741 A 10/1990 Hayhurst
4,962,929 A 10/1990 Melton, Jr.
4,968,315 A 11/1990 Gatturna
4,968,317 A 11/1990 Tormala et al.
4,969,886 A 11/1990 Cziffer et al.
4,974,488 A 12/1990 Spralja
4,974,656 A 12/1990 Judkins
4,976,736 A 12/1990 White et al.
4,978,350 A 12/1990 Wagenknecht
4,979,956 A 12/1990 Silvestrini
4,983,176 A 1/1991 Cushman et al.
4,983,184 A 1/1991 Steinemann
4,983,240 A 1/1991 Orkin et al.
4,988,351 A 1/1991 Paulos et al.
4,994,074 A 2/1991 Bezwada et al.
4,997,433 A 3/1991 Goble et al.
5,002,545 A 3/1991 Whiteside et al.
5,002,550 A 3/1991 Li
5,002,562 A 3/1991 Oberlander
5,002,574 A 3/1991 May et al.
5,007,921 A 4/1991 Brown
5,019,093 A 5/1991 Kaplan et al.
5,020,713 A 6/1991 Kunreuther
5,026,398 A 6/1991 May et al.
5,028,569 A 7/1991 Cihon
5,030,224 A 7/1991 Wright
5,030,235 A 7/1991 Campbell, Jr.
5,035,701 A 7/1991 Kabbara
5,037,422 A 8/1991 Hayhurst et al.
5,037,426 A 8/1991 Goble et al.
5,041,129 A 8/1991 Hayhurst et al.
5,046,513 A 9/1991 Gatturna et al.
5,047,030 A 9/1991 Draenert
5,053,046 A 10/1991 Janese
5,053,047 A 10/1991 Yoon
5,059,201 A 10/1991 Asnis
5,059,206 A 10/1991 Winters
5,061,277 A 10/1991 Carpentier et al.
5,062,344 A 11/1991 Gerker
5,062,843 A 11/1991 Mahony, III
5,064,431 A 11/1991 Gilbertson et al.
5,067,962 A 11/1991 Campbell et al.
5,071,420 A 12/1991 Paulos et al.
5,074,874 A 12/1991 Yoon, Inbae et al.
5,078,731 A 1/1992 Hayhurst
5,078,843 A 1/1992 Pratt
5,080,050 A 1/1992 Dale
5,080,675 A 1/1992 Lawes et al.
5,084,050 A 1/1992 Draenert
5,084,058 A 1/1992 Li
5,085,661 A 2/1992 Moss
5,087,263 A 2/1992 Li
5,087,309 A 2/1992 Melton, Jr.
5,089,012 A 2/1992 Prou
5,092,727 A 3/1992 Moghe
5,092,866 A 3/1992 Breard et al.
5,098,433 A 3/1992 Freedland
5,098,435 A 3/1992 Stednitz et al.
5,100,415 A 3/1992 Hayhurst
5,100,417 A 3/1992 Cerier
5,108,433 A 4/1992 May et al.
5,112,335 A 5/1992 Laboureau et al.
5,116,337 A 5/1992 Johnson
5,116,373 A 5/1992 Jakob et al.
5,116,375 A 5/1992 Hofmann
5,123,913 A 6/1992 Wilk et al.
5,123,914 A 6/1992 Cope
5,127,783 A 7/1992 Moghe et al.
5,127,785 A 7/1992 Faucher
5,129,901 A 7/1992 Decoste
5,129,902 A 7/1992 Goble et al.
5,129,904 A 7/1992 Illi
5,129,906 A 7/1992 Ross et al.
5,139,498 A 8/1992 Astudillo Ley
5,139,499 A 8/1992 Small et al.
5,139,520 A 8/1992 Rosenberg
5,143,498 A 9/1992 Whitman
5,147,362 A 9/1992 Goble
5,149,329 A 9/1992 Richardson
5,151,104 A 9/1992 Kenna
5,152,790 A 10/1992 Rosenberg et al.
5,154,189 A 10/1992 Oberlander
5,156,616 A 10/1992 Meadows et al.
5,163,960 A 11/1992 Bonutti
D331,626 S 12/1992 Hayhurst et al.
5,169,400 A 12/1992 Muhling et al.
5,171,274 A 12/1992 Fluckiger et al.
5,176,682 A 1/1993 Chow
5,178,629 A 1/1993 Kammerer
5,183,458 A 2/1993 Marx
5,190,545 A 3/1993 Corsi et al.
5,192,282 A 3/1993 Draenert

(56) References Cited

U.S. PATENT DOCUMENTS

| | | | |
|---|---|---|---|
| 5,197,987 | A | 3/1993 | Koch et al. |
| 5,199,135 | A | 4/1993 | Gold |
| 5,203,784 | A | 4/1993 | Ross et al. |
| 5,203,787 | A | 4/1993 | Noblitt et al. |
| 5,207,679 | A | 5/1993 | Li |
| 5,209,753 | A | 5/1993 | Biedermann et al. |
| 5,209,805 | A | 5/1993 | Spraggins |
| 5,211,647 | A | 5/1993 | Schmieding |
| 5,211,650 | A | 5/1993 | Noda |
| 5,214,987 | A | 6/1993 | Fenton, Sr. |
| 5,217,495 | A | 6/1993 | Kaplan et al. |
| 5,219,359 | A | 6/1993 | McQuilkin et al. |
| 5,222,976 | A | 6/1993 | Yoon |
| 5,224,940 | A | 7/1993 | Dann et al. |
| 5,224,946 | A | 7/1993 | Hayhurst et al. |
| 5,226,914 | A | 7/1993 | Caplan et al. |
| 5,230,699 | A | 7/1993 | Grasinger |
| 5,232,436 | A | 8/1993 | Janevski |
| 5,234,435 | A | 8/1993 | Seagrave, Jr. |
| 5,235,238 | A | 8/1993 | Nomura et al. |
| 5,236,445 | A | 8/1993 | Hayhurst et al. |
| 5,236,461 | A | 8/1993 | Forte |
| 5,242,447 | A | 9/1993 | Borzone |
| 5,246,441 | A | 9/1993 | Ross et al. |
| 5,249,899 | A | 10/1993 | Wilson |
| 5,250,053 | A | 10/1993 | Snyder |
| 5,258,015 | A | 11/1993 | Li et al. |
| 5,258,016 | A | 11/1993 | Dipoto et al. |
| 5,258,040 | A | 11/1993 | Bruchman et al. |
| 5,261,908 | A | 11/1993 | Campbell, Jr. |
| 5,268,001 | A | 12/1993 | Nicholson et al. |
| 5,269,160 | A | 12/1993 | Wood |
| 5,269,783 | A | 12/1993 | Sander |
| 5,269,806 | A | 12/1993 | Sardelis et al. |
| 5,269,809 | A | 12/1993 | Hayhurst et al. |
| 5,279,311 | A | 1/1994 | Snyder |
| 5,281,422 | A | 1/1994 | Badylak et al. |
| 5,282,809 | A | 2/1994 | Kammerer et al. |
| 5,282,832 | A | 2/1994 | Toso et al. |
| 5,282,867 | A | 2/1994 | Mikhail |
| 5,282,868 | A | 2/1994 | Bahler |
| 5,285,040 | A | 2/1994 | Brandberg et al. |
| 5,290,217 | A | 3/1994 | Campos |
| 5,290,243 | A | 3/1994 | Chodorow et al. |
| 5,306,301 | A | 4/1994 | Graf et al. |
| 5,312,410 | A | 5/1994 | Miller et al. |
| 5,312,422 | A | 5/1994 | Trott |
| 5,312,438 | A | 5/1994 | Johnson |
| 5,314,429 | A | 5/1994 | Goble |
| 5,318,566 | A | 6/1994 | Miller |
| 5,318,575 | A | 6/1994 | Chesterfield et al. |
| 5,318,577 | A | 6/1994 | Li |
| 5,318,578 | A | 6/1994 | Hasson |
| 5,320,115 | A | 6/1994 | Kenna |
| 5,320,626 | A | 6/1994 | Schmieding |
| 5,320,633 | A | 6/1994 | Allen et al. |
| 5,324,308 | A | 6/1994 | Pierce |
| 5,330,489 | A | 7/1994 | Green et al. |
| 5,330,534 | A | 7/1994 | Herrington et al. |
| 5,333,625 | A | 8/1994 | Klein |
| 5,334,204 | A | 8/1994 | Clewett et al. |
| 5,336,229 | A | 8/1994 | Noda |
| 5,336,231 | A | 8/1994 | Adair |
| 5,336,240 | A | 8/1994 | Metzler et al. |
| 5,339,870 | A | 8/1994 | Green et al. |
| 5,342,369 | A | 8/1994 | Harryman, II |
| 5,344,460 | A | 9/1994 | Turanyi et al. |
| 5,346,462 | A | 9/1994 | Barber |
| 5,350,380 | A | 9/1994 | Goble et al. |
| RE34,762 | E | 10/1994 | Goble et al. |
| 5,354,292 | A | 10/1994 | Braeuer et al. |
| 5,354,298 | A | 10/1994 | Lee et al. |
| 5,354,299 | A | 10/1994 | Coleman |
| 5,356,412 | A | 10/1994 | Golds et al. |
| 5,356,413 | A | 10/1994 | Martins et al. |
| 5,356,417 | A | 10/1994 | Golds |
| 5,358,511 | A | 10/1994 | Gatturna et al. |
| 5,358,530 | A | 10/1994 | Hodorek |
| 5,358,531 | A | 10/1994 | Goodfellow et al. |
| 5,360,431 | A | 11/1994 | Puno et al. |
| 5,362,294 | A | 11/1994 | Seitzinger |
| 5,362,911 | A | 11/1994 | Cevasco et al. |
| 5,364,400 | A | 11/1994 | Rego, Jr. et al. |
| 5,366,461 | A | 11/1994 | Blasnik |
| 5,368,599 | A | 11/1994 | Hirsch et al. |
| 5,370,646 | A | 12/1994 | Reese et al. |
| 5,370,661 | A | 12/1994 | Branch |
| 5,370,662 | A | 12/1994 | Stone et al. |
| 5,372,146 | A | 12/1994 | Branch |
| 5,372,604 | A | 12/1994 | Trott |
| 5,372,821 | A | 12/1994 | Badylak et al. |
| 5,374,268 | A | 12/1994 | Sander |
| 5,374,269 | A | 12/1994 | Rosenberg |
| 5,376,118 | A | 12/1994 | Kaplan et al. |
| 5,379,492 | A | 1/1995 | Glesser |
| 5,383,878 | A | 1/1995 | Roger et al. |
| 5,383,904 | A | 1/1995 | Totakura et al. |
| 5,385,567 | A | 1/1995 | Goble |
| 5,391,171 | A | 2/1995 | Schmieding |
| 5,391,176 | A | 2/1995 | De La Torre |
| 5,391,182 | A | 2/1995 | Chin |
| 5,393,302 | A | 2/1995 | Clark et al. |
| RE34,871 | E | 3/1995 | Mcguire et al. |
| 5,395,374 | A | 3/1995 | Miller et al. |
| 5,395,401 | A | 3/1995 | Bahler |
| 5,397,356 | A | 3/1995 | Goble et al. |
| 5,403,328 | A | 4/1995 | Shallman |
| 5,403,329 | A | 4/1995 | Hinchcliffe |
| 5,403,348 | A | 4/1995 | Bonutti |
| 5,405,359 | A | 4/1995 | Pierce |
| 5,411,550 | A | 5/1995 | Herweck et al. |
| 5,415,658 | A | 5/1995 | Kilpela et al. |
| 5,417,690 | A | 5/1995 | Sennett et al. |
| 5,417,691 | A | 5/1995 | Hayhurst |
| 5,417,698 | A | 5/1995 | Green et al. |
| 5,417,712 | A | 5/1995 | Whittaker et al. |
| 5,423,819 | A | 6/1995 | Small et al. |
| 5,423,821 | A | 6/1995 | Pasque |
| 5,423,823 | A | 6/1995 | Schmieding |
| 5,423,824 | A | 6/1995 | Akerfeldt et al. |
| 5,423,860 | A | 6/1995 | Lizardi et al. |
| 5,425,733 | A | 6/1995 | Schmieding |
| 5,425,766 | A | 6/1995 | Bowald |
| 5,433,751 | A | 7/1995 | Christel et al. |
| 5,437,680 | A | 8/1995 | Yoon |
| 5,437,685 | A | 8/1995 | Blasnik |
| 5,439,684 | A | 8/1995 | Prewett et al. |
| 5,441,508 | A | 8/1995 | Gazielly et al. |
| 5,443,468 | A | 8/1995 | Johnson |
| 5,443,482 | A | 8/1995 | Stone et al. |
| 5,443,483 | A | 8/1995 | Kirsch |
| 5,443,509 | A | 8/1995 | Boucher et al. |
| 5,445,833 | A | 8/1995 | Badylak et al. |
| 5,447,512 | A | 9/1995 | Wilson et al. |
| 5,449,361 | A | 9/1995 | Preissman |
| 5,451,203 | A | 9/1995 | Lamb |
| 5,454,811 | A | 10/1995 | Huebner |
| 5,454,821 | A | 10/1995 | Harm et al. |
| 5,456,685 | A | 10/1995 | Huebner |
| 5,456,721 | A | 10/1995 | Legrand |
| 5,456,722 | A | 10/1995 | Mcleod et al. |
| 5,458,601 | A | 10/1995 | Young, Jr. et al. |
| 5,458,604 | A | 10/1995 | Schmieding |
| 5,462,542 | A | 10/1995 | Alesi, Jr. |
| 5,462,560 | A | 10/1995 | Stevens |
| 5,464,426 | A | 11/1995 | Bonutti |
| 5,464,427 | A | 11/1995 | Curtis et al. |
| 5,464,440 | A | 11/1995 | Johansson |
| 5,466,237 | A | 11/1995 | Byrd, III et al. |
| 5,467,786 | A | 11/1995 | Allen et al. |
| 5,470,334 | A | 11/1995 | Ross et al. |
| 5,470,337 | A | 11/1995 | Moss |
| 5,470,338 | A | 11/1995 | Whitfield et al. |
| 5,470,354 | A | 11/1995 | Hershberger et al. |

(56) References Cited

U.S. PATENT DOCUMENTS 5,472,452 A 12/1995 Trott
5,474,565 A 12/1995 Trott
5,474,568 A 12/1995 Scott et al.
5,474,572 A 12/1995 Hayhurst
5,476,465 A 12/1995 Preissman
5,478,344 A 12/1995 Stone et al.
5,478,345 A 12/1995 Stone et al.
5,480,403 A 1/1996 Lee et al.
5,480,406 A 1/1996 Nolan et al.
5,480,446 A 1/1996 Goodfellow et al.
5,484,442 A 1/1996 Melker et al.
5,486,197 A 1/1996 Le et al.
5,486,359 A 1/1996 Caplan et al.
5,489,210 A 2/1996 Hanosh
5,490,750 A 2/1996 Gundy
5,495,974 A 3/1996 Deschenes et al.
5,496,290 A 3/1996 Ackerman
5,496,331 A 3/1996 Xu et al.
5,496,348 A 3/1996 Bonutti
5,498,302 A 3/1996 Davidson
5,500,000 A 3/1996 Feagin et al.
5,505,735 A 4/1996 Li
5,505,736 A 4/1996 Reimels et al.
5,507,754 A 4/1996 Green et al.
5,514,059 A 5/1996 Romney
5,520,691 A 5/1996 Branch
5,520,694 A 5/1996 Dance et al.
5,520,700 A 5/1996 Beyar et al.
5,520,702 A 5/1996 Sauer et al.
5,522,817 A 6/1996 Sander et al.
5,522,820 A 6/1996 Caspari et al.
5,522,843 A 6/1996 Zang
5,522,844 A 6/1996 Johnson
5,522,845 A 6/1996 Wenstrom, Jr.
5,522,846 A 6/1996 Bonutti
5,524,946 A 6/1996 Thompson
5,527,321 A 6/1996 Hinchliffe
5,527,342 A 6/1996 Pietrzak et al.
5,527,343 A 6/1996 Bonutti
5,531,759 A 7/1996 Kensey et al.
5,534,011 A 7/1996 Greene, Jr. et al.
5,534,012 A 7/1996 Bonutti
5,534,033 A 7/1996 Simpson
5,536,270 A 7/1996 Songer et al.
5,540,698 A 7/1996 Preissman
5,540,703 A 7/1996 Barker, Jr. et al.
5,540,718 A 7/1996 Bartlett
5,545,168 A 8/1996 Burke
5,545,178 A 8/1996 Kensey et al.
5,545,180 A 8/1996 Le et al.
5,545,228 A 8/1996 Kambin
5,549,613 A 8/1996 Goble et al.
5,549,617 A 8/1996 Green et al.
5,549,619 A 8/1996 Peters et al.
5,549,630 A 8/1996 Bonutti
5,549,631 A 8/1996 Bonutti
5,562,664 A 10/1996 Durlacher et al.
5,562,668 A 10/1996 Johnson
5,562,669 A 10/1996 Mcguire
5,562,683 A 10/1996 Chan
5,562,685 A 10/1996 Mollenauer et al.
5,562,686 A 10/1996 Sauer et al.
5,569,252 A 10/1996 Justin et al.
5,569,269 A 10/1996 Hart et al.
5,569,305 A 10/1996 Bonutti
5,569,306 A 10/1996 Thal
5,570,706 A 11/1996 Howell
5,571,090 A 11/1996 Sherts
5,571,104 A 11/1996 Li
5,571,139 A 11/1996 Jenkins, Jr.
5,572,655 A 11/1996 Tuljapurkar et al.
5,573,286 A 11/1996 Rogozinski
5,573,542 A 11/1996 Stevens
5,573,547 A 11/1996 LeVeen et al.
5,573,548 A 11/1996 Nazre et al.
5,577,299 A 11/1996 Thompson et al.
5,578,057 A 11/1996 Wenstrom, Jr.
5,584,695 A 12/1996 Sachdeva et al.
5,584,835 A 12/1996 Greenfield
5,584,836 A 12/1996 Ballintyn et al.
5,584,862 A 12/1996 Bonutti
5,586,986 A 12/1996 Hinchliffe
5,588,575 A 12/1996 Davignon
5,591,180 A 1/1997 Hinchliffe
5,591,181 A 1/1997 Stone et al.
5,591,207 A 1/1997 Coleman
5,593,407 A 1/1997 Reis
5,593,425 A 1/1997 Bonutti et al.
5,601,557 A 2/1997 Hayhurst
5,601,559 A 2/1997 Melker et al.
5,601,571 A 2/1997 Moss
5,603,716 A 2/1997 Morgan et al.
5,607,429 A 3/1997 Hayano et al.
5,607,430 A 3/1997 Bailey
5,613,971 A 3/1997 Lower et al.
5,618,290 A 4/1997 Toy et al.
5,626,611 A 5/1997 Liu et al.
5,626,614 A 5/1997 Hart
5,628,756 A 5/1997 Barker, Jr. et al.
5,628,766 A 5/1997 Johnson
5,630,824 A 5/1997 Hart
5,632,745 A 5/1997 Schwartz
5,632,748 A 5/1997 Beck, Jr. et al.
5,641,256 A 6/1997 Gundy
5,643,266 A 7/1997 Li
5,643,269 A 7/1997 Harle
5,643,273 A 7/1997 Clark
5,643,295 A 7/1997 Yoon
5,643,319 A 7/1997 Green et al.
5,643,320 A 7/1997 Lower et al.
5,643,321 A 7/1997 Mcdevitt
5,645,546 A 7/1997 Fard
5,645,547 A 7/1997 Coleman
5,645,568 A 7/1997 Chervitz et al.
5,645,588 A 7/1997 Graf et al.
5,647,874 A 7/1997 Hayhurst
5,649,959 A 7/1997 Hannam et al.
5,649,960 A 7/1997 Pavletic
5,649,963 A 7/1997 Mcdevitt
5,658,289 A 8/1997 Boucher et al.
5,658,299 A 8/1997 Hart
5,658,313 A 8/1997 Thal
5,662,658 A 9/1997 Wenstrom, Jr.
5,662,663 A 9/1997 Shallman
5,662,677 A 9/1997 Wimmer
5,662,681 A 9/1997 Nash et al.
5,665,112 A 9/1997 Thal
5,667,513 A 9/1997 Torrie et al.
5,671,695 A 9/1997 Schroeder
5,673,546 A 10/1997 Abraham et al.
5,674,224 A 10/1997 Howell et al.
5,679,723 A 10/1997 Cooper
5,681,334 A 10/1997 Evans et al.
5,681,352 A 10/1997 Clancy, III et al.
5,683,404 A 11/1997 Johnson
5,683,419 A 11/1997 Thal
5,688,284 A 11/1997 Chervitz et al.
5,688,285 A 11/1997 Yamada
5,690,655 A 11/1997 Hart et al.
5,690,676 A 11/1997 Dipoto et al.
5,690,678 A 11/1997 Johnson
5,693,046 A 12/1997 Songer et al.
5,695,497 A 12/1997 Stahelin
5,697,929 A 12/1997 Mellinger
5,697,969 A 12/1997 Schmitt et al.
5,699,657 A 12/1997 Paulson
5,700,277 A 12/1997 Nash et al.
5,702,397 A 12/1997 Goble et al.
5,702,422 A 12/1997 Stone
5,702,462 A 12/1997 Oberlander
5,702,464 A 12/1997 Lackey et al.
5,707,373 A 1/1998 Sevrain et al.
5,709,708 A 1/1998 Thal et al.
5,711,969 A 1/1998 Patel et al.

(56) References Cited

U.S. PATENT DOCUMENTS 5,713,005 A 1/1998 Proebsting
5,713,897 A 2/1998 Goble et al.
5,713,904 A 2/1998 Errico et al.
5,713,905 A 2/1998 Goble et al.
5,713,921 A 2/1998 Bonutti
5,715,578 A 2/1998 Knudson
5,716,359 A 2/1998 Ojima et al.
5,716,397 A 2/1998 Myers
5,716,616 A 2/1998 Prockop et al.
5,718,717 A 2/1998 Bonutti
5,720,747 A 2/1998 Burke
5,720,765 A 2/1998 Thal
5,720,766 A 2/1998 Zang et al.
5,722,976 A 3/1998 Brown
5,723,331 A 3/1998 Tubo et al.
5,725,529 A 3/1998 Nicholson et al.
5,725,549 A 3/1998 Lam
5,725,556 A 3/1998 Moser et al.
5,725,557 A 3/1998 Gatturna et al.
5,725,581 A 3/1998 Branemark
5,725,582 A 3/1998 Bevan et al.
5,726,722 A 3/1998 Uehara et al.
5,728,107 A 3/1998 Zlock et al.
5,728,109 A 3/1998 Schulze et al.
5,728,136 A 3/1998 Thal
5,733,293 A 3/1998 Scirica et al.
5,733,306 A 3/1998 Bonutti
5,733,307 A 3/1998 Dinsdale
5,735,875 A 4/1998 Bonutti et al.
5,741,259 A 4/1998 Chan
5,741,260 A 4/1998 Songer et al.
5,741,281 A 4/1998 Martin
5,743,912 A 4/1998 Lahille et al.
5,746,751 A 5/1998 Sherts
5,746,752 A 5/1998 Burkhart
5,746,754 A 5/1998 Chan
5,749,898 A 5/1998 Schulze et al.
5,755,729 A 5/1998 De et al.
5,755,791 A 5/1998 Whitson et al.
5,766,176 A 6/1998 Duncan
5,766,218 A 6/1998 Arnott
5,766,250 A 6/1998 Chervitz et al.
5,769,894 A 6/1998 Ferragamo
5,769,899 A 6/1998 Schwartz et al.
5,772,673 A 6/1998 Cuny et al.
5,776,196 A 7/1998 Matsuzaki et al.
5,776,200 A 7/1998 Johnson et al.
5,782,845 A 7/1998 Shewchuk
5,782,862 A 7/1998 Bonutti
5,782,864 A 7/1998 Lizardi
5,782,866 A 7/1998 Wenstrom, Jr.
5,782,925 A 7/1998 Collazo et al.
5,785,714 A 7/1998 Morgan et al.
5,786,217 A 7/1998 Tubo et al.
5,792,142 A 8/1998 Galitzer
5,792,149 A 8/1998 Sherts et al.
5,796,127 A 8/1998 Hayafuji et al.
5,797,913 A 8/1998 Dambreville et al.
5,797,915 A 8/1998 Pierson, III et al.
5,797,916 A 8/1998 McDowell
5,797,928 A 8/1998 Kogasaka
5,800,407 A 9/1998 Eldor
5,800,447 A 9/1998 Wenstrom, Jr.
5,800,543 A 9/1998 Mcleod et al.
5,810,824 A 9/1998 Chan
5,810,848 A 9/1998 Hayhurst
5,811,094 A 9/1998 Caplan et al.
5,814,056 A 9/1998 Prosst et al.
5,814,069 A 9/1998 Schulze et al.
5,814,070 A 9/1998 Borzone et al.
5,814,071 A 9/1998 Mcdevitt et al.
5,814,072 A 9/1998 Bonutti
5,814,073 A 9/1998 Bonutti
5,817,095 A 10/1998 Smith
5,823,980 A 10/1998 Kopfer
5,824,011 A 10/1998 Stone et al.
5,824,066 A 10/1998 Gross
5,827,285 A 10/1998 Bramlet
5,830,234 A 11/1998 Wojciechowicz et al.
5,836,955 A 11/1998 Buelna et al.
5,843,084 A 12/1998 Hart et al.
5,845,645 A 12/1998 Bonutti
5,846,254 A 12/1998 Schulze et al.
5,848,983 A 12/1998 Basaj et al.
5,849,012 A 12/1998 Abboudi
5,860,947 A 1/1999 Stamler
5,860,973 A 1/1999 Michelson
5,860,978 A 1/1999 Mcdevitt et al.
5,868,740 A 2/1999 LaVeen et al.
5,868,748 A 2/1999 Burke
5,868,789 A 2/1999 Huebner
5,871,456 A 2/1999 Armstrong et al.
5,871,484 A 2/1999 Spievack et al.
5,871,486 A 2/1999 Huebner
5,871,490 A 2/1999 Schulze et al.
5,871,542 A 2/1999 Goodfellow et al.
5,871,543 A 2/1999 Hofmann
5,885,294 A 3/1999 Pedlick et al.
5,891,168 A 4/1999 Thal
5,893,592 A 4/1999 Schulze et al.
5,895,395 A 4/1999 Yeung
5,897,564 A 4/1999 Schulze et al.
5,897,574 A 4/1999 Bonutti
5,899,902 A 5/1999 Brown et al.
5,899,920 A 5/1999 Desatnick et al.
5,899,938 A 5/1999 Sklar et al.
5,906,934 A 5/1999 Grande et al.
5,908,421 A 6/1999 Beger
5,908,436 A 6/1999 Cuschieri et al.
5,910,148 A 6/1999 Reimels et al.
5,911,721 A 6/1999 Nicholson et al.
5,916,557 A 6/1999 Berlowitz-Tarrant et al.
5,918,604 A 7/1999 Whelan
5,919,232 A 7/1999 Chaffringeon et al.
5,921,986 A 7/1999 Bonutti
5,925,008 A 7/1999 Douglas
5,928,231 A 7/1999 Klein et al.
5,928,267 A 7/1999 Bonutti et al.
5,928,286 A 7/1999 Ashby et al.
RE36,289 E 8/1999 Le et al.
5,931,838 A 8/1999 Vito
5,931,844 A 8/1999 Thompson et al.
5,931,869 A 8/1999 Boucher et al.
5,935,119 A 8/1999 Guy et al.
5,935,129 A 8/1999 Mcdevitt et al.
5,935,133 A 8/1999 Wagner et al.
5,935,134 A 8/1999 Pedlick et al.
5,935,149 A 8/1999 Ek
5,938,668 A 8/1999 Scirica et al.
5,941,439 A 8/1999 Kammerer et al.
5,941,900 A 8/1999 Bonutti
5,944,739 A 8/1999 Zlock et al.
5,946,783 A 9/1999 Plociennik et al.
5,947,915 A 9/1999 Thibodo, Jr.
5,947,982 A 9/1999 Duran
5,947,999 A 9/1999 Groiso
5,948,002 A 9/1999 Bonutti
5,951,559 A 9/1999 Burkhart
5,951,560 A 9/1999 Simon et al.
5,954,747 A 9/1999 Clark
5,957,953 A 9/1999 Dipoto et al.
5,961,520 A 10/1999 Beck, Jr. et al.
5,961,521 A 10/1999 Roger
5,961,524 A 10/1999 Crombie
5,963,869 A 10/1999 Fehnel
5,964,764 A 10/1999 West, Jr. et al.
5,964,767 A 10/1999 Tapia et al.
5,964,769 A 10/1999 Wagner et al.
5,964,783 A 10/1999 Grafton et al.
5,964,808 A 10/1999 Blaha et al.
5,968,045 A 10/1999 Frazier
5,968,047 A 10/1999 Reed
5,968,077 A 10/1999 Wojciechowicz et al.
5,968,078 A 10/1999 Grotz

(56) References Cited

U.S. PATENT DOCUMENTS

| | | | |
|---|---|---|---|
| 5,968,099 | A | 10/1999 | Badorf et al. |
| 5,970,697 | A | 10/1999 | Jacobs et al. |
| 5,972,006 | A | 10/1999 | Sciaino, Jr. |
| 5,976,125 | A | 11/1999 | Graham |
| 5,976,127 | A | 11/1999 | Lax |
| 5,980,473 | A | 11/1999 | Korakianitis et al. |
| 5,980,524 | A | 11/1999 | Justin et al. |
| 5,980,539 | A | 11/1999 | Kontos |
| 5,980,548 | A | 11/1999 | Evans et al. |
| 5,980,558 | A | 11/1999 | Wiley |
| 5,980,559 | A | 11/1999 | Bonutti |
| 5,989,252 | A | 11/1999 | Fumex |
| 5,989,256 | A | 11/1999 | Kuslich et al. |
| 5,989,282 | A | 11/1999 | Bonutti |
| 5,989,294 | A | 11/1999 | Marlow |
| 5,993,452 | A | 11/1999 | Vandewalle |
| 5,993,476 | A | 11/1999 | Groiso |
| 5,997,542 | A | 12/1999 | Burke |
| 5,997,552 | A | 12/1999 | Person et al. |
| 5,997,575 | A | 12/1999 | Whitson et al. |
| 6,001,100 | A | 12/1999 | Sherman et al. |
| 6,001,106 | A | 12/1999 | Ryan et al. |
| 6,004,351 | A | 12/1999 | Tomita et al. |
| 6,004,352 | A | 12/1999 | Buni |
| 6,007,538 | A | 12/1999 | Levin |
| 6,007,567 | A | 12/1999 | Bonutti |
| 6,010,525 | A | 1/2000 | Bonutti et al. |
| 6,013,103 | A | 1/2000 | Kaufman et al. |
| 6,016,727 | A | 1/2000 | Morgan |
| 6,019,767 | A | 2/2000 | Howell |
| 6,022,352 | A | 2/2000 | Vandewalle |
| 6,022,373 | A | 2/2000 | Li |
| 6,023,661 | A | 2/2000 | Sottery |
| 6,024,758 | A | 2/2000 | Thal |
| 6,027,523 | A | 2/2000 | Schmieding |
| 6,030,410 | A | 2/2000 | Zurbrugg |
| 6,033,429 | A | 3/2000 | Magovern |
| 6,033,430 | A | 3/2000 | Bonutti |
| 6,036,695 | A | 3/2000 | Smith |
| 6,039,753 | A | 3/2000 | Meislin |
| 6,041,485 | A | 3/2000 | Pedlick et al. |
| 6,042,601 | A | 3/2000 | Smith |
| 6,042,609 | A | 3/2000 | Giordano et al. |
| 6,045,551 | A | 4/2000 | Bonutti |
| 6,045,571 | A | 4/2000 | Hill et al. |
| 6,045,572 | A | 4/2000 | Johnson et al. |
| 6,045,573 | A | 4/2000 | Wenstrom, Jr. et al. |
| 6,045,574 | A | 4/2000 | Thal |
| 6,047,826 | A | 4/2000 | Kalinski et al. |
| 6,048,343 | A | 4/2000 | Mathis et al. |
| 6,051,006 | A | 4/2000 | Shluzas et al. |
| 6,051,007 | A | 4/2000 | Hogendijk et al. |
| 6,053,916 | A | 4/2000 | Moore |
| 6,053,921 | A | 4/2000 | Wagner et al. |
| 6,056,752 | A | 5/2000 | Roger |
| 6,056,772 | A | 5/2000 | Bonutti |
| 6,056,773 | A | 5/2000 | Bonutti |
| 6,059,817 | A | 5/2000 | Bonutti et al. |
| 6,059,818 | A | 5/2000 | Johnson et al. |
| 6,062,344 | A | 5/2000 | Okabe et al. |
| 6,066,146 | A | 5/2000 | Carroll et al. |
| 6,066,173 | A | 5/2000 | Mckernan et al. |
| 6,068,648 | A | 5/2000 | Cole et al. |
| 6,071,305 | A | 6/2000 | Brown et al. |
| 6,074,403 | A | 6/2000 | Nord |
| 6,077,277 | A | 6/2000 | Mollenauer et al. |
| 6,077,292 | A | 6/2000 | Bonutti |
| 6,080,185 | A | 6/2000 | Johnson et al. |
| 6,083,257 | A | 7/2000 | Taylor et al. |
| 6,086,591 | A | 7/2000 | Bojarski |
| 6,086,592 | A | 7/2000 | Rosenberg et al. |
| 6,086,608 | A | 7/2000 | Ek et al. |
| 6,093,200 | A | 7/2000 | Liu et al. |
| 6,096,060 | A | 8/2000 | Fitts et al. |
| 6,099,527 | A | 8/2000 | Hochschuler et al. |
| 6,099,530 | A | 8/2000 | Simonian et al. |
| 6,099,568 | A | 8/2000 | Simonian et al. |
| 6,102,934 | A | 8/2000 | Li |
| 6,106,545 | A | 8/2000 | Egan et al. |
| 6,110,128 | A | 8/2000 | Andelin et al. |
| 6,110,207 | A | 8/2000 | Eichhorn et al. |
| 6,113,604 | A | 9/2000 | Whittaker et al. |
| 6,117,160 | A | 9/2000 | Bonutti |
| 6,117,162 | A | 9/2000 | Schmieding et al. |
| 6,123,710 | A | 9/2000 | Pinczewski et al. |
| 6,127,596 | A | 10/2000 | Brown et al. |
| 6,132,433 | A | 10/2000 | Whelan |
| 6,132,437 | A | 10/2000 | Omurtag |
| 6,136,010 | A | 10/2000 | Modesitt et al. |
| 6,139,565 | A | 10/2000 | Stone et al. |
| RE36,974 | E | 11/2000 | Bonutti |
| 6,143,017 | A | 11/2000 | Thal |
| 6,146,406 | A | 11/2000 | Shluzas et al. |
| 6,146,408 | A | 11/2000 | Bartlett |
| 6,149,653 | A | 11/2000 | Deslauriers |
| 6,149,669 | A | 11/2000 | Li |
| 6,150,163 | A | 11/2000 | McPherson et al. |
| 6,152,928 | A | 11/2000 | Wenstrom, Jr. |
| 6,152,934 | A | 11/2000 | Harper et al. |
| 6,152,936 | A | 11/2000 | Christy et al. |
| 6,152,949 | A | 11/2000 | Bonutti |
| 6,156,039 | A | 12/2000 | Thal |
| 6,156,056 | A | 12/2000 | Kearns et al. |
| 6,159,234 | A | 12/2000 | Bonutti et al. |
| 6,165,203 | A | 12/2000 | Krebs |
| 6,168,598 | B1 | 1/2001 | Martello |
| 6,168,628 | B1 | 1/2001 | Huebner |
| 6,171,310 | B1 | 1/2001 | Giordano et al. |
| 6,174,324 | B1 | 1/2001 | Egan et al. |
| 6,179,840 | B1 | 1/2001 | Bowman |
| 6,183,461 | B1 | 2/2001 | Matsuura et al. |
| 6,183,737 | B1 | 2/2001 | Zaleske et al. |
| 6,187,025 | B1 | 2/2001 | Machek |
| 6,190,348 | B1 | 2/2001 | Tiemann |
| 6,190,401 | B1 | 2/2001 | Green et al. |
| 6,190,411 | B1 | 2/2001 | Lo |
| 6,190,415 | B1 | 2/2001 | Cooke et al. |
| 6,193,754 | B1 | 2/2001 | Seedhom |
| 6,200,318 | B1 | 3/2001 | Har-shai et al. |
| 6,200,329 | B1 | 3/2001 | Fung et al. |
| 6,200,330 | B1 | 3/2001 | Benderev et al. |
| 6,200,606 | B1 | 3/2001 | Peterson et al. |
| 6,200,685 | B1 | 3/2001 | Davidson |
| 6,203,556 | B1 | 3/2001 | Evans et al. |
| 6,203,563 | B1 | 3/2001 | Fernandez |
| 6,203,565 | B1 | 3/2001 | Bonutti et al. |
| 6,203,572 | B1 | 3/2001 | Johnson et al. |
| 6,203,576 | B1 | 3/2001 | Afriat et al. |
| 6,206,883 | B1 | 3/2001 | Tunc |
| 6,210,376 | B1 | 4/2001 | Grayson |
| 6,210,381 | B1 | 4/2001 | Morse |
| 6,210,445 | B1 | 4/2001 | Zawadzki |
| 6,214,007 | B1 | 4/2001 | Anderson |
| 6,214,012 | B1 | 4/2001 | Karpman et al. |
| 6,217,580 | B1 | 4/2001 | Levin |
| 6,221,107 | B1 | 4/2001 | Steiner |
| 6,228,096 | B1 | 5/2001 | Marchand |
| 6,231,592 | B1 | 5/2001 | Bonutti et al. |
| 6,234,980 | B1 | 5/2001 | Bell |
| 6,235,057 | B1 | 5/2001 | Roger et al. |
| 6,235,058 | B1 | 5/2001 | Huene |
| 6,238,395 | B1 | 5/2001 | Bonutti |
| 6,241,734 | B1 | 6/2001 | Scribner et al. |
| 6,241,747 | B1 | 6/2001 | Ruff |
| 6,241,771 | B1 | 6/2001 | Gresser et al. |
| 6,245,024 | B1 | 6/2001 | Montagnino et al. |
| 6,245,081 | B1 | 6/2001 | Bowman |
| 6,254,604 | B1 | 7/2001 | Howell |
| 6,258,091 | B1 | 7/2001 | Sevrain et al. |
| 6,267,766 | B1 | 7/2001 | Burkhart |
| 6,269,716 | B1 | 8/2001 | Amis |
| 6,270,518 | B1 | 8/2001 | Pedlick et al. |
| 6,273,890 | B1 | 8/2001 | Frazier |
| 6,280,474 | B1 | 8/2001 | Cassidy et al. |

(56) References Cited

U.S. PATENT DOCUMENTS

| | | | |
|---|---|---|---|
| 6,283,973 | B1 | 9/2001 | Hubbard et al. |
| 6,283,996 | B1 | 9/2001 | Chervitz et al. |
| 6,287,307 | B1 | 9/2001 | Abboudi |
| 6,287,325 | B1 | 9/2001 | Bonutti |
| 6,293,929 | B1 | 9/2001 | Smith et al. |
| 6,293,961 | B2 | 9/2001 | Schwartz et al. |
| 6,296,659 | B1 | 10/2001 | Foerster |
| 6,299,615 | B1 | 10/2001 | Huebner |
| 6,302,888 | B1 | 10/2001 | Mellinger et al. |
| 6,302,899 | B1 | 10/2001 | Johnson et al. |
| 6,302,915 | B1 | 10/2001 | Cooney, III et al. |
| 6,303,158 | B1 | 10/2001 | Odgaard et al. |
| 6,306,156 | B1 | 10/2001 | Clark |
| 6,306,158 | B1 | 10/2001 | Bartlett |
| 6,306,159 | B1 | 10/2001 | Schwartz et al. |
| 6,309,124 | B1 | 10/2001 | Gueret |
| 6,309,405 | B1 | 10/2001 | Bonutti |
| 6,312,448 | B1 | 11/2001 | Bonutti |
| 6,315,788 | B1 | 11/2001 | Roby |
| 6,319,224 | B1 | 11/2001 | Stout et al. |
| 6,319,271 | B1 | 11/2001 | Schwartz et al. |
| 6,328,758 | B1 | 12/2001 | Tornier et al. |
| 6,334,064 | B1 | 12/2001 | Fiddian-Green |
| 6,342,060 | B1 | 1/2002 | Adams |
| 6,343,531 | B2 | 2/2002 | Amis |
| 6,355,066 | B1 | 3/2002 | Kim et al. |
| 6,358,270 | B1 | 3/2002 | Lemer |
| 6,364,897 | B1 | 4/2002 | Bonutti |
| 6,368,322 | B1 | 4/2002 | Luks et al. |
| 6,368,326 | B1 | 4/2002 | Dakin et al. |
| 6,368,343 | B1 | 4/2002 | Bonutti et al. |
| 6,371,124 | B1 | 4/2002 | Whelan |
| 6,379,361 | B1 | 4/2002 | Beck, Jr. et al. |
| 6,383,190 | B1 | 5/2002 | Preissman |
| 6,383,199 | B2 | 5/2002 | Carter et al. |
| 6,387,111 | B1 | 5/2002 | Barber |
| 6,387,113 | B1 | 5/2002 | Hawkins et al. |
| 6,387,129 | B2 | 5/2002 | Rieser et al. |
| 6,391,030 | B1 | 5/2002 | Wagner et al. |
| 6,398,785 | B2 | 6/2002 | Carchidi et al. |
| 6,406,456 | B1 | 6/2002 | Slate et al. |
| 6,406,479 | B1 | 6/2002 | Justin et al. |
| 6,409,743 | B1 | 6/2002 | Fenton, Jr. |
| 6,413,260 | B1 | 7/2002 | Berrevoets et al. |
| 6,423,073 | B2 | 7/2002 | Bowman |
| 6,423,088 | B1 | 7/2002 | Fenton, Jr. |
| 6,425,924 | B1 | 7/2002 | Rousseau |
| 6,428,562 | B2 | 8/2002 | Bonutti |
| 6,432,123 | B2 | 8/2002 | Schwartz et al. |
| 6,436,123 | B1 | 8/2002 | Magovern |
| 6,436,124 | B1 | 8/2002 | Anderson et al. |
| 6,440,134 | B1 | 8/2002 | Zaccherotti et al. |
| 6,440,136 | B1 | 8/2002 | Gambale et al. |
| 6,447,516 | B1 | 9/2002 | Bonutti |
| 6,451,030 | B2 | 9/2002 | Li et al. |
| 6,454,768 | B1 | 9/2002 | Jackson |
| 6,458,134 | B1 | 10/2002 | Songer et al. |
| 6,458,161 | B1 | 10/2002 | Gibbs et al. |
| 6,461,373 | B2 | 10/2002 | Wyman et al. |
| 6,464,690 | B1 | 10/2002 | Castaneda et al. |
| 6,464,713 | B2 | 10/2002 | Bonutti |
| 6,468,293 | B2 | 10/2002 | Bonutti et al. |
| 6,471,707 | B1 | 10/2002 | Miller et al. |
| 6,475,230 | B1 | 11/2002 | Bonutti et al. |
| 6,478,753 | B2 | 11/2002 | Reay-young |
| 6,482,210 | B1 | 11/2002 | Skiba et al. |
| 6,485,504 | B1 | 11/2002 | Johnson et al. |
| 6,491,714 | B1 | 12/2002 | Bennett |
| 6,497,901 | B1 | 12/2002 | Royer |
| 6,500,184 | B1 | 12/2002 | Chan et al. |
| 6,500,195 | B2 | 12/2002 | Bonutti |
| 6,500,208 | B1 | 12/2002 | Metzger et al. |
| RE37,963 | E | 1/2003 | Thal |
| 6,503,267 | B2 | 1/2003 | Bonutti et al. |
| 6,506,190 | B1 | 1/2003 | Walshe |
| 6,508,820 | B2 | 1/2003 | Bales |
| 6,508,821 | B1 | 1/2003 | Schwartz et al. |
| 6,508,830 | B2 | 1/2003 | Steiner |
| 6,511,498 | B1 | 1/2003 | Fumex |
| 6,511,499 | B2 | 1/2003 | Schmieding et al. |
| 6,514,274 | B1 | 2/2003 | Boucher et al. |
| 6,517,542 | B1 | 2/2003 | Papay et al. |
| 6,517,552 | B1 | 2/2003 | Nord et al. |
| 6,517,564 | B1 | 2/2003 | Grafton et al. |
| 6,517,578 | B2 | 2/2003 | Hein |
| 6,517,579 | B1 | 2/2003 | Paulos et al. |
| 6,520,964 | B2 | 2/2003 | Tallarida et al. |
| 6,520,980 | B1 | 2/2003 | Foerster |
| 6,524,317 | B1 | 2/2003 | Ritchart et al. |
| 6,527,777 | B2 | 3/2003 | Justin |
| 6,527,794 | B1 | 3/2003 | Mcdevitt et al. |
| 6,527,795 | B1 | 3/2003 | Lizardi |
| 6,533,795 | B1 | 3/2003 | Tran et al. |
| 6,533,802 | B2 | 3/2003 | Bojarski et al. |
| 6,537,319 | B2 | 3/2003 | Whelan |
| 6,540,750 | B2 | 4/2003 | Burkhart |
| 6,540,769 | B1 | 4/2003 | Miller, III |
| 6,540,770 | B1 | 4/2003 | Tornier et al. |
| 6,540,783 | B1 | 4/2003 | Whittaker et al. |
| 6,543,094 | B2 | 4/2003 | D'addario |
| 6,544,281 | B2 | 4/2003 | Elattrache et al. |
| 6,547,564 | B1 | 4/2003 | Hansson |
| 6,547,778 | B1 | 4/2003 | Sklar et al. |
| 6,547,800 | B2 | 4/2003 | Foerster et al. |
| 6,551,330 | B1 | 4/2003 | Bain et al. |
| 6,551,343 | B1 | 4/2003 | Tormala et al. |
| 6,551,353 | B1 | 4/2003 | Baker et al. |
| 6,553,802 | B1 | 4/2003 | Jacob |
| 6,554,830 | B1 | 4/2003 | Chappius |
| 6,554,852 | B1 | 4/2003 | Oberlander |
| 6,554,862 | B2 | 4/2003 | Hays et al. |
| 6,558,389 | B2 | 5/2003 | Clark et al. |
| 6,562,071 | B2 | 5/2003 | Järvinen |
| 6,565,572 | B2 | 5/2003 | Chappius |
| 6,565,573 | B1 | 5/2003 | Ferrante |
| 6,569,167 | B1 | 5/2003 | Bobechko et al. |
| 6,569,186 | B1 | 5/2003 | Winters et al. |
| 6,569,187 | B1 | 5/2003 | Bonutti et al. |
| 6,572,635 | B1 | 6/2003 | Bonutti |
| 6,572,655 | B1 | 6/2003 | Johnson |
| 6,575,925 | B1 | 6/2003 | Noble |
| 6,579,295 | B1 | 6/2003 | Supinski |
| 6,582,453 | B1 | 6/2003 | Tran et al. |
| 6,585,730 | B1 | 7/2003 | Foerster |
| 6,585,740 | B2 | 7/2003 | Schlapfer et al. |
| 6,585,750 | B2 | 7/2003 | Bonutti et al. |
| 6,589,245 | B1 | 7/2003 | Weiler et al. |
| 6,589,246 | B1 | 7/2003 | Hack et al. |
| 6,592,609 | B1 | 7/2003 | Bonutti |
| 6,592,622 | B1 | 7/2003 | Ferguson |
| 6,595,911 | B2 | 7/2003 | Lovuolo |
| 6,599,289 | B1 | 7/2003 | Bojarski et al. |
| 6,599,319 | B2 | 7/2003 | Knudsen et al. |
| 6,605,096 | B1 | 8/2003 | Ritchart |
| 6,607,548 | B2 | 8/2003 | Pohjonen et al. |
| 6,610,064 | B1 | 8/2003 | Goble et al. |
| 6,610,079 | B1 | 8/2003 | Li et al. |
| 6,613,018 | B2 | 9/2003 | Bagga et al. |
| 6,616,694 | B1 | 9/2003 | Hart |
| 6,620,166 | B1 | 9/2003 | Wenstrom, Jr. et al. |
| 6,620,185 | B1 | 9/2003 | Harvie et al. |
| 6,620,195 | B2 | 9/2003 | Goble et al. |
| 6,620,329 | B2 | 9/2003 | Rosen et al. |
| 6,620,349 | B1 | 9/2003 | Lopez |
| 6,623,492 | B1 | 9/2003 | Berube et al. |
| 6,623,524 | B2 | 9/2003 | Schmieding |
| 6,626,910 | B1 | 9/2003 | Hugues |
| 6,626,919 | B1 | 9/2003 | Swanstrom |
| 6,626,930 | B1 | 9/2003 | Allen et al. |
| 6,629,977 | B1 | 10/2003 | Wolf |
| 6,629,997 | B2 | 10/2003 | Mansmann |
| 6,632,245 | B2 | 10/2003 | Kim |
| 6,635,073 | B2 | 10/2003 | Bonutti |
| 6,638,279 | B2 | 10/2003 | Bonutti |

(56) References Cited

U.S. PATENT DOCUMENTS 6,638,286 B1 10/2003 Burbank et al.
6,638,312 B2 10/2003 Plouhar et al.
6,641,596 B1 11/2003 Lizardi
6,641,597 B2 11/2003 Burkhart et al.
6,645,169 B1 11/2003 Slate et al.
6,645,211 B2 11/2003 Magana
6,645,227 B2 11/2003 Fallin et al.
6,648,903 B1 11/2003 Pierson, III
6,648,921 B2 11/2003 Anderson et al.
6,652,450 B2 11/2003 Neisz et al.
6,652,533 B2 11/2003 O'neil
6,652,560 B1 11/2003 Gerke et al.
6,652,562 B2 11/2003 Collier et al.
6,652,563 B2 11/2003 Dreyfuss
6,656,182 B1 12/2003 Hayhurst
6,656,183 B2 12/2003 Colleran et al.
6,658,182 B1 12/2003 Gonthier
6,660,008 B1 12/2003 Foerster et al.
6,660,022 B1 12/2003 Li et al.
6,663,634 B2 12/2003 Ahrens et al.
6,663,656 B2 12/2003 Schmieding et al.
6,666,868 B2 12/2003 Fallin
6,666,877 B2 12/2003 Morgan et al.
6,669,707 B1 12/2003 Swanstrom et al.
6,679,889 B1 1/2004 West, Jr. et al.
6,682,533 B1 1/2004 Dinsdale et al.
6,682,549 B2 1/2004 Bartlett
6,685,728 B2 2/2004 Sinnott et al.
6,689,137 B2 2/2004 Reed
6,689,153 B1 2/2004 Skiba
6,689,154 B2 2/2004 Bartlett
6,692,499 B2 2/2004 Tormala et al.
6,692,516 B2 2/2004 West, Jr. et al.
6,695,852 B2 2/2004 Gleason
6,712,849 B2 3/2004 Re et al.
6,712,859 B2 3/2004 Rousseau
6,716,190 B1 4/2004 Glines et al.
6,716,224 B2 4/2004 Singhatat
6,716,234 B2 4/2004 Grafton et al.
6,716,957 B2 4/2004 Tunc
6,730,092 B2 5/2004 Songer
6,730,124 B2 5/2004 Steiner
6,736,799 B1 5/2004 Erbe et al.
6,737,053 B1 5/2004 Goh et al.
6,746,483 B1 6/2004 Bojarski et al.
6,752,780 B2 6/2004 Stout et al.
6,752,810 B1 6/2004 Gao et al.
6,752,831 B2 6/2004 Sybert et al.
6,755,836 B1 6/2004 Lewis
6,755,868 B2 6/2004 Rousseau
6,761,722 B2 7/2004 Cole et al.
6,761,739 B2 7/2004 Shepard
6,767,037 B2 7/2004 Wenstrom, Jr.
6,770,076 B2 8/2004 Foerster
6,770,084 B1 8/2004 Bain et al.
6,773,450 B2 8/2004 Leung et al.
6,779,701 B2 8/2004 Bailly et al.
6,780,190 B2 8/2004 Maroney
6,780,198 B1 8/2004 Gregoire et al.
6,790,210 B1 9/2004 Cragg et al.
6,793,595 B1 9/2004 Monnet
6,802,862 B1 10/2004 Roger et al.
6,808,502 B2 10/2004 Nguyen
6,808,526 B1 10/2004 Magerl et al.
6,814,741 B2 11/2004 Bowman et al.
6,830,572 B2 12/2004 Mcdevitt et al.
6,833,005 B1 12/2004 Mantas
6,835,377 B2 12/2004 Goldberg et al.
6,840,953 B2 1/2005 Martinek
6,860,885 B2 3/2005 Bonutti
6,860,895 B1 3/2005 Akerfeldt et al.
6,863,671 B1 3/2005 Strobel et al.
6,872,040 B2 3/2005 Deeg et al.
6,872,210 B2 3/2005 Hearn
6,875,216 B2 4/2005 Wolf
6,884,249 B2 4/2005 May et al.
6,887,243 B2 5/2005 Culbert
6,887,259 B2 5/2005 Lizardi
6,887,271 B2 5/2005 Justin et al.
6,890,354 B2 5/2005 Steiner et al.
6,893,448 B2 5/2005 O'quinn et al.
6,896,686 B2 5/2005 Weber
6,899,722 B2 5/2005 Bonutti
6,902,573 B2 6/2005 Strobel et al.
6,905,513 B1 6/2005 Metzger
6,908,466 B1 6/2005 Bonutti et al.
6,911,202 B2 6/2005 Amir et al.
6,916,292 B2 7/2005 Morawski et al.
6,916,321 B2 7/2005 Tenhuisen et al.
6,921,402 B2 7/2005 Contiliano et al.
6,923,823 B1 8/2005 Bartlett et al.
6,923,824 B2 8/2005 Morgan et al.
6,923,832 B1 8/2005 Sharkey et al.
6,939,379 B2 9/2005 Sklar
6,946,001 B2 9/2005 Sanford et al.
6,949,102 B2 9/2005 Andrews
6,951,565 B2 10/2005 Keane et al.
6,960,214 B2 11/2005 Burkinshaw
6,966,887 B1 11/2005 Chin
6,966,916 B2 11/2005 Kumar
6,969,391 B1 11/2005 Gazzani
6,969,398 B2 11/2005 Stevens et al.
6,972,027 B2 12/2005 Fallin et al.
6,980,903 B2 12/2005 Daniels et al.
6,984,237 B2 1/2006 Hatch et al.
6,986,781 B2 1/2006 Smith
6,989,034 B2 1/2006 Hammer et al.
6,994,719 B2 2/2006 Grafton
6,994,725 B1 2/2006 Goble
7,001,429 B2 2/2006 Ferguson
7,004,959 B2 2/2006 Bonutti
7,008,451 B2 3/2006 Justin et al.
7,011,682 B2 3/2006 Lashinski et al.
7,033,397 B2 4/2006 Webster et al.
7,048,754 B2 5/2006 Martin et al.
7,052,499 B2 5/2006 Steger et al.
7,060,101 B2 6/2006 O'Connor et al.
7,066,942 B2 6/2006 Treace
7,066,944 B2 6/2006 Laufer et al.
7,081,126 B2 7/2006 Mcdevitt et al.
7,083,638 B2 8/2006 Foerster
7,087,064 B1 8/2006 Hyde
7,087,073 B2 8/2006 Bonutti
7,090,690 B2 8/2006 Foerster et al.
7,097,654 B1 8/2006 Freedland
7,101,395 B2 9/2006 Tremulis et al.
7,105,010 B2 9/2006 Hart et al.
7,105,026 B2 9/2006 Johnson et al.
7,112,221 B2 9/2006 Harris
7,118,578 B2 10/2006 West, Jr. et al.
7,118,583 B2 10/2006 O'quinn et al.
7,125,421 B2 10/2006 Tremulis et al.
7,131,467 B2 11/2006 Gao et al.
7,137,996 B2 11/2006 Steiner et al.
7,141,066 B2 11/2006 Steiner et al.
7,144,414 B2 12/2006 Harvie et al.
7,148,209 B2 12/2006 Hoemann et al.
7,153,127 B2 12/2006 Struble et al.
7,153,307 B2 12/2006 Scribner
7,153,312 B1 12/2006 Torrie et al.
7,153,327 B1 12/2006 Metzger
7,160,285 B2 1/2007 Sklar et al.
7,160,333 B2 1/2007 Plouhar et al.
7,172,626 B1 2/2007 Andrews
7,179,259 B1 2/2007 Gibbs
7,201,722 B2 4/2007 Krueger
7,207,993 B1 4/2007 Baldwin et al.
7,229,441 B2 6/2007 Trieu et al.
7,235,091 B2 6/2007 Thornes
7,255,675 B2 8/2007 Gertner et al.
7,255,700 B2 8/2007 Kaiser et al.
7,255,715 B2 8/2007 Metzger
7,261,716 B2 8/2007 Strobel et al.
7,264,634 B2 9/2007 Schmieding

(56) References Cited

U.S. PATENT DOCUMENTS 7,279,008 B2 10/2007 Brown et al.
7,285,124 B2 10/2007 Foerster
7,291,177 B2 11/2007 Gibbs
7,303,577 B1 12/2007 Dean
7,306,417 B2 12/2007 Dorstewitz
7,309,355 B2 12/2007 Donnelly et al.
7,326,222 B2 2/2008 Dreyfuss et al.
7,329,272 B2 2/2008 Burkhart et al.
7,354,354 B2 4/2008 Palumbo et al.
7,361,179 B2 4/2008 Rousseau et al.
7,377,845 B2 5/2008 Stewart et al.
7,390,329 B2 6/2008 Westra et al.
7,390,332 B2 6/2008 Selvitelli et al.
7,399,018 B1 7/2008 Khachaturian
7,442,210 B2 10/2008 Segal et al.
7,462,198 B2 12/2008 Webster et al.
7,463,198 B2 12/2008 Deaett et al.
7,465,308 B2 12/2008 Sikora et al.
7,468,074 B2 12/2008 Caborn
7,481,814 B1 1/2009 Metzger
7,484,539 B1 2/2009 Huang
7,485,149 B1 2/2009 White
7,494,496 B2 2/2009 Swain et al.
7,494,506 B2 2/2009 Brulez et al.
D587,807 S 3/2009 Wolf et al.
7,500,983 B1 3/2009 Kaiser et al.
7,513,910 B2 4/2009 Buskirk et al.
7,517,357 B2 4/2009 Abrams et al.
7,572,275 B2 8/2009 Fallin et al.
7,572,298 B2 8/2009 Roller et al.
7,578,825 B2 8/2009 Huebner
7,585,311 B2 9/2009 Green et al.
7,588,587 B2 9/2009 Barbieri et al.
7,591,823 B2 9/2009 Tipirneni
7,597,705 B2 10/2009 Forsberg et al.
7,601,165 B2 10/2009 Stone
7,604,636 B1 10/2009 Walters et al.
7,608,092 B1 10/2009 Schaffhasen
7,608,098 B1 10/2009 Stone et al.
7,615,076 B2 11/2009 Cauthen, III et al.
7,621,937 B2 11/2009 Pipenhagen et al.
7,632,287 B2 12/2009 Baker et al.
7,651,509 B2 1/2010 Bojarski et al.
7,658,750 B2 2/2010 Li
7,658,751 B2 2/2010 Stone et al.
7,670,279 B2 3/2010 Gertner
7,678,123 B2 3/2010 Chanduszko
7,686,810 B2 3/2010 West, Jr. et al.
7,691,112 B2 4/2010 Chanduszko et al.
7,695,493 B2 4/2010 Saadat et al.
7,695,503 B1 4/2010 Kaiser
7,703,372 B1 4/2010 Shakespeare
7,713,188 B2 5/2010 Bouffier
7,713,285 B1 5/2010 Stone et al.
7,717,929 B2 5/2010 Fallman
7,731,732 B2 6/2010 Ken
7,736,364 B2 6/2010 Stone
7,736,379 B2 6/2010 Ewers et al.
7,749,250 B2 7/2010 Stone et al.
7,758,594 B2 7/2010 Lamson et al.
7,758,611 B2 7/2010 Kato
7,762,942 B2 7/2010 Neisz et al.
7,771,482 B1 8/2010 Karmon
7,776,041 B1 8/2010 Walters
7,780,701 B1 8/2010 Meridew et al.
7,790,945 B1 9/2010 Watson, Jr.
7,803,173 B2 9/2010 Burkhart et al.
7,819,895 B2 10/2010 Ginn et al.
7,828,820 B2 11/2010 Stone et al.
7,828,850 B2 11/2010 Cauthen, III et al.
7,856,698 B2 12/2010 Hays
7,857,830 B2 12/2010 Stone et al.
7,867,252 B2 1/2011 Criscuolo et al.
7,867,264 B2 1/2011 Mcdevitt et al.
7,875,058 B2 1/2011 Holmes, Jr.
7,878,058 B2 2/2011 Blendinger et al.
7,887,586 B2 2/2011 Linares
7,896,907 B2 3/2011 Mcdevitt et al.
7,905,903 B2 3/2011 Stone et al.
7,905,904 B2 3/2011 Stone et al.
7,909,851 B2 3/2011 Stone et al.
7,914,539 B2 3/2011 Stone et al.
7,938,847 B2 5/2011 Fanton et al.
7,951,198 B2 5/2011 Sucec et al.
7,955,388 B2 6/2011 Jensen et al.
7,959,650 B2 6/2011 Kaiser et al.
7,976,565 B1 7/2011 Meridew
7,981,140 B2 7/2011 Burkhart
7,998,203 B2 8/2011 Blum
8,034,090 B2 10/2011 Stone et al.
8,062,334 B2 11/2011 Green et al.
8,066,776 B2 11/2011 O'Connor et al.
8,075,574 B2 12/2011 May et al.
8,075,626 B2 12/2011 Dun
8,088,108 B2 1/2012 Kraft
8,088,130 B2 1/2012 Kaiser et al.
8,109,867 B2 2/2012 Rosenblatt
8,114,127 B2 2/2012 West, Jr.
8,114,128 B2 2/2012 Cauldwell et al.
8,118,835 B2 2/2012 Weisel et al.
8,118,836 B2 2/2012 Denham et al.
8,118,868 B2 2/2012 May et al.
8,128,658 B2 3/2012 Kaiser et al.
8,137,354 B2 3/2012 Stone
8,137,382 B2 3/2012 Denham et al.
8,137,407 B2 3/2012 Todd et al.
8,142,510 B2 3/2012 Lee et al.
8,147,557 B2 4/2012 Lee et al.
8,147,558 B2 4/2012 Lee et al.
8,162,997 B2 4/2012 Struhl
8,167,906 B2 5/2012 Cauldwell et al.
8,177,810 B2 5/2012 Ferree
8,202,295 B2 6/2012 Kaplan
8,202,318 B2 6/2012 Willobee
8,221,454 B2 7/2012 Schaffhasen
8,231,654 B2 7/2012 Kaiser et al.
8,251,998 B2 8/2012 Hoeppner et al.
8,252,022 B2 8/2012 Holman et al.
8,273,106 B2 9/2012 Stone et al.
8,292,921 B2 10/2012 Stone et al.
8,298,262 B2 10/2012 Stone et al.
8,298,284 B2 10/2012 Cassani
8,303,589 B2 11/2012 Tyber et al.
8,303,604 B2 11/2012 Stone et al.
8,317,825 B2 11/2012 Stone
8,328,806 B2 12/2012 Tyber et al.
8,333,788 B2 12/2012 Maiorino
8,337,525 B2 12/2012 Stone et al.
8,343,155 B2 1/2013 Fisher et al.
8,343,227 B2 1/2013 Metzger et al.
8,361,054 B2 1/2013 Ducharme et al.
8,361,113 B2 1/2013 Stone et al.
8,409,253 B2 4/2013 Stone et al.
8,454,635 B2 6/2013 Paolitto et al.
8,486,114 B2 7/2013 Gillard et al.
8,500,818 B2 8/2013 Metzger et al.
8,506,597 B2 8/2013 Kaiser et al.
8,545,535 B2 10/2013 Hirotsuka et al.
8,551,140 B2 10/2013 Denham et al.
8,562,645 B2 10/2013 Stone et al.
8,562,647 B2 10/2013 Kaiser et al.
8,574,235 B2 11/2013 Stone
8,579,901 B1 11/2013 Foerster
8,579,944 B2 11/2013 Holloway et al.
8,591,544 B2 11/2013 Jolly et al.
8,597,327 B2 12/2013 Stone et al.
8,608,777 B2 12/2013 Kaiser et al.
8,632,566 B2 1/2014 Olson
8,632,569 B2 1/2014 Stone et al.
8,652,171 B2 2/2014 Stone et al.
8,652,172 B2 2/2014 Denham et al.
8,672,904 B1 3/2014 Schultz
8,672,968 B2 3/2014 Stone et al.
8,672,969 B2 3/2014 Stone et al.

(56) References Cited

U.S. PATENT DOCUMENTS 8,702,718 B2 4/2014 Bhatnagar et al.
8,715,297 B1 5/2014 Foerster et al.
8,721,650 B2 5/2014 Fanton et al.
8,721,684 B2 5/2014 Denham et al.
8,771,316 B2 7/2014 Denham et al.
8,771,352 B2 7/2014 Conner et al.
8,777,956 B2 7/2014 Hoeppner et al.
8,801,783 B2 8/2014 Stone et al.
8,808,374 B2 8/2014 Eggli
8,814,903 B2 8/2014 Sengun et al.
8,828,067 B2 9/2014 Tipirneni et al.
8,840,645 B2 9/2014 Denham et al.
8,858,642 B2 10/2014 Metzger et al.
8,894,715 B2 11/2014 Metzger et al.
8,900,314 B2 12/2014 Metzger et al.
8,926,613 B2 1/2015 Kaiser et al.
8,932,331 B2 1/2015 Kaiser et al.
8,936,621 B2 1/2015 Denham et al.
8,961,548 B2 2/2015 Buser
8,968,364 B2 3/2015 Berelsman
8,998,949 B2 4/2015 Stone et al.
9,005,287 B2 4/2015 Stone
9,017,381 B2 4/2015 Kaiser et al.
9,023,058 B2 5/2015 Jaramillo et al.
9,028,509 B2 5/2015 Chu et al.
9,078,644 B2 7/2015 Stone
9,149,267 B2 10/2015 Norton et al.
9,173,651 B2 11/2015 Stone et al.
9,179,950 B2 11/2015 Zajac et al.
9,198,673 B2 12/2015 Stone
9,216,078 B2 12/2015 Conner et al.
9,271,713 B2 3/2016 Denham et al.
9,271,826 B2 3/2016 Eggli et al.
9,289,285 B2 3/2016 Eggli
9,314,235 B2 4/2016 Bojarski et al.
9,314,241 B2 4/2016 Stone et al.
9,357,991 B2 6/2016 Denham et al.
9,357,992 B2 6/2016 Stone et al.
9,370,350 B2 6/2016 Norton
9,381,013 B2 7/2016 Norton
9,402,621 B2 8/2016 Stone et al.
9,408,599 B2 8/2016 Kaiser et al.
9,414,833 B2 8/2016 Stone et al.
9,414,925 B2 8/2016 Metzger et al.
9,468,433 B2 10/2016 Denham et al.
9,486,211 B2 11/2016 Stone et al.
9,492,158 B2 11/2016 Stone et al.
9,498,204 B2 11/2016 Denham et al.
9,504,460 B2 11/2016 Stone et al.
9,510,819 B2 12/2016 Stone et al.
9,510,821 B2 12/2016 Denham et al.
9,532,777 B2 1/2017 Kaiser et al.
9,538,998 B2 1/2017 Stone et al.
9,539,003 B2 1/2017 Stone et al.
9,561,025 B2 2/2017 Stone et al.
9,572,655 B2 2/2017 Denham
9,585,651 B2 3/2017 Lam et al.
9,603,591 B2 3/2017 Denham et al.
9,622,736 B2 4/2017 Stone et al.
9,642,661 B2 5/2017 Stone et al.
9,681,940 B2 6/2017 Stone et al.
9,724,090 B2 8/2017 Kaiser et al.
9,743,919 B2 8/2017 Manos et al.
9,757,119 B2 9/2017 Norton et al.
9,763,656 B2 9/2017 Stone et al.
9,782,245 B2 10/2017 Mujwid et al.
9,788,876 B2 10/2017 Stone
9,801,620 B2 10/2017 Kaiser et al.
9,801,708 B2 10/2017 Denham et al.
9,833,230 B2 12/2017 Stone
9,861,351 B2 1/2018 Kaiser et al.
9,918,826 B2 3/2018 Berelsman et al.
9,918,827 B2 3/2018 Berelsman et al.
9,993,241 B2 6/2018 Denham et al.
10,004,489 B2 6/2018 Kaiser et al.
10,004,493 B2 6/2018 Stone et al.
10,004,588 B2 6/2018 Berelsman et al.
10,022,118 B2 7/2018 Norton et al.
10,092,288 B2 10/2018 Denham et al.
10,098,629 B2 10/2018 Kaiser et al.
10,154,837 B2 12/2018 Stone et al.
10,167,582 B1 1/2019 Pilgeram et al.
10,251,637 B2 4/2019 Stone et al.
10,265,064 B2 4/2019 Stone et al.
10,265,159 B2 4/2019 Denham et al.
10,321,906 B2 6/2019 Stone et al.
10,349,931 B2 7/2019 Stone
10,363,028 B2 7/2019 Norton
10,368,856 B2 8/2019 Stone et al.
10,398,428 B2 9/2019 Denham et al.
10,398,430 B2 9/2019 Stone et al.
10,441,264 B2 10/2019 Stone et al.
10,517,587 B2 12/2019 Denham et al.
10,517,714 B2 12/2019 Stone et al.
10,542,967 B2 1/2020 Kaiser et al.
10,595,851 B2 * 3/2020 Kaiser ................ A61B 17/0487
10,603,029 B2 3/2020 Kaiser et al.
10,610,217 B2 4/2020 Stone et al.
10,675,073 B2 6/2020 Stone et al.
10,687,803 B2 6/2020 Denham et al.
10,695,045 B2 6/2020 Kaiser et al.
10,695,052 B2 6/2020 Denham et al.
10,702,259 B2 7/2020 Stone et al.
10,716,557 B2 7/2020 Denham et al.
10,729,421 B2 8/2020 Stone et al.
10,729,423 B2 8/2020 Kaiser et al.
10,729,430 B2 8/2020 Denham et al.
10,743,925 B2 8/2020 Stone et al.
10,758,221 B2 9/2020 Berelsman et al.
10,835,232 B2 11/2020 Stone et al.
10,932,770 B2 3/2021 Stone et al.
10,973,507 B2 4/2021 Stone et al.
10,987,099 B2 4/2021 Stone et al.
11,039,826 B2 6/2021 Denham et al.
11,065,103 B2 7/2021 Berelsman et al.
11,096,684 B2 8/2021 Stone et al.
11,109,857 B2 9/2021 Stone et al.
11,116,495 B2 9/2021 Stone et al.
11,185,320 B2 11/2021 Kaiser et al.
11,241,305 B2 2/2022 Denham et al.
11,259,792 B2 3/2022 Denham et al.
11,259,794 B2 3/2022 Stone et al.
11,284,884 B2 3/2022 Denham et al.
11,311,287 B2 4/2022 Stone et al.
11,317,907 B2 5/2022 Denham et al.
11,376,115 B2 7/2022 Stone et al.
11,446,019 B2 9/2022 Stone et al.
11,471,147 B2 * 10/2022 Kaiser .............. A61B 17/06166
11,534,157 B2 12/2022 Norton
11,534,159 B2 12/2022 Denham et al.
11,589,859 B2 2/2023 Kaiser et al.
11,612,391 B2 3/2023 Stone et al.
11,617,572 B2 4/2023 Stone et al.
11,672,527 B2 * 6/2023 Stone .................... A61F 2/0811
606/232
11,723,648 B2 8/2023 Stone et al.
11,730,464 B2 8/2023 Stone et al.
11,786,236 B2 10/2023 Denham et al.
11,819,205 B2 11/2023 Stone et al.
11,896,210 B2 2/2024 Stone et al.
11,998,185 B2 6/2024 Kaiser et al.
12,064,101 B2 8/2024 Denham et al.
12,096,928 B2 9/2024 Kaiser et al.
12,096,931 B2 9/2024 Denham et al.
12,245,759 B2 3/2025 Kaiser et al.
12,251,093 B2 3/2025 Kaiser et al.
12,251,100 B2 * 3/2025 Norton ............... A61B 17/0401
12,303,122 B2 5/2025 Kaiser et al.
12,329,373 B2 6/2025 Stone et al.
12,336,701 B2 6/2025 Stone et al.
2001/0002439 A1 5/2001 Bonutti et al.
2001/0010005 A1 7/2001 Kammerer et al.
2001/0014825 A1 8/2001 Burke et al.
2001/0019649 A1 9/2001 Field et al.

(56) References Cited

U.S. PATENT DOCUMENTS

| | | | |
|---|---|---|---|
| 2001/0027341 | A1 | 10/2001 | Gianotti |
| 2001/0029387 | A1 | 10/2001 | Wolf et al. |
| 2001/0037131 | A1 | 11/2001 | Schmieding et al. |
| 2001/0037153 | A1 | 11/2001 | Charles, Jr. et al. |
| 2001/0041916 | A1 | 11/2001 | Bonutti |
| 2001/0041937 | A1 | 11/2001 | Rieser et al. |
| 2001/0041938 | A1 | 11/2001 | Hein |
| 2001/0044627 | A1 | 11/2001 | Justin |
| 2001/0044639 | A1 | 11/2001 | Levinson |
| 2001/0047206 | A1 | 11/2001 | Sklar et al. |
| 2001/0051815 | A1 | 12/2001 | Esplin |
| 2001/0051816 | A1 | 12/2001 | Enzerink et al. |
| 2001/0053934 | A1 | 12/2001 | Schmieding |
| 2001/0056299 | A1 | 12/2001 | Thompson |
| 2002/0001964 | A1 | 1/2002 | Choi |
| 2002/0004669 | A1 | 1/2002 | Bartlett |
| 2002/0007182 | A1 | 1/2002 | Kim |
| 2002/0010513 | A1 | 1/2002 | Schmieding |
| 2002/0013607 | A1 | 1/2002 | Lemer |
| 2002/0013608 | A1 | 1/2002 | Elattrache et al. |
| 2002/0019649 | A1 | 2/2002 | Sikora et al. |
| 2002/0029048 | A1 | 3/2002 | Miller |
| 2002/0029066 | A1 | 3/2002 | Foerster |
| 2002/0032465 | A1 | 3/2002 | Lemer |
| 2002/0045902 | A1 | 4/2002 | Bonutti |
| 2002/0052628 | A1 | 5/2002 | Bowman |
| 2002/0055780 | A1 | 5/2002 | Sklar |
| 2002/0058966 | A1 | 5/2002 | Tormala et al. |
| 2002/0068254 | A1 | 6/2002 | Campbell |
| 2002/0077629 | A1 | 6/2002 | Hoffman et al. |
| 2002/0077659 | A1 | 6/2002 | Johnson et al. |
| 2002/0082220 | A1 | 6/2002 | Hoemann et al. |
| 2002/0091391 | A1 | 7/2002 | Cole et al. |
| 2002/0099411 | A1 | 7/2002 | Bartlett |
| 2002/0111591 | A1 | 8/2002 | Mckinnon et al. |
| 2002/0111653 | A1 | 8/2002 | Foerster |
| 2002/0120270 | A1 | 8/2002 | Trieu et al. |
| 2002/0120292 | A1 | 8/2002 | Morgan |
| 2002/0123752 | A1 | 9/2002 | Schultheiss et al. |
| 2002/0128654 | A1 | 9/2002 | Steger et al. |
| 2002/0128684 | A1 | 9/2002 | Foerster |
| 2002/0129820 | A1 | 9/2002 | Ryan et al. |
| 2002/0143336 | A1 | 10/2002 | Hearn |
| 2002/0147463 | A1 | 10/2002 | Martinek |
| 2002/0156475 | A1 | 10/2002 | Lerch et al. |
| 2002/0161401 | A1 | 10/2002 | Steiner |
| 2002/0161439 | A1 | 10/2002 | Strobel et al. |
| 2002/0165548 | A1 | 11/2002 | Jutley |
| 2002/0165611 | A1 | 11/2002 | Enzerink et al. |
| 2002/0169452 | A1 | 11/2002 | Tormala et al. |
| 2002/0169477 | A1 | 11/2002 | Demopulos et al. |
| 2002/0169478 | A1 | 11/2002 | Schwartz et al. |
| 2002/0173788 | A1 | 11/2002 | Bojarski et al. |
| 2002/0177853 | A1 | 11/2002 | Chervitz et al. |
| 2002/0188298 | A1 | 12/2002 | Chan |
| 2002/0193830 | A1 | 12/2002 | Bonutti |
| 2003/0004545 | A1 | 1/2003 | Burkhart et al. |
| 2003/0009235 | A1 | 1/2003 | Manrique et al. |
| 2003/0023268 | A1 | 1/2003 | Lizardi |
| 2003/0032961 | A1 | 2/2003 | Pelo et al. |
| 2003/0033021 | A1 | 2/2003 | Plouhar et al. |
| 2003/0033022 | A1 | 2/2003 | Plouhar et al. |
| 2003/0036797 | A1 | 2/2003 | Malaviya et al. |
| 2003/0036801 | A1 | 2/2003 | Schwartz et al. |
| 2003/0050667 | A1 | 3/2003 | Grafton et al. |
| 2003/0065361 | A1 | 4/2003 | Dreyfuss |
| 2003/0065391 | A1 | 4/2003 | Re et al. |
| 2003/0065402 | A1 | 4/2003 | Anderson et al. |
| 2003/0078585 | A1 | 4/2003 | Johnson et al. |
| 2003/0078603 | A1 | 4/2003 | Schaller et al. |
| 2003/0078617 | A1 | 4/2003 | Schwartz et al. |
| 2003/0083662 | A1 | 5/2003 | Middleton |
| 2003/0083694 | A1 | 5/2003 | Archibald, III |
| 2003/0088251 | A1 | 5/2003 | Braun et al. |
| 2003/0088272 | A1 | 5/2003 | Smith |
| 2003/0093156 | A1 | 5/2003 | Metzger et al. |
| 2003/0105477 | A1 | 6/2003 | Schwartz et al. |
| 2003/0105489 | A1 | 6/2003 | Eichhorn et al. |
| 2003/0114929 | A1 | 6/2003 | Knudsen |
| 2003/0120309 | A1 | 6/2003 | Colleran et al. |
| 2003/0130670 | A1 | 7/2003 | Anderson et al. |
| 2003/0130694 | A1 | 7/2003 | Bojarski et al. |
| 2003/0130695 | A1 | 7/2003 | Mcdevitt et al. |
| 2003/0135214 | A1 | 7/2003 | Fetto |
| 2003/0135239 | A1 | 7/2003 | Gabriel et al. |
| 2003/0135265 | A1 | 7/2003 | Stinson |
| 2003/0135963 | A1 | 7/2003 | Holbrook et al. |
| 2003/0139752 | A1 | 7/2003 | Pasricha et al. |
| 2003/0139775 | A1 | 7/2003 | Grafton |
| 2003/0144696 | A1 | 7/2003 | Sinnott et al. |
| 2003/0149448 | A1 | 8/2003 | Foerster et al. |
| 2003/0152522 | A1 | 8/2003 | Miller et al. |
| 2003/0153947 | A1 | 8/2003 | Koseki |
| 2003/0167072 | A1 | 9/2003 | Oberlander |
| 2003/0167090 | A1 | 9/2003 | Chervitz et al. |
| 2003/0171811 | A1 | 9/2003 | Steiner et al. |
| 2003/0176865 | A1 | 9/2003 | Supinski |
| 2003/0176919 | A1 | 9/2003 | Schmieding |
| 2003/0176920 | A1 | 9/2003 | Sklar et al. |
| 2003/0181925 | A1 | 9/2003 | Bain et al. |
| 2003/0187510 | A1 | 10/2003 | Hyde |
| 2003/0195528 | A1 | 10/2003 | Ritchart |
| 2003/0195564 | A1 | 10/2003 | Tran et al. |
| 2003/0195565 | A1 | 10/2003 | Bonutti |
| 2003/0208209 | A1 | 11/2003 | Gambale et al. |
| 2003/0208210 | A1 | 11/2003 | Dreyfuss et al. |
| 2003/0212456 | A1 | 11/2003 | Lipchitz et al. |
| 2003/0216809 | A1 | 11/2003 | Ferguson |
| 2003/0220646 | A1 | 11/2003 | Thelen et al. |
| 2003/0220660 | A1 | 11/2003 | Kortenbach et al. |
| 2003/0225459 | A1 | 12/2003 | Hammer et al. |
| 2003/0229361 | A1 | 12/2003 | Jackson |
| 2003/0229396 | A1 | 12/2003 | Andrews |
| 2003/0236555 | A1 | 12/2003 | Thornes |
| 2004/0002734 | A1 | 1/2004 | Fallin et al. |
| 2004/0006345 | A1 | 1/2004 | Vlahos et al. |
| 2004/0006346 | A1 | 1/2004 | Holmen et al. |
| 2004/0013380 | A1 | 1/2004 | Jimenez |
| 2004/0015171 | A1 | 1/2004 | Bojarski et al. |
| 2004/0015172 | A1 | 1/2004 | Biedermann et al. |
| 2004/0024456 | A1 | 2/2004 | Charles, Jr. et al. |
| 2004/0024457 | A1 | 2/2004 | Boyce et al. |
| 2004/0039389 | A1 | 2/2004 | Hugh, Jr. et al. |
| 2004/0044351 | A1 | 3/2004 | Searle |
| 2004/0044391 | A1 | 3/2004 | Porter |
| 2004/0059357 | A1 | 3/2004 | Koseki |
| 2004/0073176 | A1 | 4/2004 | Utterberg |
| 2004/0087981 | A1 | 5/2004 | Berube et al. |
| 2004/0092936 | A1 | 5/2004 | Miller et al. |
| 2004/0093031 | A1 | 5/2004 | Burkhart et al. |
| 2004/0093032 | A1 | 5/2004 | Sinnott et al. |
| 2004/0098051 | A1 | 5/2004 | Fallin et al. |
| 2004/0098053 | A1 | 5/2004 | Tran |
| 2004/0098099 | A1 | 5/2004 | McCullagh et al. |
| 2004/0111117 | A1 | 6/2004 | Colleran et al. |
| 2004/0122431 | A1 | 6/2004 | Biedermann et al. |
| 2004/0122454 | A1 | 6/2004 | Wang et al. |
| 2004/0122456 | A1 | 6/2004 | Saadat et al. |
| 2004/0127907 | A1 | 7/2004 | Dakin et al. |
| 2004/0133206 | A1 | 7/2004 | Stevens et al. |
| 2004/0133211 | A1 | 7/2004 | Raskin et al. |
| 2004/0133238 | A1 | 7/2004 | Cerier |
| 2004/0133239 | A1 | 7/2004 | Singhatat |
| 2004/0138664 | A1 | 7/2004 | Bowman |
| 2004/0138683 | A1 | 7/2004 | Shelton et al. |
| 2004/0138704 | A1 | 7/2004 | Gambale et al. |
| 2004/0138706 | A1 | 7/2004 | Abrams et al. |
| 2004/0138747 | A1 | 7/2004 | Kaladelfos |
| 2004/0138755 | A1 | 7/2004 | O'connor et al. |
| 2004/0143344 | A1 | 7/2004 | Malaviya et al. |
| 2004/0144535 | A1 | 7/2004 | Kalman et al. |
| 2004/0147932 | A1 | 7/2004 | Burkinshaw et al. |
| 2004/0147958 | A1 | 7/2004 | Lam et al. |
| 2004/0148030 | A1 | 7/2004 | Ek |

(56) References Cited

U.S. PATENT DOCUMENTS

| | | | |
|---|---|---|---|
| 2004/0153103 | A1 | 8/2004 | Schwartz et al. |
| 2004/0153153 | A1 | 8/2004 | Elson et al. |
| 2004/0162579 | A1 | 8/2004 | Foerster |
| 2004/0166169 | A1 | 8/2004 | Malaviya et al. |
| 2004/0181234 | A1 | 9/2004 | Mcdevitt et al. |
| 2004/0182968 | A1 | 9/2004 | Gentry |
| 2004/0187314 | A1 | 9/2004 | Johnson |
| 2004/0193185 | A1 | 9/2004 | Mcbrayer |
| 2004/0199169 | A1 | 10/2004 | Koons et al. |
| 2004/0204722 | A1 | 10/2004 | Sikora et al. |
| 2004/0220574 | A1 | 11/2004 | Pelo et al. |
| 2004/0225183 | A1 | 11/2004 | Michlitsch et al. |
| 2004/0225292 | A1 | 11/2004 | Sasso et al. |
| 2004/0225305 | A1 | 11/2004 | Ewers et al. |
| 2004/0230302 | A1 | 11/2004 | May et al. |
| 2004/0236353 | A1 | 11/2004 | Bain et al. |
| 2004/0236373 | A1 | 11/2004 | William, III |
| 2004/0243139 | A1 | 12/2004 | Lewis et al. |
| 2004/0243178 | A1 | 12/2004 | Haut et al. |
| 2004/0243180 | A1 | 12/2004 | Donnelly et al. |
| 2004/0243235 | A1 | 12/2004 | Goh et al. |
| 2004/0249394 | A1 | 12/2004 | Morris et al. |
| 2004/0260296 | A1 | 12/2004 | Kaiser et al. |
| 2004/0260298 | A1 | 12/2004 | Kaiser et al. |
| 2004/0267164 | A1 | 12/2004 | Rhodes et al. |
| 2004/0267265 | A1 | 12/2004 | Kyle |
| 2004/0267270 | A1 | 12/2004 | Jacobs et al. |
| 2004/0267276 | A1 | 12/2004 | Camino et al. |
| 2004/0267277 | A1 | 12/2004 | Zannis et al. |
| 2004/0267286 | A1 | 12/2004 | Gao et al. |
| 2004/0267304 | A1 | 12/2004 | Zannis et al. |
| 2004/0267309 | A1 | 12/2004 | Garvin |
| 2004/0267317 | A1 | 12/2004 | Higgins et al. |
| 2004/0267361 | A1 | 12/2004 | Donnelly et al. |
| 2004/0267362 | A1 | 12/2004 | Hwang et al. |
| 2005/0004670 | A1 | 1/2005 | Gebhardt et al. |
| 2005/0021087 | A1 | 1/2005 | Koseki |
| 2005/0021148 | A1 | 1/2005 | Gibbs |
| 2005/0027307 | A1 | 2/2005 | Schwartz et al. |
| 2005/0033289 | A1 | 2/2005 | Warren et al. |
| 2005/0033362 | A1 | 2/2005 | Grafton |
| 2005/0033363 | A1 | 2/2005 | Bojarski et al. |
| 2005/0038426 | A1 | 2/2005 | Chan |
| 2005/0049598 | A1 | 3/2005 | West et al. |
| 2005/0055027 | A1 | 3/2005 | Yeung et al. |
| 2005/0055037 | A1 | 3/2005 | Fathauer |
| 2005/0064042 | A1 | 3/2005 | Vunjak-novakovic et al. |
| 2005/0065521 | A1 | 3/2005 | Steger et al. |
| 2005/0065526 | A1 | 3/2005 | Drew et al. |
| 2005/0070906 | A1 | 3/2005 | Clark et al. |
| 2005/0070928 | A1 | 3/2005 | Heino et al. |
| 2005/0074495 | A1 | 4/2005 | Schwartz et al. |
| 2005/0076478 | A1 | 4/2005 | Miyazaki et al. |
| 2005/0085819 | A1 | 4/2005 | Ellis et al. |
| 2005/0090827 | A1 | 4/2005 | Gedebou |
| 2005/0090828 | A1 | 4/2005 | Alford |
| 2005/0090862 | A1 | 4/2005 | Mcdevitt et al. |
| 2005/0096696 | A1 | 5/2005 | Forsberg |
| 2005/0096697 | A1 | 5/2005 | Forsberg et al. |
| 2005/0096743 | A1 | 5/2005 | Schmieding et al. |
| 2005/0101957 | A1 | 5/2005 | Buskirk et al. |
| 2005/0107795 | A1 | 5/2005 | Morris et al. |
| 2005/0107828 | A1 | 5/2005 | Reese |
| 2005/0107882 | A1 | 5/2005 | Stone et al. |
| 2005/0119531 | A1 | 6/2005 | Sharratt |
| 2005/0119696 | A1 | 6/2005 | Walters et al. |
| 2005/0124996 | A1 | 6/2005 | Hearn |
| 2005/0125031 | A1 | 6/2005 | Pipenhagen et al. |
| 2005/0125036 | A1 | 6/2005 | Roby |
| 2005/0125073 | A1 | 6/2005 | Orban et al. |
| 2005/0130301 | A1 | 6/2005 | Mckay et al. |
| 2005/0131413 | A1 | 6/2005 | O'driscoll et al. |
| 2005/0137600 | A1 | 6/2005 | Jacobs et al. |
| 2005/0137624 | A1 | 6/2005 | Fallman |
| 2005/0143734 | A1 | 6/2005 | Cachia et al. |
| 2005/0149033 | A1 | 7/2005 | Mcguire et al. |
| 2005/0149118 | A1 | 7/2005 | Koyfman et al. |
| 2005/0149119 | A1 | 7/2005 | Koyfman et al. |
| 2005/0149122 | A1 | 7/2005 | Mcdevitt et al. |
| 2005/0149187 | A1 | 7/2005 | Clark et al. |
| 2005/0154471 | A1 | 7/2005 | Aram et al. |
| 2005/0159812 | A1 | 7/2005 | Dinger, III et al. |
| 2005/0160656 | A1 | 7/2005 | Safwat et al. |
| 2005/0165416 | A1 | 7/2005 | Bojarski et al. |
| 2005/0165482 | A1 | 7/2005 | Goldhahn et al. |
| 2005/0171547 | A1 | 8/2005 | Aram |
| 2005/0171603 | A1 | 8/2005 | Justin et al. |
| 2005/0171604 | A1 | 8/2005 | Michalow |
| 2005/0177237 | A1 | 8/2005 | Shappley et al. |
| 2005/0187565 | A1 | 8/2005 | Baker et al. |
| 2005/0187577 | A1 | 8/2005 | Selvitelli et al. |
| 2005/0187635 | A1 | 8/2005 | Metzger |
| 2005/0192581 | A1 | 9/2005 | Molz et al. |
| 2005/0192632 | A1 | 9/2005 | Geissler et al. |
| 2005/0197711 | A1 | 9/2005 | Cachia |
| 2005/0203620 | A1 | 9/2005 | Steiner et al. |
| 2005/0209703 | A1 | 9/2005 | Fell |
| 2005/0222618 | A1 | 10/2005 | Dreyfuss et al. |
| 2005/0222619 | A1 | 10/2005 | Dreyfuss et al. |
| 2005/0228448 | A1 | 10/2005 | Li |
| 2005/0229433 | A1 | 10/2005 | Cachia |
| 2005/0234472 | A1 | 10/2005 | Huebner |
| 2005/0234549 | A1 | 10/2005 | Kladakis et al. |
| 2005/0240198 | A1 | 10/2005 | Albertson et al. |
| 2005/0251153 | A1 | 11/2005 | Sakamoto et al. |
| 2005/0251159 | A1 | 11/2005 | Ewers et al. |
| 2005/0251177 | A1 | 11/2005 | Saadat et al. |
| 2005/0251207 | A1 | 11/2005 | Flores et al. |
| 2005/0251208 | A1 | 11/2005 | Elmer et al. |
| 2005/0251209 | A1 | 11/2005 | Saadat et al. |
| 2005/0251210 | A1 | 11/2005 | Westra et al. |
| 2005/0261642 | A1 | 11/2005 | Weston |
| 2005/0267479 | A1 | 12/2005 | Morgan et al. |
| 2005/0267533 | A1 | 12/2005 | Gertner |
| 2005/0277088 | A1 | 12/2005 | Fischer et al. |
| 2005/0277939 | A1 | 12/2005 | Miller, III |
| 2005/0277961 | A1 | 12/2005 | Stone et al. |
| 2005/0277985 | A1 | 12/2005 | Wert et al. |
| 2005/0283040 | A1 | 12/2005 | Greenhalgh |
| 2005/0283156 | A1 | 12/2005 | Schmieding et al. |
| 2005/0283158 | A1 | 12/2005 | West |
| 2005/0283192 | A1 | 12/2005 | Torrie et al. |
| 2005/0283220 | A1 | 12/2005 | Gobran et al. |
| 2005/0288710 | A1 | 12/2005 | Fallin et al. |
| 2006/0004364 | A1 | 1/2006 | Green et al. |
| 2006/0004410 | A1 | 1/2006 | Nobis et al. |
| 2006/0004460 | A1 | 1/2006 | Engh et al. |
| 2006/0015103 | A1 | 1/2006 | Burke |
| 2006/0015106 | A1 | 1/2006 | Lerch et al. |
| 2006/0015107 | A1 | 1/2006 | Sklar |
| 2006/0030884 | A1 | 2/2006 | Yeung et al. |
| 2006/0030948 | A1 | 2/2006 | Manrique et al. |
| 2006/0036265 | A1 | 2/2006 | Dant et al. |
| 2006/0052787 | A1 | 3/2006 | Re et al. |
| 2006/0052818 | A1 | 3/2006 | Drake et al. |
| 2006/0064125 | A1 | 3/2006 | Henderson et al. |
| 2006/0064126 | A1 | 3/2006 | Fallin et al. |
| 2006/0069334 | A1 | 3/2006 | Moskowitz |
| 2006/0079904 | A1 | 4/2006 | Thal |
| 2006/0084943 | A1 | 4/2006 | Rosenman et al. |
| 2006/0085000 | A1 | 4/2006 | Mohr et al. |
| 2006/0089525 | A1 | 4/2006 | Mamo et al. |
| 2006/0089672 | A1 | 4/2006 | Martinek |
| 2006/0095130 | A1 | 5/2006 | Caborn et al. |
| 2006/0095131 | A1 | 5/2006 | Justin et al. |
| 2006/0100627 | A1 | 5/2006 | Stone et al. |
| 2006/0100637 | A1 | 5/2006 | Rathbun et al. |
| 2006/0106423 | A1 | 5/2006 | Weisel et al. |
| 2006/0111721 | A1 | 5/2006 | Puricelli |
| 2006/0116685 | A1 | 6/2006 | Urbanski et al. |
| 2006/0121084 | A1 | 6/2006 | Borden et al. |
| 2006/0122608 | A1 | 6/2006 | Fallin et al. |
| 2006/0122611 | A1 | 6/2006 | Morales et al. |
| 2006/0135958 | A1 | 6/2006 | Marissen et al. |

(56) References Cited

U.S. PATENT DOCUMENTS

2006/0149258 A1 7/2006 Sousa
2006/0149266 A1 7/2006 Cordasco
2006/0155287 A1 7/2006 Montgomery et al.
2006/0155328 A1 7/2006 Foerster
2006/0161161 A1 7/2006 Shifrin et al.
2006/0167458 A1 7/2006 Gabele
2006/0167481 A1 7/2006 Baker et al.
2006/0167482 A1 7/2006 Swain et al.
2006/0173492 A1 8/2006 Akerfeldt et al.
2006/0178680 A1 8/2006 Nelson et al.
2006/0178701 A1 8/2006 Schmieding
2006/0178743 A1 8/2006 Carter
2006/0189993 A1 8/2006 Stone
2006/0190041 A1 8/2006 Fallin et al.
2006/0190042 A1 8/2006 Stone et al.
2006/0195101 A1 8/2006 Stevens
2006/0195106 A1 8/2006 Jones et al.
2006/0200235 A1 9/2006 Bianchi et al.
2006/0212055 A1 9/2006 Karabey et al.
2006/0229623 A1 10/2006 Bonutti et al.
2006/0229671 A1 10/2006 Steiner et al.
2006/0229676 A1 10/2006 Doll et al.
2006/0235407 A1 10/2006 Wang et al.
2006/0235413 A1 10/2006 Denham et al.
2006/0241624 A1 10/2006 Kizuka et al.
2006/0241776 A1 10/2006 Brown et al.
2006/0241781 A1 10/2006 Brown et al.
2006/0247642 A1 11/2006 Stone et al.
2006/0253130 A1 11/2006 Wolniewicz, III
2006/0259048 A1 11/2006 Koseki
2006/0259076 A1 11/2006 Burkhart
2006/0264944 A1 11/2006 Cole
2006/0271192 A1 11/2006 Olsen et al.
2006/0276793 A1 12/2006 Berry
2006/0276809 A1 12/2006 Oliveira
2006/0276818 A1 12/2006 Buser et al.
2006/0276841 A1 12/2006 Barbieri et al.
2006/0276896 A1 12/2006 Fallin et al.
2006/0280768 A1 12/2006 Hwang et al.
2006/0280803 A1 12/2006 Kumar et al.
2006/0282082 A1 12/2006 Fanton et al.
2006/0282083 A1 12/2006 Fanton et al.
2006/0282085 A1 12/2006 Stone
2006/0293709 A1 12/2006 Bojarski et al.
2007/0005068 A1 1/2007 Sklar
2007/0005080 A1 1/2007 Wolniewicz et al.
2007/0010857 A1 1/2007 Sugimoto et al.
2007/0016305 A1 1/2007 Chudik
2007/0021779 A1 1/2007 Garvin et al.
2007/0027476 A1 2/2007 Harris et al.
2007/0032800 A1 2/2007 Ortiz et al.
2007/0032823 A1 2/2007 Tegg
2007/0038218 A1 2/2007 Grevious
2007/0043371 A1 2/2007 Teague
2007/0055249 A1 3/2007 Jensen et al.
2007/0055251 A1 3/2007 Huebner et al.
2007/0055255 A1 3/2007 Siegel
2007/0060922 A1 3/2007 Dreyfuss
2007/0067025 A1 3/2007 Schwartz
2007/0071568 A1 3/2007 Dorstewitz
2007/0073307 A1 3/2007 Scribner et al.
2007/0073319 A1 3/2007 Mikkaichi et al.
2007/0073322 A1 3/2007 Mikkaichi et al.
2007/0078435 A1 4/2007 Stone et al.
2007/0078517 A1 4/2007 Engh et al.
2007/0083236 A1 4/2007 Sikora et al.
2007/0088362 A1 4/2007 Bonutti et al.
2007/0093847 A1 4/2007 Scribner et al.
2007/0100350 A1 5/2007 Deffenbaugh et al.
2007/0112384 A1 5/2007 Conlon et al.
2007/0118217 A1 5/2007 Brulez et al.
2007/0123883 A1 5/2007 Ellis et al.
2007/0123984 A1 5/2007 Hodorek
2007/0129809 A1 6/2007 Meridew et al.
2007/0135843 A1 6/2007 Burkhart
2007/0142838 A1 6/2007 Jordan
2007/0156174 A1 7/2007 Kaiser et al.
2007/0162018 A1 7/2007 Jensen et al.
2007/0162120 A1 7/2007 Bouffier
2007/0167926 A1 7/2007 Blott et al.
2007/0167950 A1 7/2007 Tauro et al.
2007/0173948 A1 7/2007 Meridew et al.
2007/0185488 A1 8/2007 Pohjonen et al.
2007/0185532 A1 8/2007 Stone et al.
2007/0185568 A1 8/2007 Schwartz
2007/0191849 A1 8/2007 Elattrache et al.
2007/0191853 A1 8/2007 Stone
2007/0198022 A1 8/2007 Lang et al.
2007/0198036 A1 8/2007 Sklar et al.
2007/0219558 A1 9/2007 Deutsch
2007/0225715 A1 9/2007 Deffenbaugh et al.
2007/0225719 A1 9/2007 Stone et al.
2007/0225763 A1 9/2007 Zwolinski et al.
2007/0225805 A1 9/2007 Schmieding
2007/0233241 A1 10/2007 Graf et al.
2007/0239209 A1 10/2007 Fallman
2007/0239275 A1 10/2007 Willobee
2007/0244565 A1 10/2007 Stchur
2007/0250059 A1 10/2007 Weisshaupt et al.
2007/0250163 A1 10/2007 Cassani
2007/0250175 A1 10/2007 Meridew et al.
2007/0255282 A1 11/2007 Simonton et al.
2007/0260251 A1 11/2007 Weier et al.
2007/0260279 A1 11/2007 Hotter et al.
2007/0265704 A1 11/2007 Mayer et al.
2007/0270856 A1 11/2007 Morales et al.
2007/0270878 A1 11/2007 Leisinger
2007/0276387 A1 11/2007 Morales et al.
2007/0288023 A1 12/2007 Pellegrino et al.
2008/0009904 A1 1/2008 Bourque et al.
2008/0027430 A1 1/2008 Montgomery et al.
2008/0027440 A1 1/2008 Marissen et al.
2008/0027446 A1 1/2008 Stone et al.
2008/0033549 A1 2/2008 Marshall et al.
2008/0046009 A1 2/2008 Albertorio et al.
2008/0051834 A1 2/2008 Mazzocca et al.
2008/0051836 A1 2/2008 Foerster et al.
2008/0058787 A1 3/2008 Gertner
2008/0065114 A1 3/2008 Stone et al.
2008/0071299 A1 3/2008 Allinniemi et al.
2008/0082101 A1 4/2008 Reisberg
2008/0082127 A1 4/2008 Stone et al.
2008/0082128 A1* 4/2008 Stone ............... A61B 17/06166
606/232
2008/0086138 A1 4/2008 Stone et al.
2008/0097430 A1 4/2008 Bernstein et al.
2008/0103528 A1 5/2008 Zirps et al.
2008/0114460 A1 5/2008 Willobee et al.
2008/0119892 A1 5/2008 Brailovski et al.
2008/0132753 A1 6/2008 Goddard
2008/0132932 A1 6/2008 Hoeppner et al.
2008/0132948 A1 6/2008 Surti et al.
2008/0133007 A1 6/2008 Donnelly et al.
2008/0137624 A1 6/2008 Silverstrim et al.
2008/0140092 A1 6/2008 Stone et al.
2008/0140093 A1 6/2008 Stone et al.
2008/0140128 A1 6/2008 Smisson et al.
2008/0147127 A1 6/2008 Tipirneni et al.
2008/0147187 A1 6/2008 Bollinger et al.
2008/0154260 A1 6/2008 Hoof
2008/0154314 A1 6/2008 Mcdevitt
2008/0161806 A1 7/2008 Donnelly et al.
2008/0161852 A1 7/2008 Kaiser et al.
2008/0161861 A1 7/2008 Huebner
2008/0161864 A1 7/2008 Beck et al.
2008/0166421 A1 7/2008 Buhr et al.
2008/0172097 A1 7/2008 Lerch et al.
2008/0177302 A1 7/2008 Shurnas
2008/0183290 A1 7/2008 Baird et al.
2008/0188933 A1 8/2008 Koob et al.
2008/0188935 A1 8/2008 Saylor et al.
2008/0188936 A1 8/2008 Ball et al.
2008/0208252 A1 8/2008 Holmes
2008/0217263 A1 9/2008 Higgins et al.

(56) References Cited

U.S. PATENT DOCUMENTS

| | | | |
|---|---|---|---|
| 2008/0221527 | A1 | 9/2008 | Bradley et al. |
| 2008/0221578 | A1 | 9/2008 | Zeitani |
| 2008/0228186 | A1 | 9/2008 | Gall et al. |
| 2008/0228271 | A1 | 9/2008 | Stone et al. |
| 2008/0234730 | A1 | 9/2008 | Cotton et al. |
| 2008/0243260 | A1 | 10/2008 | Lee et al. |
| 2008/0243261 | A1 | 10/2008 | Wyss et al. |
| 2008/0243262 | A1 | 10/2008 | Lee |
| 2008/0255613 | A1* | 10/2008 | Kaiser .................. A61F 2/0811 606/232 |
| 2008/0257363 | A1 | 10/2008 | Schoenefeld et al. |
| 2008/0262544 | A1 | 10/2008 | Burkhart |
| 2008/0268064 | A1 | 10/2008 | Woodell-may |
| 2008/0269674 | A1 | 10/2008 | Stone |
| 2008/0275469 | A1 | 11/2008 | Fanton et al. |
| 2008/0275477 | A1 | 11/2008 | Sterrett et al. |
| 2008/0281428 | A1 | 11/2008 | Meyers et al. |
| 2008/0288070 | A1 | 11/2008 | Lo |
| 2008/0300611 | A1 | 12/2008 | Houser et al. |
| 2008/0312689 | A1 | 12/2008 | Denham et al. |
| 2008/0319478 | A1 | 12/2008 | Foerster et al. |
| 2009/0018589 | A1 | 1/2009 | Smisson, III et al. |
| 2009/0018654 | A1 | 1/2009 | Schmieding et al. |
| 2009/0018655 | A1 | 1/2009 | Brunelle et al. |
| 2009/0043342 | A1 | 2/2009 | Freedland |
| 2009/0054928 | A1 | 2/2009 | Denham et al. |
| 2009/0062847 | A1 | 3/2009 | Ken |
| 2009/0062854 | A1* | 3/2009 | Kaiser ................ A61B 17/0401 606/232 |
| 2009/0082790 | A1 | 3/2009 | Shad et al. |
| 2009/0082805 | A1* | 3/2009 | Kaiser .............. A61B 17/06166 606/228 |
| 2009/0084491 | A1 | 4/2009 | Uthgenannt et al. |
| 2009/0099598 | A1 | 4/2009 | Mcdevitt et al. |
| 2009/0105717 | A1 | 4/2009 | Bluechel |
| 2009/0105754 | A1 | 4/2009 | Sethi |
| 2009/0118774 | A1 | 5/2009 | Miller, III |
| 2009/0118775 | A1 | 5/2009 | Burke |
| 2009/0125073 | A1 | 5/2009 | Rehm |
| 2009/0138002 | A1 | 5/2009 | Fenton |
| 2009/0138054 | A1 | 5/2009 | Teague et al. |
| 2009/0156997 | A1 | 6/2009 | Trenhaile |
| 2009/0163949 | A1 | 6/2009 | Rolnick et al. |
| 2009/0177233 | A1 | 7/2009 | Malek |
| 2009/0182335 | A1 | 7/2009 | Struhl |
| 2009/0192468 | A1 | 7/2009 | Stone |
| 2009/0198277 | A1 | 8/2009 | Gordon et al. |
| 2009/0204146 | A1 | 8/2009 | Kaiser et al. |
| 2009/0216325 | A1 | 8/2009 | May et al. |
| 2009/0228015 | A1 | 9/2009 | Ellis |
| 2009/0228042 | A1 | 9/2009 | Koogle, Jr. et al. |
| 2009/0234357 | A1 | 9/2009 | Morales et al. |
| 2009/0234358 | A1 | 9/2009 | Morales et al. |
| 2009/0234451 | A1 | 9/2009 | Manderson |
| 2009/0240251 | A1 | 9/2009 | Gabele |
| 2009/0240335 | A1 | 9/2009 | Arcenio et al. |
| 2009/0241497 | A1 | 10/2009 | Imai et al. |
| 2009/0248091 | A1 | 10/2009 | Teague et al. |
| 2009/0254089 | A1 | 10/2009 | Tipirneni et al. |
| 2009/0265014 | A1 | 10/2009 | May et al. |
| 2009/0265015 | A1 | 10/2009 | May et al. |
| 2009/0287215 | A1 | 11/2009 | Fisher et al. |
| 2009/0299409 | A1 | 12/2009 | Coe et al. |
| 2009/0306711 | A1 | 12/2009 | Stone et al. |
| 2009/0312776 | A1 | 12/2009 | Kaiser et al. |
| 2009/0312793 | A1 | 12/2009 | Huxel et al. |
| 2009/0318960 | A1 | 12/2009 | Burkhart |
| 2009/0318961 | A1 | 12/2009 | Stone et al. |
| 2009/0318965 | A1 | 12/2009 | Burkhart |
| 2010/0016891 | A1 | 1/2010 | Kennedy et al. |
| 2010/0016899 | A1 | 1/2010 | Gelfand |
| 2010/0030321 | A1 | 2/2010 | Mach |
| 2010/0042114 | A1 | 2/2010 | Schaffhausen et al. |
| 2010/0063540 | A1 | 3/2010 | Maiorino |
| 2010/0063541 | A1 | 3/2010 | Brunelle et al. |
| 2010/0087857 | A1 | 4/2010 | Stone et al. |
| 2010/0094341 | A1 | 4/2010 | Raju |
| 2010/0094355 | A1 | 4/2010 | Trenhaile |
| 2010/0106254 | A1 | 4/2010 | Delsignore |
| 2010/0121348 | A1 | 5/2010 | Van Der Burg et al. |
| 2010/0145384 | A1 | 6/2010 | Stone et al. |
| 2010/0152752 | A1 | 6/2010 | Denove et al. |
| 2010/0191319 | A1 | 7/2010 | Lilburn et al. |
| 2010/0191342 | A1 | 7/2010 | Byrd et al. |
| 2010/0204700 | A1 | 8/2010 | Falahee |
| 2010/0211071 | A1 | 8/2010 | Lettmann et al. |
| 2010/0211075 | A1 | 8/2010 | Stone |
| 2010/0256677 | A1 | 10/2010 | Albertorio et al. |
| 2010/0268273 | A1 | 10/2010 | Albertorio et al. |
| 2010/0268275 | A1 | 10/2010 | Stone et al. |
| 2010/0270306 | A1 | 10/2010 | Shiffer |
| 2010/0274282 | A1 | 10/2010 | Olson |
| 2010/0292792 | A1 | 11/2010 | Stone et al. |
| 2010/0298872 | A1 | 11/2010 | Berndt et al. |
| 2010/0298952 | A1 | 11/2010 | Busold et al. |
| 2010/0305698 | A1 | 12/2010 | Metzger et al. |
| 2010/0305709 | A1 | 12/2010 | Metzger et al. |
| 2010/0305710 | A1 | 12/2010 | Metzger |
| 2010/0312245 | A1 | 12/2010 | Tipirneni et al. |
| 2010/0312341 | A1 | 12/2010 | Kaiser et al. |
| 2010/0324676 | A1 | 12/2010 | Albertorio |
| 2010/0331881 | A1 | 12/2010 | Hart |
| 2011/0009885 | A1 | 1/2011 | Graf et al. |
| 2011/0022083 | A1 | 1/2011 | Dimatteo et al. |
| 2011/0026141 | A1 | 2/2011 | Barrows |
| 2011/0040387 | A1 | 2/2011 | Ries et al. |
| 2011/0046733 | A1 | 2/2011 | Eggli |
| 2011/0087225 | A1 | 4/2011 | Fritzinger |
| 2011/0087280 | A1 | 4/2011 | Albertorio |
| 2011/0087284 | A1 | 4/2011 | Stone et al. |
| 2011/0098727 | A1 | 4/2011 | Kaiser et al. |
| 2011/0106153 | A1 | 5/2011 | Stone et al. |
| 2011/0112537 | A1 | 5/2011 | Bernstein et al. |
| 2011/0112538 | A1 | 5/2011 | Dell'oca |
| 2011/0124954 | A1 | 5/2011 | Ogdahl et al. |
| 2011/0125153 | A1 | 5/2011 | Tyber et al. |
| 2011/0160767 | A1 | 6/2011 | Stone et al. |
| 2011/0160768 | A1 | 6/2011 | Stone et al. |
| 2011/0166608 | A1 | 7/2011 | Duggal et al. |
| 2011/0184227 | A1 | 7/2011 | Altman et al. |
| 2011/0208239 | A1 | 8/2011 | Stone et al. |
| 2011/0208240 | A1 | 8/2011 | Stone et al. |
| 2011/0213367 | A1 | 9/2011 | Tyber et al. |
| 2011/0213416 | A1 | 9/2011 | Kaiser |
| 2011/0218625 | A1 | 9/2011 | Berelsman et al. |
| 2011/0224799 | A1 | 9/2011 | Stone |
| 2011/0245868 | A1 | 10/2011 | Teeslink et al. |
| 2011/0264141 | A1 | 10/2011 | Denham et al. |
| 2011/0270278 | A1 | 11/2011 | Overes et al. |
| 2011/0270306 | A1 | 11/2011 | Denham et al. |
| 2011/0295284 | A1 | 12/2011 | Purdue et al. |
| 2011/0319932 | A1 | 12/2011 | Avelar et al. |
| 2012/0004669 | A1 | 1/2012 | Overes et al. |
| 2012/0024134 | A1 | 2/2012 | Dow et al. |
| 2012/0029561 | A1 | 2/2012 | Olson |
| 2012/0041485 | A1 | 2/2012 | Kaiser et al. |
| 2012/0041486 | A1 | 2/2012 | Stone et al. |
| 2012/0041496 | A1 | 2/2012 | Walker |
| 2012/0042768 | A1 | 2/2012 | Chou et al. |
| 2012/0046693 | A1 | 2/2012 | Denham et al. |
| 2012/0053630 | A1 | 3/2012 | Denham et al. |
| 2012/0059417 | A1 | 3/2012 | Norton et al. |
| 2012/0059418 | A1 | 3/2012 | Denham et al. |
| 2012/0059468 | A1 | 3/2012 | Mattern et al. |
| 2012/0060278 | A1 | 3/2012 | Mccurdy |
| 2012/0083837 | A1 | 4/2012 | Ferragamo et al. |
| 2012/0089193 | A1 | 4/2012 | Stone et al. |
| 2012/0095470 | A1 | 4/2012 | Kaiser et al. |
| 2012/0109156 | A1 | 5/2012 | Overes et al. |
| 2012/0116409 | A1 | 5/2012 | Stone |
| 2012/0116450 | A1 | 5/2012 | Mcdevitt et al. |
| 2012/0116452 | A1 | 5/2012 | Stone et al. |
| 2012/0123447 | A1 | 5/2012 | Corrao et al. |
| 2012/0123474 | A1 | 5/2012 | Zajac et al. |

(56) References Cited

U.S. PATENT DOCUMENTS

| | | | |
|---|---|---|---|
| 2012/0123541 | A1 | 5/2012 | Albertorio et al. |
| 2012/0130423 | A1 | 5/2012 | Sengun et al. |
| 2012/0130492 | A1 | 5/2012 | Eggli et al. |
| 2012/0143215 | A1 | 6/2012 | Corrao et al. |
| 2012/0150223 | A1 | 6/2012 | Manos et al. |
| 2012/0150297 | A1 | 6/2012 | Denham et al. |
| 2012/0165864 | A1 | 6/2012 | Hernandez et al. |
| 2012/0165866 | A1 | 6/2012 | Kaiser et al. |
| 2012/0165867 | A1 | 6/2012 | Denham et al. |
| 2012/0165938 | A1 | 6/2012 | Denham et al. |
| 2012/0192455 | A1 | 8/2012 | Hansen et al. |
| 2012/0197271 | A1 | 8/2012 | Astorino et al. |
| 2012/0215257 | A1 | 8/2012 | Mcdevitt et al. |
| 2012/0239159 | A1 | 9/2012 | Metzger et al. |
| 2012/0245585 | A1 | 9/2012 | Kaiser et al. |
| 2012/0265219 | A1 | 10/2012 | Rushdy et al. |
| 2012/0265294 | A1 | 10/2012 | Nishigishi |
| 2012/0271403 | A1 | 10/2012 | Gries |
| 2012/0273085 | A1 | 11/2012 | David et al. |
| 2012/0290002 | A1 | 11/2012 | Astorino |
| 2012/0290003 | A1 | 11/2012 | Dreyfuss |
| 2012/0290004 | A1 | 11/2012 | Lombardo et al. |
| 2012/0296427 | A1 | 11/2012 | Conner et al. |
| 2012/0310245 | A1 | 12/2012 | Hoeppner et al. |
| 2013/0018375 | A1 | 1/2013 | Dell'oca |
| 2013/0018416 | A1 | 1/2013 | Lombardo et al. |
| 2013/0023928 | A1 | 1/2013 | Dreyfuss |
| 2013/0023929 | A1 | 1/2013 | Sullivan et al. |
| 2013/0023930 | A1 | 1/2013 | Stone et al. |
| 2013/0035698 | A1 | 2/2013 | Stone |
| 2013/0035722 | A1 | 2/2013 | Mcdevitt et al. |
| 2013/0046341 | A1 | 2/2013 | Stone et al. |
| 2013/0060323 | A1 | 3/2013 | Mchugo |
| 2013/0090720 | A1 | 4/2013 | Mahr et al. |
| 2013/0090731 | A1 | 4/2013 | Walker |
| 2013/0103082 | A1 | 4/2013 | Kaiser et al. |
| 2013/0110165 | A1 | 5/2013 | Burkhart et al. |
| 2013/0110251 | A1 | 5/2013 | Metzger et al. |
| 2013/0116730 | A1 | 5/2013 | Denham |
| 2013/0123810 | A1 | 5/2013 | Brown et al. |
| 2013/0123813 | A1 | 5/2013 | Stone et al. |
| 2013/0131722 | A1 | 5/2013 | Marchand et al. |
| 2013/0138123 | A1 | 5/2013 | Stone et al. |
| 2013/0144337 | A1 | 6/2013 | Stone et al. |
| 2013/0144338 | A1 | 6/2013 | Stone et al. |
| 2013/0158599 | A1 | 6/2013 | Hester et al. |
| 2013/0158601 | A1 | 6/2013 | Stone et al. |
| 2013/0172942 | A1 | 7/2013 | Lewis et al. |
| 2013/0190818 | A1 | 7/2013 | Norton |
| 2013/0190819 | A1 | 7/2013 | Norton |
| 2013/0204276 | A1 | 8/2013 | Stone et al. |
| 2013/0211452 | A1 | 8/2013 | Stone et al. |
| 2013/0231700 | A1 | 9/2013 | Gedet et al. |
| 2013/0237997 | A1 | 9/2013 | Arai et al. |
| 2013/0245761 | A1 | 9/2013 | Conner et al. |
| 2013/0267956 | A1 | 10/2013 | Terrill et al. |
| 2013/0274812 | A1 | 10/2013 | Dell'oca |
| 2013/0289564 | A1 | 10/2013 | Bernstein et al. |
| 2013/0317621 | A1 | 11/2013 | Metzger et al. |
| 2013/0331742 | A1 | 12/2013 | Aupperle et al. |
| 2013/0331848 | A1 | 12/2013 | Kaiser et al. |
| 2014/0005754 | A1 | 1/2014 | Finley et al. |
| 2014/0018804 | A1 | 1/2014 | Foerster |
| 2014/0046367 | A1 | 2/2014 | Stone et al. |
| 2014/0046368 | A1 | 2/2014 | Kaiser et al. |
| 2014/0052179 | A1 | 2/2014 | Dreyfuss et al. |
| 2014/0058436 | A1 | 2/2014 | Rosenbluth et al. |
| 2014/0067081 | A1 | 3/2014 | Stone |
| 2014/0081322 | A1 | 3/2014 | Sengun et al. |
| 2014/0088655 | A1 | 3/2014 | Stone et al. |
| 2014/0094913 | A1 | 4/2014 | Berelsman et al. |
| 2014/0128985 | A1 | 5/2014 | Sanders et al. |
| 2014/0135835 | A1 | 5/2014 | Stone et al. |
| 2014/0163613 | A1 | 6/2014 | Stone et al. |
| 2014/0163614 | A1 | 6/2014 | Denham et al. |
| 2014/0194927 | A1 | 7/2014 | Kaiser et al. |
| 2014/0200583 | A1 | 7/2014 | Stone et al. |
| 2014/0257378 | A1 | 9/2014 | Norton et al. |
| 2014/0276992 | A1 | 9/2014 | Stone et al. |
| 2014/0277447 | A1 | 9/2014 | Berelsman et al. |
| 2014/0324101 | A1 | 10/2014 | Denham et al. |
| 2014/0330311 | A1 | 11/2014 | Denham et al. |
| 2014/0336760 | A1 | 11/2014 | Eggli |
| 2014/0350674 | A1 | 11/2014 | Stone et al. |
| 2015/0012094 | A1 | 1/2015 | Denham et al. |
| 2015/0032216 | A1 | 1/2015 | Metzger et al. |
| 2015/0057665 | A1 | 2/2015 | Neal et al. |
| 2015/0057757 | A1 | 2/2015 | Metzger et al. |
| 2015/0066081 | A1 | 3/2015 | Martin |
| 2015/0119890 | A1 | 4/2015 | Kaiser et al. |
| 2015/0127051 | A1 | 5/2015 | Kaiser et al. |
| 2015/0128792 | A1 | 5/2015 | Zachariades et al. |
| 2015/0134000 | A1 | 5/2015 | Denham et al. |
| 2015/0143981 | A1 | 5/2015 | Dunker |
| 2015/0148888 | A1 | 5/2015 | Milner et al. |
| 2015/0173753 | A1 | 6/2015 | Spivey et al. |
| 2015/0173887 | A1 | 6/2015 | Berelsman et al. |
| 2015/0257750 | A1 | 9/2015 | Kaiser et al. |
| 2015/0320026 | A1 | 11/2015 | Toddes |
| 2016/0000483 | A1 | 1/2016 | Stone |
| 2016/0022261 | A1 | 1/2016 | Stone et al. |
| 2016/0038187 | A1 | 2/2016 | Mcdonnell |
| 2016/0058436 | A1 | 3/2016 | Stone et al. |
| 2016/0058484 | A1 | 3/2016 | Mccombs-stearnes et al. |
| 2016/0074049 | A1 | 3/2016 | Russell et al. |
| 2016/0081789 | A1 | 3/2016 | Denham et al. |
| 2016/0106414 | A1 | 4/2016 | Stone et al. |
| 2016/0128684 | A1 | 5/2016 | Stone et al. |
| 2016/0183935 | A1 | 6/2016 | Stone |
| 2016/0199053 | A1 | 7/2016 | Norton et al. |
| 2016/0213369 | A1 | 7/2016 | Stone et al. |
| 2016/0242760 | A1 | 8/2016 | Kaiser et al. |
| 2017/0014225 | A1 | 1/2017 | Denham et al. |
| 2017/0020507 | A1 | 1/2017 | Denham et al. |
| 2017/0020569 | A1 | 1/2017 | Grant |
| 2017/0035411 | A1 | 2/2017 | Kaiser et al. |
| 2017/0049557 | A1 | 2/2017 | Denham et al. |
| 2017/0065278 | A1 | 3/2017 | Stone |
| 2017/0071593 | A1 | 3/2017 | Stone |
| 2017/0071595 | A1 | 3/2017 | Stone et al. |
| 2017/0086816 | A1 | 3/2017 | Norton |
| 2017/0119382 | A1 | 5/2017 | Denham et al. |
| 2017/0128061 | A1 | 5/2017 | Stone et al. |
| 2017/0181746 | A1 | 6/2017 | Denham et al. |
| 2017/0189011 | A1 | 7/2017 | Stone et al. |
| 2017/0189197 | A1 | 7/2017 | Werber et al. |
| 2017/0202587 | A1 | 7/2017 | Stone et al. |
| 2017/0231752 | A1 | 8/2017 | Rodriguez et al. |
| 2017/0273686 | A1 | 9/2017 | Denham et al. |
| 2017/0311947 | A1 | 11/2017 | Kaiser et al. |
| 2017/0319194 | A1 | 11/2017 | Mayeski et al. |
| 2017/0319195 | A1 | 11/2017 | Denham et al. |
| 2017/0319204 | A1 | 11/2017 | Norton et al. |
| 2017/0325808 | A1 | 11/2017 | Stone et al. |
| 2017/0333176 | A1 | 11/2017 | Stone et al. |
| 2017/0360425 | A1 | 12/2017 | Stone et al. |
| 2018/0000477 | A1 | 1/2018 | Kaiser et al. |
| 2018/0014864 | A1 | 1/2018 | Stone et al. |
| 2018/0020762 | A1 | 1/2018 | Jamison |
| 2018/0021036 | A1 | 1/2018 | Kaiser et al. |
| 2018/0021125 | A1 | 1/2018 | Berelsman et al. |
| 2018/0042609 | A1 | 2/2018 | Denham et al. |
| 2018/0098858 | A1 | 4/2018 | Valderrabano et al. |
| 2018/0125476 | A1 | 5/2018 | Kaiser et al. |
| 2018/0125477 | A1 | 5/2018 | Stone |
| 2018/0153538 | A1 | 6/2018 | Kaiser et al. |
| 2018/0153558 | A1 | 6/2018 | Bake et al. |
| 2018/0161030 | A1 | 6/2018 | Stone et al. |
| 2018/0177501 | A1 | 6/2018 | Kaiser et al. |
| 2018/0193015 | A1 | 7/2018 | Denham et al. |
| 2018/0221017 | A1 | 8/2018 | Stone et al. |
| 2018/0235747 | A1 | 8/2018 | Berelsman et al. |
| 2018/0249997 | A1 | 9/2018 | Stone et al. |
| 2018/0256153 | A1 | 9/2018 | Stone et al. |

(56) References Cited

U.S. PATENT DOCUMENTS

2019/0083233 A1 3/2019 Denham et al.
2019/0150909 A1 5/2019 Stone et al.
2019/0150923 A1 5/2019 Stone et al.
2019/0231348 A1 8/2019 Stone et al.
2019/0254652 A1 8/2019 Stone et al.
2019/0274681 A1 9/2019 Denham et al.
2019/0282227 A1 9/2019 Norton
2019/0290258 A1 9/2019 Denham et al.
2019/0298345 A1 10/2019 Denham et al.
2019/0328382 A1 10/2019 Stone et al.
2019/0365376 A1 12/2019 Stone et al.
2020/0029955 A1 1/2020 Stone et al.
2020/0085562 A1 3/2020 Stone et al.
2020/0178959 A1 6/2020 Denham et al.
2020/0187932 A1 6/2020 Kaiser et al.
2020/0187933 A1 6/2020 Kaiser et al.
2020/0197002 A1 6/2020 Stone et al.
2020/0297338 A1 9/2020 Stone et al.
2020/0367880 A1 11/2020 Stone et al.
2021/0177397 A1 6/2021 Stone et al.
2021/0228203 A1 7/2021 Denham et al.
2021/0361286 A1 11/2021 Stone et al.
2022/0015757 A1 1/2022 Stone et al.
2022/0054123 A1 2/2022 Kaiser et al.
2022/0096074 A1 3/2022 Denham et al.
2022/0096081 A1 3/2022 Denham et al.
2022/0133296 A1 5/2022 Stone et al.
2023/0000484 A1 1/2023 Kaiser et al.
2023/0084732 A1 3/2023 Norton
2023/0146316 A1 5/2023 Stone et al.
2023/0165580 A1 6/2023 Kaiser et al.
2023/0172602 A1 6/2023 Kaiser et al.
2023/0248356 A1 8/2023 Stone et al.
2023/0293165 A1 9/2023 Stone et al.
2023/0389916 A1 12/2023 Denham et al.
2024/0081807 A1 3/2024 Stone et al.
2024/0081810 A1 3/2024 Stone et al.
2024/0108328 A1 4/2024 Stone et al.
2024/0130723 A1 4/2024 Denham et al.
2024/0130727 A1 4/2024 Stone et al.
2024/0188952 A1 6/2024 Kaiser et al.

FOREIGN PATENT DOCUMENTS

AU 4381268 A 4/1970
AU 5850469 A 1/1971
AU 5963869 A 2/1971
AU 1505470 A 11/1971
AU 2223767 A 5/1973
AU 3615171 A 5/1973
AU 440266 B2 9/1973
AU 5028569 A 9/1973
AU 7110887 A 10/1987
AU 639410 A 11/1989
AU 1713188 A 11/1989
AU 651929 B2 8/1994
AU 3877493 B2 8/1994
BE 1010569 A6 10/1998
CN 1720872 A 1/2006
CN 1777450 A 5/2006
CN 101083954 A 12/2007
CN 101584592 A 11/2009
CN 105208970 A 12/2015
DE 2529669 A1 3/1976
DE 2747312 A1 4/1979
DE 2818254 A1 10/1979
DE 2919009 A1 11/1979
DE 3027138 A1 12/1981
DE 3225620 A1 2/1983
DE 3136083 A1 3/1983
DE 233303 A1 2/1986
DE 4127550 A1 2/1993
DE 4302397 A 7/1993
DE 29621340 U1 4/1998
DE 19841252 A1 3/2000
DE 29922088 U1 4/2000
DE 20207781 U1 8/2002
EP 0019062 A 11/1980
EP 0108912 A 5/1984
EP 0129422 A2 12/1984
EP 0129442 A1 12/1984
EP 0172130 A2 2/1986
EP 0241240 A2 10/1987
EP 0241792 A1 10/1987
EP 0260970 A2 3/1988
EP 0270704 A1 6/1988
EP 0282789 A2 9/1988
EP 0315371 A2 5/1989
EP 0317406 A1 5/1989
EP 0340159 A1 11/1989
EP 0346183 A1 12/1989
EP 0349173 A1 1/1990
EP 0374088 A1 6/1990
EP 0409364 A2 1/1991
EP 0415915 A1 3/1991
EP 0440991 A1 8/1991
EP 0441065 A2 8/1991
EP 0447065 A2 9/1991
EP 0451932 A2 10/1991
EP 0464480 A1 1/1992
EP 0490417 A1 6/1992
EP 0497079 A1 8/1992
EP 0502509 A1 9/1992
EP 0502698 A1 9/1992
EP 0520177 A1 12/1992
EP 0546726 A1 6/1993
EP 0552950 A1 7/1993
EP 0574707 A1 12/1993
EP 0582514 A1 2/1994
EP 0591991 A2 4/1994
EP 0598219 A2 5/1994
EP 0611551 A1 8/1994
EP 0627203 A2 12/1994
EP 0651979 A1 5/1995
EP 0669110 A2 8/1995
EP 0686373 A1 12/1995
EP 2723528 A1 2/1996
EP 0702933 A1 3/1996
EP 2734709 A1 12/1996
EP 0775473 A1 5/1997
EP 2744010 A1 8/1997
EP 0913123 A1 5/1999
EP 0913131 A2 5/1999
EP 0995409 A1 4/2000
EP 1013229 A2 6/2000
EP 1093773 A1 4/2001
EP 1093774 A1 4/2001
EP 1555945 A2 7/2005
EP 1741412 A2 1/2007
EP 1864617 A2 12/2007
EP 2238944 A2 10/2010
EP 2544607 A1 1/2013
EP 2709557 A1 3/2014
EP 2895112 A1 7/2015
EP 2934379 A1 10/2015
EP 2434987 B1 6/2016
EP 2775935 B1 5/2017
FR 2622790 A1 5/1989
FR 2634373 A1 1/1990
FR 2655840 A1 6/1991
FR 2663837 A1 1/1992
FR 2682867 A1 4/1993
FR 2687911 A1 9/1993
FR 2688689 A1 9/1993
FR 2704140 A3 10/1994
FR 2717070 A1 9/1995
FR 2745999 A1 9/1997
FR 2770764 A1 5/1999
GB 401677 A 11/1933
GB 1413477 A 11/1975
GB 1485681 A 9/1977
GB 2083751 A 3/1982
GB 2118474 A 11/1983
GB 2129306 A 5/1984

(56) References Cited

FOREIGN PATENT DOCUMENTS

| | | | |
|---|---|---|---|
| GB | 2227175 | A | 7/1990 |
| GB | 2253147 | A | 9/1992 |
| GB | 2312376 | A | 10/1997 |
| GB | 2403416 | A | 1/2005 |
| GB | 2454251 | A | 5/2009 |
| JP | 5362911 | U | 5/1978 |
| JP | 5362912 | U | 5/1978 |
| JP | 5374942 | U | 6/1978 |
| JP | 5378230 | U | 9/1978 |
| JP | 54166092 | U | 11/1979 |
| JP | 54166093 | U | 11/1979 |
| JP | 54176284 | U | 12/1979 |
| JP | 54178988 | U | 12/1979 |
| JP | 5362911 | A | 7/1987 |
| JP | 62159647 | A | 7/1987 |
| JP | 62159647 | U | 10/1987 |
| JP | 62295657 | A | 12/1987 |
| JP | 5269160 | A | 10/1993 |
| JP | 5300917 | A | 11/1993 |
| JP | 751292 | A | 2/1995 |
| JP | 10127672 | A | 5/1998 |
| JP | 10211213 | A | 8/1998 |
| JP | 5362911 | B2 | 12/2013 |
| JP | 5362912 | B2 | 12/2013 |
| JP | 5374942 | B2 | 12/2013 |
| JP | 5378230 | B2 | 12/2013 |
| RU | 2051647 | C1 | 1/1996 |
| RU | 2076667 | C1 | 4/1997 |
| WO | WO-8300615 | A1 | 3/1983 |
| WO | WO-8603666 | A1 | 7/1986 |
| WO | WO-8701270 | A1 | 3/1987 |
| WO | WO-8901767 | A1 | 3/1989 |
| WO | WO-8909030 | A1 | 10/1989 |
| WO | WO-8910096 | A1 | 11/1989 |
| WO | WO-9008510 | A1 | 8/1990 |
| WO | WO-9203980 | A1 | 3/1992 |
| WO | WO-9314705 | A1 | 8/1993 |
| WO | WO-9315694 | A1 | 8/1993 |
| WO | WO-9502373 | A1 | 1/1995 |
| WO | WO-9503003 | A1 | 2/1995 |
| WO | WO-9529637 | A1 | 11/1995 |
| WO | WO-9532670 | A1 | 12/1995 |
| WO | WO-9609797 | A1 | 4/1996 |
| WO | WO-9629029 | A1 | 9/1996 |
| WO | WO-9737603 | A1 | 10/1997 |
| WO | WO-9812991 | A1 | 4/1998 |
| WO | WO-9812992 | A1 | 4/1998 |
| WO | WO-9822047 | A1 | 5/1998 |
| WO | WO-9822048 | A1 | 5/1998 |
| WO | WO-9901084 | A2 | 1/1999 |
| WO | WO-9912480 | A1 | 3/1999 |
| WO | WO-9937219 | A1 | 7/1999 |
| WO | WO-9944544 | A | 9/1999 |
| WO | WO-9952472 | A1 | 10/1999 |
| WO | WO-0004159 | A1 | 1/2000 |
| WO | WO-0040159 | A1 | 7/2000 |
| WO | WO-0139671 | A1 | 6/2001 |
| WO | WO-0236020 | A1 | 5/2002 |
| WO | WO-03005914 | A1 | 1/2003 |
| WO | WO-03071962 | A2 | 9/2003 |
| WO | WO-03077772 | A1 | 9/2003 |
| WO | WO-03092551 | A1 | 11/2003 |
| WO | WO-2004091412 | A1 | 10/2004 |
| WO | WO-05104992 | A1 | 11/2005 |
| WO | WO-2005122954 | A1 | 12/2005 |
| WO | WO-2006011786 | A1 | 2/2006 |
| WO | WO-2006023661 | A2 | 3/2006 |
| WO | WO-2006055823 | A2 | 5/2006 |
| WO | WO-2007045460 | A2 | 4/2007 |
| WO | WO-2007103562 | A2 | 9/2007 |
| WO | WO-2007109280 | A2 | 9/2007 |
| WO | WO-2007119057 | A1 | 10/2007 |
| WO | WO-2008002550 | A2 | 1/2008 |
| WO | WO-2008015171 | A1 | 2/2008 |
| WO | WO-2008073588 | A2 | 6/2008 |
| WO | WO-2009012021 | A1 | 1/2009 |
| WO | WO-2009083047 | A1 | 7/2009 |
| WO | WO-2009131820 | A1 | 10/2009 |
| WO | WO-2010138832 | A1 | 12/2010 |
| WO | WO-2011112371 | A1 | 9/2011 |
| WO | WO-2011150238 | A1 | 12/2011 |
| WO | WO-2012134999 | A1 | 10/2012 |
| WO | WO-2012158583 | A1 | 11/2012 |
| WO | WO-2013066974 | A1 | 5/2013 |
| WO | WO-2013074525 | A1 | 5/2013 |
| WO | WO-2014043078 | A1 | 3/2014 |
| WO | WO-2014100109 | A1 | 6/2014 |
| WO | WO-2014151766 | A1 | 9/2014 |

OTHER PUBLICATIONS

"U.S. Appl. No. 17/516,664, Response filed Sep. 18, 2024 to Non Final Office Action mailed Jun. 20, 2024", 10 pgs.

"U.S. Appl. No. 17/232,672, Notice of Allowance mailed Apr. 16, 2024", 11 pgs.

"U.S. Appl. No. 17/232,672, Preliminary Amendment filed Apr. 19, 2021", 5 pgs.

"U.S. Appl. No. 17/232,672, Response filed Feb. 29, 2024 to Restriction Requirement mailed Feb. 26, 2024", 6 pgs.

"U.S. Appl. No. 17/232,672, Restriction Requirement mailed Feb. 26, 2024", 6 pgs.

"U.S. Appl. No. 17/392,971, Examiner Interview Summary mailed Oct. 7, 2024", 2 pgs.

"U.S. Appl. No. 17/392,971, Examiner Interview Summary mailed Oct. 11, 2024", 3 pgs.

"U.S. Appl. No. 17/392,971, Non Final Action with Restriction Requirement mailed Apr. 18, 2024", 8 pgs.

"U.S. Appl. No. 17/392,971, Non Final Office Action mailed Apr. 18, 2024", 8 pgs.

"U.S. Appl. No. 17/392,971, Notice of Allowance mailed Sep. 18, 2024", 8 pgs.

"U.S. Appl. No. 17/392,971, Response filed Jul. 17, 2024 to Non Final Office Action mailed Apr. 18, 2024", 9 pgs.

"U.S. Appl. No. 17/392,971, Response filed Jul. 17, 2024 to Non Final Office Action mailed Apr. 18, 2024", 10 pgs.

"U.S. Appl. No. 17/392,971, Supplemental Preliminary Amendment filed Jan. 12, 2024", 7 pgs.

"U.S. Appl. No. 17/516,664, Non Final Office Action mailed Jun. 20, 20224", 16 pgs.

"U.S. Appl. No. 17/516,664, Notice of Allowance mailed Jan. 31, 2025", 8 pgs.

"U.S. Appl. No. 17/550,074, Notice of Allowance mailed Jun. 3, 2024", 9 pgs.

"U.S. Appl. No. 17/577,188, Supplemental Preliminary Amendment filed Dec. 21, 2023", 5 pgs.

"U.S. Appl. No. 17/940,022, Notice of Allowance mailed Feb. 7, 2024", 8 pgs.

"U.S. Appl. No. 18/093,114, Notice of Allowance mailed May 8, 2025", 10 pgs.

"U.S. Appl. No. 18/093,114, PTO Response to Rule 312 Communication mailed May 19, 2025", 2 pgs.

"U.S. Appl. No. 18/093,114, PTO Response to Rule 312 Communication mailed May 20, 2025", 2 pgs.

"U.S. Appl. No. 18/093,114, Response filed Apr. 7, 2025 to Restriction Requirement mailed Mar. 31, 2025", 7 pgs.

"U.S. Appl. No. 18/093,114, Restriction Requirement mailed Mar. 31, 2025", 6 pgs.

"U.S. Appl. No. 18/101,490, Non Final Office Action mailed Jun. 12, 2024", 20 pgs.

"U.S. Appl. No. 18/101,490, Notice of Allowance mailed Nov. 14, 2024", 10 pgs.

"U.S. Appl. No. 18/101,490, Response filed Sep. 12, 2024 to Non Final Office Action mailed Jun. 12, 2024", 10 pgs.

"U.S. Appl. No. 18/102,518, Corrected Notice of Allowability mailed Aug. 27, 2024", 2 pgs.

"U.S. Appl. No. 18/102,518, Notice of Allowance mailed Apr. 18, 2024", 11 pgs.

(56) References Cited

OTHER PUBLICATIONS

"U.S. Appl. No. 18/126,022, Notice of Allowance mailed Jul. 29, 2025", 12 pgs.
"U.S. Appl. No. 18/126,022, Response filed Jun. 5, 2025 to Restriction Requirement mailed Apr. 30, 2025", 6 pgs.
"U.S. Appl. No. 18/126,022, Restriction Requirement mailed Apr. 30, 2025", 8 pgs.
"U.S. Appl. No. 18/134,897, Notice of Allowance mailed May 15, 2025", 11 pgs.
"U.S. Appl. No. 18/134,897, Response filed Apr. 9, 2025 to Restriction Requirement mailed Apr. 2, 2025", 9 pgs.
"U.S. Appl. No. 18/134,897, Restriction Requirement mailed Apr. 2, 2025", 6 pgs.
"U.S. Appl. No. 18/134,897, Supplemental Amendment filed Nov. 1, 2023", 8 pgs.
"U.S. Appl. No. 18/235,540, Advisory Action mailed Apr. 4, 2025", 3 pgs.
"U.S. Appl. No. 18/235,540, Final Office Action mailed Feb. 28, 2025", 19 pgs.
"U.S. Appl. No. 18/235,540, Non Final Office Action mailed Nov. 14, 2024", 17 pgs.
"U.S. Appl. No. 18/235,540, Notice of Allowance mailed Jun. 4, 2025", 12 pgs.
"U.S. Appl. No. 18/235,540, Response filed Mar. 27, 2025 to Final Office Action mailed Feb. 28, 2025", 8 pgs.
"U.S. Appl. No. 18/235,540, Response filed Dec. 13, 2024 to Non Final Office Action mailed Nov. 14, 2024", 11 pgs.
"U.S. Appl. No. 18/471,089, Response filed Jul. 18, 2025 to Restriction Requirement mailed Jun. 5, 2025", 8 pgs.
"U.S. Appl. No. 18/471,089, Restriction Requirement mailed Jun. 5, 2025", 6 pgs.
"U.S. Appl. No. 18/514,936, Preliminary Amendment filed Nov. 20, 2023", 4 pgs.
"U.S. Appl. No. 18/514,936, Restriction Requirement mailed Jul. 28, 2025", 7 pgs.
"U.S. Appl. No. 18/514,936, Supplemental Amendment filed Nov. 22, 2023", 6 pgs.
"U.S. Appl. No. 18/531,362, Supplemental Preliminary Amendment filed Dec. 21, 2023", 6 pgs.
"U.S. Appl. No. 18/531,396, Supplemental Amendment filed Jan. 18, 2024", 10 pgs.
"U.S. Appl. No. 18/531,431, Supplemental Preliminary Amendment filed Jan. 19, 2024", 5 pgs.
"U.S. Appl. No. 18/583,499, Corrected Notice of Allowability mailed Dec. 4, 2024", 2 pgs.
"U.S. Appl. No. 18/583,499, Notice of Allowance mailed Nov. 21, 2024", 9 pgs.
"U.S. Appl. No. 18/583,499, Preliminary Amendment filed Feb. 26, 2024", 6 pgs.
"AperFix® System Surgical Technique Guide. Single Tunnel Double Bundle.™", Cayenne Medical brochure, (Aug. 2008), 8 pgs.
"U.S. Appl. No. 10/984,624, Final Office Action mailed Jan. 5, 2009", 9 pgs.
"U.S. Appl. No. 10/984,624, Non Final Office Action mailed Jul. 10, 2008", 9 pgs.
"U.S. Appl. No. 10/984,624, Notice of Allowance mailed Jun. 12, 2009", 9 pgs.
"U.S. Appl. No. 10/984,624, Response filed Apr. 1, 2009 to Final Office Action mailed Jan. 5, 2009", 16 pgs.
"U.S. Appl. No. 10/984,624, Response filed Apr. 15, 2008 to Restriction Requirement mailed Mar. 24, 2008", 1 pg.
"U.S. Appl. No. 10/984,624, Response filed Oct. 10, 2008 to Non Final Office Action mailed Jul. 10, 2008", 12 pgs.
"U.S. Appl. No. 10/984,624, Restriction Requirement mailed Mar. 24, 2008", 5 pgs.
"U.S. Appl. No. 11/294,694, Final Office Action mailed Sep. 1, 2010", 14 pgs.
"U.S. Appl. No. 11/294,694, Non Final Office Action mailed Mar. 16, 2010", 19 pgs.
"U.S. Appl. No. 11/294,694, Notice of Allowance mailed Nov. 17, 2010", 4 pgs.
"U.S. Appl. No. 11/294,694, Preliminary Amendment filed Jan. 13, 2010", 9 pgs.
"U.S. Appl. No. 11/294,694, Response filed Jun. 16, 2010 to Non Final Office Action mailed Mar. 16, 2010", 16 pgs.
"U.S. Appl. No. 11/294,694, Response filed Nov. 1, 2010 to Final Office Action mailed Sep. 1, 2010", 10 pgs.
"U.S. Appl. No. 11/294,694, Response filed Dec. 22, 2009 to Restriction Requirement mailed Nov. 25, 2009", 1 pg.
"U.S. Appl. No. 11/294,694, Restriction Requirement mailed Nov. 25, 2009", 9 pgs.
"U.S. Appl. No. 11/347,661, Examiner Interview Summary mailed Sep. 11, 2009", 2 pgs.
"U.S. Appl. No. 11/347,661, Final Office Action mailed Mar. 3, 2009", 15 pgs.
"U.S. Appl. No. 11/347,661, Non Final Office Action mailed Aug. 13, 2009", 19 pgs.
"U.S. Appl. No. 11/347,661, Non Final Office Action mailed Aug. 21, 2008", 11 pgs.
"U.S. Appl. No. 11/347,661, Notice of Allowance mailed Feb. 24, 2010", 8 pgs.
"U.S. Appl. No. 11/347,661, Notice of Allowance mailed May 5, 2010", 8 pgs.
"U.S. Appl. No. 11/347,661, Response filed May 29, 2008 to Restriction Requirement mailed Apr. 30, 2008", 1 pg.
"U.S. Appl. No. 11/347,661, Response filed Jun. 3, 2009 to Final Office Action mailed Mar. 3, 2009", 19 pgs.
"U.S. Appl. No. 11/347,661, Response filed Nov. 6, 2009 to Non Final Office Action mailed Aug. 13, 2009", 16 pgs.
"U.S. Appl. No. 11/347,661, Response filed Nov. 19, 2008 to Non Final Office Action mailed Aug. 21, 2008", 12 pgs.
"U.S. Appl. No. 11/347,661, Restriction Requirement mailed Apr. 30, 2008", 6 pgs.
"U.S. Appl. No. 11/347,662, Examiner Interview Summary mailed Jun. 24, 2010", 3 pgs.
"U.S. Appl. No. 11/347,662, Examiner Interview Summary mailed Nov. 9, 2009", 3 pgs.
"U.S. Appl. No. 11/347,662, Final Office Action mailed Sep. 16, 2009", 13 pgs.
"U.S. Appl. No. 11/347,662, Final Office Action mailed Oct. 26, 2010", 10 pgs.
"U.S. Appl. No. 11/347,662, Non Final Office Action mailed Mar. 9, 2009", 11 pgs.
"U.S. Appl. No. 11/347,662, Non Final Office Action mailed May 21, 2010", 19 pgs.
"U.S. Appl. No. 11/347,662, Non Final Office Action mailed Oct. 28, 2008", 13 pgs.
"U.S. Appl. No. 11/347,662, Response filed Jan. 16, 2009 to Non Final Office Action mailed Oct. 28, 2008", 16 pgs.
"U.S. Appl. No. 11/347,662, Response filed Feb. 12, 2010 to Final Office Action mailed Sep. 16, 2009", 21 pgs.
"U.S. Appl. No. 11/347,662, Response filed Jun. 5, 2009 to Non Final Office Action mailed Mar. 9, 2009", 13 pgs.
"U.S. Appl. No. 11/347,662, Response filed Aug. 20, 2010 to Non Final Office Action mailed May 21, 2010", 13 pgs.
"U.S. Appl. No. 11/386,071, Advisory Action mailed Dec. 23, 2010", 3 pgs.
"U.S. Appl. No. 11/386,071, Examiner Interview Summary mailed Jan. 31, 2011", 3 pgs.
"U.S. Appl. No. 11/386,071, Examiner Interview Summary mailed Jul. 21, 2010", 3 pgs.
"U.S. Appl. No. 11/386,071, Final Office Action mailed Oct. 27, 2010", 10 pgs.
"U.S. Appl. No. 11/386,071, Non Final Office Action mailed May 12, 2010", 13 pgs.
"U.S. Appl. No. 11/386,071, Notice of Allowance mailed Jun. 6, 2011", 6 pgs.
"U.S. Appl. No. 11/386,071, Response filed Jan. 26, 2011 to Advisory Action mailed Dec. 23, 2010", 13 pgs.
"U.S. Appl. No. 11/386,071, Response filed Aug. 12, 2010 to Non Final Office Action mailed May 12, 2010", 14 pgs.

(56) References Cited

OTHER PUBLICATIONS

"U.S. Appl. No. 11/386,071, Response filed Dec. 15, 2010 to Final Office Action mailed Oct. 27, 2010", 14 pgs.
"U.S. Appl. No. 11/408,282, Final Office Action mailed Dec. 15, 2008", 8 pgs.
"U.S. Appl. No. 11/408,282, Non Final Office Action mailed May 23, 2008", 12 pgs.
"U.S. Appl. No. 11/408,282, Response filed Aug. 21, 2008 to Non Final Office Action mailed May 23, 2008", 10 pgs.
"U.S. Appl. No. 11/504,882, Examiner Interview Summary mailed Sep. 2, 2010", 3 pgs.
"U.S. Appl. No. 11/504,882, Final Office Action mailed Dec. 21, 2010", 7 pgs.
"U.S. Appl. No. 11/504,882, Non Final Office Action mailed Jun. 19, 2014", 11 pgs.
"U.S. Appl. No. 11/504,882, Non Final Office Action mailed Jun. 23, 2010", 8 pgs.
"U.S. Appl. No. 11/504,882, Non Final Office Action mailed Nov. 13, 2013", 13 pgs.
"U.S. Appl. No. 11/504,882, Notice of Allowance mailed Dec. 1, 2014", 9 pgs.
"U.S. Appl. No. 11/504,882, Response filed Feb. 10, 2014 to Non Final Office Action mailed Nov. 13, 2013", 11 pgs.
"U.S. Appl. No. 11/504,882, Response filed Mar. 18, 2011 to Final Office Action mailed Dec. 21, 2010", 11 pgs.
"U.S. Appl. No. 11/504,882, Response filed Sep. 17, 2014 to Non Final Office Action mailed Jun. 19, 2014", 14 pgs.
"U.S. Appl. No. 11/504,882, Response filed Sep. 23, 2010 to Non Final Office Action mailed Jun. 23, 2010", 12 pgs.
"U.S. Appl. No. 11/504,882, Supplemental Notice of Allowability mailed Mar. 12, 2015", 5 pgs.
"U.S. Appl. No. 11/541,505, Non Final Office Action mailed May 19, 2009", 7 pgs.
"U.S. Appl. No. 11/541,505, Notice of Allowance mailed Sep. 18, 2009", 8 pgs.
"U.S. Appl. No. 11/541,505, Response filed Apr. 9, 2009 to Restriction Requirement mailed Mar. 9, 2009", 1 pg.
"U.S. Appl. No. 11/541,505, Response filed Jun. 18, 2009 to Non Final Office Action mailed May 19, 2009", 5 pgs.
"U.S. Appl. No. 11/541,505, Restriction Requirement mailed Mar. 9, 2009", 9 pgs.
"U.S. Appl. No. 11/541,506, Notice of Allowance mailed Jun. 1, 2009", 10 pgs.
"U.S. Appl. No. 11/541,506, Notice of Allowance mailed Jun. 29, 2009", 8 pgs.
"U.S. Appl. No. 11/541,506, Response filed Apr. 9, 2009 to Restriction Requirement mailed Mar. 9, 2009", 1 pg.
"U.S. Appl. No. 11/541,506, Restriction Requirement mailed Mar. 9, 2009", 6 pgs.
"U.S. Appl. No. 11/739,768, Examiner Interview Summary mailed May 11, 2011", 3 pgs.
"U.S. Appl. No. 11/739,768, Examiner Interview Summary mailed Oct. 4, 2011", 3 pgs.
"U.S. Appl. No. 11/739,768, Final Office Action mailed Aug. 22, 2011", 14 pgs.
"U.S. Appl. No. 11/739,768, Non Final Office Action mailed Mar. 4, 2011", 11 pgs.
"U.S. Appl. No. 11/739,768, Notice of Allowance mailed Nov. 15, 2011", 5 pgs.
"U.S. Appl. No. 11/739,768, Response filed Jun. 6, 2011 to Non Final Office Action mailed Mar. 4, 2011", 15 pgs.
"U.S. Appl. No. 11/739,768, Response filed Oct. 26, 2011 to Final Office Action mailed Aug. 22, 2011", 14 pgs.
"U.S. Appl. No. 11/740,035, Final Office Action mailed Aug. 7, 2008", 9 pgs.
"U.S. Appl. No. 11/740,035, Non Final Office Action mailed Jan. 3, 2008", 9 pgs.
"U.S. Appl. No. 11/740,035, Response filed Apr. 3, 2008 to Non Final Office Action mailed Jan. 3, 2008", 6 pgs.
"U.S. Appl. No. 11/784,821, Corrected Notice of Allowance mailed Dec. 24, 2014", 4 pgs.
"U.S. Appl. No. 11/784,821, Examiner Interview Summary mailed Jun. 26, 2014", 3 pgs.
"U.S. Appl. No. 11/784,821, Examiner Interview Summary mailed Nov. 17, 2009", 3 pgs.
"U.S. Appl. No. 11/784,821, Final Office Action mailed Mar. 10, 2010", 11 pgs.
"U.S. Appl. No. 11/784,821, Non Final Office Action mailed Mar. 28, 2014", 14 pgs.
"U.S. Appl. No. 11/784,821, Non Final Office Action mailed Sep. 4, 2009", 12 pgs.
"U.S. Appl. No. 11/784,821, Notice of Allowance mailed Oct. 21, 2014", 10 pgs.
"U.S. Appl. No. 11/784,821, Response filed Jun. 10, 2010 to Final Office Action mailed Mar. 10, 2010", 20 pgs.
"U.S. Appl. No. 11/784,821, Response filed Jun. 15, 2009 to Restriction Requirement mailed May 13, 2009", 2 pgs.
"U.S. Appl. No. 11/784,821, Response filed Jun. 26, 2014 to Non Final Office Action mailed Mar. 28, 2014", 16 pgs.
"U.S. Appl. No. 11/784,821, Response filed Nov. 23, 2009 to Non Final Office Action mailed Sep. 4, 2009", 17 pgs.
"U.S. Appl. No. 11/784,821, Restriction Requirement mailed May 13, 2009", 6 pgs.
"U.S. Appl. No. 11/869,440, Examiner Interview Summary mailed Mar. 25, 2010", 3 pgs.
"U.S. Appl. No. 11/869,440, Non Final Office Action mailed Mar. 1, 2010", 13 pgs.
"U.S. Appl. No. 11/869,440, Notice of Allowance mailed Aug. 19, 2010", 10 pgs.
"U.S. Appl. No. 11/869,440, Response filed Jun. 1, 2010 to Non Final Office Action mailed Mar. 1, 2010", 14 pgs.
"U.S. Appl. No. 11/935,681, Examiner Interview Summary mailed Jul. 19, 2010", 3 pgs.
"U.S. Appl. No. 11/935,681, Non Final Office Action mailed May 24, 2010", 12 pgs.
"U.S. Appl. No. 11/935,681, Notice of Allowance mailed Nov. 8, 2010", 10 pgs.
"U.S. Appl. No. 11/935,681, Response filed Apr. 19, 2010 to Restriction Requirement mailed Mar. 17, 2010", 4 pgs.
"U.S. Appl. No. 11/935,681, Response filed Aug. 24, 2010 to Non Final Office Action mailed May 24, 2010", 13 pgs.
"U.S. Appl. No. 11/935,681, Restriction Requirement mailed Mar. 17, 2010", 6 pgs.
"U.S. Appl. No. 12/014,340, Examiner Interview Summary mailed Jun. 22, 2010", 3 pgs.
"U.S. Appl. No. 12/014,340, Non Final Office Action mailed May 25, 2010", 12 pgs.
"U.S. Appl. No. 12/014,340, Notice of Allowance mailed Nov. 8, 2010", 9 pgs.
"U.S. Appl. No. 12/014,340, Preliminary Amendment filed May 21, 2010", 11 pgs.
"U.S. Appl. No. 12/014,340, Response filed Apr. 26, 2010 to Restriction Requirement mailed Mar. 25, 2010", 2 pgs.
"U.S. Appl. No. 12/014,340, Response filed Aug. 25, 2010 to Non Final Office Action mailed May 25, 2010", 16 pgs.
"U.S. Appl. No. 12/014,340, Restriction Requirement mailed Mar. 25, 2010", 9 pgs.
"U.S. Appl. No. 12/014,399, Examiner Interview Summary mailed Jun. 23, 2010", 3 pgs.
"U.S. Appl. No. 12/014,399, Non Final Office Action mailed May 26, 2010", 13 pgs.
"U.S. Appl. No. 12/014,399, Notice of Allowance mailed Nov. 12, 2010", 11 pgs.
"U.S. Appl. No. 12/014,399, Preliminary Amendment filed May 25, 2010", 10 pgs.
"U.S. Appl. No. 12/014,399, Response filed May 5, 2010 to Restriction Requirement mailed Apr. 6, 2010", 2 pgs.
"U.S. Appl. No. 12/014,399, Response filed Aug. 25, 2010 to Non Final Office Action mailed May 26, 2010", 14 pgs.
"U.S. Appl. No. 12/014,399, Restriction Requirement mailed Apr. 6, 2010", 9 pgs.

(56) References Cited

OTHER PUBLICATIONS

"U.S. Appl. No. 12/029,861, Examiner Interview Summary mailed Jan. 27, 2012", 3 pgs.
"U.S. Appl. No. 12/029,861, Final Office Action mailed Dec. 8, 2011", 11 pgs.
"U.S. Appl. No. 12/029,861, Non Final Office Action mailed Jul. 26, 2011", 11 pgs.
"U.S. Appl. No. 12/029,861, Notice of Allowance mailed Apr. 26, 2012", 5 pgs.
"U.S. Appl. No. 12/029,861, Response filed Jan. 26, 2012 to Final Office Action mailed Dec. 8, 2011", 15 pgs.
"U.S. Appl. No. 12/029,861, Response filed May 6, 2011 to Restriction Requirement mailed Apr. 7, 2011", 10 pgs.
"U.S. Appl. No. 12/029,861, Response filed Jun. 23, 2011 to Restriction Requirement mailed May 24, 2011", 1 pgs.
"U.S. Appl. No. 12/029,861, Response filed Oct. 14, 2011 to Non Final Office Action mailed Jul. 26, 2011", 11 pgs.
"U.S. Appl. No. 12/029,861, Restriction Requirement mailed Apr. 7, 2011", 8 pgs.
"U.S. Appl. No. 12/029,861, Restriction Requirement mailed May 24, 2011", 6 pgs.
"U.S. Appl. No. 12/107,437, Examiner Interview Summary mailed May 10, 2010", 4 pgs.
"U.S. Appl. No. 12/107,437, Non Final Office Action mailed Mar. 17, 10", 9 pgs.
"U.S. Appl. No. 12/107,437, Preliminary Amendment filed Feb. 23, 2010", 9 pgs.
"U.S. Appl. No. 12/107,437, Response filed Jan. 29, 2010 to Restriction Requirement mailed Jan. 13, 2010", 1 pgs.
"U.S. Appl. No. 12/107,437, Restriction Requirement mailed Jan. 13, 2010", 7 pgs.
"U.S. Appl. No. 12/196,398, Examiner Interview Summary mailed Nov. 8, 2010", 3 pgs.
"U.S. Appl. No. 12/196,398, Notice of Allowance mailed Feb. 3, 2011", 12 pgs.
"U.S. Appl. No. 12/196,398, Preliminary Amendment filed Nov. 10, 2008", 3 pgs.
"U.S. Appl. No. 12/196,398, Preliminary Amendment filed Dec. 1, 2010", 12 pgs.
"U.S. Appl. No. 12/196,398, Preliminary Amendment filed Dec. 9, 2008", 46 pgs.
"U.S. Appl. No. 12/196,398, Response filed Oct. 29, 2010 to Restriction Requirement mailed Sep. 29, 2010", 2 pgs.
"U.S. Appl. No. 12/196,398, Restriction Requirement mailed Sep. 29, 2010", 6 pgs.
"U.S. Appl. No. 12/196,398, Supplemental Notice of Allowability mailed Mar. 9, 2011", 4 pgs.
"U.S. Appl. No. 12/196,398, Supplemental Notice of Allowability mailed Apr. 15, 2011", 4 pgs.
"U.S. Appl. No. 12/196,405, Examiner Interview Summary mailed Jun. 20, 2011", 3 pgs.
"U.S. Appl. No. 12/196,405, Non Final Office Action mailed Apr. 11, 2011", 13 pgs.
"U.S. Appl. No. 12/196,405, Notice of Allowance mailed Oct. 26, 2011", 11 pgs.
"U.S. Appl. No. 12/196,405, Preliminary Amendment filed Nov. 10, 2008", 3 pgs.
"U.S. Appl. No. 12/196,405, Response filed Mar. 16, 2011 to Restriction Requirement mailed Feb. 14, 2011", 1 pgs.
"U.S. Appl. No. 12/196,405, Response filed Jul. 12, 2011 to Non Final Office Action mailed Apr. 11, 2011", 19 pgs.
"U.S. Appl. No. 12/196,405, Restriction Requirement mailed Feb. 14, 2011", 6 pgs.
"U.S. Appl. No. 12/196,405, Supplemental Amendment filed Oct. 3, 2011", 12 pgs.
"U.S. Appl. No. 12/196,407, Examiner Interview Summary mailed Jul. 14, 2011", 3 pgs.
"U.S. Appl. No. 12/196,407, Non Final Office Action mailed May 4, 2011", 11 pgs.
"U.S. Appl. No. 12/196,407, Notice of Allowance mailed Oct. 26, 2011", 10 pgs.
"U.S. Appl. No. 12/196,407, Preliminary Amendment filed Nov. 10, 2008", 3 pgs.
"U.S. Appl. No. 12/196,407, Response filed Apr. 20, 2011 to Restriction Requirement mailed Mar. 22, 2011", 12 pgs.
"U.S. Appl. No. 12/196,407, Response filed Aug. 2, 2011 to Non Final Office Action mailed May 4, 2011", 27 pgs.
"U.S. Appl. No. 12/196,407, Restriction Requirement mailed Mar. 22, 2011", 6 pgs.
"U.S. Appl. No. 12/196,407, Supplemental Response to Non Final Office Action filed Oct. 3, 2011", 18 pgs.
"U.S. Appl. No. 12/196,410, Examiner Interview Summary mailed Jul. 14, 2011", 3 pgs.
"U.S. Appl. No. 12/196,410, Non Final Office Action mailed May 9, 2011", 9 pgs.
"U.S. Appl. No. 12/196,410, Notice of Allowance mailed Oct. 13, 2011", 8 pgs.
"U.S. Appl. No. 12/196,410, Response filed Apr. 20, 2011 to Restriction Requirement mailed Mar. 22, 2011", 13 pgs.
"U.S. Appl. No. 12/196,410, Response filed Aug. 1, 2011 to Non Final Office Action mailed May 9, 2011", 23 pgs.
"U.S. Appl. No. 12/196,410, Restriction Requirement mailed Mar. 22, 2011", 6 pgs.
"U.S. Appl. No. 12/196,410, Supplemental Amendment filed Oct. 3, 2011", 15 pgs.
"U.S. Appl. No. 12/398,548, Examiner Interview Summary mailed Jul. 12, 2011", 3 pgs.
"U.S. Appl. No. 12/398,548, Non Final Office Action mailed Apr. 12, 2011", 7 pgs.
"U.S. Appl. No. 12/398,548, Notice of Allowance mailed Oct. 18, 2011", 7 pgs.
"U.S. Appl. No. 12/398,548, Response filed Jul. 12, 2011 to Non Final Office Action mailed Apr. 12, 2011", 15 pgs.
"U.S. Appl. No. 12/398,548, Supplemental Preliminary Amendment filed Sep. 7, 2010", 11 pgs.
"U.S. Appl. No. 12/419,491, Examiner Interview Summary mailed May 30, 2012", 3 pgs.
"U.S. Appl. No. 12/419,491, Examiner Interview Summary mailed Nov. 29, 2011", 3 pgs.
"U.S. Appl. No. 12/419,491, Final Office Action mailed Apr. 12, 2012", 12 pgs.
"U.S. Appl. No. 12/419,491, Non Final Office Action mailed Sep. 22, 2011", 12 pgs.
"U.S. Appl. No. 12/419,491, Notice of Allowance mailed Jul. 13, 2012", 10 pgs.
"U.S. Appl. No. 12/419,491, Response filed May 30, 2012 to Final Office Action mailed Apr. 12, 2012", 12 pgs.
"U.S. Appl. No. 12/419,491, Response filed Dec. 9, 2011 to Non Final Office Action mailed Sep. 22, 2011", 17 pgs.
"U.S. Appl. No. 12/474,802, Notice of Allowance mailed Aug. 31, 2011", 13 pgs.
"U.S. Appl. No. 12/474,802, Notice of Allowance mailed Oct. 26, 2011", 4 pgs.
"U.S. Appl. No. 12/474,802, Response filed Mar. 28, 2011 to Restriction Requirement mailed Feb. 24, 2011", 12 pgs.
"U.S. Appl. No. 12/474,802, Restriction Requirement mailed Feb. 24, 2011", 6 pgs.
"U.S. Appl. No. 12/489,168, Examiner Interview Summary mailed Feb. 21, 2012", 3 pgs.
"U.S. Appl. No. 12/489,168, Non Final Office Action mailed Dec. 7, 2011", 10 pgs.
"U.S. Appl. No. 12/489,168, Notice of Allowance mailed Apr. 26, 2012", 8 pgs.
"U.S. Appl. No. 12/489,168, Notice of Allowance mailed Sep. 5, 2012", 8 pgs.
"U.S. Appl. No. 12/489,168, Preliminary Amendment filed Oct. 22, 2009", 3 pgs.
"U.S. Appl. No. 12/489,168, Response filed Feb. 27, 2012 to Non Final Office Action mailed Dec. 7, 2011", 15 pgs.
"U.S. Appl. No. 12/489,168, Response filed Nov. 11, 2011 to Restriction Requirement mailed Oct. 20, 2011", 1 pg.

(56) References Cited

OTHER PUBLICATIONS

"U.S. Appl. No. 12/489,168, Restriction Requirement mailed Oct. 20, 2011", 8 pgs.
"U.S. Appl. No. 12/489,181, Examiner Interview Summary mailed Feb. 13, 2012", 3 pgs.
"U.S. Appl. No. 12/489,181, Non Final Office Action mailed Jan. 3, 2012", 9 pgs.
"U.S. Appl. No. 12/489,181, Notice of Allowance mailed May 23, 2012", 9 pgs.
"U.S. Appl. No. 12/489,181, Preliminary Amendment filed Mar. 31, 2011", 10 pgs.
"U.S. Appl. No. 12/489,181, Preliminary Amendment filed Oct. 22, 2009", 3 pgs.
"U.S. Appl. No. 12/489,181, Response filed Mar. 27, 2012 to Non Final Office Action mailed Jan. 3, 2012", 12 pgs.
"U.S. Appl. No. 12/489,181, Response filed Dec. 5, 2011 to Restriction Requirement mailed Nov. 4, 2011", 1 pg.
"U.S. Appl. No. 12/489,181, Restriction Requirement mailed Nov. 4, 2011", 7 pgs.
"U.S. Appl. No. 12/570,854, Examiner Interview Summary mailed Apr. 16, 2012", 3 pgs.
"U.S. Appl. No. 12/570,854, Non Final Office Action mailed Feb. 10, 2012", 8 pgs.
"U.S. Appl. No. 12/570,854, Notice of Allowance mailed Jun. 29, 2012", 10 pgs.
"U.S. Appl. No. 12/570,854, Notice of Allowance mailed Sep. 19, 2012", 6 pgs.
"U.S. Appl. No. 12/570,854, Response filed May 10, 2012 to Non Final Office Action mailed Feb. 10, 2012", 27 pgs.
"U.S. Appl. No. 12/570,854, Response filed Dec. 20, 2011 to Restriction Requirement mailed Dec. 14, 2011", 1 pg.
"U.S. Appl. No. 12/570,854, Restriction Requirement mailed Dec. 14, 2011", 6 pgs.
"U.S. Appl. No. 12/702,067, Non Final Office Action mailed Mar. 5, 2013", 8 pgs.
"U.S. Appl. No. 12/702,067, Notice of Allowance mailed Oct. 7, 2013", 11 pgs.
"U.S. Appl. No. 12/702,067, Preliminary Amendment filed Jan. 11, 2011", 13 pgs.
"U.S. Appl. No. 12/702,067, Response filed Jun. 5, 2013 to Non Final Office Action mailed Mar. 5, 2013", 17 pgs.
"U.S. Appl. No. 12/702,067, Response filed Oct. 2, 2012 to Restriction Requirement mailed Sep. 4, 2012", 1 pg.
"U.S. Appl. No. 12/702,067, Restriction Requirement mailed Sep. 4, 2012", 9 pgs.
"U.S. Appl. No. 12/719,337, Advisory Action mailed Sep. 30, 2014", 4 pgs.
"U.S. Appl. No. 12/719,337, Examiner Interview Summary mailed Apr. 4, 2014", 4 pgs.
"U.S. Appl. No. 12/719,337, Examiner Interview Summary mailed May 14, 2013", 3 pgs.
"U.S. Appl. No. 12/719,337, Examiner Interview Summary mailed Sep. 18, 2014", 3 pgs.
"U.S. Appl. No. 12/719,337, Final Office Action mailed Mar. 12, 2013", 8 pgs.
"U.S. Appl. No. 12/719,337, Final Office Action mailed Jul. 18, 2014", 15 pgs.
"U.S. Appl. No. 12/719,337, Non Final Office Action mailed Jan. 10, 2014", 14 pgs.
"U.S. Appl. No. 12/719,337, Non Final Office Action mailed Sep. 5, 2012", 7 pgs.
"U.S. Appl. No. 12/719,337, Notice of Allowance mailed Mar. 11, 2015", 10 pgs.
"U.S. Appl. No. 12/719,337, Notice of Non-Compliant Amendment mailed May 2, 2014", 3 pgs.
"U.S. Appl. No. 12/719,337, Response filed Apr. 10, 2014 to Non Final Office Action mailed Jan. 10, 2014", 16 pgs.
"U.S. Appl. No. 12/719,337, Response filed May 25, 2012 to Restriction Requirement mailed Apr. 26, 2012", 9 pgs.
"U.S. Appl. No. 12/719,337, Response filed Jun. 5, 13 to Final Office Action mailed Mar. 12, 2013", 16 pgs.
"U.S. Appl. No. 12/719,337, Response filed Jun. 25, 2014 to Notice of Non-Compliant Amendment mailed May 2, 2014", 10 pgs.
"U.S. Appl. No. 12/719,337, Response filed Sep. 18, 2014 to Final Office Action mailed Jul. 18, 2014", 13 pgs.
"U.S. Appl. No. 12/719,337, Response filed Nov. 28, 2012 to Non Final Office Action mailed Sep. 5, 2012", 14 pgs.
"U.S. Appl. No. 12/719,337, Restriction Requirement mailed Apr. 26, 2012", 8 pgs.
"U.S. Appl. No. 12/788,966, Examiner Interview Summary mailed Jun. 1, 2012", 3 pgs.
"U.S. Appl. No. 12/788,966, Final Office Action mailed May 4, 2012", 16 pgs.
"U.S. Appl. No. 12/788,966, Non Final Office Action mailed Jan. 4, 2012", 12 pgs.
"U.S. Appl. No. 12/788,966, Notice of Allowance mailed Aug. 16, 2012", 10 pgs.
"U.S. Appl. No. 12/788,966, Notice of Allowance mailed Nov. 23, 2012", 2 pgs.
"U.S. Appl. No. 12/788,966, Response filed Apr. 4, 2012 to Non Final Office Action mailed Jan. 4, 2012", 15 pgs.
"U.S. Appl. No. 12/788,966, Response filed Aug. 6, 2012 to Final Office Action mailed May 4, 2012", 12 pgs.
"U.S. Appl. No. 12/788,966, Response filed Dec. 16, 2011 to Restriction Requirement mailed Dec. 7, 2011", 11 pgs.
"U.S. Appl. No. 12/788,966, Restriction Requirement mailed Dec. 7, 2011", 9 pgs.
"U.S. Appl. No. 12/788,973, Advisory Action mailed Jan. 23, 2013", 3 pgs.
"U.S. Appl. No. 12/788,973, Advisory Action mailed Dec. 27, 2012", 8 pgs.
"U.S. Appl. No. 12/788,973, Final Office Action mailed Sep. 18, 2012", 16 pgs.
"U.S. Appl. No. 12/788,973, Non Final Office Action mailed May 8, 2012", 12 pgs.
"U.S. Appl. No. 12/788,973, Notice of Allowance mailed Mar. 21, 2013", 6 pgs.
"U.S. Appl. No. 12/788,973, Response filed Jan. 16, 2013 to Advisory Action mailed Dec. 27, 2012", 9 pgs.
"U.S. Appl. No. 12/788,973, Response filed Jul. 19, 2012 to Non Final Office Action mailed May 8, 2012", 21 pgs.
"U.S. Appl. No. 12/788,973, Response filed Dec. 16, 2011 to Restriction Requirement mailed Dec. 6, 2011", 11 pgs.
"U.S. Appl. No. 12/788,973, Response filed Dec. 17, 2012 to Final Office Action mailed Sep. 18, 2012", 15 pgs.
"U.S. Appl. No. 12/788,973, Restriction Requirement mailed Dec. 6, 2011", 9 pgs.
"U.S. Appl. No. 12/788,973, Supplemental Notice of Allowance mailed May 24, 2013", 2 pgs.
"U.S. Appl. No. 12/788,978, Advisory Action mailed Dec. 24, 2013", 4 pgs.
"U.S. Appl. No. 12/788,978, Applicant's Summary of Examiner Interview filed Dec. 12, 2013", 2 pgs.
"U.S. Appl. No. 12/788,978, Corrected Notice of Allowance mailed Apr. 30, 2014", 2 pgs.
"U.S. Appl. No. 12/788,978, Examiner Interview Summary mailed Jan. 28, 2014", 3 pgs.
"U.S. Appl. No. 12/788,978, Examiner Interview Summary mailed Mar. 22, 2013", 3 pgs.
"U.S. Appl. No. 12/788,978, Examiner Interview Summary mailed Sep. 11, 2012", 3 pgs.
"U.S. Appl. No. 12/788,978, Examiner Interview Summary mailed Oct. 29, 2013", 4 pgs.
"U.S. Appl. No. 12/788,978, Examiner Interview Summary mailed Dec. 16, 2013", 3 pgs.
"U.S. Appl. No. 12/788,978, Examiner Interview Summary mailed Dec. 27, 2012", 3 pgs.
"U.S. Appl. No. 12/788,978, Final Office Action mailed Aug. 20, 2013", 17 pgs.
"U.S. Appl. No. 12/788,978, Final Office Action mailed Nov. 2, 2012", 14 pgs.

(56) References Cited

OTHER PUBLICATIONS

"U.S. Appl. No. 12/788,978, Non Final Office Action mailed Jan. 11, 2013", 16 pgs.
"U.S. Appl. No. 12/788,978, Non Final Office Action mailed Jul. 13, 2012", 17 pgs.
"U.S. Appl. No. 12/788,978, Notice of Allowance mailed Jan. 24, 2014", 9 pgs.
"U.S. Appl. No. 12/788,978, Notice of Non-Compliant Amendment mailed Jun. 6, 2013", 3 pgs.
"U.S. Appl. No. 12/788,978, Response filed Jan. 2, 2013 to Final Office Action mailed Nov. 2, 2012", 13 pgs.
"U.S. Appl. No. 12/788,978, Response filed Jan. 20, 2014 to Advisory Action mailed Dec. 24, 2013", 4 pgs.
"U.S. Appl. No. 12/788,978, Response filed Apr. 8, 2013 to Non Final Office Action mailed Jan. 11, 2013", 16 pgs.
"U.S. Appl. No. 12/788,978, Response filed May 21, 2012 to Restriction Requirement mailed Apr. 20, 2012", 12 pgs.
"U.S. Appl. No. 12/788,978, Response filed Jul. 3, 2013 to Notice of Non-Compliant Amendment mailed Jun. 6, 2013", 17 pgs.
"U.S. Appl. No. 12/788,978, Response filed Oct. 5, 2012 to Non Final Office Action mailed Jul. 13, 2012", 20 pgs.
"U.S. Appl. No. 12/788,978, Response filed Nov. 20, 2013 to Final Office Action mailed Aug. 20, 2013", 15 pgs.
"U.S. Appl. No. 12/788,978, Restriction Requirement mailed Apr. 20, 2012", 8 pgs.
"U.S. Appl. No. 12/828,977, Examiner Interview Summary mailed Jul. 9, 2012", 3 pgs.
"U.S. Appl. No. 12/828,977, Non Final Office Action mailed May 3, 2012", 9 pgs.
"U.S. Appl. No. 12/828,977, Notice of Allowance mailed Sep. 5, 2012", 9 pgs.
"U.S. Appl. No. 12/828,977, Preliminary Amendment filed Jul. 19, 2011", 10 pgs.
"U.S. Appl. No. 12/828,977, Response filed Mar. 14, 2012 to Restriction Requirement mailed Feb. 13, 2012", 9 pgs.
"U.S. Appl. No. 12/828,977, Response filed Jul. 25, 2012 to Non Final Office Action mailed May 3, 2012", 11 pgs.
"U.S. Appl. No. 12/828,977, Restriction Requirement mailed Feb. 13, 2012", 7 pgs.
"U.S. Appl. No. 12/915,962, Examiner Interview Summary mailed Jul. 25, 2012", 3 pgs.
"U.S. Appl. No. 12/915,962, Non Final Office Action mailed May 7, 2012", 11 pgs.
"U.S. Appl. No. 12/915,962, Non Final Office Action mailed Oct. 15, 2012", 9 pgs.
"U.S. Appl. No. 12/915,962, Notice of Allowance mailed Jun. 10, 2013", 12 pgs.
"U.S. Appl. No. 12/915,962, Response filed Jan. 10, 2013 to Non Final Office Action mailed Oct. 15, 2012", 21 pgs.
"U.S. Appl. No. 12/915,962, Response filed Mar. 16, 2012 to Restriction Requirement mailed Feb. 15, 2012", 15 pgs.
"U.S. Appl. No. 12/915,962, Response filed Aug. 7, 2012 to Non Final Office Action mailed May 7, 2012", 26 pgs.
"U.S. Appl. No. 12/915,962, Restriction Requirement mailed Feb. 15, 2012", 8 pgs.
"U.S. Appl. No. 12/938,902, Examiner Interview Summary mailed Dec. 3, 2012", 3 pgs.
"U.S. Appl. No. 12/938,902, Non Final Office Action mailed Sep. 17, 2012", 11 pgs.
"U.S. Appl. No. 12/938,902, Notice of Allowance mailed Jun. 21, 2013", 13 pgs.
"U.S. Appl. No. 12/938,902, Notice of Allowance mailed Oct. 1, 2013", 9 pgs.
"U.S. Appl. No. 12/938,902, Response filed Aug. 6, 2012 to Restriction Requirement mailed Jul. 6, 2012", 14 pgs.
"U.S. Appl. No. 12/938,902, Response filed Dec. 10, 2012 to Non Final Office Action mailed Sep. 17, 2012", 20 pgs.
"U.S. Appl. No. 12/938,902, Restriction Requirement mailed Jul. 6, 2012", 8 pgs.
"U.S. Appl. No. 12/976,328, Examiner Interview Summary mailed Feb. 13, 2012", 3 pgs.
"U.S. Appl. No. 12/976,328, Non Final Office Action mailed Dec. 15, 2011", 13 pgs.
"U.S. Appl. No. 12/976,328, Notice of Allowance mailed Apr. 30, 2012", 9 pgs.
"U.S. Appl. No. 12/976,328, Response filed Mar. 2, 2012 to Non Final Office Action mailed Dec. 15, 2011", 15 pgs.
"U.S. Appl. No. 13/045,689, Examiner Interview Summary mailed May 14, 2012", 3 pgs.
"U.S. Appl. No. 13/045,689, Non Final Office Action mailed Mar. 20, 2012", 11 pgs.
"U.S. Appl. No. 13/045,689, Notice of Allowance mailed Aug. 10, 2012", 10 pgs.
"U.S. Appl. No. 13/045,689, Notice of Allowance mailed Sep. 24, 2012", 7 pgs.
"U.S. Appl. No. 13/045,689, Response filed Jan. 30, 2012 to Restriction Requirement mailed Dec. 29, 2011", 13 pgs.
"U.S. Appl. No. 13/045,689, Response filed Jun. 8, 2012 to Non Final Office Action mailed Mar. 20, 2012", 15 pgs.
"U.S. Appl. No. 13/045,689, Restriction Requirement mailed Dec. 29, 2011", 6 pgs.
"U.S. Appl. No. 13/045,691, Examiner Interview Summary mailed May 14, 2012", 3 pgs.
"U.S. Appl. No. 13/045,691, Non Final Office Action mailed Mar. 20, 2012", 12 pgs.
"U.S. Appl. No. 13/045,691, Notice of Allowance mailed Jun. 19, 2012", 10 pgs.
"U.S. Appl. No. 13/045,691, Response filed Feb. 9, 2012 to Restriction Requirement mailed Jan. 9, 2012", 1 pg.
"U.S. Appl. No. 13/045,691, Response filed Jun. 8, 2012 to Non Final Office Action mailed Mar. 20, 2012", 17 pgs.
"U.S. Appl. No. 13/045,691, Restriction Requirement mailed Jan. 9, 2012", 6 pgs.
"U.S. Appl. No. 13/071,563, Final Office Action mailed May 23, 2014", 13 pgs.
"U.S. Appl. No. 13/071,563, Non Final Office Action mailed Oct. 23, 2013", 18 pgs.
"U.S. Appl. No. 13/071,563, Notice of Allowance mailed Aug. 15, 2014", 7 pgs.
"U.S. Appl. No. 13/071,563, Preliminary Amendment filed May 1, 2012", 8 pgs.
"U.S. Appl. No. 13/071,563, Preliminary Amendment filed Dec. 6, 2011", 7 pgs.
"U.S. Appl. No. 13/071,563, Response filed Jan. 21, 2014 to Non Final Office Action mailed Oct. 23, 2013", 13 pgs.
"U.S. Appl. No. 13/071,563, Response filed Jul. 23, 2014 to Final Office Action mailed May 23, 2014", 14 pgs.
"U.S. Appl. No. 13/071,563, Response filed Sep. 19, 2013 to Restriction Requirement mailed Aug. 19, 2013", 11 pgs.
"U.S. Appl. No. 13/071,563, Restriction Requirement mailed Aug. 19, 2013", 7 pgs.
"U.S. Appl. No. 13/098,897, Examiner Interview Summary mailed Nov. 27, 2012", 3 pgs.
"U.S. Appl. No. 13/098,897, Non Final Office Action mailed Sep. 21, 2012", 9 pgs.
"U.S. Appl. No. 13/098,897, Notice of Allowance mailed Jun. 11, 2013", 13 pgs.
"U.S. Appl. No. 13/098,897, Response filed Aug. 30, 2012 to Restriction Requirement mailed Jul. 30, 2012", 16 pgs.
"U.S. Appl. No. 13/098,897, Response filed Dec. 18, 2012 to Non Final Office Action mailed Sep. 21, 2012", 21 pgs.
"U.S. Appl. No. 13/098,897, Restriction Requirement mailed Jul. 30, 2012", 8 pgs.
"U.S. Appl. No. 13/098,927, Advisory Action mailed Aug. 8, 2013", 3 pgs.
"U.S. Appl. No. 13/098,927, Applicant's Summary of Examiner Interview filed Sep. 23, 2013", 12 pgs.
"U.S. Appl. No. 13/098,927, Examiner Interview Summary mailed Jun. 28, 2013", 3 pgs.
"U.S. Appl. No. 13/098,927, Examiner Interview Summary mailed Sep. 20, 2013", 3 pgs.

(56) References Cited

OTHER PUBLICATIONS

"U.S. Appl. No. 13/098,927, Final Office Action mailed May 22, 2013", 10 pgs.
"U.S. Appl. No. 13/098,927, Non Final Office Action mailed Sep. 24, 2012", 12 pgs.
"U.S. Appl. No. 13/098,927, Notice of Allowance mailed Jan. 8, 2014", 5 pgs.
"U.S. Appl. No. 13/098,927, Notice of Allowance mailed Sep. 26, 2013", 14 pgs.
"U.S. Appl. No. 13/098,927, Response filed Jul. 22, 2015 to Final Office Action mailed May 22, 2013", 17 pgs.
"U.S. Appl. No. 13/098,927, Response filed Aug. 27, 2012 to Restriction Requirement mailed Jul. 25, 2012", 14 pgs.
"U.S. Appl. No. 13/098,927, Response filed Dec. 21, 2012 to Non Final Office Action mailed Sep. 24, 2012", 21 pgs.
"U.S. Appl. No. 13/098,927, Restriction Requirement mailed Jul. 25, 2012", 8 pgs.
"U.S. Appl. No. 13/102,182, Notice of Allowance mailed Mar. 22, 2012", 10 pgs.
"U.S. Appl. No. 13/109,667, Advisory Action mailed Feb. 4, 2014", 4 pgs.
"U.S. Appl. No. 13/109,667, Examiner Interview Summary mailed Dec. 20, 2013", 3 pgs.
"U.S. Appl. No. 13/109,667, Final Office Action mailed Oct. 11, 2013", 19 pgs.
"U.S. Appl. No. 13/109,667, Non Final Office Action mailed May 21, 2013", 21 pgs.
"U.S. Appl. No. 13/109,667, Notice of Allowance mailed Feb. 18, 2014", 10 pgs.
"U.S. Appl. No. 13/109,667, Response filed Jan. 13, 2014 to Final Office Action mailed Oct. 11, 2013", 20 pgs.
"U.S. Appl. No. 13/109,667, Response filed May 2, 2013 to Restriction Requirement mailed Apr. 2, 2013", 1 pg.
"U.S. Appl. No. 13/109,667, Response filed Aug. 21, 2013 to Non Final Office Action mailed May 21, 2013", 27 pgs.
"U.S. Appl. No. 13/109,667, Restriction Requirement mailed Apr. 2, 2013", 8 pgs.
"U.S. Appl. No. 13/109,667, Supplemental Notice of Allowability mailed Jun. 12, 2014", 3 pgs.
"U.S. Appl. No. 13/109,667, Supplemental Notice of Allowance mailed May 28, 2014", 2 pgs.
"U.S. Appl. No. 13/109,667, Supplemental Preliminary Amendment filed Feb. 4, 2014", 16 pgs.
"U.S. Appl. No. 13/109,672, 312 Amendment filed Jan. 15, 2015", 3 pgs.
"U.S. Appl. No. 13/109,672, Non Final Office Action mailed May 15, 2014", 10 pgs.
"U.S. Appl. No. 13/109,672, Notice of Allowance mailed Feb. 3, 2015", 2 pgs.
"U.S. Appl. No. 13/109,672, Notice of Allowance mailed Sep. 29, 2014", 9 pgs.
"U.S. Appl. No. 13/109,672, PTO Response to Rule 312 Communication mailed Jan. 27, 2015", 2 pgs.
"U.S. Appl. No. 13/109,672, Response filed Apr. 14, 2014 to Restriction Requirement mailed Feb. 14, 2014", 15 pgs.
"U.S. Appl. No. 13/109,672, Response filed Aug. 15, 2014 to Non Final Office Action mailed May 15, 2014", 20 pgs.
"U.S. Appl. No. 13/109,672, Response filed Nov. 4, 2013 to Restriction Requirement mailed Oct. 2, 2013", 10 pgs.
"U.S. Appl. No. 13/109,672, Restriction Requirement mailed Feb. 14, 2014", 7 pgs.
"U.S. Appl. No. 13/109,672, Restriction Requirement mailed Oct. 2, 2013", 7 pgs.
"U.S. Appl. No. 13/111,564, Corrected Notice of Allowance mailed Oct. 9, 2013", 2 pgs.
"U.S. Appl. No. 13/111,564, Examiner Interview Summary mailed Jun. 18, 2013", 3 pgs.
"U.S. Appl. No. 13/111,564, Non Final Office Action mailed Mar. 18, 2013", 8 pgs.
"U.S. Appl. No. 13/111,564, Notice of Allowance mailed Jun. 28, 2013", 12 pgs.
"U.S. Appl. No. 13/111,564, Response filed Feb. 4, 2013 to Restriction Requirement mailed Jan. 3, 2013", 20 pgs.
"U.S. Appl. No. 13/111,564, Response filed Jun. 18, 2013 to Non Final Office Action mailed Mar. 18, 2013", 25 pgs.
"U.S. Appl. No. 13/111,564, Restriction Requirement mailed Jan. 3, 2013", 5 pgs.
"U.S. Appl. No. 13/177,153, Final Office Action mailed May 28, 2013", 11 pgs.
"U.S. Appl. No. 13/177,153, Non Final Office Action mailed Oct. 2, 2012", 11 pgs.
"U.S. Appl. No. 13/177,153, Notice of Allowance mailed Jan. 7, 2014", 4 pgs.
"U.S. Appl. No. 13/177,153, Notice of Allowance mailed Sep. 17, 2013", 13 pgs.
"U.S. Appl. No. 13/177,153, Response filed Aug. 28, 2013 to Final Office Action mailed May 28, 2013", 19 pgs.
"U.S. Appl. No. 13/177,153, Response filed Sep. 4, 2012 to Restriction Requirement mailed Aug. 2, 2012", 15 pgs.
"U.S. Appl. No. 13/177,153, Response filed Dec. 20, 2012 to Non Final Office Action mailed Oct. 2, 2012", 16 pgs.
"U.S. Appl. No. 13/177,153, Restriction Requirement mailed Aug. 2, 2012", 9 pgs.
"U.S. Appl. No. 13/181,729, Examiner Interview Summary mailed May 9, 2013", 3 pgs.
"U.S. Appl. No. 13/181,729, Final Office Action mailed Mar. 13, 2013", 14 pgs.
"U.S. Appl. No. 13/181,729, Non Final Office Action mailed Oct. 2, 2012", 7 pgs.
"U.S. Appl. No. 13/181,729, Notice of Allowance mailed May 23, 2013", 9 pgs.
"U.S. Appl. No. 13/181,729, Response filed May 13, 2013 to Final Office Action mailed Mar. 13, 2013", 13 pgs.
"U.S. Appl. No. 13/181,729, Response filed Dec. 20, 2012 to Non Final Office Action mailed Oct. 2, 2012", 15 pgs.
"U.S. Appl. No. 13/269,097, Final Office Action mailed Aug. 8, 2013", 7 pgs.
"U.S. Appl. No. 13/269,097, Non Final Office Action mailed Feb. 12, 2013", 10 pgs.
"U.S. Appl. No. 13/269,097, Notice of Allowance mailed Feb. 3, 2014", 5 pgs.
"U.S. Appl. No. 13/269,097, Notice of Allowance mailed Oct. 21, 2013", 9 pgs.
"U.S. Appl. No. 13/269,097, Response filed May 13, 2013 to Non Final Office Action mailed Feb. 12, 2013", 17 pgs.
"U.S. Appl. No. 13/269,097, Response filed Oct. 8, 2013 to Final Office Action mailed Aug. 8, 2013", 12 pgs.
"U.S. Appl. No. 13/269,097, Response filed Nov. 13, 2012 to Restriction Requirement mailed Oct. 17, 2012", 1 pg.
"U.S. Appl. No. 13/269,097, Restriction Requirement mailed Oct. 17, 2012", 8 pgs.
"U.S. Appl. No. 13/278,341, Notice of Allowance mailed Jun. 18, 2013", 10 pgs.
"U.S. Appl. No. 13/278,341, Response filed Mar. 8, 2013 to Restriction Requirement mailed Feb. 11, 2013", 1 pg.
"U.S. Appl. No. 13/278,341, Restriction Requirement mailed Feb. 11, 2013", 6 pgs.
"U.S. Appl. No. 13/281,009, Corrected Notice of Allowance mailed Nov. 18, 2016", 4 pgs.
"U.S. Appl. No. 13/281,009, Corrected Notice of Allowance mailed Dec. 12, 2016", 2 pgs.
"U.S. Appl. No. 13/281,009, Examiner Interview Summary mailed Nov. 18, 2016", 2 pgs.
"U.S. Appl. No. 13/281,009, Non Final Office Action mailed Jun. 2, 2015", 9 pgs.
"U.S. Appl. No. 13/281,009, Notice of Allowance mailed Feb. 24, 2016", 9 pgs.
"U.S. Appl. No. 13/281,009, Notice of Allowance mailed Jun. 23, 2016", 9 pgs.
"U.S. Appl. No. 13/281,009, Notice of Allowance mailed Oct. 29, 2015", 8 pgs.

(56) References Cited

OTHER PUBLICATIONS

"U.S. Appl. No. 13/281,009, Response filed Sep. 2, 2015 to Non Final Office Action mailed Jun. 2, 2015", 13 pgs.
"U.S. Appl. No. 13/281,009, Restriction Requirement mailed Feb. 11, 2015", 6 pgs.
"U.S. Appl. No. 13/288,459, Corrected Notice of Allowance mailed Aug. 3, 2016", 4 pgs.
"U.S. Appl. No. 13/288,459, Corrected Notice of Allowance mailed Sep. 9, 2016", 4 pgs.
"U.S. Appl. No. 13/288,459, Corrected Notice of Allowance mailed Sep. 23, 2016", 4 pgs.
"U.S. Appl. No. 13/288,459, Examiner Interview Summary mailed Feb. 6, 2015", 3 pgs.
"U.S. Appl. No. 13/288,459, Examiner Interview Summary mailed Jan. 11, 2016", 1 pg.
"U.S. Appl. No. 13/288,459, Non Final Office Action mailed Jun. 24, 2015", 10 pgs.
"U.S. Appl. No. 13/288,459, Non Final Office Action mailed Nov. 4, 2014", 15 pgs.
"U.S. Appl. No. 13/288,459, Notice of Allowance mailed Jan. 11, 2016", 13 pgs.
"U.S. Appl. No. 13/288,459, Notice of Allowance mailed May 10, 2016", 7 pgs.
"U.S. Appl. No. 13/288,459, Response filed Mar. 3, 2015 to Non Final Office Action mailed Nov. 4, 2014", 16 pgs.
"U.S. Appl. No. 13/288,459, Response filed Oct. 13, 2014 to Restriction Requirement mailed Aug. 11, 2014", 15 pgs.
"U.S. Appl. No. 13/288,459, Response filed Oct. 23, 2015 to Non Final Office Action mailed Jun. 24, 2015", 14 pgs.
"U.S. Appl. No. 13/288,459, Restriction Requirement mailed Aug. 11, 2014", 9 pgs.
"U.S. Appl. No. 13/288,463, Examiner Interview Summary mailed Jun. 3, 2014", 3 pgs.
"U.S. Appl. No. 13/288,463, Non Final Office Action mailed Feb. 24, 2014", 13 pgs.
"U.S. Appl. No. 13/288,463, Notice of Allowance mailed Aug. 27, 2014", 9 pgs.
"U.S. Appl. No. 13/288,463, Response filed May 27, 2014 to Non Final Office Action mailed Feb. 24, 2014", 15 pgs.
"U.S. Appl. No. 13/288,463, Supplemental Notice of Allowability mailed Dec. 8, 2014", 5 pgs.
"U.S. Appl. No. 13/288,463, Supplemental Notice of Allowability mailed Dec. 19, 2014", 5 pgs.
"U.S. Appl. No. 13/293,825, Notice of Allowability mailed Jun. 22, 2015", 7 pgs.
"U.S. Appl. No. 13/293,825, Notice of Allowance mailed May 19, 2015", 9 pgs.
"U.S. Appl. No. 13/293,825, Response filed Apr. 15, 2015 to Restriction Requirement mailed Feb. 12, 2015", 17 pgs.
"U.S. Appl. No. 13/293,825, Restriction Requirement mailed Feb. 12, 2015", 9 pgs.
"U.S. Appl. No. 13/295,126, Non Final Office Action mailed May 19, 2015", 9 pgs.
"U.S. Appl. No. 13/295,126, Notice of Allowance mailed Oct. 22, 2015", 9 pgs.
"U.S. Appl. No. 13/295,126, Response filed Apr. 13, 2015 to Restriction Requirement mailed Feb. 12, 2015", 1 pgs.
"U.S. Appl. No. 13/295,126, Response filed Aug. 17, 2015 to Non Final Office Action mailed May 19, 2015", 21 pgs.
"U.S. Appl. No. 13/295,126, Restriction Requirement mailed Feb. 12, 2015", 9 pgs.
"U.S. Appl. No. 13/311,936, Examiner Interview Summary mailed Feb. 12, 2015", 2 pgs.
"U.S. Appl. No. 13/311,936, Non Final Office Action mailed Feb. 9, 2015", 13 pgs.
"U.S. Appl. No. 13/311,936, Non Final Office Action mailed Oct. 19, 2015", 8 pgs.
"U.S. Appl. No. 13/311,936, Notice of Allowance mailed Mar. 29, 2016", 8 pgs.
"U.S. Appl. No. 13/311,936, PTO Response to Rule 312 Communication mailed May 10, 2016", 2 pgs.
"U.S. Appl. No. 13/311,936, Response filed Jan. 18, 2016 to Non Final Office Action mailed Oct. 19, 2015", 8 pgs.
"U.S. Appl. No. 13/311,936, Response filed Jun. 9, 2015 to Non Final Office Action mailed Feb. 9, 2015", 12 pgs.
"U.S. Appl. No. 13/311,936, Response filed Oct. 3, 2014 to Restriction Requirement mailed Aug. 5, 2014", 10 pgs.
"U.S. Appl. No. 13/311,936, Restriction Requirement mailed Aug. 5, 2014", 7 pgs.
"U.S. Appl. No. 13/350,985, Final Office Action mailed Apr. 16, 2015", 8 pgs.
"U.S. Appl. No. 13/350,985, Non Final Office Action mailed Dec. 15, 2014", 8 pgs.
"U.S. Appl. No. 13/350,985, Notice of Allowance mailed Jul. 27, 2015", 5 pgs.
"U.S. Appl. No. 13/350,985, Response filed Mar. 13, 2015 to Non Final Office Action mailed Dec. 15, 2014", 10 pgs.
"U.S. Appl. No. 13/350,985, Response filed Jul. 9, 2015 to Final Office Action mailed Apr. 16, 2015", 8 pgs.
"U.S. Appl. No. 13/350,985, Response filed Dec. 2, 2014 to Restriction Requirement mailed Oct. 2, 2014", 9 pgs.
"U.S. Appl. No. 13/350,985, Restriction Requirement mailed Oct. 2, 2014", 6 pgs.
"U.S. Appl. No. 13/399,125, Corrected Notice of Allowance mailed Aug. 28, 2014", 2 pgs.
"U.S. Appl. No. 13/399,125, Examiner Interview Summary mailed May 17, 2013", 3 pgs.
"U.S. Appl. No. 13/399,125, Final Office Action mailed Mar. 20, 2013", 12 pgs.
"U.S. Appl. No. 13/399, 125, Non Final Office Action mailed Oct. 24, 2012", 12 pgs.
"U.S. Appl. No. 13/399,125, Notice of Allowance mailed May 16, 2014", 8 pgs.
"U.S. Appl. No. 13/399,125, Response filed Jan. 10, 2013 to Non Final Office Action mailed Oct. 24, 2012", 15 pgs.
"U.S. Appl. No. 13/399,125, Response filed May 20, 2013 to Final Office Action mailed Mar. 20, 2013", 14 pgs.
"U.S. Appl. No. 13/412,105, Advisory Action mailed Feb. 24, 2014", 3 pgs.
"U.S. Appl. No. 13/412,105, Examiner Interview Summary mailed Feb. 6, 2014", 3 pgs.
"U.S. Appl. No. 13/412,105, Examiner Interview Summary mailed Oct. 11, 2013", 3 pgs.
"U.S. Appl. No. 13/412,105, Final Office Action mailed Dec. 13, 2013", 9 pgs.
"U.S. Appl. No. 13/412,105, Non Final Office Action mailed Jul. 15, 2013", 10 pgs.
"U.S. Appl. No. 13/412,105, Notice of Allowance mailed Aug. 18, 2014", 9 pgs.
"U.S. Appl. No. 13/412,105, Response filed Feb. 10, 2014 to Final Office Action mailed Dec. 13, 2013", 14 pgs.
"U.S. Appl. No. 13/412,105, Response filed Mar. 13, 2014 to Advisory Action mailed Feb. 24, 2014", 19 pgs.
"U.S. Appl. No. 13/412,105, Response filed May 6, 2013 to Restriction Requirement mailed Apr. 5, 2013", 9 pgs.
"U.S. Appl. No. 13/412,105, Response filed Oct. 14, 2013 mailed Jul. 15, 2013", 13 pgs.
"U.S. Appl. No. 13/412,105, Restriction Requirement mailed Apr. 5, 2013", 9 pgs.
"U.S. Appl. No. 13/412,116, Corrected Notice of Allowance mailed Jun. 2, 2014", 2 pgs.
"U.S. Appl. No. 13/412,116, Examiner Interview Summary mailed Dec. 13, 2013", 3 pgs.
"U.S. Appl. No. 13/412,116, Non Final Office Action mailed Sep. 11, 2013", 9 pgs.
"U.S. Appl. No. 13/412,116, Notice of Allowance mailed Feb. 19, 2014", 9 pgs.
"U.S. Appl. No. 13/412,116, Response filed Jul. 3, 2013 to Restriction Requirement mailed Jun. 19, 2013", 1 pg.
"U.S. Appl. No. 13/412,116, Response filed Dec. 11, 2013 to Non Final Office Action mailed Sep. 11, 2013", 11 pgs.

(56) References Cited

OTHER PUBLICATIONS

"U.S. Appl. No. 13/412,116, Restriction Requirement mailed Jun. 19, 2013", 9 pgs.
"U.S. Appl. No. 13/412,127, Examiner Interview Summary mailed Nov. 5, 2013", 3 pgs.
"U.S. Appl. No. 13/412,127, Non Final Office Action mailed Aug. 7, 2013", 15 pgs.
"U.S. Appl. No. 13/412,127, Notice of Allowance mailed Dec. 24, 2013", 10 pgs.
"U.S. Appl. No. 13/412,127, Response filed May 23, 2013 to Restriction Requirement mailed Apr. 24, 2013", 2 pgs.
"U.S. Appl. No. 13/412,127, Response filed Nov. 5, 2013 to Non Final Office Action mailed Aug. 7, 2013", 16 pgs.
"U.S. Appl. No. 13/412,127, Restriction Requirement mailed Apr. 24, 2013", 10 pgs.
"U.S. Appl. No. 13/587,374, Final Office Action mailed Nov. 6, 2013", 9 pgs.
"U.S. Appl. No. 13/587,374, Non Final Office Action mailed Jul. 17, 2013", 8 pgs.
"U.S. Appl. No. 13/587,374, Notice of Allowance mailed Feb. 28, 2014", 5 pgs.
"U.S. Appl. No. 13/587,374, Preliminary Amendment filed Jun. 21, 2013", 9 pgs.
"U.S. Appl. No. 13/587,374, Response filed Jan. 24, 2014 to Final Office Action mailed Nov. 6, 2013", 15 pgs.
"U.S. Appl. No. 13/587,374, Response filed Oct. 14, 2013 to Non Final Office Action mailed Jul. 17, 2013", 14 pgs.
"U.S. Appl. No. 13/609,389, 312 Amendment filed Sep. 15, 2014", 4 pgs.
"U.S. Appl. No. 13/609,389, Examiner Interview Summary mailed Feb. 4, 2014", 4 pgs.
"U.S. Appl. No. 13/609,389, Final Office Action mailed May 5, 2014", 14 pgs.
"U.S. Appl. No. 13/609,389, Non Final Office Action mailed Nov. 27, 2013", 12 pgs.
"U.S. Appl. No. 13/609,389, Notice of Allowance mailed Jul. 23, 2014", 5 pgs.
"U.S. Appl. No. 13/609,389, PTO Response to Rule 312 Communication mailed Oct. 16, 2014", 2 pgs.
"U.S. Appl. No. 13/609,389, Response filed Feb. 27, 2014 to Non Final Office Action mailed Nov. 27, 2013", 18 pgs.
"U.S. Appl. No. 13/609,389, Response filed Jul. 10, 2014 to Final Office Action mailed May 5, 2014", 12 pgs.
"U.S. Appl. No. 13/625,413, Final Office Action mailed Oct. 30, 2015", 8 pgs.
"U.S. Appl. No. 13/625,413, Non Final Office Action mailed Jun. 8, 2015", 11 pgs.
"U.S. Appl. No. 13/625,413, Notice of Allowance mailed Apr. 1, 2016", 8 pgs.
"U.S. Appl. No. 13/625,413, Notice of Allowance mailed Dec. 11, 2015", 9 pgs.
"U.S. Appl. No. 13/625,413, Response filed May 11, 2015 to Restriction Requirement mailed Mar. 10, 2015", 1 pg.
"U.S. Appl. No. 13/625,413, Response filed Sep. 8, 2015 to Non Final Office Action mailed Jun. 8, 2015", 16 pgs.
"U.S. Appl. No. 13/625,413, Response filed Dec. 1, 2015 to Final Office Action mailed Oct. 30, 2015", 9 pgs.
"U.S. Appl. No. 13/625,413, Restriction Requirement mailed Mar. 10, 2015", 7 pgs.
"U.S. Appl. No. 13/645,964, Advisory Action mailed Feb. 4, 2016", 2 pgs.
"U.S. Appl. No. 13/645,964, Final Office Action mailed Oct. 6, 2015", 17 pgs.
"U.S. Appl. No. 13/645,964, Non Final Office Action mailed Mar. 15, 2016", 15 pgs.
"U.S. Appl. No. 13/645,964, Non Final Office Action mailed Mar. 17, 2015", 15 pgs.
"U.S. Appl. No. 13/645,964, Notice of Allowance mailed Jul. 21, 2016", 9 pgs.
"U.S. Appl. No. 13/645,964, Response filed Jun. 13, 2016 to Non Final Office Action mailed Mar. 15, 2016", 11 pgs.
"U.S. Appl. No. 13/645,964, Response filed Jul. 17, 2015 to Non Final Office Action mailed Mar. 17, 2015", 17 pgs.
"U.S. Appl. No. 13/645,964, Response filed Dec. 4, 2015 to Final Office Action mailed Oct. 6, 2015", 14 pgs.
"U.S. Appl. No. 13/656,821, Notice of Allowance mailed Jun. 18, 2015", 11 pgs.
"U.S. Appl. No. 13/656,821, Response filed May 11, 2015 to Restriction Requirement mailed Mar. 10, 2015", 1 pg.
"U.S. Appl. No. 13/656,821, Restriction Requirement mailed Mar. 10, 2015", 6 pgs.
"U.S. Appl. No. 13/720,631, Final Office Action mailed Jun. 25, 2014", 10 pgs.
"U.S. Appl. No. 13/720,631, Non Final Office Action mailed Mar. 6, 2014", 7 pgs.
"U.S. Appl. No. 13/720,631, Notice of Allowance mailed Jul. 25, 2014", 5 pgs.
"U.S. Appl. No. 13/720,631, Response filed Jun. 6, 2014 to Non Final Office Action mailed Mar. 6, 2014", 11 pgs.
"U.S. Appl. No. 13/720,631, Response filed Jul. 14, 2014 to Final Office Action mailed Jun. 25, 2014", 6 pgs.
"U.S. Appl. No. 13/720,631, Supplemental Notice of Allowance mailed Sep. 8, 2014", 2 pgs.
"U.S. Appl. No. 13/720,648, Final Office Action mailed Nov. 16, 2015", 7 pgs.
"U.S. Appl. No. 13/720,648, Non Final Office Action mailed Jun. 10, 2015", 11 pgs.
"U.S. Appl. No. 13/720,648, Notice of Allowance mailed Feb. 5, 2016", 11 pgs.
"U.S. Appl. No. 13/720,648, Response filed Jan. 13, 2016 to Final Office Action mailed Nov. 16, 2015", 9 pgs.
"U.S. Appl. No. 13/720,648, Response filed May 11, 2015 to Restriction Requirement mailed Mar. 10, 2015", 8 pgs.
"U.S. Appl. No. 13/720,648, Response filed Oct. 9, 2015 to Non Final Office Action mailed Jun. 10, 2015", 12 pgs.
"U.S. Appl. No. 13/720,648, Restriction Requirement mailed Mar. 10, 2015", 8 pgs.
"U.S. Appl. No. 13/721,970, Notice of Allowance mailed Aug. 12, 2013", 13 pgs.
"U.S. Appl. No. 13/721,970, Preliminary Amendment filed Mar. 15, 2013", 13 pgs.
"U.S. Appl. No. 13/721,970, Response filed May 8, 2013 to Restriction Requirement mailed Apr. 11, 2013", 1 pgs.
"U.S. Appl. No. 13/721,970, Restriction Requirement mailed Apr. 11, 2013", 6 pgs.
"U.S. Appl. No. 13/751,846, Final Office Action mailed Nov. 17, 2015", 9 pgs.
"U.S. Appl. No. 13/751,846, Non Final Office Action mailed Jun. 15, 2015", 10 pgs.
"U.S. Appl. No. 13/751,846, Notice of Allowance mailed Mar. 16, 2016", 11 pgs.
"U.S. Appl. No. 13/751,846, Notice of Allowance mailed Jul. 6, 2016", 9 pgs.
"U.S. Appl. No. 13/751,846, Response filed Feb. 5, 2016 to Final Office Action mailed Nov. 17, 2015", 14 pgs.
"U.S. Appl. No. 13/751,846, Response filed May 11, 2015 to Restriction Requirement mailed Mar. 10, 2015", 15 pgs.
"U.S. Appl. No. 13/751,846, Response filed Oct. 9, 2015 to Non Final Office Action mailed Jun. 15, 2015", 20 pgs.
"U.S. Appl. No. 13/751,846, Restriction Requirement mailed Mar. 10, 2015", 7 pgs.
"U.S. Appl. No. 13/757,003, Non Final Office Action mailed Jun. 25, 2015", 8 pgs.
"U.S. Appl. No. 13/757,003, Notice of Allowance mailed Feb. 8, 2016", 10 pgs.
"U.S. Appl. No. 13/757,003, Response filed May 12, 2015 to Restriction Requirement mailed Mar. 12, 2015", 9 pgs.
"U.S. Appl. No. 13/757,003, Response filed Oct. 26, 2015 to Non Final Office Action mailed Jul. 25, 2015", 8 pgs.
"U.S. Appl. No. 13/757,003, Restriction Requirement mailed Mar. 12, 2015", 6 pgs.

(56) References Cited

OTHER PUBLICATIONS

"U.S. Appl. No. 13/757,019, Non Final Office Action mailed Jun. 25, 2015", 11 pgs.
"U.S. Appl. No. 13/757,019, Notice of Allowance mailed Dec. 10, 2015", 10 pgs.
"U.S. Appl. No. 13/757,019, Response filed May 11, 2015 to Restriction Requirement mailed Mar. 11, 2015", 9 pgs.
"U.S. Appl. No. 13/757,019, Response filed Oct. 26, 2015 to Non Final Office Action mailed Jun. 25, 2015", 9 pgs.
"U.S. Appl. No. 13/757,019, Restriction Requirement mailed Mar. 11, 2015", 10 pgs.
"U.S. Appl. No. 13/767,401, Non Final Office Action mailed Aug. 26, 2015", 9 pgs.
"U.S. Appl. No. 13/767,401, Notice of Allowance mailed Apr. 8, 2016", 9 pgs.
"U.S. Appl. No. 13/767,401, Notice of Allowance mailed Dec. 30, 2015", 9 pgs.
"U.S. Appl. No. 13/767,401, Response filed May 18, 2015 to Restriction Requirement mailed Mar. 17, 2015", 15 pgs.
"U.S. Appl. No. 13/767,401, Response filed Nov. 6, 2015 to Non Final Office Action mailed Aug. 26, 2015", 12 pgs.
"U.S. Appl. No. 13/767,401, Restriction Requirement mailed Mar. 17, 2015", 8 pgs.
"U.S. Appl. No. 13/790,982, Examiner Interview Summary mailed Jun. 9, 2015", 3 pgs.
"U.S. Appl. No. 13/790,982, Non Final Office Action mailed Sep. 16, 2015", 11 pgs.
"U.S. Appl. No. 13/790,982, Notice of Allowance mailed Feb. 24, 2016", 10 pgs.
"U.S. Appl. No. 13/790,982, Response filed Jun. 2, 2015 to Restriction Requirement mailed Apr. 2, 2015", 11 pgs.
"U.S. Appl. No. 13/790,982, Response filed Dec. 16, 2015 to Non Final Office Action mailed Sep. 16, 2015", 10 pgs.
"U.S. Appl. No. 13/790,982, Restriction Requirement mailed Apr. 2, 2015", 10 pgs.
"U.S. Appl. No. 13/790,997, Examiner Interview Summary mailed Jun. 8, 2015", 3 pgs.
"U.S. Appl. No. 13/790,997, Non Final Office Action mailed Sep. 21, 2015", 8 pgs.
"U.S. Appl. No. 13/790,997, Notice of Allowance mailed Mar. 2, 2016", 9 pgs.
"U.S. Appl. No. 13/790,997, Response filed Jun. 2, 2015 to Restriction Requirement mailed Apr. 2, 2015", 12 pgs.
"U.S. Appl. No. 13/790,997, Response filed Dec. 18, 2015 to Non Final Office Action mailed Sep. 21, 2015", 9 pgs.
"U.S. Appl. No. 13/790,997, Restriction Requirement mailed Apr. 2, 2015", 8 pgs.
"U.S. Appl. No. 13/791,014, Final Office Action mailed Jan. 8, 2016", 11 pgs.
"U.S. Appl. No. 13/791,014, Non Final Office Action mailed Aug. 14, 2015", 9 pgs.
"U.S. Appl. No. 13/791,014, Notice of Allowability mailed Jul. 27, 2017", 2 pgs.
"U.S. Appl. No. 13/791,014, Notice of Allowance mailed Jan. 10, 2017", 15 pgs.
"U.S. Appl. No. 13/791,014, Notice of Allowance mailed Apr. 27, 2017", 8 pgs.
"U.S. Appl. No. 13/791,014, Response filed Jun. 6, 2016 to Final Office Action mailed Jan. 8, 2016", 13 pgs.
"U.S. Appl. No. 13/791,014, Response filed Aug. 3, 2015 to Restriction Requirement mailed May 1, 2015", 9 pgs.
"U.S. Appl. No. 13/791,014, Response filed Nov. 10, 2015 to Non Final Office Action mailed Aug. 14, 2015", 13 pgs.
"U.S. Appl. No. 13/791,014, Restriction Requirement mailed May 1, 2015", 6 pgs.
"U.S. Appl. No. 13/833,567, Advisory Action mailed Apr. 28, 2016", 3 pgs.
"U.S. Appl. No. 13/833,567, Final Office Action mailed Mar. 9, 2016", 9 pgs.
"U.S. Appl. No. 13/833,567, Non Final Office Action mailed May 27, 2016", 9 pgs.
"U.S. Appl. No. 13/833,567, Non Final Office Action mailed Oct. 23, 2015", 10 pgs.
"U.S. Appl. No. 13/833,567, Notice of Allowance mailed Sep. 27, 2016", 9 pgs.
"U.S. Appl. No. 13/833,567, Response filed Jan. 22, 2016 to Non Final Office Action mailed Oct. 23, 2015", 11 pgs.
"U.S. Appl. No. 13/833,567, Response filed Apr. 20, 2016 to Final Office Action mailed Mar. 9, 2016", 10 pgs.
"U.S. Appl. No. 13/833,567, Response filed Jun. 25, 2015 to Restriction Requirement mailed Apr. 3, 2015", 10 pgs.
"U.S. Appl. No. 13/833,567, Response filed Aug. 4, 2016 to Non Final Office Action mailed May 27, 2016", 11 pgs.
"U.S. Appl. No. 13/833,567, Restriction Requirement mailed Apr. 3, 2015", 6 pgs.
"U.S. Appl. No. 13/838,755, Final Office Action mailed Feb. 22, 2016", 9 pgs.
"U.S. Appl. No. 13/838,755, Non Final Office Action mailed Sep. 17, 2015", 11 pgs.
"U.S. Appl. No. 13/838,755, Notice of Allowance mailed Apr. 27, 2016", 7 pgs.
"U.S. Appl. No. 13/838,755, Notice of Allowance mailed Aug. 3, 2016", 8 pgs.
"U.S. Appl. No. 13/838,755, Response filed Apr. 15, 2016 to Final Office Action mailed Feb. 22, 2016", 11 pgs.
"U.S. Appl. No. 13/838,755, Response filed Jun. 8, 2015 to Restriction Requirement mailed Apr. 6, 2015", 1 pg.
"U.S. Appl. No. 13/838,755, Response filed Dec. 1, 2015 to Non Final Office Action mailed Sep. 17, 2015", 13 pgs.
"U.S. Appl. No. 13/838,755, Restriction Requirement mailed Apr. 6, 2015", 6 pgs.
"U.S. Appl. No. 13/889,851, Non Final Office Action mailed Apr. 6, 2015", 10 pgs.
"U.S. Appl. No. 13/889,851, Notice of Allowance mailed Aug. 12, 2015", 8 pgs.
"U.S. Appl. No. 13/889,851, Response filed Feb. 26, 2015 to Restriction Requirement mailed Jan. 21, 2015", 12 pgs.
"U.S. Appl. No. 13/889,851, Response filed Jul. 6, 2015 to Non Final Office Action mailed Apr. 6, 2015", 14 pgs.
"U.S. Appl. No. 13/889,851, Restriction Requirement mailed Jan. 21, 2015", 6 pgs.
"U.S. Appl. No. 13/889,851, Supplemental Amendment and Response filed Jul. 6, 2015 to Non Final Office Action mailed Apr. 6, 2015", 8 pgs.
"U.S. Appl. No. 13/959,145, Examiner Interview Summary mailed Sep. 16, 2015", 3 pgs.
"U.S. Appl. No. 13/959,145, Final Office Action mailed Jan. 29, 2016", 16 pgs.
"U.S. Appl. No. 13/959,145, Final Office Action mailed Feb. 5, 2015", 22 pgs.
"U.S. Appl. No. 13/959,145, Non Final Office Action mailed Jul. 31, 2015", 21 pgs.
"U.S. Appl. No. 13/959,145, Non Final Office Action mailed Sep. 15, 2014", 20 pgs.
"U.S. Appl. No. 13/959,145, Notice of Allowability mailed Jun. 14, 2016", 2 pgs.
"U.S. Appl. No. 13/959,145, Notice of Allowance mailed Apr. 13, 2016", 5 pgs.
"U.S. Appl. No. 13/959,145, Response filed Mar. 28, 2016 to Final Office Action mailed Jan. 29, 2016", 10 pgs.
"U.S. Appl. No. 13/959,145, Response filed Jul. 6, 2015 to Final Office Action mailed Feb. 5, 2015", 18 pgs.
"U.S. Appl. No. 13/959,145, Response filed Oct. 30, 2015 to Non Final Office Action mailed Jul. 31, 2015", 14 pgs.
"U.S. Appl. No. 13/959,145, Response filed Dec. 15, 2014 to Non Final Office Action mailed Sep. 15, 2014", 21 pgs.
"U.S. Appl. No. 14/055,172, Final Office Action mailed Dec. 22, 2016", 8 pgs.
"U.S. Appl. No. 14/055,172, Non Final Office Action mailed Jul. 14, 2016", 12 pgs.
"U.S. Appl. No. 14/055,172, Notice of Allowance mailed Mar. 29, 2017", 10 pgs.

(56) References Cited

OTHER PUBLICATIONS

"U.S. Appl. No. 14/055,172, Response filed Feb. 22, 2017 to Final Office Action mailed Dec. 22, 2016", 11 pgs.
"U.S. Appl. No. 14/055,172, Response filed May 4, 2016 to Restriction Requirement mailed Mar. 4, 2016", 8 pgs.
"U.S. Appl. No. 14/055,172, Response filed Nov. 14, 2016 to Non Final Office Action mailed Jul. 14, 2016", 19 pgs.
"U.S. Appl. No. 14/055,172, Restriction Requirement mailed Mar. 4, 2016", 6 pgs.
"U.S. Appl. No. 14/055,191, Non Final Office Action mailed May 16, 2016", 8 pgs.
"U.S. Appl. No. 14/055,191, Notice of Allowability mailed Sep. 8, 2016", 7 pgs.
"U.S. Appl. No. 14/055,191, Notice of Allowance mailed Aug. 31, 2016", 13 pgs.
"U.S. Appl. No. 14/055,191, Response filed Apr. 29, 2016 to Restriction Requirement mailed Mar. 7, 2016", 8 pgs.
"U.S. Appl. No. 14/055,191, Response filed Aug. 3, 2016 to Non Final Office Action mailed May 16, 2016", 11 pgs.
"U.S. Appl. No. 14/055,191, Restriction Requirement mailed Mar. 7, 2016", 6 pgs.
"U.S. Appl. No. 14/071,295, Non Final Office Action mailed Aug. 15, 2014", 6 pgs.
"U.S. Appl. No. 14/071,295, Notice of Allowance mailed Dec. 10, 2014", 8 pgs.
"U.S. Appl. No. 14/071,295, Response filed Nov. 17, 2014 to Non Final Office Action mailed Aug. 15, 2014", 14 pgs.
"U.S. Appl. No. 14/071,295, Supplemental Notice of Allowability mailed Jan. 26, 2015", 2 pgs.
"U.S. Appl. No. 14/094,311, Corrected Notice of Allowance mailed Mar. 28, 2017", 5 pgs.
"U.S. Appl. No. 14/094,311, Notice of Allowance mailed Aug. 16, 2016", 12 pgs.
"U.S. Appl. No. 14/094,311, Notice of Allowance mailed Dec. 27, 2016", 8 pgs.
"U.S. Appl. No. 14/094,311, Response filed Jul. 26, 2016 to Restriction Requirement mailed Jun. 22, 2016", 10 pgs.
"U.S. Appl. No. 14/094,311, Restriction Requirement mailed Jun. 22, 2016", 6 pgs.
"U.S. Appl. No. 14/095,614, Non Final Office Action mailed Jan. 19, 2017", 9 pgs.
"U.S. Appl. No. 14/095,614, Notice of Allowance mailed May 8, 2017", 8 pgs.
"U.S. Appl. No. 14/095,614, Notice of Allowance mailed Nov. 6, 2017", 9 pgs.
"U.S. Appl. No. 14/095,614, Preliminary Amendment filed Apr. 15, 2014", 17 pgs.
"U.S. Appl. No. 14/095,614, Response filed Mar. 2, 2017 to Non Final Office Action mailed Jan. 19, 2017", 14 pgs.
"U.S. Appl. No. 14/095,614, Response filed Sep. 12, 2016 to Restriction Requirement mailed Jul. 11, 2016", 11 pgs.
"U.S. Appl. No. 14/095,614, Restriction Requirement mailed Jul. 11, 2016", 8 pgs.
"U.S. Appl. No. 14/095,639, Non Final Office Action mailed Jan. 18, 2017", 10 pgs.
"U.S. Appl. No. 14/095,639, Notice of Allowance mailed Apr. 13, 2017", 9 pgs.
"U.S. Appl. No. 14/095,639, Notice of Allowance mailed Oct. 30, 2017", 9 pgs.
"U.S. Appl. No. 14/095,639, Response filed Mar. 2, 2017 to Non Final Office Action mailed Jan. 18, 2017", 9 pgs.
"U.S. Appl. No. 14/095,639, Response filed Sep. 12, 2016 to Restriction Requirement mailed Jul. 19, 2016", 7 pgs.
"U.S. Appl. No. 14/095,639, Restriction Requirement mailed Jul. 19, 2016", 8 pgs.
"U.S. Appl. No. 14/107,350, Notice of Allowance mailed Feb. 26, 2016", 11 pgs.
"U.S. Appl. No. 14/107,350, Notice of Allowance mailed Jul. 27, 2016", 7 pgs.
"U.S. Appl. No. 14/107,350, Preliminary Amendment filed Feb. 28, 2014", 4 pgs.
"U.S. Appl. No. 14/159,094, Examiner Interview Summary mailed Nov. 29, 2016", 1 pg.
"U.S. Appl. No. 14/159,094, Non Final Office Action mailed Jun. 29, 2016", 15 pgs.
"U.S. Appl. No. 14/159,094, Notice of Allowance mailed Nov. 29, 2016", Examiner Interview Summary from Nov. 29, 2016 included, 11 pgs.
"U.S. Appl. No. 14/159,094, Response filed Jun. 3, 2016 to Restriction Requirement mailed Apr. 20, 2016", 9 pgs.
"U.S. Appl. No. 14/159,094, Response filed Sep. 19, 2016 to Non Final Office Action mailed Jun. 29, 2016", 13 pgs.
"U.S. Appl. No. 14/159,094, Restriction Requirement mailed Apr. 20, 2016", 6 pgs.
"U.S. Appl. No. 14/182,038, Advisory Action mailed Mar. 1, 2017", 3 pgs.
"U.S. Appl. No. 14/182,038, Final Office Action mailed Dec. 19, 2016", 8 pgs.
"U.S. Appl. No. 14/182,038, Non Final Office Action mailed Jul. 19, 2016", 10 pgs.
"U.S. Appl. No. 14/182,038, Notice of Allowance mailed May 24, 2017", 9 pgs.
"U.S. Appl. No. 14/182,038, Response filed Feb. 20, 2017 to Final Office Action mailed Dec. 19, 2016", 11 pgs.
"U.S. Appl. No. 14/182,038, Response filed Jun. 27, 2016 to Restriction Requirement mailed Apr. 26, 2016", 8 pgs.
"U.S. Appl. No. 14/182,038, Response filed Oct. 19, 2016 to Non Final Office Action mailed Jul. 19, 2016", 15 pgs.
"U.S. Appl. No. 14/182,038, Restriction Requirement mailed Apr. 26, 2016", 7 pgs.
"U.S. Appl. No. 14/182,046, Corrected Notice of Allowance mailed Jan. 20, 2017", 6 pgs.
"U.S. Appl. No. 14/182,046, Non Final Office Action mailed Jul. 15, 2016", 9 pgs.
"U.S. Appl. No. 14/182,046, Notice of Allowance mailed Dec. 8, 2016", 7 pgs.
"U.S. Appl. No. 14/182,046, Response filed Jun. 27, 2016 to Restriction Requirement mailed Apr. 26, 2016", 7 pgs.
"U.S. Appl. No. 14/182,046, Response filed Oct. 17, 2016 to Non Final Office Action mailed Jul. 15, 2016", 11 pgs.
"U.S. Appl. No. 14/182,046, Restriction Requirement mailed Apr. 26, 2016", 6 pgs.
"U.S. Appl. No. 14/211,977, Notice of Allowance mailed Jul. 12, 2016", 9 pgs.
"U.S. Appl. No. 14/211,977, Preliminary Amendment filed Mar. 2, 2016", 7 pgs.
"U.S. Appl. No. 14/211,977, Response filed Apr. 29, 2016 to Restriction Requirement mailed Mar. 11, 2016", 8 pgs.
"U.S. Appl. No. 14/211,977, Restriction Requirement mailed Mar. 11, 2016", 6 pgs.
"U.S. Appl. No. 14/215,550, Corrected Notice of Allowance mailed Jul. 27, 2017", 2 pgs.
"U.S. Appl. No. 14/215,550, Examiner Interview Summary mailed Mar. 9, 2017", 3 pgs.
"U.S. Appl. No. 14/215,550, Final Office Action mailed Feb. 1, 2017", 11 pgs.
"U.S. Appl. No. 14/215,550, Non Final Office Action mailed Jul. 19, 2016", 12 pgs.
"U.S. Appl. No. 14/215,550, Notice of Allowance mailed Jun. 21, 2017", 8 pgs.
"U.S. Appl. No. 14/215,550, Response filed May 1, 2017 to Final Office Action mailed Feb. 1, 2017", 10 pgs.
"U.S. Appl. No. 14/215,550, Response filed Jun. 22, 2016 to Restriction Requirement mailed Apr. 28, 2016", 7 pgs.
"U.S. Appl. No. 14/215,550, Response filed Dec. 5, 16 to Non Final Office Action mailed Jul. 19, 2016", 13 pgs.
"U.S. Appl. No. 14/215,550, Restriction Requirement mailed Apr. 28, 2016", 6 pgs.
"U.S. Appl. No. 14/275,548, Examiner Interview Summary mailed May 25, 2016", 3 pgs.
"U.S. Appl. No. 14/275,548, Non Final Office Action mailed Feb. 19, 2016", 14 pgs.

(56) References Cited

OTHER PUBLICATIONS

"U.S. Appl. No. 14/275,548, Notice of Allowance mailed Jul. 27, 2016", 7 pgs.
"U.S. Appl. No. 14/275,548, Response filed May 19, 2016 to Non Final Office Action mailed Feb. 19, 2016", 19 pgs.
"U.S. Appl. No. 14/324,688, Corrected Notice of Allowance mailed Sep. 22, 2016", 2 pgs.
"U.S. Appl. No. 14/324,688, Non Final Office Action mailed Jan. 8, 2016", 18 pgs.
"U.S. Appl. No. 14/324,688, Notice of Allowance mailed Jun. 9, 2016", 7 pgs.
"U.S. Appl. No. 14/324,688, Response filed Apr. 8, 2016 to Non Final Office Action mailed Jan. 8, 2016", 15 pgs.
"U.S. Appl. No. 14/456,286, Advisory Action mailed Jun. 21, 2016", 3 pgs.
"U.S. Appl. No. 14/456,286, Final Office Action mailed May 27, 2016", 15 pgs.
"U.S. Appl. No. 14/456,286, Non Final Office Action mailed Oct. 17, 2016", 17 pgs.
"U.S. Appl. No. 14/456,286, Non Final Office Action mailed Dec. 30, 2015", 16 pgs.
"U.S. Appl. No. 14/456,286, Notice of Allowance mailed Feb. 15, 2017", 9 pgs.
"U.S. Appl. No. 14/456,286, Response filed Mar. 30, 2016 to Non Final Office Action mailed Dec. 30, 2015", 15 pgs.
"U.S. Appl. No. 14/456,286, Response filed Jun. 13, 2016 to Final Office Action mailed May 27, 2016", 10 pgs.
"U.S. Appl. No. 14/456,286, Response filed Nov. 16, 2016 to Non Final Office Action mailed Oct. 17, 2016", 9 pgs.
"U.S. Appl. No. 14/456,286, Response filed Dec. 11, 2015 to Restriction Requirement mailed Oct. 29, 2015", 6 pgs.
"U.S. Appl. No. 14/456,286, Restriction Requirement mailed Oct. 29, 2015", 9 pgs.
"U.S. Appl. No. 14/492,590, Notice of Allowance mailed Oct. 5, 2016", 10 pgs.
"U.S. Appl. No. 14/492,590, Response filed Sep. 15, 2016 to Restriction Requirement mailed Jul. 25, 2015", 7 pgs.
"U.S. Appl. No. 14/492,590, Restriction Requirement mailed Jul. 25, 2016", 6 pgs.
"U.S. Appl. No. 14/492,590, Supplemental Response filed Sep. 26, 2016 to Restriction Requirement mailed Jul. 25, 2016", 10 pgs.
"U.S. Appl. No. 14/514,453, Final Office Action mailed Mar. 17, 2016", 17 pgs.
"U.S. Appl. No. 14/514,453, Non Final Office Action mailed Sep. 24, 2015", 11 pgs.
"U.S. Appl. No. 14/514,453, Response filed Dec. 16, 2015 to Non Final Office Action mailed Sep. 24, 2015", 14 pgs.
"U.S. Appl. No. 14/532,333, Response filed Apr. 7, 2016 to Restriction Requirement mailed Feb. 8, 2016", 10 pgs.
"U.S. Appl. No. 14/532,333, Restriction Requirement mailed Feb. 8, 2016", 6 pgs.
"U.S. Appl. No. 14/589,101, Advisory Action mailed Feb. 21, 2017", 5 pgs.
"U.S. Appl. No. 14/589,101, Advisory Action mailed May 22, 2018", 3 pgs.
"U.S. Appl. No. 14/589,101, Examiner Interview Summary mailed Jan. 30, 2017", 3 pgs.
"U.S. Appl. No. 14/589,101, Final Office Action mailed Feb. 22, 2018", 15 pgs.
"U.S. Appl. No. 14/589,101, Final Office Action mailed Oct. 2, 2015", 10 pgs.
"U.S. Appl. No. 14/589,101, Final Office Action mailed Nov. 16, 2016", 12 pgs.
"U.S. Appl. No. 14/589,101, Non Final Office Action mailed Feb. 12, 2015", 10 pgs.
"U.S. Appl. No. 14/589,101, Non Final Office Action mailed May 5, 2016", 14 pgs.
"U.S. Appl. No. 14/589,101, Non Final Office Action mailed Sep. 14, 2017", 13 pgs.
"U.S. Appl. No. 14/589,101, Response filed Jan. 23, 2017 to Final Office Action mailed Nov. 16, 2016", 9 pgs.
"U.S. Appl. No. 14/589,101, Response filed Apr. 10, 2018 to Final Office Action mailed Feb. 22, 2018", 10 pgs.
"U.S. Appl. No. 14/589, 101, Response filed Jun. 12, 2015 mailed Feb. 12, 2015", 11 pgs.
"U.S. Appl. No. 14/589,101, Response filed Nov. 13, 2017 mailed Sep. 14, 2017", 10 pgs.
"U.S. Appl. No. 14/589,101, Response filed Dec. 29, 2015 to Final Office Action mailed Oct. 2, 2015", 15 pgs.
"U.S. Appl. No. 14/589,191, Response filed Aug. 5, 2016 to Non Final Office Action mailed May 5, 2016", 16 pgs.
"U.S. Appl. No. 14/594,285, Final Office Action mailed May 22, 2017", 12 pgs.
"U.S. Appl. No. 14/594,285, Non Final Office Action mailed Jan. 11, 2017", 15 pgs.
"U.S. Appl. No. 14/594,285, Notice of Allowance mailed Jun. 27, 2017", 10 pgs.
"U.S. Appl. No. 14/594,285, Response filed Apr. 11, 2017 to Non Final Office Action mailed Jan. 11, 2017", 12 pgs.
"U.S. Appl. No. 14/594,285, Response filed Jun. 14, 2017 to Final Office Action mailed May 22, 2017", 9 pgs.
"U.S. Appl. No. 14/594,285, Response filed Dec. 14, 2016 to Restriction Requirement mailed Nov. 7, 2016", 8 pgs.
"U.S. Appl. No. 14/594,285, Restriction Requirement mailed Nov. 7, 2016", 6 pgs.
"U.S. Appl. No. 14/599,909, Non Final Office Action mailed Jul. 27, 2017", 18 pgs.
"U.S. Appl. No. 14/599,909, Notice of Allowance mailed Feb. 13, 2018", 9 pgs.
"U.S. Appl. No. 14/599,909, Response filed Sep. 21, 2017 to Non Final Office Action mailed Jul. 27, 2017", 10 pgs.
"U.S. Appl. No. 14/635,055, Non Final Office Action mailed Aug. 28, 2017", 8 pgs.
"U.S. Appl. No. 14/635,055, Notice of Allowance mailed Feb. 28, 2018", 11 pgs.
"U.S. Appl. No. 14/635,055, Response filed Jun. 27, 2017 to Restriction Requirement mailed Apr. 27, 2017", 11 pgs.
"U.S. Appl. No. 14/635,055, Response filed Nov. 28, 2017 to Non Final Office Action mailed Aug. 28, 2017", 13 pgs.
"U.S. Appl. No. 14/635,055, Restriction Requirement mailed Apr. 27, 2017", 7 pgs.
"U.S. Appl. No. 14/697,140, Advisory Action mailed Aug. 11, 2017", 3 pgs.
"U.S. Appl. No. 14/697,140, Final Office Action mailed Jun. 30, 2017", 13 pgs.
"U.S. Appl. No. 14/697,140, Final Office Action mailed Sep. 23, 2016", 10 pgs.
"U.S. Appl. No. 14/697,140, Non Final Office Action mailed Jan. 10, 2017", 12 pgs.
"U.S. Appl. No. 14/697,140, Non Final Office Action mailed Apr. 8, 2016", 8 pgs.
"U.S. Appl. No. 14/697,140, Notice of Allowance mailed Sep. 5, 2017", 7 pgs.
"U.S. Appl. No. 14/697,140, Response filed Mar. 1, 2017 to Non Final Office Action mailed Jan. 10, 2017", 11 pgs.
"U.S. Appl. No. 14/697,140, Response filed Jun. 13, 2016 to Non Final Office Action mailed Apr. 8, 2016", 10 pgs.
"U.S. Appl. No. 14/697,140, Response filed Jul. 27, 2017 to Final Office Action mailed Jun. 30, 2017", 10 pgs.
"U.S. Appl. No. 14/697,140, Response filed Nov. 16, 2016 to Final Office Action mailed Sep. 23, 2016", 13 pgs.
"U.S. Appl. No. 14/794,309, Final Office Action mailed Mar. 20, 2017", 18 pgs.
"U.S. Appl. No. 14/794,309, Non Final Office Action mailed Jun. 20, 2017", 16 pgs.
"U.S. Appl. No. 14/794,309, Non Final Office Action mailed Nov. 22, 2016", 13 pgs.
"U.S. Appl. No. 14/794,309, Notice of Allowance mailed Sep. 18, 2017", 5 pgs.
"U.S. Appl. No. 14/794,309, Preliminary Amendment filed Sep. 22, 2015", 6 pgs.

(56) References Cited

OTHER PUBLICATIONS

"U.S. Appl. No. 14/794,309, Response filed Feb. 22, 2017 to Non Final Office Action mailed Nov. 22, 2016", 12 pgs.
"U.S. Appl. No. 14/794,309, Response filed May 22, 2017 to Final Office Action mailed Mar. 20, 2017", 13 pgs.
"U.S. Appl. No. 14/794,309, Response filed Aug. 17, 2017 to Non Final Office Action mailed Jun. 20, 2017", 12 pgs.
"U.S. Appl. No. 14/794,309, Supplemental Preliminary Amendment filed Mar. 3, 2016", 8 pgs.
"U.S. Appl. No. 14/854,308, Notice of Allowance mailed Mar. 16, 2018", 11 pgs.
"U.S. Appl. No. 14/854,308, Response filed Dec. 20, 2017 to Restriction Requirement mailed Oct. 20, 2017", 8 pgs.
"U.S. Appl. No. 14/854,308, Restriction Requirement mailed Oct. 20, 2017", 8 pgs.
"U.S. Appl. No. 14/854,308, Supplemental Preliminary Amendment Filed Aug. 31, 2017", 3 pgs.
"U.S. Appl. No. 14/876,167, Final Office Action mailed Jul. 31, 2018", 8 pgs.
"U.S. Appl. No. 14/876,167, Non Final Office Action mailed Mar. 13, 2018", 8 pgs.
"U.S. Appl. No. 14/876,167, Notice of Allowance mailed Dec. 10, 2018", 8 pgs.
"U.S. Appl. No. 14/876,167, Preliminary Amendment filed Oct. 27, 2015", 8 pgs.
"U.S. Appl. No. 14/876,167, Response filed Jan. 9, 2018 to Restriction Requirement mailed Nov. 22, 2017", 6 pgs.
"U.S. Appl. No. 14/876,167, Response filed Jun. 6, 2018 to Non Final Office Action mailed Mar. 13, 2018", 9 pgs.
"U.S. Appl. No. 14/876,167, Response filed Sep. 28, 2018 to Final Office Action mailed Jul. 31, 2018", 10 pgs.
"U.S. Appl. No. 14/876,167, Restriction Requirement mailed Nov. 22, 2017", 9 pgs.
"U.S. Appl. No. 14/936,831, Advisory Action mailed Jan. 29, 2019", 3 pgs.
"U.S. Appl. No. 14/936,831, Final Office Action mailed Nov. 20, 2018", 8 pgs.
"U.S. Appl. No. 14/936,831, Non Final Office Action mailed May 16, 2018", 11 pgs.
"U.S. Appl. No. 14/936,831, Notice of Allowance mailed Jul. 3, 2019", 8 pgs.
"U.S. Appl. No. 14/936,831, Notice of Non-Compliant Amendment mailed Mar. 14, 2018", 2 pgs.
"U.S. Appl. No. 14/936,831, Preliminary Amendment filed Nov. 11, 2015", 6 pgs.
"U.S. Appl. No. 14/936,831, Response filed Jan. 10, 2018 to Restriction Requirement mailed Nov. 22, 2017", 6 pgs.
"U.S. Appl. No. 14/936,831, Response filed Jan. 21, 2019 to Final Office Action mailed Nov. 20, 2018", 9 pgs.
"U.S. Appl. No. 14/936,831, Response filed Mar. 26, 2018 to Notice of Non-Compliant Amendment mailed Mar. 14, 2018", 6 pgs.
"U.S. Appl. No. 14/936,831, Response filed Aug. 16, 2018 to Non Final Office Action mailed May 16, 2018", 9 pgs.
"U.S. Appl. No. 14/936,831, Restriction Requirement mailed Nov. 22, 2017", 8 pgs.
"U.S. Appl. No. 14/956,724, Examiner Interview Summary mailed Jun. 20, 2017", 3 pgs.
"U.S. Appl. No. 14/956,724, Non Final Office Action mailed Mar. 31, 2017", 17 pgs.
"U.S. Appl. No. 14/956,724, Notice of Allowance mailed Aug. 23, 2017", 9 pgs.
"U.S. Appl. No. 14/956,724, Preliminary Amendment filed Dec. 7, 2015", 8 pgs.
"U.S. Appl. No. 14/956,724, Response filed Jun. 16, 2017 to Non Final Office Action mailed Mar. 31, 2017", 12 pgs.
"U.S. Appl. No. 14/956,724, Supplemental Preliminary Amendment filed Feb. 11, 2016", 7 pgs.
"U.S. Appl. No. 14/956,724, Supplemental Preliminary Amendment filed Oct. 3, 2016", 8 pgs.
"U.S. Appl. No. 14/983,108, Final Office Action mailed Aug. 30, 2018", 9 pgs.
"U.S. Appl. No. 14/983,108, Non Final Office Action mailed Apr. 10, 2018", 7 pgs.
"U.S. Appl. No. 14/983,108, Non Final Office Action mailed Nov. 5, 2018", 8 pgs.
"U.S. Appl. No. 14/983,108, Notice of Allowance mailed Mar. 8, 2019", 8 pgs.
"U.S. Appl. No. 14/983,108, Preliminary Amendment filed Dec. 30, 2015", 7 pgs.
"U.S. Appl. No. 14/983,108, Response filed Jan. 24, 2018 to Restriction Requirement mailed Dec. 4, 2017", 6 pgs.
"U.S. Appl. No. 14/983,108, Response filed Feb. 4, 2019 to Non Final Office Action mailed Nov. 5, 2018", 8 pgs.
"U.S. Appl. No. 14/983,108, Response filed Jun. 13, 2018 to Non Final Office Action mailed Apr. 10, 2018", 10 pgs.
"U.S. Appl. No. 14/983,108, Response filed Oct. 22, 2018 to Final Office Action mailed Aug. 30, 2018", 9 pgs.
"U.S. Appl. No. 14/983,108, Restriction Requirement mailed Dec. 4, 2017", 7 pgs.
"U.S. Appl. No. 14/983,747, Non Final Office Action mailed Apr. 9, 2018", 13 pgs.
"U.S. Appl. No. 14/983,747, Notice of Allowance mailed Sep. 24, 2018", 14 pgs.
"U.S. Appl. No. 14/983,747, Preliminary Amendment filed Jan. 4, 2016", 5 pgs.
"U.S. Appl. No. 14/983,747, Response filed Jan. 24, 2018 to Restriction Requirement mailed Dec. 20, 2017", 5 pgs.
"U.S. Appl. No. 14/983,747, Response filed Jun. 13, 2018 to Non Final Office Action mailed Apr. 9, 2018", 9 pgs.
"U.S. Appl. No. 14/983,747, Restriction Requirement mailed Dec. 20, 2017", 7 pgs.
"U.S. Appl. No. 14/983,747, Supplemental Response to Restriction Requirement filed Jan. 24, 2018", 5 pgs.
"U.S. Appl. No. 15/060,007, Corrected Notice of Allowability mailed May 1, 2019", 2 pgs.
"U.S. Appl. No. 15/060,007, Final Office Action mailed Jan. 3, 2019", 9 pgs.
"U.S. Appl. No. 15/060,007, Non Final Office Action mailed Nov. 9, 2018", 17 pgs.
"U.S. Appl. No. 15/060,007, Notice of Allowance mailed Mar. 6, 2019", 5 pgs.
"U.S. Appl. No. 15/060,007, Preliminary Amendment filed Mar. 9, 2016", 9 pgs.
"U.S. Appl. No. 15/060,007, Response filed Feb. 15, 2019 to Final Office Action mailed Jan. 3, 2019", 9 pgs.
"U.S. Appl. No. 15/060,007, Response filed Nov. 26, 2018 to Non Final Office Action mailed Nov. 9, 2018", 10 pgs.
"U.S. Appl. No. 15/061,352, Corrected Notice of Allowance mailed Feb. 12, 2018", 2 pgs.
"U.S. Appl. No. 15/061,352, Non Final Office Action mailed Nov. 17, 2017", 6 pgs.
"U.S. Appl. No. 15/061,352, Notice of Allowance mailed Jan. 19, 2018", 10 pgs.
"U.S. Appl. No. 15/061,352, Preliminary Amendment filed Mar. 7, 2016", 8 pgs.
"U.S. Appl. No. 15/061,352, Response filed Dec. 12, 2017 to Non Final Office Action mailed Nov. 17, 2017", 9 pgs.
"U.S. Appl. No. 15/074,553, Corrected Notice of Allowance mailed Feb. 12, 2018", 2 pgs.
"U.S. Appl. No. 15/074,553, Non Final Office Action mailed Nov. 17, 2017", 6 pgs.
"U.S. Appl. No. 15/074,553, Notice of Allowance mailed Jan. 19, 2018", 10 pgs.
"U.S. Appl. No. 15/074,553, Preliminary Amendment filed Mar. 21, 2016", 8 pgs.
"U.S. Appl. No. 15/074,553, Response filed Dec. 12, 2017 to Non Final Office Action mailed Nov. 17, 2017", 8 pgs.
"U.S. Appl. No. 15/131,663, Non Final Office Action mailed Oct. 2, 2018", 7 pgs.
"U.S. Appl. No. 15/131,663, Notice of Allowance mailed Mar. 19, 2019", 8 pgs.

(56) References Cited

OTHER PUBLICATIONS

"U.S. Appl. No. 15/131,663, Preliminary Amendment filed Dec. 21, 2016", 6 pgs.
"U.S. Appl. No. 15/131,663, Response Filed Jan. 2, 2019 to Non-Final Office Action Mailed Oct. 2, 2018", 9 pgs.
"U.S. Appl. No. 15/131,663, Response filed Jul. 13, 2018 to Restriction Requirement mailed May 18, 2018", 8 pgs.
"U.S. Appl. No. 15/131,663, Restriction Requirement mailed May 18, 2018", 7 pgs.
"U.S. Appl. No. 15/166,480, Notice of Allowance mailed Sep. 20, 2018", 12 pgs.
"U.S. Appl. No. 15/166,480, Response filed Jul. 18, 2018 to Restriction Requirement mailed May 21, 2018", 6 pgs.
"U.S. Appl. No. 15/166,480, Restriction Requirement mailed May 21, 2018", 6 pgs.
"U.S. Appl. No. 15/166,480, Supplemental Preliminary Amendment filed Jul. 18, 2017", 7 pgs.
"U.S. Appl. No. 15/200,546, Non Final Office Action mailed Oct. 15, 2018", 10 pgs.
"U.S. Appl. No. 15/200,546, Notice of Allowance mailed Mar. 19, 2019", 7 pgs.
"U.S. Appl. No. 15/200,546, Preliminary Amendment filed Dec. 21, 2016", 6 pgs.
"U.S. Appl. No. 15/200,546, Response Filed Jan. 15, 2019 to Non-Final Office Action Mailed Oct. 15, 2018", 10 pgs.
"U.S. Appl. No. 15/200,546, Response filed Sep. 17, 2018 to Restriction Requirement Mailed Jul. 16, 2018", 8 pgs.
"U.S. Appl. No. 15/200,546, Restriction Requirement mailed Jul. 16, 2018", 6 pgs.
"U.S. Appl. No. 15/278,777, Non Final Office Action mailed Feb. 28, 2018", 14 pgs.
"U.S. Appl. No. 15/278,777, Notice of Allowance mailed Jul. 16, 2018", 8 pgs.
"U.S. Appl. No. 15/278,777, Preliminary Amendment filed Oct. 3, 2016", 7 pgs.
"U.S. Appl. No. 15/278,777, Response filed May 29, 2018 to Non Final Office action mailed Feb. 28, 2018", 11 pgs.
"U.S. Appl. No. 15/288,183, Corrected Notice of Allowability mailed Jun. 21, 2019", 7 pgs.
"U.S. Appl. No. 15/288,183, Non Final Office Action mailed Dec. 10, 2018", 13 pgs.
"U.S. Appl. No. 15/288,183, Notice of Allowance mailed May 9, 2019", 11 pgs.
"U.S. Appl. No. 15/288,183, Preliminary Amendment filed Oct. 31, 2016", 7 pgs.
"U.S. Appl. No. 15/288,183, Response filed Feb. 27, 2019 to Non Final Office Action mailed Dec. 10, 2018", 11 pgs.
"U.S. Appl. No. 15/288,183, Response filed Oct. 25, 2018 to Restriction Requirement mailed Sep. 12, 2018", 7 pgs.
"U.S. Appl. No. 15/288,183, Restriction Requirement mailed Sep. 12, 2018", 6 pgs.
"U.S. Appl. No. 15/288,183, Supplemental Preliminary Amendment filed Jul. 27, 2017", 7 pgs.
"U.S. Appl. No. 15/294,994, Examiner Interview Summary mailed Feb. 26, 2019", 3 pgs.
"U.S. Appl. No. 15/294,994, Final Office Action mailed Jan. 25, 2019", 13 pgs.
"U.S. Appl. No. 15/294,994, Non Final Office Action mailed Aug. 9, 2018", 9 pgs.
"U.S. Appl. No. 15/294,994, Notice of Allowance mailed May 22, 2019", 10 pgs.
"U.S. Appl. No. 15/294,994, Preliminary Amendment filed Jan. 25, 2017", 8 pgs.
"U.S. Appl. No. 15/294,994, Response filed Feb. 27, 2019 to Final Office Action mailed Jan. 25, 2019", 9 pgs.
"U.S. Appl. No. 15/294,994, Response filed Oct. 25, 2018 to Non Final Office Action mailed Aug. 9, 2018", 10 pgs.
"U.S. Appl. No. 15/294,994, Supplemental Preliminary Amendment filed May 31, 2017", 6 pgs.
"U.S. Appl. No. 15/297,844, Notice of Allowance mailed Aug. 30, 2018", 10 pgs.
"U.S. Appl. No. 15/297,844, Preliminary Amendment filed Oct. 20, 2016", 7 pgs.
"U.S. Appl. No. 15/297,844, Supplemental Preliminary Amendment filed Jan. 25, 2018", 6 pgs.
"U.S. Appl. No. 15/332,590, Notice of Allowance mailed Dec. 5, 2018", 13 pgs.
"U.S. Appl. No. 15/332,590, Preliminary Amendment filed Nov. 22, 2016", 5 pgs.
"U.S. Appl. No. 15/361,917, Advisory Action mailed Nov. 19, 2019", 3 pgs.
"U.S. Appl. No. 15/361,917, Final Office Action mailed Sep. 3, 2019", 8 pgs.
"U.S. Appl. No. 15/361,917, Non Final Office Action mailed Apr. 19, 2019", 11 pgs.
"U.S. Appl. No. 15/361,917, Notice of Allowance mailed Mar. 4, 2020", 8 pgs.
"U.S. Appl. No. 15/361,917, Preliminary Amendment filed Nov. 30, 2016", 6 pgs.
"U.S. Appl. No. 15/361,917, Response filed Feb. 14, 2019 to Restriction Requirement mailed Jan. 3, 2019", 6 pgs.
"U.S. Appl. No. 15/361,917, Response filed Jun. 19, 2019 to Non Final Office Action mailed Apr. 19, 2019", 9 pgs.
"U.S. Appl. No. 15/361,917, Response filed Nov. 4, 2019 to Final Office Action mailed Sep. 3, 2019", 8 pgs.
"U.S. Appl. No. 15/361,917, Restriction Requirement mailed Jan. 3, 2019", 6 pgs.
"U.S. Appl. No. 15/401,768, Non Final Office Action mailed Jul. 22, 2019", 10 pgs.
"U.S. Appl. No. 15/401,768, Notice of Allowance mailed Nov. 20, 2019", 9 pgs.
"U.S. Appl. No. 15/401,768, Preliminary Amendment filed Mar. 23, 2017", 6 pgs.
"U.S. Appl. No. 15/401,768, Response filed May 15, 2019 to Restriction Requirement mailed Mar. 15, 2019", 7 pgs.
"U.S. Appl. No. 15/401,768, Response filed Aug. 28, 2019 to Non Final Office Action mailed Jul. 22, 2019", 10 pgs.
"U.S. Appl. No. 15/401,768, Restriction Requirement mailed Mar. 15, 2019", 6 pgs.
"U.S. Appl. No. 15/401,768, Supplemental Preliminary Amendment filed Jun. 22, 2017", 7 pgs.
"U.S. Appl. No. 15/412,676, Non Final Office Action mailed Jul. 23, 2019", 11 pgs.
"U.S. Appl. No. 15/412,676, Notice of Allowance mailed Dec. 30, 2019", 8 pgs.
"U.S. Appl. No. 15/412,676, Preliminary Amendment filed Jul. 3, 2017", 7 pgs.
"U.S. Appl. No. 15/412,676, Response filed May 15, 2019 to Restriction Requirement mailed Mar. 15, 2019", 7 pgs.
"U.S. Appl. No. 15/412,676, Response filed Oct. 23, 2019 to Non Final Office Action mailed Jul. 23, 2019", 12 pgs.
"U.S. Appl. No. 15/412,676, Restriction Requirement mailed Mar. 15, 2019", 6 pgs.
"U.S. Appl. No. 15/455,895, Examiner Interview Summary mailed Nov. 25, 2019", 3 pgs.
"U.S. Appl. No. 15/455,895, Non Final Office Action mailed Sep. 5, 2019", 11 pgs.
"U.S. Appl. No. 15/455,895, Notice of Allowance mailed Feb. 13, 2020", 7 pgs.
"U.S. Appl. No. 15/455,895, Preliminary Amendment filed Mar. 13, 2017", 6 pgs.
"U.S. Appl. No. 15/455,895, Response filed Jan. 28, 2020 to Non Final Office Action mailed Sep. 5, 2019", 14 pgs.
"U.S. Appl. No. 15/455,895, Supplemental Preliminary Amendment filed May 24, 2019", 6 pgs.
"U.S. Appl. No. 15/461,675, Non Final Office Action mailed Aug. 9, 2019", 10 pgs.
"U.S. Appl. No. 15/461,675, Notice of Allowance mailed Jan. 30, 2020", 7 pgs.
"U.S. Appl. No. 15/461,675, Preliminary Amendment filed Jun. 24, 2017", 6 pgs.

(56) References Cited

OTHER PUBLICATIONS

"U.S. Appl. No. 15/461,675, Response filed May 24, 2019 to Restriction Requirement mailed Mar. 26, 2019", 6 pgs.
"U.S. Appl. No. 15/461,675, Response filed Nov. 12, 2019 to Non Final Office Action mailed Aug. 9, 2019", 11 pgs.
"U.S. Appl. No. 15/461,675, Restriction Requirement mailed Mar. 26, 2019", 6 pgs.
"U.S. Appl. No. 15/461,675, Supplemental Preliminary Amendment filed Jun. 28, 2018", 7 pgs.
"U.S. Appl. No. 15/622,718, Examiner Interview Summary mailed Nov. 22, 2019", 3 pgs.
"U.S. Appl. No. 15/622,718, Non Final Office Action mailed Aug. 28, 2019", 14 pgs.
"U.S. Appl. No. 15/622,718, Notice of Allowance mailed Feb. 13, 2020", 8 pgs.
"U.S. Appl. No. 15/622,718, Preliminary Amendment filed Jun. 15, 2017", 7 pgs.
"U.S. Appl. No. 15/622,718, Response filed Jan. 28, 2020 to Non Final Office Action mailed Aug. 28, 2019", 11 pgs.
"U.S. Appl. No. 15/622,718, Response filed Jul. 31, 2019 to Restriction Requirement mailed Jun. 7, 2019", 8 pgs.
"U.S. Appl. No. 15/622,718, Restriction Requirement mailed Jun. 7, 2019", 6 pgs.
"U.S. Appl. No. 15/626,384, Non Final Office Action mailed May 3, 2019", 14 pgs.
"U.S. Appl. No. 15/626,384, Notice of Allowability mailed Oct. 18, 2019", 2 pgs.
"U.S. Appl. No. 15/626,384, Notice of Allowance mailed Aug. 21, 2019", 7 pgs.
"U.S. Appl. No. 15/626,384, Preliminary Amendment filed Aug. 10, 2018", 11 pgs.
"U.S. Appl. No. 15/626,384, Response filed Jul. 31, 2019 to Non-Final Office Action mailed May 3, 2019", 13 pgs.
"U.S. Appl. No. 15/654,386, Non Final Office Action mailed Nov. 7, 2019", 10 pgs.
"U.S. Appl. No. 15/654,386, Notice of Allowance mailed Feb. 20, 2020", 8 pgs.
"U.S. Appl. No. 15/654,386, Preliminary Amendment filed Aug. 30, 2017", 11 pgs.
"U.S. Appl. No. 15/654,386, Response filed Feb. 5, 2020 to Non Final Office Action mailed Nov. 7, 2019", 12 pgs.
"U.S. Appl. No. 15/654,386, Response filed Aug. 23, 2019 to Restriction Requirement mailed Jul. 16, 2019", 9 pgs.
"U.S. Appl. No. 15/654,386, Restriction Requirement mailed Jul. 16, 2019", 6 pgs.
"U.S. Appl. No. 15/659,689, Non Final Office Action mailed Oct. 31, 2018", 13 pgs.
"U.S. Appl. No. 15/659,689, Preliminary Amendment filed Jul. 26, 2017", 7 pgs.
"U.S. Appl. No. 15/662,572, Non Final Office Action mailed Oct. 10, 2019", 14 pgs.
"U.S. Appl. No. 15/662,572, Notice of Allowance mailed Mar. 11, 2020", 9 pgs.
"U.S. Appl. No. 15/662,572, Preliminary Amendment filed Jul. 31, 2017", 7 pgs.
"U.S. Appl. No. 15/662,572, Response filed Jan. 8, 2020 to Non Final Office Action mailed Oct. 10, 2019", 10 pgs.
"U.S. Appl. No. 15/662,572, Response filed Aug. 23, 2019 to Restriction Requirement mailed Jul. 1, 2019", 8 pgs.
"U.S. Appl. No. 15/662,572, Restriction Requirement mailed Jul. 1, 2019", 6 pgs.
"U.S. Appl. No. 15/664,572, Non Final Office Action mailed May 15, 2019", 8 pgs.
"U.S. Appl. No. 15/664,572, Notice of Allowance mailed Jun. 12, 2019", 8 pgs.
"U.S. Appl. No. 15/664,572, Preliminary Amendment filed Aug. 3, 2017", 7 pgs.
"U.S. Appl. No. 15/664,572, Response filed May 17, 2019 to Non Final Office Action mailed May 15, 2019", 9 pgs.
"U.S. Appl. No. 15/682,187, Non Final Office Action mailed Dec. 16, 2019", 10 pgs.
"U.S. Appl. No. 15/682,187, Notice of Allowance mailed Mar. 25, 2020", 9 pgs.
"U.S. Appl. No. 15/682,187, Preliminary Amendment filed Sep. 7, 2017", 6 pgs.
"U.S. Appl. No. 15/682,187, Response filed Feb. 2027, to Non Final Office Action mailed Dec. 16, 2019", 11 pgs.
"U.S. Appl. No. 15/682,187, Response filed Sep. 18, 2019 to Restriction Requirement mailed Aug. 9, 2019", 7 pgs.
"U.S. Appl. No. 15/682,187, Restriction Requirement mailed Aug. 9, 2019", 6 pgs.
"U.S. Appl. No. 15/703,727, Non Final Office Action mailed Aug. 1, 2019", 11 pgs.
"U.S. Appl. No. 15/703,727, Notice of Allowance mailed Nov. 20, 2019", 7 pgs.
"U.S. Appl. No. 15/703,727, Preliminary Amendment filed Sep. 14, 2017", 7 pgs.
"U.S. Appl. No. 15/703,727, Response filed Nov. 1, 2019 to Non Final Office Action mailed Aug. 1, 2019", 10 pgs.
"U.S. Appl. No. 15/715,731, Non Final Office Action mailed Jan. 21, 2020", 8 pgs.
"U.S. Appl. No. 15/715,731, Notice of Allowance mailed Apr. 8, 2020", 9 pgs.
"U.S. Appl. No. 15/715,731, Preliminary Amendment Filed Sep. 26, 2017", 9 pgs.
"U.S. Appl. No. 15/715,731, Response filed Feb. 27, 2020 to Non Final Office Action mailed Jan. 21, 2020", 12 pgs.
"U.S. Appl. No. 15/715,731, Response Filed Nov. 4, 2019 to Restriction Requirement Mailed Sep. 4, 2019", 9 pgs.
"U.S. Appl. No. 15/715,731, Restriction Requirement mailed Sep. 4, 2019", 6 pgs.
"U.S. Appl. No. 15/715,731, Supplemental Preliminary Amendment filed Dec. 29, 2017", 8 pgs.
"U.S. Appl. No. 15/720,997, Advisory Action mailed Jun. 15, 2021", 3 pgs.
"U.S. Appl. No. 15/720,997, Advisory Action mailed Oct. 13, 2020", 2 pgs.
"U.S. Appl. No. 15/720,997, Final Office Action mailed Apr. 7, 2021", 9 pgs.
"U.S. Appl. No. 15/720,997, Final Office Action mailed Aug. 4, 2020", 10 pgs.
"U.S. Appl. No. 15/720,997, Non Final Office Action mailed Jan. 6, 2020", 10 pgs.
"U.S. Appl. No. 15/720,997, Non Final Office Action mailed Jul. 16, 2019", 11 pgs.
"U.S. Appl. No. 15/720,997, Non Final Office Action mailed Nov. 23, 2020", 7 pgs.
"U.S. Appl. No. 15/720,997, Notice of Allowance mailed Jul. 29, 2021", 7 pgs.
"U.S. Appl. No. 15/720,997, Preliminary Amendment filed Oct. 2, 2017", 6 pgs.
"U.S. Appl. No. 15/720,997, Response filed Jan. 25, 2021 to Non Final Office Action mailed Nov. 23, 2020", 9 pgs.
"U.S. Appl. No. 15/720,997, Response filed Mar. 27, 2020 to Non Final Office Action mailed Jan. 6, 2020", 10 pgs.
"U.S. Appl. No. 15/720,997, Response filed Jun. 2, 2021 to Final Office Action mailed Apr. 7, 2021", 9 pgs.
"U.S. Appl. No. 15/720,997, Response filed Jul. 7, 2021 to Advisory Action mailed Jun. 21, 2021", 6 pgs.
"U.S. Appl. No. 15/720,997, Response filed Sep. 30, 2020 to Final Office Action mailed Aug. 4, 2020", 11 pgs.
"U.S. Appl. No. 15/720,997, Response filed Oct. 3, 2019 to Non-Final Office Action mailed Jul. 16, 2019", 9 pgs.
"U.S. Appl. No. 15/722,002, Non Final Office Action mailed Feb. 4, 2020", 8 pgs.
"U.S. Appl. No. 15/722,002, Notice of Allowance mailed Apr. 8, 2020", 7 pgs.
"U.S. Appl. No. 15/722,002, Preliminary Amendment filed Jun. 29, 2018", 5 pgs.
"U.S. Appl. No. 15/722,002, Response filed Mar. 5, 2020 to Non Final Office Action mailed Feb. 4, 2020", 7 pgs.

(56) References Cited

OTHER PUBLICATIONS

"U.S. Appl. No. 15/722,002, Response filed Nov. 14, 2019 to Restriction Requirement mailed Sep. 17, 2019", 6 pgs.
"U.S. Appl. No. 15/722,002, Restriction Requirement mailed Sep. 17, 2019", 6 pgs.
"U.S. Appl. No. 15/793,216, Examiner Interview Summary mailed Nov. 4, 2019", 4 pgs.
"U.S. Appl. No. 15/793,216, Non Final Office Action mailed Aug. 1, 2019", 21 pgs.
"U.S. Appl. No. 15/793,216, Notice of Allowance mailed Mar. 23, 2020", 7 pgs.
"U.S. Appl. No. 15/793,216, Preliminary Amendment filed Oct. 26, 2017", 8 pgs.
"U.S. Appl. No. 15/793,216, Response filed Jan. 28, 2020 to Non Final Office Action mailed Aug. 1, 2019", 13 pgs.
"U.S. Appl. No. 15/865,938, Notice of Allowance mailed Sep. 17, 2019", 11 pgs.
"U.S. Appl. No. 15/865,938, Preliminary Amendment filed Jan. 10, 2018", 7 pgs.
"U.S. Appl. No. 15/866,089, Corrected Notice of Allowability mailed Aug. 27, 2020", 2 pgs.
"U.S. Appl. No. 15/866,089, Final Office Action mailed Mar. 25, 2020", 15 pgs.
"U.S. Appl. No. 15/866,089, Non Final Office Action mailed Dec. 4, 2019", 16 pgs.
"U.S. Appl. No. 15/866,089, Notice of Allowance mailed Jul. 15, 2020", 5 pgs.
"U.S. Appl. No. 15/866,089, Preliminary Amendment filed Jan. 10, 2018", 10 pgs.
"U.S. Appl. No. 15/866,089, Response filed Feb. 27, 2020 to Non Final Office Action mailed Dec. 4, 2019", 10 pgs.
"U.S. Appl. No. 15/866,089, Response filed Jun. 18, 2020 to Final Office Action mailed Mar. 25, 2020", 11 pgs.
"U.S. Appl. No. 15/886,712, Non Final Office Action mailed Sep. 27, 2019", 8 pgs.
"U.S. Appl. No. 15/886,712, Notice of Allowance mailed Nov. 14, 2019", 7 pgs.
"U.S. Appl. No. 15/886,712, Preliminary Amendment filed Feb. 2, 2018", 8 pgs.
"U.S. Appl. No. 15/886,712, Response filed Oct. 18, 2019 to Non Final Office Action mailed Sep. 27, 2019", 9 pgs.
"U.S. Appl. No. 15/891,049, Examiner Interview Summary mailed Aug. 10, 2020", 3 pgs.
"U.S. Appl. No. 15/891,049, Examiner Interview Summary mailed Dec. 4, 2020", 2 pgs.
"U.S. Appl. No. 15/891,049, Final Office Action mailed Nov. 10, 2020", 10 pgs.
"U.S. Appl. No. 15/891,049, Non Final Office Action mailed Jul. 14, 2020", 16 pgs.
"U.S. Appl. No. 15/891,049, Notice of Allowance mailed Dec. 22, 2020", 8 pgs.
"U.S. Appl. No. 15/891,049, Preliminary Amendment filed Feb. 8, 2018", 6 pgs.
"U.S. Appl. No. 15/891,049, Response filed May 29, 2020 to Restriction Requirement mailed May 5, 2020", 9 pgs.
"U.S. Appl. No. 15/891,049, Response filed Aug. 17, 2020 to Non Final Office Action mailed Jul. 14, 2020", 18 pgs.
"U.S. Appl. No. 15/891,049, Response filed Dec. 1, 2020 to Final Office Action mailed Nov. 10, 2020", 12 pgs.
"U.S. Appl. No. 15/891,049, Restriction Requirement mailed May 5, 2020", 6 pgs.
"U.S. Appl. No. 15/891,049, Supplemental Preliminary Amendment filed Dec. 20, 2019", 8 pgs.
"U.S. Appl. No. 15/903,261, Notice of Allowance mailed Mar. 26, 2020", 9 pgs.
"U.S. Appl. No. 15/903,261, Preliminary Amendment filed Feb. 28, 2018", 6 pgs.
"U.S. Appl. No. 15/917,143, Non Final Office Action mailed Aug. 7, 2020", 6 pgs.
"U.S. Appl. No. 15/917,143, Notice of Allowance mailed Feb. 24, 2021", 8 pgs.
"U.S. Appl. No. 15/917,143, Preliminary Amendment filed Mar. 14, 2018", 7 pgs.
"U.S. Appl. No. 15/917,143, Response filed Jun. 17, 2020 to Restriction Requirement mailed May 5, 2020", 8 pgs.
"U.S. Appl. No. 15/917,143, Response filed Oct. 29, 2020 to Non Final Office Action mailed Aug. 7, 2020", 11 pgs.
"U.S. Appl. No. 15/917,143, Restriction Requirement mailed May 5, 2020", 6 pgs.
"U.S. Appl. No. 15/941,481, Non Final Office Action mailed Aug. 14, 2020", 21 pgs.
"U.S. Appl. No. 15/941,481, Notice of Allowance mailed Dec. 3, 2020", 8 pgs.
"U.S. Appl. No. 15/941,481, Preliminary Amendment filed Mar. 30, 2018", 7 pgs.
"U.S. Appl. No. 15/941,481, Response filed Jun. 24, 2020 to Restriction Requirement mailed May 19, 2020", 8 pgs.
"U.S. Appl. No. 15/941,481, Response filed Nov. 16, 2020 to Non Final Office Action mailed Aug. 14, 2020", 15 pgs.
"U.S. Appl. No. 15/941,481, Restriction Requirement mailed May 19, 2020", 7 pgs.
"U.S. Appl. No. 15/945,425, Non Final Office Action mailed Aug. 25, 2020", 11 pgs.
"U.S. Appl. No. 15/945,425, Notice of Allowance mailed Dec. 24, 2020", 8 pgs.
"U.S. Appl. No. 15/945,425, Preliminary Amendment filed Apr. 5, 2018", 8 pgs.
"U.S. Appl. No. 15/945,425, Response filed Jun. 24, 2020 to Restriction Requirement mailed May 19, 2020", 7 pgs.
"U.S. Appl. No. 15/945,425, Response filed Nov. 23, 2020 to Non Final Office Action mailed Aug. 25, 2020", 10 pgs.
"U.S. Appl. No. 15/945,425, Restriction Requirement mailed May 19, 20", 7 pgs.
"U.S. Appl. No. 15/945,425, Supplemental Preliminary Amendment filed May 10, 2018", 6 pgs.
"U.S. Appl. No. 15/956,444, Non Final Office Action mailed Dec. 7, 2020", 7 pgs.
"U.S. Appl. No. 15/956,444, Notice of Allowance mailed Mar. 11, 2021", 8 pgs.
"U.S. Appl. No. 15/956,444, Preliminary Amendment filed Apr. 19, 2018", 7 pgs.
"U.S. Appl. No. 15/956,444, PTO Response to Rule 312 Communication mailed Jun. 8, 2021", 2 pgs.
"U.S. Appl. No. 15/956,444, Response filed Feb. 23, 2021 to Non Final Office Action mailed Dec. 7, 2020", 11 pgs.
"U.S. Appl. No. 15/956,444, Response filed Sep. 14, 2020 to Restriction Requirement mailed Jul. 14, 2020", 8 pgs.
"U.S. Appl. No. 15/956,444, Restriction Requirement mailed Jul. 14, 2020", 7 pgs.
"U.S. Appl. No. 15/972,646, Non Final Office Action mailed Dec. 7, 2020", 11 pgs.
"U.S. Appl. No. 15/972,646, Notice of Allowance mailed Apr. 21, 2021", 8 pgs.
"U.S. Appl. No. 15/972,646, Preliminary Amendment filed May 9, 2018", 6 pgs.
"U.S. Appl. No. 15/972,646, Response filed Feb. 22, 2021 to Non Final Office Action mailed Dec. 7, 2020", 13 pgs.
"U.S. Appl. No. 15/972,646, Response filed Sep. 21, 2020 mailed Jul. 27, 2020", 7 pgs.
"U.S. Appl. No. 15/972,646, Restriction Requirement mailed Jul. 27, 2020", 6 pgs.
"U.S. Appl. No. 16/160,559, 312 Amendment filed Dec. 9, 2021", 7 pgs.
"U.S. Appl. No. 16/160,559, Non Final Office Action mailed May 14, 2021", 12 pgs.
"U.S. Appl. No. 16/160,559, Notice of Allowance mailed Sep. 16, 2021", 14 pgs.
"U.S. Appl. No. 16/160,559, Preliminary Amendment filed Oct. 17, 2018", 6 pgs.
"U.S. Appl. No. 16/160,559, PTO Response to Rule 312 Communication mailed Dec. 24, 2021", 2 pgs.

(56) References Cited

OTHER PUBLICATIONS

"U.S. Appl. No. 16/160,559, Response filed Mar. 2, 2021 to Restriction Requirement mailed Jan. 27, 2021", 7 pgs.
"U.S. Appl. No. 16/160,559, Response filed Aug. 11, 2021 to Non Final Office Action mailed May 14, 2021", 10 pgs.
"U.S. Appl. No. 16/160,559, Restriction Requirement mailed Jan. 27, 2021", 6 pgs.
"U.S. Appl. No. 16/251,342, Notice of Allowance mailed Jul. 26, 2021", 8 pgs.
"U.S. Appl. No. 16/251,342, Preliminary Amendment filed Jan. 21, 2019", 6 pgs.
"U.S. Appl. No. 16/251,342, Response filed May 3, 2021 to Restriction Requirement mailed Apr. 30, 2021", 8 pgs.
"U.S. Appl. No. 16/251,342, Restriction Requirement mailed Apr. 30, 2021", 6 pgs.
"U.S. Appl. No. 16/251,342, Supplemental Preliminary Amendment filed Oct. 28, 2020", 7 pgs.
"U.S. Appl. No. 16/251,342, Supplemental Preliminary Amendment filed Nov. 4, 2020", 7 pgs.
"U.S. Appl. No. 16/255,300 Supplemental Preliminary Amendment Filed Nov. 12, 2020", 8 pgs.
"U.S. Appl. No. 16/255,300, Notice of Allowance mailed Jul. 19, 2021", 10 pgs.
"U.S. Appl. No. 16/255,300, Preliminary Amendment filed Jan. 24, 2019", 6 pgs.
"U.S. Appl. No. 16/380,742, Notice of Allowance mailed Jan. 3, 2022", 13 pgs.
"U.S. Appl. No. 16/380,742, Preliminary Amendment filed Apr. 12, 2019", 6 pgs.
"U.S. Appl. No. 16/380,742, Response filed Oct. 20, 2021 to Restriction Requirement mailed Aug. 20, 2021", 6 pgs.
"U.S. Appl. No. 16/380,742, Restriction Requirement mailed Aug. 20, 2021", 7 pgs.
"U.S. Appl. No. 16/380,742, Supplemental Preliminary Amendment filed Mar. 1, 2021", 5 pgs.
"U.S. Appl. No. 16/400,199, Non Final Office Action mailed Feb. 10, 2022", 8 pgs.
"U.S. Appl. No. 16/400,199, Notice of Allowance mailed May 11, 2022", 8 pgs.
"U.S. Appl. No. 16/400,199, Preliminary Amendment filed May 7, 2019", 7 pgs.
"U.S. Appl. No. 16/400,199, Response filed Apr. 13, 2022 to Non Final Office Action mailed Feb. 10, 2022", 11 pgs.
"U.S. Appl. No. 16/400,199, Response filed Nov. 15, 2021 to Restriction Requirement mailed Oct. 1, 2021", 8 pgs.
"U.S. Appl. No. 16/400,199, Restriction Requirement mailed Oct. 1, 2021", 7 pgs.
"U.S. Appl. No. 16/420,676, Non Final Office Action mailed Jul. 20, 2021", 11 pgs.
"U.S. Appl. No. 16/420,676, Notice of Allowance mailed Nov. 15, 2021", 9 pgs.
"U.S. Appl. No. 16/420,676, Preliminary Amendment filed Jun. 3, 2019", 5 pgs.
"U.S. Appl. No. 16/420,676, Response filed Oct. 20, 2021 to Non Final Office Action mailed Jul. 20, 2021", 14 pgs.
"U.S. Appl. No. 16/428,277, Corrected Notice of Allowability mailed Sep. 16, 2022", 6 pgs.
"U.S. Appl. No. 16/428,277, Non Final Office Action mailed May 24, 2022", 7 pgs.
"U.S. Appl. No. 16/428,277, Notice of Allowance mailed Aug. 25, 2022", 9 pgs.
"U.S. Appl. No. 16/428,277, Preliminary Amendment filed Jun. 3, 2019", 5 pgs.
"U.S. Appl. No. 16/428,277, Response filed Apr. 11, 2022 to Restriction Requirement mailed Feb. 11, 2022", 8 pgs.
"U.S. Appl. No. 16/428,277, Response filed Aug. 3, 2022 to Non Final Office Action mailed May 24, 2022", 8 pgs.
"U.S. Appl. No. 16/428,277, Restriction Requirement mailed Feb. 11, 2022", 6 pgs.
"U.S. Appl. No. 16/436,023, Examiner Interview Summary mailed Aug. 23, 2021", 2 pgs.
"U.S. Appl. No. 16/436,023, Non Final Office Action mailed May 19, 2021", 18 pgs.
"U.S. Appl. No. 16/436,023, Notice of Allowance mailed Oct. 27, 2021", 8 pgs.
"U.S. Appl. No. 16/436,023, Preliminary Amendment filed Jun. 12, 2019", 6 pgs.
"U.S. Appl. No. 16/436,023, Response filed Aug. 19, 2021 to Non Final Office actio mailed May 19, 2021", 9 pgs.
"U.S. Appl. No. 16/443,391, Non Final Office Action mailed Aug. 31, 2021", 11 pgs.
"U.S. Appl. No. 16/443,391, Notice of Allowance mailed Jan. 7, 2022", 5 pgs.
"U.S. Appl. No. 16/443,391, Preliminary Amendment filed Jun. 19, 2019", 6 pgs.
"U.S. Appl. No. 16/443,391, Response filed Nov. 15, 2021 to Non Final Office Action mailed Aug. 31, 2021", 9 pgs.
"U.S. Appl. No. 16/508,764, Notice of Allowance mailed Oct. 20, 2021", 10 pgs.
"U.S. Appl. No. 16/508,764, Preliminary Amendment filed Jul. 12, 2019", 7 pgs.
"U.S. Appl. No. 16/508,764, Supplemental Amendment filed Sep. 30, 2021", 6 pgs.
"U.S. Appl. No. 16/544,293, Corrected Notice of Allowability mailed Mar. 17, 2023", 7 pgs.
"U.S. Appl. No. 16/544,293, Non Final Office Action mailed Sep. 21, 2022", 14 pgs.
"U.S. Appl. No. 16/544,293, Notice of Allowance mailed Mar. 8, 2023", 11 pgs.
"U.S. Appl. No. 16/544,293, Preliminary Amendment filed Aug. 21, 2019", 7 pgs.
"U.S. Appl. No. 16/544,293, Response filed Aug. 15, 2022 to Restriction Requirement mailed Jul. 7, 2022", 7 pgs.
"U.S. Appl. No. 16/544,293, Response filed Nov. 28, 2022 to Non-Final Office Action mailed Sep. 21, 2022", 10 pgs.
"U.S. Appl. No. 16/544,293, Restriction Requirement mailed Jul. 7, 2022", 6 pgs.
"U.S. Appl. No. 16/544,293, Supplemental Preliminary Amendment filed Oct. 28, 2020", 6 pgs.
"U.S. Appl. No. 16/593,022, Preliminary Amendment filed Oct. 30, 2019", 8 pgs.
"U.S. Appl. No. 16/593,022, Response filed Sep. 9, 2022 to Restriction Requirement mailed Sep. 6, 2022", 8 pgs.
"U.S. Appl. No. 16/593,022, Response filed Nov. 4, 2022 to Restriction Requirement mailed Oct. 31, 2022", 8 pgs.
"U.S. Appl. No. 16/593,022, Restriction Requirement mailed Sep. 6, 2022", 6 pgs.
"U.S. Appl. No. 16/593,022, Restriction Requirement mailed Oct. 31, 2022", 6 pgs.
"U.S. Appl. No. 16/593,022, Supplemental Amendment filed Nov. 7, 2022 to Restriction Requirement mailed Oct. 31, 2022", 9 pgs.
"U.S. Appl. No. 16/593,022, Supplemental Preliminary Amendment filed Oct. 21, 2020", 8 pgs.
"U.S. Appl. No. 16/593,022, Supplemental Preliminary Amendment filed Dec. 5, 2019", 8 pgs.
"U.S. Appl. No. 16/593,022, Supplemental Preliminary Amendment filed Dec. 20, 2019", 5 pgs.
"U.S. Appl. No. 16/690,671, Non Final Office Action mailed Nov. 15, 2021", 8 pgs.
"U.S. Appl. No. 16/690,671, Notice of Allowance mailed Mar. 2, 2022", 7 pgs.
"U.S. Appl. No. 16/690,671, Preliminary Amendment filed Dec. 11, 2019", 7 pgs.
"U.S. Appl. No. 16/690,671, Response filed Feb. 4, 2022 to Non Final Office Action mailed Nov. 15, 2021", 10 pgs.
"U.S. Appl. No. 16/795,181, Examiner Interview Summary mailed Apr. 15, 2022", 2 pgs.
"U.S. Appl. No. 16/795,181, Final Office Action mailed Jun. 7, 2022", 12 pgs.
"U.S. Appl. No. 16/795, 181,Non Final Office Action mailed Jan. 24, 2022", 12 pgs.

(56) References Cited

OTHER PUBLICATIONS

"U.S. Appl. No. 16/795, 181, Notice of Allowance mailed Aug. 25, 2022", 7 pgs.
"U.S. Appl. No. 16/795,181, Preliminary Amendment filed Feb. 20, 2020", 6 pgs.
"U.S. Appl. No. 16/795,181, Response filed Apr. 14, 2022 to Non Final Office Action mailed Jan. 24, 2022", 9 pgs.
"U.S. Appl. No. 16/795,181, Response filed Aug. 3, 2022 to Final Office Action mailed Jun. 7, 2022", 8 pgs.
"U.S. Appl. No. 16/802,228, Notice of Allowance mailed Jun. 15, 2022", 10 pgs.
"U.S. Appl. No. 16/802,228, Preliminary Amendment filed Mar. 4, 2020", 7 pgs.
"U.S. Appl. No. 16/802,248, Non Final Office Action mailed Jun. 17, 2022", 18 pgs.
"U.S. Appl. No. 16/802,248, Notice of Allowance mailed Oct. 28, 2022", 9 pgs.
"U.S. Appl. No. 16/802,248, Preliminary Amendment filed Mar. 5, 2020", 8 pgs.
"U.S. Appl. No. 16/802,248, Response filed Sep. 14, 2022 to Non Final Office Action mailed Jun. 17, 2022", 12 pgs.
"U.S. Appl. No. 16/806,611, Notice of Allowance mailed Feb. 15, 2023", 10 pgs.
"U.S. Appl. No. 16/806,611, Preliminary Amendment filed Mar. 4, 2020", 7 pgs.
"U.S. Appl. No. 16/806,611, Response filed Sep. 9, 2022 to Restriction Requirement mailed Aug. 26, 2022", 9 pgs.
"U.S. Appl. No. 16/806,611, Response filed Nov. 7, 2022 to Restriction Requirement mailed Nov. 1, 2022", 9 pgs.
"U.S. Appl. No. 16/806,611, Restriction Requirement mailed Aug. 26, 2022", 6 pgs.
"U.S. Appl. No. 16/806,611, Restriction Requirement mailed Nov. 1, 2022", 6 pgs.
"U.S. Appl. No. 16/895,246, Non Final Office Action mailed Dec. 13, 2022", 8 pgs.
"U.S. Appl. No. 16/895,246, Notice of Allowance mailed Apr. 5, 2023", 13 pgs.
"U.S. Appl. No. 16/895,246, Preliminary Amendment filed Jun. 9, 2020", 6 pgs.
"U.S. Appl. No. 16/895,246, Response filed Jan. 11, 2023 to Non Final Office Action mailed Dec. 13, 2022", 8 pgs.
"U.S. Appl. No. 16/895,246, Response filed Sep. 28, 2022 to Restriction Requirement mailed Sep. 9, 2022", 7 pgs.
"U.S. Appl. No. 16/895,246, Restriction Requirement mailed Sep. 9, 2022", 6 pgs.
"U.S. Appl. No. 16/987,001, Notice of Allowance mailed Feb. 17, 2023", 15 pgs.
"U.S. Appl. No. 16/989,386, Non Final Office Action mailed Mar. 15, 2023", 13 pgs.
"U.S. Appl. No. 16/989,386, Notice of Allowance mailed Jul. 26, 2023", 9 pgs.
"U.S. Appl. No. 16/989,386, PTO Response to Rule 312 Communication mailed Oct. 19, 2023", 2 pgs.
"U.S. Appl. No. 16/989,386, Response filed May 19, 2023 to Non Final Office Action mailed Mar. 15, 2023", 11 pgs.
"U.S. Appl. No. 16/989,386, Response filed Dec. 5, 2022 to Restriction Requirement mailed Nov. 14, 2022", 9 pgs.
"U.S. Appl. No. 16/989,386, Restriction Requirement mailed Nov. 14, 2022", 6 pgs.
"U.S. Appl. No. 16/989,386, Supplemental Preliminary Amendment filed Oct. 21, 2020", 8 pgs.
"U.S. Appl. No. 17/190,686, Notice of Allowance mailed Oct. 5, 2023", 8 pgs.
"U.S. Appl. No. 17/190,686, Preliminary Amendment filed Mar. 10, 2021", 7 pgs.
"U.S. Appl. No. 17/190,686, Restriction Requirement mailed Jun. 6, 2023", 7 pgs.
"U.S. Appl. No. 17/190,686, Supplemental Amendment filed Apr. 12, 2023", 9 pgs.
"U.S. Appl. No. 17/392,971, Preliminary Amendment filed Aug. 18, 2021", 9 pgs.
"U.S. Appl. No. 17/492,082, Notice of Allowance mailed Apr. 17, 2023", 8 pgs.
"U.S. Appl. No. 17/492,082, Preliminary Amendment filed Oct. 25, 2021", 6 pgs.
"U.S. Appl. No. 17/516,664, Preliminary Amendment filed Nov. 10, 2021", 6 pgs.
"U.S. Appl. No. 17/545,668, Notice of Allowance mailed Jun. 22, 2023", 7 pgs.
"U.S. Appl. No. 17/545,668, Preliminary Amendment filed Dec. 9, 2021", 5 pgs.
"U.S. Appl. No. 17/550,074, Preliminary Amendment filed Dec. 15, 2021", 5 pgs.
"U.S. Appl. No. 17/577,188, Preliminary Amendment filed Jan. 19, 2022", 7 pgs.
"U.S. Appl. No. 17/940,022, Preliminary Amendment filed Sep. 26, 2022", 6 pgs.
"U.S. Appl. No. 17/991,832, Preliminary Amendment filed Dec. 14, 2022", 6 pgs.
"U.S. Appl. No. 17/190,686, Response filed Aug. 3, 2023 to Restriction Requirement mailed Jun. 6, 2023", 9 pgs.
"U.S. Appl. No. 18/093,114, Supplemental Amendment filed Jan. 11, 2023", 6 pgs.
"U.S. Appl. No. 18/101,490, Supplemental Preliminary Amendment filed Jan. 26, 2023", 7 pgs.
"U.S. Appl. No. 18/102,518, Preliminary Amendment filed Jan. 30, 2023", 6 pgs.
"U.S. Appl. No. 18/126,022, Preliminary Amendment filed Apr. 28, 2023", 6 pgs.
"U.S. Appl. No. 18/134,897, Supplemental Preliminary Amendment filed Apr. 17, 2023", 6 pgs.
"U.S. Appl. No. 18/235,540, Supplemental Preliminary Amendment filed Aug. 30, 2023", 5 pgs.
"U.S. Appl. No. 18/471,089, Supplemental Preliminary Amendment filed Sep. 21, 2023", 7 pgs.
"Arthroscopic Meniscal Repair using the Meniscal Cinch™", Surgical Technique brochure. Arthrex®, 6 sheets, (2008), 6 sheets.
"Australian Application Serial No. 2014236885, First Examination Report mailed Dec. 11, 2017", 2 pgs.
"Australian Application Serial No. 2014236885, Response filed Feb. 14, 2018 to First Examination Report mailed Dec. 11, 2017", 6 pgs.
"Bio-Intrafix Tibial Soft Tissue Fastener, Building on the Legacy of IntraFix", DePuy Mitek brochure, (Feb. 2007), 6 pgs.
"Bio-Intrafix (TCP/PLA) & Intrafix, Tibial Soft Tissue Fasteners", DePuy Mitek, ((date unknown)), 6 pgs.
"Biomechanical Evaluation of the Biomet Sports Medicine JurggerKnot™ Soft Anchor in Porcine Bone", Study completed Jan. 2010. Biomet Sports Medicine Research and Develo ment, Warsaw, Indiana, (Jan. 2010), 2 pgs.
"Canadian Application Serial No. 2906596, Office Action mailed Feb. 26, 2018", 3 pgs.
"Chinese Application Serial No. 201480027708.4, Office Action mailed Feb. 14, 2017", (W/ English Translation), 18 pgs.
"Chinese Application Serial No. 201480027708.4, Office Action mailed May 26, 2016", W/ English Translation, 15 pgs.
"Chinese Application Serial No. 201480027708.4, Office Action mailed Aug. 18, 2017", (W/ English Translation), 8 pgs.
"Chinese Application Serial No. 201480027708.4, Response filed May 2, 2017 to Office Action mailed Feb. 14, 2017", (W/ English Translation), 17 pgs.
"Chinese Application Serial No. 201480027708.4, Response filed Oct. 10, 2016 to Office Action mailed May 26, 2016", (W/ English Translation of Claims), 14 pgs.
"Chinese Application Serial No. 201480027708.4, Response filed Oct. 31, 2017 to Office Action mailed Aug. 18, 2017", (W/ English Claims), 7 pgs.
"Declaration of John White regarding PSCD and Customized Device and Exhibits 1-5".
"Do your next distal tendon repair with . . . The Lubbers Technique", Teno Fix® brochure, Ortheon® Medical, (2003), 2 pgs.

(56) References Cited

OTHER PUBLICATIONS

"European Application No. 16168202.6, Extended European Search Report mailed Aug. 16, 2017", 11 pgs.
"European Application No. 16168202.6, Response filed Nov. 3, 2017 to Extended European Search Report mailed Aug. 16, 2017", 9 pgs.
"European Application Serial No. 10727548.9, Examination Notification Art. 94(3) mailed Sep. 18, 2014", 6 pgs.
"European Application Serial No. 10727548.9, Office Action mailed Jan. 11, 2016", 6 pgs.
"European Application Serial No. 10727548.9, Office Action mailed Jan. 19, 2012", 2 pgs.
"European Application Serial No. 10727548.9, Response filed Mar. 19, 2015 to Examination Notification Art. 94(3) mailed Sep. 18, 2014", 23 pgs.
"European Application Serial No. 11707316.3, Examination Notification Art. 94(3) mailed Feb. 4, 2014", 3 pgs.
"European Application Serial No. 11707316.3, Examination Notification Art. 94(3) mailed Dec. 17, 2014", 5 pgs.
"European Application Serial No. 11707316.3, Office Action mailed Nov. 10, 2015", 6 pgs.
"European Application Serial No. 11707316.3, Response filed Jun. 5, 2014 to Examination Notification Art. 94(3) mailed Feb. 4, 2014", 7 pgs.
"European Application Serial No. 11707316.3, Response filed Jun. 29, 2015 to Examination Notification Art. 94(3) mailed Dec. 17, 2014", 25 pgs.
"European Application Serial No. 12721676.0, Communication pursuant to Article 94(3) EPC mailed Sep. 30, 2015", 4 pgs.
"European Application Serial No. 12721676.0, Office Action mailed Jan. 3, 2014", 2 pgs.
"European Application Serial No. 12721676.0, Preliminary Amendment filed Nov. 19, 2013", 9 pgs.
"European Application Serial No. 12721676.0, Response filed Apr. 11, 2016 to Communication pursuant to Article 94(3) EPC mailed Sep. 30, 2015", 38 pgs.
"European Application Serial No. 12721676.0, Response filed Jul. 10, 2014 to Office Action mailed Jan. 3, 2014", 2 pgs.
"European Application Serial No. 12791902.5, Examination Notification Art. 94(3) mailed Aug. 14, 2015", 4 pgs.
"European Application Serial No. 12791902.5, Office Action mailed Jul. 15, 2014", 2 pgs.
"European Application Serial No. 12791902.5, Response filed Feb. 23, 2016 to Examination Notification Art. 94(3) mailed Aug. 14, 2015", 12 pgs.
"European Application Serial No. 12806211.4, Examination Notification Art. 94(3) mailed Aug. 13, 2015", 5 pgs.
"European Application Serial No. 12806211.4, Office Action mailed Jul. 18, 2014", 2 pgs.
"European Application Serial No. 12806211.4, Response filed Feb. 23, 2016 to Communication Pursuant to Article 94(3) EPC mailed Aug. 13, 2015", 11 pgs.
"European Application Serial No. 13818131.8, Office Action mailed Jul. 28, 2015", 2 pgs.
"European Application Serial No. 13818131.8, Response filed Feb. 8, 2016 to Office Action mailed Jul. 28, 2015", 14 pgs.
"European Application Serial No. 14716173.1, Communication Pursuant to Article 94(3) EPC mailed Jul. 13, 2020", 4 pgs.
"European Application Serial No. 14716173.1, Office Action mailed Nov. 5, 2015", 2 pgs.
"European Application Serial No. 14716173.1, Response filed May 16, 2016 to Communication pursuant to Rules 161(1) and 162 EPC mailed Nov. 5, 2015", 10 pgs.
"European Application Serial No. 14716173.1, Response filed Sep. 25, 2017 to Office Action mailed Mar. 14, 2017", 12 pgs.
"European Application Serial No. 16168202.6, Communication Pursuant to Article 94(3) EPC mailed Apr. 25, 2018", 5 pgs.
"European Application Serial No. 16168202.6, Communication pursuant to Article 94(3) EPC mailed Dec. 11, 2018", 6 pgs.
"European Application Serial No. 16168202.6, Partial European Search Report mailed May 9, 2017", 12 pgs.
"European Application Serial No. 16168202.6, Response filed Sep. 5, 2018 to Communication Pursuant to Article 94(3) EPC mailed Apr. 25, 2018", 13 pgs.
"European Application Serial No. 17169003.5, Extended European Search Report mailed May 11, 2018", 8 pgs.
"European Application Serial No. 17169003.5, Response Filed Dec. 19, 2018 to Extended European Search Report mailed May 11, 2018", 22 pgs.
"European Application Serial No. 12806211.4, Communication Pursuant to Article 94(3) EPC mailed Jun. 23, 2016", 4 pgs.
"EZ Loc Femoral Fixation Device", copyright 2005 Arthrotek, Inc, (2005), 8 pgs.
"Information of Polydioxanone", Dolphin Sutures, [Online] Retrieved from the internet: <https://www.dolphinsutures.com/resoucres/information-on-polydioxanone>, (2018), 2 pgs.
"International Application Serial No. PCT/US2009/039580, International Preliminary Report on Patentability mailed Nov. 4, 2010", 9 pgs.
"International Application Serial No. PCT/US2009/039580, International Search Report mailed Jul. 30, 2009", 4 pgs.
"International Application Serial No. PCT/US2009/039580, Written Opinion mailed Jul. 3, 2009", 7 pgs.
"International Application Serial No. PCT/US2010/036602, International Preliminary Report on Patentability mailed Dec. 8, 2011", 9 pgs.
"International Application Serial No. PCT/US2010/036602, International Search Report mailed Nov. 8, 2010", 6 pgs.
"International Application Serial No. PCT/US2010/036602, Written Opinion mailed Nov. 8, 2010", 7 pgs.
"International Application Serial No. PCT/US2011/026349, International Preliminary Report on Patentability mailed Sep. 20, 2012", 11 pgs.
"International Application Serial No. PCT/US2011/026349, International Search Report mailed Jul. 28, 2011", 6 pgs.
"International Application Serial No. PCT/US2011/026349, Invitation to Pay Additional Fees mailed Jun. 9, 2011", 5 pgs.
"International Application Serial No. PCT/US2011/026349, Written Opinion mailed Jul. 28, 2011", 9 pgs.
"International Application Serial No. PCT/US2011/038188, International Preliminary Report on Patentability mailed Dec. 6, 2012", 14 pgs.
"International Application Serial No. PCT/US2011/038188, International Search Report mailed Oct. 14, 2011", 6 pgs.
"International Application Serial No. PCT/US2011/038188, Invitation to Pay Additional Fees mailed Aug. 5, 2011", 5 pgs.
"International Application Serial No. PCT/US2011/038188, Written Opinion mailed Oct. 14, 2011", 12 pgs.
"International Application Serial No. PCT/US2012/030294, International Preliminary Report on Patentability mailed Oct. 10, 2013", 9 pgs.
"International Application Serial No. PCT/US2012/030294, International Search Report mailed May 23, 2012", 6 pgs.
"International Application Serial No. PCT/US2012/030294, Written Opinion mailed Mat 23, 2012", 7 pgs.
"International Application Serial No. PCT/US2012/037703, International Preliminary Report on Patentability mailed Nov. 28, 2013", 10 pgs.
"International Application Serial No. PCT/US2012/037703, International Search Report mailed Sep. 21, 2012", 6 pgs.
"International Application Serial No. PCT/US2012/037703, Invitation to Pay Additional Fees mailed Jul. 19, 2012", 7 pgs.
"International Application Serial No. PCT/US2012/037703, Written Opinion mailed Sep. 21, 2012", 8 pgs.
"International Application Serial No. PCT/US2012/062738, International Preliminary Report on Patentability mailed May 15, 2014", 9 pgs.
"International Application Serial No. PCT/US2012/062738, International Search Report mailed Mar. 6, 2013", 6 pgs.
"International Application Serial No. PCT/US2012/062738, Written Opinion mailed Mar. 6, 2013", 7 pgs.

(56) References Cited

OTHER PUBLICATIONS

"International Application Serial No. PCT/US2012/064832, International Preliminary Report on Patentability mailed May 30, 2014", 9 pgs.
"International Application Serial No. PCT/US2012/064832, International Search Report mailed Feb. 6, 2013", 3 pgs.
"International Application Serial No. PCT/US2012/064832, Written Opinion mailed Feb. 6, 2013", 7 pgs.
"International Application Serial No. PCT/US2013/058921, International Preliminary Report on Patentability mailed Mar. 26, 2015", 9 pgs.
"International Application Serial No. PCT/US2013/058921, International Search Report mailed Oct. 21, 2013", 5 pgs.
"International Application Serial No. PCT/US2013/058921, Written Opinion mailed Oct. 21, 2013", 6 pgs.
"International Application Serial No. PCT/US2013/075989, International Preliminary Report on Patentability mailed Jul. 2, 2015", 10 pgs.
"International Application Serial No. PCT/US2013/075989, International Search Report mailed Mar. 6, 2014", 4 pgs.
"International Application Serial No. PCT/US2013/075989, Written Opinion mailed Mar. 6, 2014", 7 pgs.
"International Application Serial No. PCT/US2014/026413, International Preliminary Report on Patentability mailed Sep. 24, 2015", 10 pgs.
"International Application Serial No. PCT/US2014/026413, International Search Report mailed Jun. 6, 2014", 5 pgs.
"International Application Serial No. PCT/US2014/026413, Written Opinion mailed Jun. 6, 2014", 8 pgs.
"JuggerKnot™ Soft Anchor Midfoot Repair", brochure. Biomet Sports Medicine, (Jul. 2011), 12 pgs.
"JuggerKnot™ Soft Anchor. It's Small. It's strong. And it's all suture . . . ", Ordering Information brochure. Biomet Sports Medicine, (Jun. 2011), 2 pgs.
"JuggerKnot™ Soft Anchor. Labral Repair", brochure. Biomet Sports Medicine, (Apr. 2011), 12 pgs.
"JuggerKnot™ Soft Anchor: Arthroscopic and Mini-Open Rotator Cuff Repair Using JuggerKnot™ Soft Anchor—2.9mm with ALLthread™ Knotless Anchor Surgical Technique", brochure, Biomet® Sports Medicine, (2013), 16 pgs.
"Make your next tendon repair an open-and-shut case. The Teno Fix® Tendon Repair System", Teno Fix® brochure, Ortheon® Medical, (2003), 2 pgs.
"Mallory-Head Modular Calcar Revision System", Biomet Orthopedics, Inc., (2006), 20 pgs.
"Next Generation in Knee Ligament Reconstruction & Repair Technology", Suture Tensioner w/Tensiometer, Arthrex®, Inc. catalog, (2009).
"PANALOK Anchor with PDS II and ETHIBOND Suture", Mitek Products ETHICON, (1997), 12 pgs.
"Rapid Sternal Closure", KLS Martin L.P., [Online] retrieved from the internet: USPTO Private Pair, U.S. Appl. No. 13/645,964 , Matter No. 5394.230US2, (2006).
"Rotator Cuff Fixation", Acufex Fastenator System: Shoulder Arthroscopy; H-2—H-22, 22 pgs.
"SE Graft Tensioning System Surgical Technique", Linvatec Corporation copyright 2003, (2004), 12 pgs.
"SportMesh™ Soft Tissue Reinforcment, Made from . . . Artelon® optimal tissue repair", Biomet® Sports Medicine, Inc., (2007), 8 pgs.
"Sternal Cable System", Pioneer®, [Online] retrieved from the internet: U.S. Appl. No. 13/645,964 , (2010).
"The AutoCuff System", Opus Medical, [Online]. Retrieved from the Internet: <www.opusmedical.com>, (2003), 4 pgs.
"Toggleloc™ Femoral Fixation Device", Arthrotek, (Mar. 31, 2006), 8 pgs.
"TriTis™ Tibial Fixation System and Implant", brochure. Scandius Biomedical, (2006).
Albritton, Mark J, et al., "Toggleloc Fixation Device with Ziploop Technology: Biceps Tendon Reattachment", Biomet Sports Medicine, a Biomet Company Brochure 2099, (2011), 1-12.
Alford, J Winslow, et al., "Cartilage Restoration, Part 1. Basic Science, Historical Perspective, Patient Evaluation, and Treatment Options", The American Journal of Sports Medicine, 33(2), (2005), 295-306.
Andrews, James R, "Toggleloc™ Fixation Device with Ziploop™ Technology: ACL Reconstruction Bone-Tendon-Bone", Biomet Sports Medicine, a Biomet Company Brochure, (2013), 1-20.
Anitua, Eduardo, et al., "Autologous platelets as a source of proteins for healing and tissue regeneration", Thromb Haemost, vol. 91, (2004), 4-15.
Arthrotek, "A Biomet Company; Sure fire Hybrid Meniscal Device", Fall AANA, (2004), 37 pgs.
Barber, Alan F, "Uses and Abuses of Sutures and Anchors", Shoulder Scope, San Diego Shoulder Arthroscopy Library, (Jul. 1999), 6 pgs.
Barber, Alan F, "Using Sutures and Anchors", San Diego Shoulder Arthroscopy Course, 17th Annual Meetina, (Jun. 14, 2000), 9 pgs.
Charlton, Timothy, "Ziptight™ Fixation System Featuring Zip Loop™ Technology. Ankle Syndesmosis. Surgical Protocol", Biomet Sports® Medicine brochure, (Jun. 15, 2011), 8 pgs.
Edwards, Andrew, et al., "The Attachments of the Fiber Bundles of the Posterior Cruciate ligament: An Anatomic Study", Arthroscopy: The Journal of Arthroscopic and Related Surgery, vol. 23, No. 3, (Mar. 2008), 284-290.
Flavia, Namie Azato, "Traction endurance biomechanical study of metallic suture anchors at different insertion angles", Acta Ortop. Bras., vol. 11, No. 1, Sao Paulo, (Jan./Mar. 2003), pp. 25-31.
Floryan, K, et al., "Home Study Program: Intraoperative use of Autologous Platelet-Rich and Platelet-Poor Plasma for Orthopedic Surgery Patients", AORN Journal: Home Study Program, 80(4), (Oct. 2004), 667-678.
Fromm, Stuart M.D. E, Rapidloc, Meniscal Repair System, Mitek Products, Ethicon, (2001), 6 pgs.
Haynesworth, S E, et al., "Mitogenic Stimulation of Human Mesenchymal Stem Cells by Platelet Releasate Suggests a Mechanism for Enhancement of Bone Repair by Platelet Concentrate", 48th Annual Meeting of the Orthopaedic Research Society Poster No. 0462, (2002), 1 pg.
Hecker, AT, et al., "Pull-out strength of suture anchors for rotator cuff and Bankart lesion repairs", The American Journal of Sports Medicine 21(6), (1993), 874-879.
Hunt, Patrick, et al., "Development of a Perforated Biodegradable Interference Screw; Arthroscopy:", The Journal of Arthroscopic and Related Surgery, vol. 21, No. 3;, (Mar. 2005), 258-265.
Lawhorn, M D, et al., "MaxFire™ Meniscal Repair Device with Zip Loop™ Technology", Biomet Sports Medicine, (Feb. 29, 2008), 12 pgs.
Majors, Md, Roy Alan, "Meniscal repairs: proven techniques and current trends", Lippincott Williams & Wilkins, Inc.;, (2002), 30-36.
Miller, Mark D, et al., "Pitfalls Associated with FasT-Fix Meniscal Repair", Arthroscopy: The Journal of Arthroscopic and Related Surgery, vol. 18 No. 8 :, (Oct. 2002), 939-943.
Mithoefer, Kai Md, et al., "The Microfracture Technique for the Treatment of Articular Cartilage Lesions in the Knee. A Prospective Cohort Study", The Journal of Bone and Joint Surgery 87(9), (Sep. 2005), 1911-1920.
Nixon, A J, "Platelet Enriched Plasma Provides an Intensely Anabolic Vehicle for Sustained Chondrocyte Function After Implantation", 52nd Annual Meeting of the Orthopedic Research Society: Paper No. 1416, (2005), 2 pgs.
Roseberg, Md, Thomas D, "ACL Reconstruction with Acufex Director Drill Guide and Endobutton CL Fixation System", Smith & Nephew: Knee Series, Technique Guide, (2005), 12 pgs.
Saxena, Pankaj, et al., "Use of Double Wires in Sternal Closure, A Useful Technique", Texas Heart® Institute. Journal List> Tex Heart Inst J > v.33(4), (2006).
Smith, et al., "Endoscopic Meniscal Repair Using the T-Fix", (1996), 16 pgs.
Smith, et al., "Fast-Fix", Meniscal Repair System;, (2001), 3 pgs.

(56) References Cited

OTHER PUBLICATIONS

Steadman, et al., "Microfracture: Surgical Technique and Rehabilitation to Treat Chondral Defects", Clinical Orthopaedics and Related Research 391, (2001), S362-S369.
Thomas, Roseberg D, "Technique for ACL Reconstruction with Acufex Director Drill Guide and Endobutton CL", Smith & Nephew, Technique Guide, (1999), 18 pgs.
Weiler, A, et al., "Biodegradierbare Interferenzschrauben in der Kreuzbandchirurgie", Opjournal 14, (1998), 278-284.
Zeitani, Jacob M.D, "A New Sternal Reinforcement Device to Prevent and Treat Sternal Dehiscence", CTSNet, [Online]. Retrieved from the Internet: < URL: http://www.ctsnet.org/print/article/new-sternal-reinforcement-device-prevent-and-treat-sternal-dehiscence>, (Jun. 30, 2008), 6 pgs.

* cited by examiner

METHOD AND APPARATUS FOR SOFT TISSUE FIXATION

CROSS-REFERENCE TO RELATED APPLICATIONS

This application is a continuation of U.S. patent Ser. No. 18/134,897 filed on Apr. 14, 2023, which is a continuation of U.S. patent Ser. No. 18/093,114 filed on Jan. 4, 2023, which is a continuation of U.S. patent Ser. No. 16/895,246 filed on Jun. 8, 2020, now U.S. Pat. No. 11,723,648 issued on Aug. 15, 2023, which is a continuation of U.S. patent Ser. No. 15/682,187 filed on Aug. 21, 2017, now U.S. Pat. No. 10,729,421 issued on Aug. 4, 2020, which is a continuation of U.S. patent Ser. No. 14/182,038 filed on Feb. 17, 2014, now U.S. Pat. No. 9,763,656 issued on Sep. 19, 2017, which is a divisional of U.S. patent application Ser. No. 13/098,927 filed on May 2, 2011, now U.S. Pat. No. 8,652,171 issued on Feb. 18, 2014.

The entire disclosures of the aforementioned references are expressly incorporated herein by reference.

FIELD

The present disclosure relates to methods and apparatuses for securing soft tissue using a flexible suture construct and, more particularly, to flexible suture constructs including adjustable loops.

BACKGROUND

This section provides background information related to the present disclosure which is not necessarily prior art.

Surgical procedures are often performed on a body, for example, a human body or anatomy, to repair or replace various portions thereof. For example, the soft tissues of the body may need to be reattached to bones or a tear in the soft tissue may need repaired due to trauma, overuse, surgical Intervention, or disease.

Soft tissues can be reattached to a bone or repaired using fastening devices such as screws, staples, and various types of suture anchors. Soft tissues are often fixed to various positions on the bone. For example, to replace a natural tendon fixation point or to replace the tendon itself, it may be desired to fix a graft to a selected bone area. One method of fixing a soft tissue to the selected area is to pass one end of a suture through a selected portion of the soft tissue to form a knot and fix another end of the suture to a selected area on the bone with a suture anchor. The present teachings provide surgical methods and apparatuses for improving engagement between a suture construct and a soft tissue.

SUMMARY

This section provides a general summary of the disclosure, and is not a comprehensive disclosure of its full scope or all of its features.

The present teachings provide surgical methods of attaching a first tissue to a second tissue. In one example, an exemplary method can include passing at least two adjustable loops through at least the first tissue to extend from an outer surface of the first tissue opposite a tissue engaging surface facing the second tissue, and attaching the two adjustable loops to a first selected area of the second tissue. The method can further include positioning a locking member within the two adjustable loops such that the locking member extends between the two adjustable loops adjacent the outer surface, engaging the locking member with the outer surface by drawing the two adjustable loops towards the outer surface, and compressing the first tissue between the locking member and the second tissue by tensioning the two adjustable loops.

In another example, the method can include attaching a suture anchor including a flexible construct to the second tissue, wherein the flexible construct extends from the suture anchor and includes at least two self-locking adjustable loops and tensioning members extending from the two adjustable loops. The method can further include passing the at least two self-locking adjustable loops and the tensioning members through the first tissue to extend from an outer surface of the first tissue opposite a tissue engaging surface facing the second tissue. The method can further include positioning an elongated locking member within the two self-locking adjustable loops such that the locking member extends between the two self-locking adjustable loops adjacent the outer surface. The method can further include cinching the two self-locking adjustable loops around the locking member by selectively pulling on the tensioning members, engaging the locking member with the outer surface of the first tissue, and compressing the first tissue between the locking member and the second tissue by selectively pulling on the tensioning members.

In another example, the method can include attaching a self-locking, first adjustable loop to a first anchor at a first end of the first adjustable loop and a second anchor at a second end of the first adjustable loop, wherein the first adjustable loop includes a first tensioning member. The method can further include attaching a self-locking, second adjustable loop to a third anchor at a first end of the second adjustable loop and a fourth anchor at a second end of the second adjustable loop, wherein the second adjustable loop includes a second tensioning member. The method can further include passing the first ends of the first and second adjustable loops through separate apertures in the first tissue to extend from an outer surface of the first tissue opposite a tissue engaging surface facing the second tissue. The method can further include attaching the first and third anchors to the second tissue in a first selected area overlapping the first tissue, and attaching the second and fourth anchors to the second tissue in a second selected area spaced apart from the first selected area. The method can further include positioning a locking member between the outer surface and the first and second adjustable loops, and engaging the first and second adjustable loops with the locking member by pulling on the first and second tensioning members. The method can further include engaging the locking member with the outer surface of the first tissue, and compressing the first tissue between the locking member and the second tissue by pulling on the first and second tensioning members. The second selected area can be disposed adjacent an end of the first tissue.

The present teachings also provide tissue fixation apparatuses that can be used to attach a first tissue to a second tissue. In one example, an exemplary tissue fixation apparatus can include a flexible construct and an elongated locking member. The flexible construct can include at least two adjustable loops, tensioning members, and an anchor. The two adjustable loops can be configured to pass through the first tissue, and to be spaced apart along an outer surface of the first tissue in a first direction. The tensioning members can extend from the two adjustable loops, and can be configured to reduce the two adjustable loops from a first size to a second size. The anchor can be configured to attach the flexible construct to the second tissue in a first selected area of the second tissue. The locking member can be configured to be received within the two adjustable loops at the first size, and to engage the two adjustable loops at the second size.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
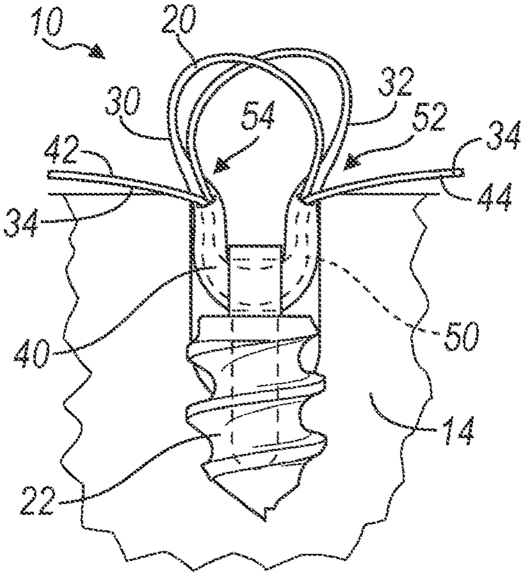
FIGS. 1-3 are fragmentary side views illustrating an exemplary tissue fixation device and method for affixing two tissues together using the tissue fixation device according to the present teachings.
Figure 2:
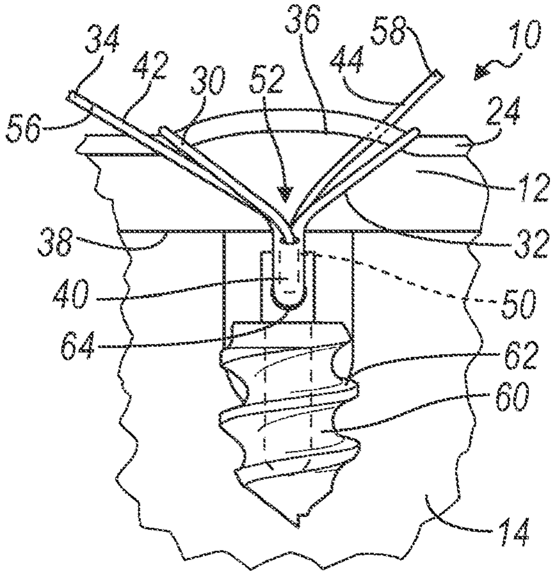
Figure 3:
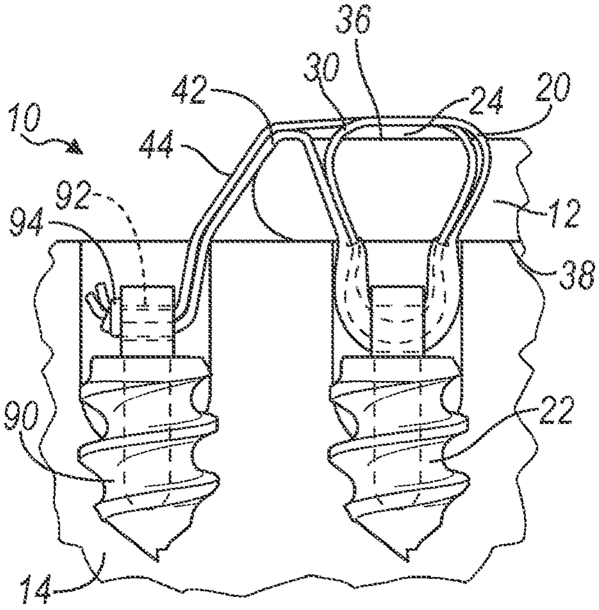

With particular reference to FIGS. 1-3, an exemplary tissue fixation device (TFD) 10 for affixing a first tissue 12 to a second tissue 14 is shown. The first tissue 12 and the second tissue 14 can be independently selected from soft tissue or bone to provide any one of a soft tissue-to-bone, a soft tissue-to-soft tissue, or a bone-to-bone connection. For purposes of the example shown in FIGS. 1-3, a soft tissue-to-bone connection is described. Various components of the TFD 10 are described first and then various surgical methods for affixing the first tissue 12 to the second tissue 14 using the TFD 10 are described.

Generally, the TFD 10 can be composed of various biocompatible materials, including bioresorbable and non-bioresorbable materials. The TFD 10 can include a flexible suture construct 20, a suture anchoring member 22, and a locking member 24. Generally, the suture construct 20 can be formed of a monofilament, a braided fiber or strand, or other flexible member or suture used to affix the tissues 12, 14. The suture construct 20 can include at least two adjustable loops 30, 32 and at least one tensioning member 34. In various implementations, as illustrated by the examples discussed below, a tensioning member 34 may be provided for each of the loops 30, 32. Additionally, the loops 30, 32 and the tensioning member or members 34 can be formed from a single suture construct.

Together, the loops 30, 32 and the tensioning member or members 34 can cooperate to cinch the loops 30, 32 and to create tension in the suture construct 20. In this way, the loops 30, 32 and the tensioning member or members 34 can cooperate to draw and/or compress the tissues 12, 14 together. The loops 30, 32 can be adapted to both receive and engage the locking member 24. In various implementations, the loops 30, 32 can be self-locking adjustable loops, as illustrated by the examples discussed below. Together, the loops 30, 32 and the locking member 24 can cooperate to engage a major or outer surface 36 of the first tissue 12 opposite a tissue engaging surface 38 to be engaged with the second tissue 14. The tensioning member or members 34 can be configured to adjust the suture construct 20 between an untensioned state and a tensioned state.

The loops 30, 32, the tensioning member or members 34, and/or the suture anchoring member 22 can be created using various surgical methods and suture constructs. For example, whip and/or mattress stitching methods employing a suture thread can be used. As another example, self-locking adjustable loop suture constructs can be employed. Exemplary self-locking adjustable loop suture constructs are disclosed in commonly assigned U.S. Pat. Nos. 7,658,751 and 7,601,165, the entire disclosures of which are expressly incorporated herein by reference.

According to the example shown in FIGS. 1-3, the suture construct 20 can include a braided body 40 and tensioning strands 42, 44 that form self-locking adjustable loops 30, 32 and separate tensioning members 34 for each of the loops 30, 32. The braided body 40 and the tensioning strands 42, 44 can be formed in a single suture construct using a braiding process for braiding fibers composed of a biocompatible material. The braided body 40 can define a longitudinal passage 50 and apertures 52, 54 longitudinally spaced along and in communication with the longitudinal passage 50. The apertures 52, 54 can be created during the braiding process as loose portions between pairs of fibers. The tensioning strands 42, 44 can be created using one or more of the fibers used to create the braided body. In this way, the tensioning strands 42, 44 can be integral to the braided body 40.

An end 56 of the tensioning strand 42 can be inserted through the aperture 52 and passed through the longitudinal passage 50 and out the aperture 54 to create the loop 30. Similarly, an end 58 of the tensioning strand 44 can be inserted through the aperture 54 and passed through the longitudinal passage 50 and out the aperture 52 to create the loop 32. Sizes or diameters of the loops 30, 32 can be adjusted by retracting or advancing the tensioning strands 42, 44, respectively, within the longitudinal passage 50.

The suture anchoring member 22 can be configured to affix the suture construct 20 to the second tissue 14. In various implementations, the suture anchoring member 22 can be created by the suture construct 20 alone, or in combination with, a separate component. According to the example shown in FIGS. 1-3, the suture anchoring member 22 can be a separate fastener or suture anchor 60 including external threads 62 configured to threadingly engage the second tissue 14 and an eyelet 64 configured to receive the braided body 40. It should be understood that the suture anchor 60 is merely exemplary in nature, and that other suture anchors can be used. For example, threaded or non-threaded suture anchors can be used. The suture anchor 60 can be composed of various bio resorbable materials such as, for example, the LactoSorb® material available from Biomet Sports Medicine, LLC of Warsaw, Indiana. Alternately, or additionally, the suture anchor may be composed of other non-bioresorbable materials, such as, for example, titanium-based materials. Various bioresorbable and non-bioresorbable, soft and hard suture anchors are available from, for example, Biomet Sports Medicine, LLC of Warsaw, Indiana.

The locking member 24 can be an elongated member that is received within each of the loops 30, 32, and that spans a lateral distance between the loops 30, 32. The locking member 24 can be further configured to engage and thereby restrain the loops 30, 32 from pulling through the first tissue 12 and to maintain the lateral distance between the loops 30, 32, when the suture construct 20 is in the tensioned state. For example, the locking member 24 can be constructed to have a predetermined strength for a period after implantation for resisting pull through by the loops 30, 32. The locking member 24 can be further sized to provide a predetermined bearing surface for distributing compressive loads to the first tissue 12 generated by the suture construct 20 in the tensioned state. More specifically, the locking member 24 can transmit compressive loads received from the loops 30, 32 to the first tissue 12.

Generally, the locking member 24 can be composed of various bioresorbable or non-bioresorbable materials. The locking member 24 can include flexible and/or semi-rigid sections that enable the locking member 24 to conform to the outer surface 36 of the first tissue 12, yet distribute the compressive loads to the first tissue 12 in a predetermined manner. According to the example shown in FIGS. 1-3, the locking member 24 can be a length of a flexible strip of surgical fabric such as, for example, surgical tape. The surgical tape can include braided fibers. The locking member 24 can be cut to a predetermined length and/or cut to a custom length during a surgical procedure based on a particular patient.

Figure 4:
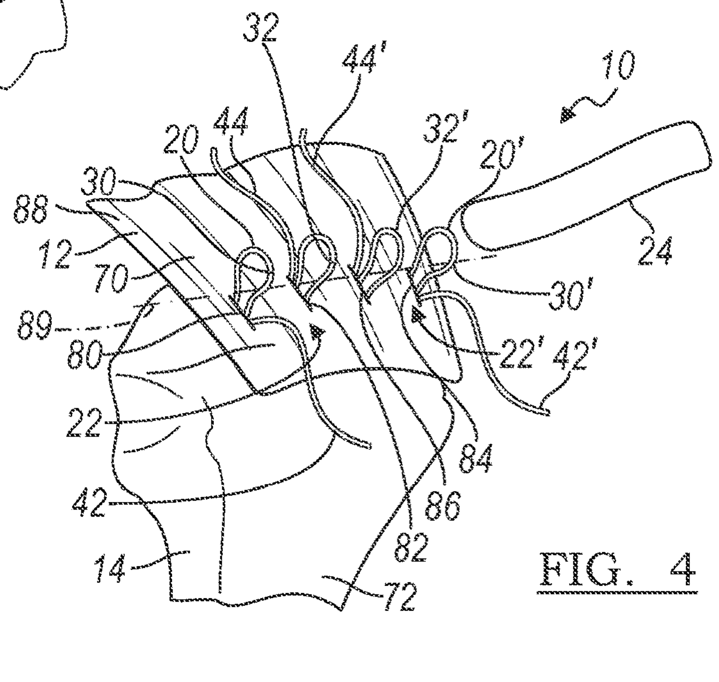
FIGS. 4-6 are fragmentary environmental perspective views illustrating an exemplary method of using the tissue fixation device shown in FIGS. 1-3 to affix a rotator cuff to a humerus.
Figure 5:
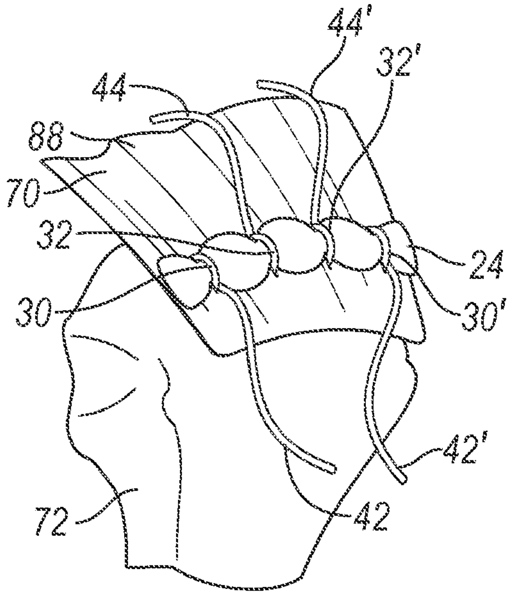
Figure 6:
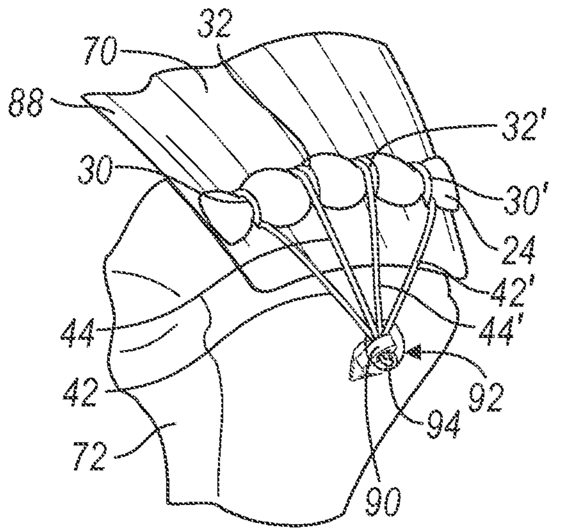

With additional reference to FIGS. 4-6, an exemplary surgical method for affixing the tissues 12, 14 together using the TFD 10 according to the present teachings will now be described. For exemplary purposes, the method includes affixing a rotator cuff 70 to a humerus 72. In various implementations, the TFD 10 and the corresponding method can include two or more suture constructs, such as the suture construct 20, with a single locking member, such as the locking member 24. As illustrated in FIGS. 4-6, the TFD 10 can further include a second suture construct 20' substantially similar to the suture construct 20. The second suture construct 20' can be coupled to the second tissue 14 via a second suture anchoring member 22' substantially similar to the suture anchoring member 22. For purposes of the following description, corresponding reference numerals are used to indicate corresponding parts of the suture constructs 20, 20' throughout the several views of the drawings.

With continued reference to FIGS. 1-6 the method can include preparing the humerus 72 to receive suture anchoring members 22, 22' in a selected area where the rotator cuff 70 is to be attached. The humerus 72 can be prepared by creating threaded holes in the humerus 72 in selected areas, each at a desired angle of insertion. The threaded holes can be created to a depth that enables the suture anchoring members 22, 22' and/or portions of the suture constructs 20, 20' to be located beneath an outer surface of the humerus 72.

Next, suture constructs 20, 20' can be coupled to the humerus 72 via the suture anchoring members 22, 22', respectively. The suture constructs 20, 20' can be coupled to the suture anchoring members 22, 22' prior to, at the same time, or after securing the suture anchoring members 22, 22' to the humerus 72. According to the examples shown in FIGS. 1-6, the suture construct 20 can be coupled to the suture anchoring member 22 prior to threadingly engaging the suture anchoring member 22 with the humerus 72. More particularly, tensioning strand 42 can be inserted through the eyelet 64 until the braided body 40 is approximately centered within the eyelet 64. Next, the tensioning strands 42, 44 can be passed through the longitudinal passage 50 to create the loops 30, 32 as discussed above. The suture construct 20' can be coupled to the suture anchoring member 22' and subsequently to the tissue 14 in a similar manner.

Next, with particular reference to FIG. 4, the loops 30, 32 and tensioning strands 42, 44 can be passed through incisions or apertures 80, 82 formed into the rotator cuff 70. Similarly, the loops 30', 32' and tensioning strands 42', 44' can be passed through apertures 84, 86 of the rotator cuff 70. The apertures 80, 82, 84, 86 can be spaced apart and can extend generally parallel to one another as shown. In various implementations, one or more of the tensioning strands 42, 44, 42', 44' can be passed between the tissues 12, 14, rather than through the corresponding apertures 80, 82, 84, 86. The apertures 80, 82, 84, 86 can be created prior to or at the same time as the passing of the corresponding loops 30, 32, 30', 32' and the tensioning strands 42, 44, 42', 44'. The loops 30, 32, 30', 32' and tensioning strands 42, 44, 42', 44' can be passed using a separate needle or other suitable suture passer or device. For example, suitable devices include devices sold under the trade names "BiPass™", SpeedPass™", and "ArthroPass™", all made by Barnet Sports Medicine, LLC of Warsaw, Indiana.

The loops 30, 32, 30', 32' can be passed such that distal ends of the loops 30, 32, 30', 32' are spaced apart along a major or outer surface 88 of the rotator cuff 70. The loops 30, 32, 30', 32' can be spaced apart along a line or axis 89 to face or open towards each other as shown. The loops 30, 32, 30', 32' can be spaced apart to span a selected area of the rotator cuff 70 to be attached to the humerus 72. The tensioning strands 42, 44, 42', 44' can be passed through the same apertures 80, 82, 84, 86 as the corresponding loops 30, 32, 30', 32' as shown, or through separate, spaced apertures as discussed in further detail below. Next, as shown between FIGS. 4-5, the locking member 24 can be passed through and positioned within each of the loops 30, 32, 30', 32'. Sizes or diameters of the loops 30, 32, 30', 32' can be adjusted to enable the locking member 24 to be passed through the loops 30, 32, 30', 32'. The diameters can be adjusted as discussed above prior to or when positioning the locking member 24.

With the locking member 24 thus positioned, the tensioning strands 42, 44, 42', 44' can be selectively pulled to cinch the loops 30, 32, 30', 32' around the locking member 24 and to draw the locking member 24 into engagement with the rotator cuff 70. With the locking member 24 engaged, the tensioning strands 42, 44, 42', 44' can be further pulled to further close and tension the loops 30, 32, 30', 32' and draw the locking member 24 towards the suture anchoring members 22, 22'. Further drawing the locking member 24 can draw the rotator cuff 70 in close proximity with the humerus 72 and subsequently compress the rotator cuff 70, thereby creating tension in the suture constructs 20, 20'. More specifically, the rotator cuff 70 can be drawn into a desired relationship with the humerus 72. FIGS. 1 and 4 illustrate the suture constructs 20, 20' in an untensioned state. FIGS. 2, 3, and 5 illustrate the suture constructs 20, 20' in a tensioned state.

Tension in the loops 30, 32, 30', 32' can be retained by the self-locking features of the constructs 20, 20' without continuing to pull on the tensioning strands 42, 44, 42', 44'. Although not specifically shown, with the rotator cuff 70 and the humerus 72 in the desired relationship, one or more of the tensioning strands 42, 44, 42', 44' can be cut to a desired length, for example, flush to the outer surface 88. In this way, excess length can be removed. Alternately, the tensioning strands 42, 44, 42', 44' can be drawn past an end of the rotator cuff 70 and attached to a selected area of the humerus 72 as shown in FIG. 6. More particularly, the tensioning strands 42, 44, 42', 44' can be drawn and attached so as to extend in a direction generally parallel to a direction in which the rotator cuff 70 contracts during muscle action. Tensioning strands 44, 44' can be drawn around the locking member 24 and positioned to adjoin the loops 32, 32', respectively, as shown.

The tensioning strands 42, 44, 42', 44' can be attached using another suture anchoring member 90 substantially similar to the suture anchoring member 22. The tensioning strands 42, 44, 42', 44' can be coupled to the suture anchoring member 90 by passing the tensioning strands 42, 44, 42', 44' through an eyelet 92 of the suture anchoring member 90 and creating a knot 94. The humerus 72 can be prepared to receive the suture anchoring member 90 in substantially the same manner as the suture anchoring members 22, 22'.

Figure 7:
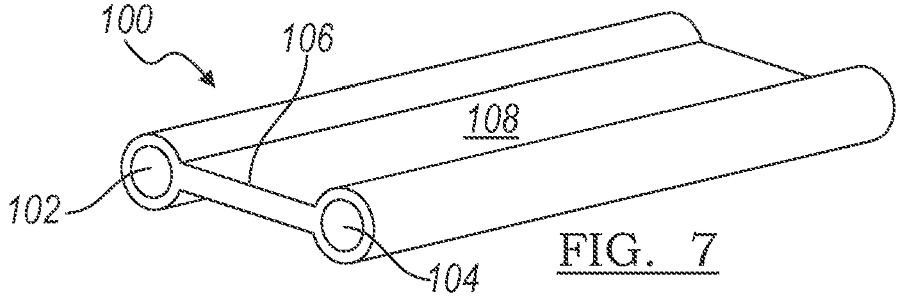
FIG. 7 is a perspective view illustrating an exemplary locking member according to the present teachings.
Figure 8:
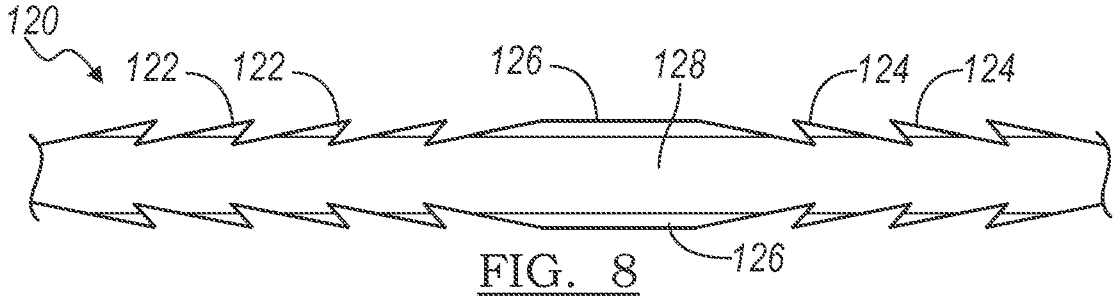
FIG. 8 is a fragmentary top view illustrating another exemplary locking member according to the present teachings.
Figure 9:
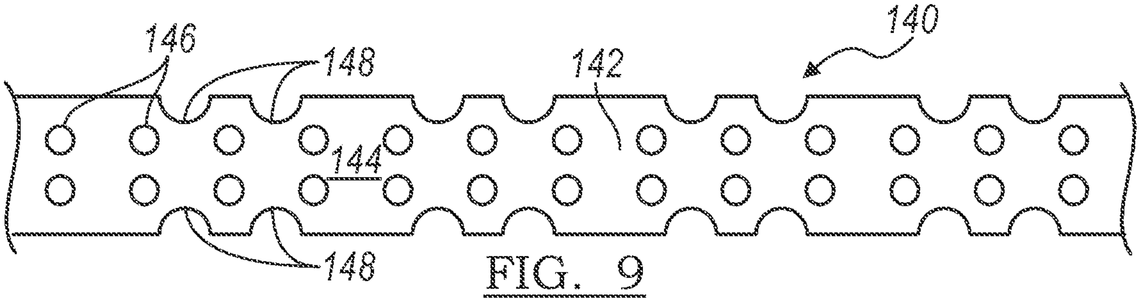
FIG. 9 is a fragmentary top view illustrating another exemplary locking member according to the present teachings.

With particular reference to FIGS. 7-14, various other exemplary configurations of the locking member 24 according to the present teachings are shown. FIGS. 7-9 illustrate various flexible, elongated, and generally thin, flat configurations that can be cut to a desired length and/or width from a larger stock of material prior to and/or during a surgical procedure. With particular reference to FIG. 7, an exemplary locking member 100 can include monofilament fibers 102, 104 connected along a length by a fabric of intertwined threads, or braided fabric 106. The monofilament fibers 102, 104 can have diameters greater than a thickness of the braided fabric 106. The braided fabric 106 can circumscribe the monofilament fibers 102, 104 and include a central section 108 that spans a width between the monofilament fibers 102, 104. The locking member 100 can be oriented between adjacent loops (e.g., loops 30, 32) of a suture construct so that the monofilament fibers 102, 104 span a distance between the loops. Alternately, the locking member 100 can be oriented so that the central section 108 spans the distance between the loops and the larger side sections created by the monofilament fibers 102, 104 engage opposite sides of the loops. In this way, the monofilament fibers 102, 104 can provide a loop engaging feature for fixing ends of the locking member 100 relative to the loops and/or for fixing the distance between the loops.

Referring now to FIG. 8, another exemplary locking member 120 can include outwardly extending edges or protrusions 122, 124 that create peripheral recesses along a length that are configured to engage two or more loops (e.g., loops 30, 32) of a suture construct. At least two protrusions 122, 124 can be provided to fixedly position the loops and thereby maintain a distance between the loops when the loops are engaged. The protrusions 122, 124 can extend at an angle, for example towards each other, to create barbs or hooks as shown for engaging and securely holding the loops at a separated distance. In an exemplary construction, the locking member 120 can include monofilament fibers 126 connected along a length by a braided fabric 128 in a substantially similar way as the locking member 100. The protrusions 122, 124 can be created using various methods. For example, the protrusions 122, 124 can be created during the braiding process used to create the braided fabric 128. As another example, a cutting process, for example a die cutting process, can be used to create the protrusions 122, 124.

Referring now to FIG. 9, another exemplary locking member 140 can include a length or strip of a non-woven bio-textile 142, such as, for example, the Scaftex® materials offered by Biomedical Structures of Warwick, Rhode Island. Non-woven bio-textiles can be manufactured from a variety of synthetic, absorbable polymeric fibers, including polyglycolic acid (PGA), poly-L-lactide (PLLA), poly DL-lactide-co-glycolide acid (PLGA), blends, and other fibers. The bio-textile 142 can include first regions 144 having a higher density than second regions 146. The first and second regions 144, 146 can have a predetermined and regular arrangement with respect to a broad or major surface of the locking member 140 configured to engage loops of a suture construct. The bio-textile 142 can be die cut from a sheet to include peripheral depressions 148 along opposite sides configured to engage the loops of the suture construct. The peripheral depressions 148 can adjoin the higher density first regions 144. In this way, the bops can engage and be retained in higher density regions specifically suited to restrain the loops from pulling through the adjoining tissue.

FIGS. 10-14 illustrate various adjustable locking members according to the present teachings. Generally, the locking members are flexible and elongate configurations created using various adjustable loop constructions. The adjustable loop constructions can enable adjustments to sizes or diameters of one or more loop sections and an overall length of the locking members prior to and during a surgical procedure. The adjustments can further enable loop engaging members at opposite ends of the locking members to be brought into engagement with one or more loops of a suture construct. The loop engaging members can be deformable between a first configuration when the locking members are untensioned and/or unengaged with loops of a suture construct and a second configuration facilitating engagement between the locking members and the loops. Additional suitable adjustable loop constructions are disclosed in commonly assigned U.S. patent application Ser. No. 11/541,506, the entire disclosure of which is expressly incorporated herein by reference.

Figure 10:
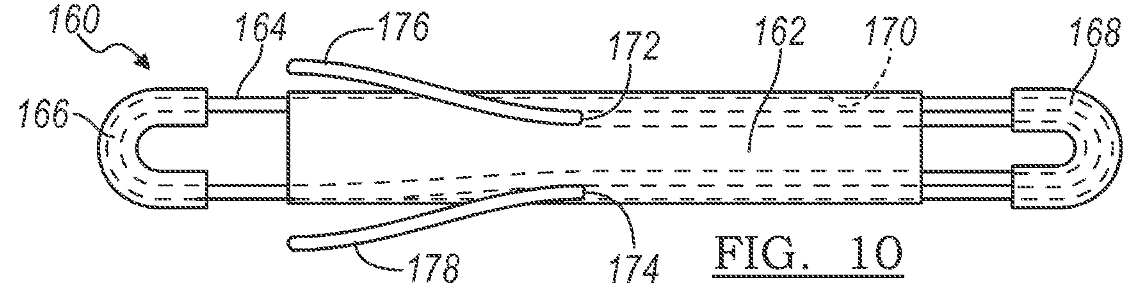
FIG. 10 is a top view illustrating an exemplary adjustable locking member according to the present teachings.

With particular reference to FIG. 10, an exemplary adjustable locking member 160 can include an adjustable loop construct including a sleeve 162, a fiber or strand 164, and sleeves 166, 168. The sleeve 162 can have a braided construction and can define a longitudinal passage 170 and apertures 172, 174. The strand 164 can be wrapped into a single loop or coil passing through the longitudinal passage 170 and the sleeves 166, 168 as shown to create adjustable loop sections that extend from opposite ends of the sleeve 162. Ends 176, 178 of the strand 164 can pass through the apertures 172, 174 and can be used as tensioning members used to adjust sizes or diameters of the adjustable loop sections and thereby adjust an overall length of the locking member 160 or, more specifically, a distance between the sleeves 166, 168. The sleeves 166, 168 can have a braided construction similar to the sleeve 162 and can function as loop engaging members.

Figure 11:
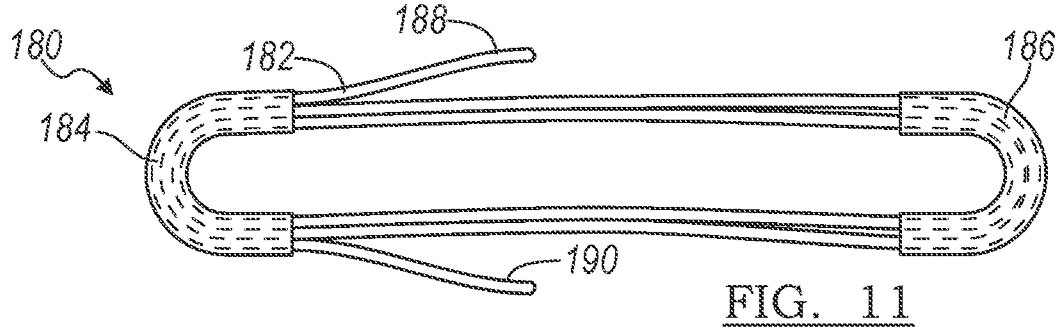
FIG. 11 is a top view illustrating another exemplary adjustable locking member according to the present teachings.

Referring now to FIG. 11, another exemplary adjustable locking member 180 can include an adjustable loop construct including a fiber or strand 182 and sleeves 184, 186. The strand 182 can be wrapped into a single loop or coil passing through the sleeves 184, 186 as shown to create an adjustable closed loop configuration. Ends 188, 190 of the strand 182 can extend through the sleeves 184, 186 and exit at opposite ends of the sleeve 184. A size or diameter of the loop or coil and an overall distance between the sleeves 184, 186 can be adjusted by pulling on one or both the first and second ends 188, 190. The sleeves 184, 186 can include flexible sections to facilitate adjustments and/or semi-rigid sections to maintain a predetermined curvature or diameter of the sleeves 184, 186 after the adjustments. The sleeves 184, 186 can also function as loop engaging members deformable between a first configuration and a second configuration. The first configuration can be a first shape configured to maintain an overall shape of the locking member 180 prior to engaging the locking member 180 with loops of a suture construct, for example, the shape shown in FIG. 11. The second configuration can be a second shape different from the first shape configured to facilitate engagement between the locking member 180 and the loops of the suture construct, for example, the cinched shape shown in FIG. 16 and discussed below.

Figure 12:
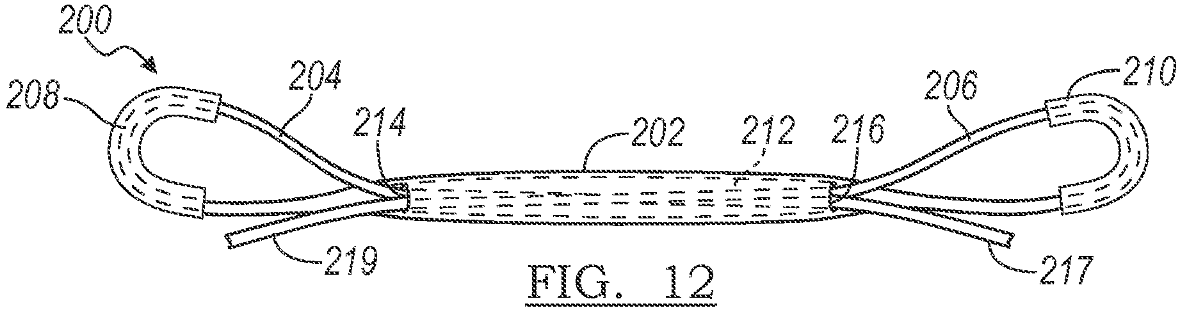
FIG. 12 is a top view illustrating another exemplary adjustable locking member according to the present teachings.

Referring now to FIG. 12, another exemplary adjustable locking member 200 can include a self-locking adjustable loop construct formed from a braided suture construct. The locking member 200 can include a braided body 202, fibers or strands 204, 206, and sleeves 208, 210. The braided body 204 can have a longitudinal passage 212 and apertures 214, 216. The longitudinal passage 212 and the apertures 214, 216 can be sized relative to the strands 204, 206 to provide the self locking feature. A first end 217 of the strand 204 can be passed through the sleeve 208, then through the aperture 214 and the longitudinal passage 212 and out the aperture 216 to create a first self-locking adjustable loop at one end of the adjustable locking member 200. A second end 219 of the strand 206 can be passed through the sleeve 210, then through the aperture 216 and the longitudinal passage 212 and out the aperture 214 to create a second self-locking adjustable loop at an opposite end.

The apertures 214, 216 can be loose portions between pairs of fibers forming the braided body 204. While two apertures 214, 216 are shown, additional apertures can be provided so that each of the strands 204, 206 can be passed through separate apertures to create the adjustable loops. Sizes or diameters of the adjustable loops can be separately adjusted by selectively pulling on the first and second ends 217, 219. By adjusting the diameter of one or both of the loops, an overall length of the adjustable locking member 200 and, more particularly, a distance between the sleeves 208, 210 can be adjusted.

Figure 13:
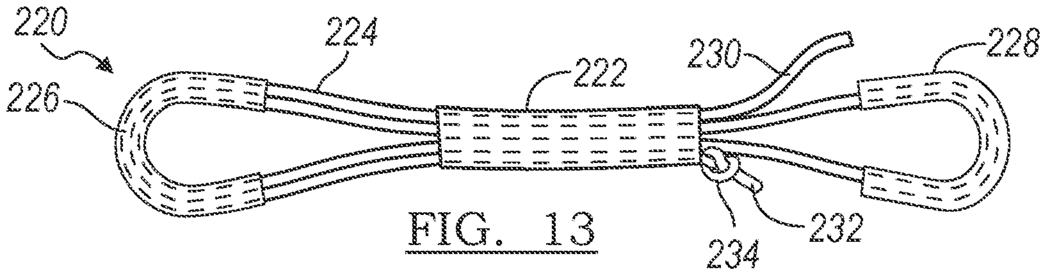
FIG. 13 is a top view illustrating another exemplary adjustable locking member according to the present teachings.

Referring now to FIG. 13, another exemplary adjustable locking member 220 can include an adjustable loop construct including a tubular body 222, a fiber or strand 224, and sleeves 226, 228. The strand 224 can be wound in a single loop or coil passing through the tubular body 222 and the sleeves 226, 228, as shown to create two adjustable loop sections extending from opposite ends of the tubular body 222. First and second ends 230, 232 of the strand 224 can pass through the tubular body 222 to exit at one of the opposite ends. The first end 230 can be a free end that functions as a tensioning member that can be pulled to simultaneously adjust sizes or diameters of the adjustable loop sections and thereby adjust a distance between the sleeves 226, 228. The second end 232 can be tied in a knot 234 that engages the tubular body 222 to prevent the second end 232 from pulling through the tubular body 222 when making adjustments.

Figure 14:
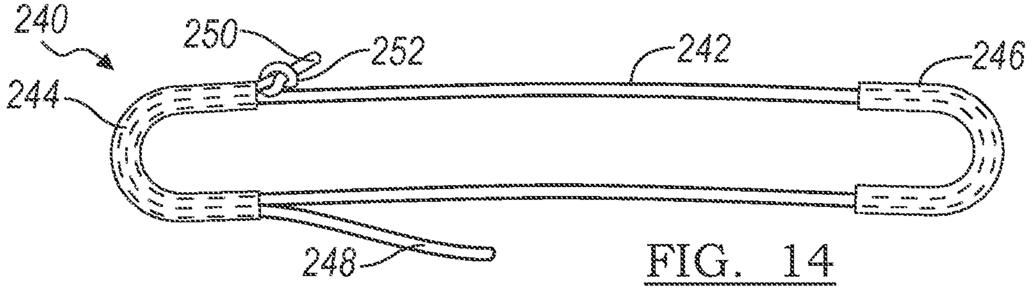
FIG. 14 is a top view illustrating another exemplary adjustable locking member according to the present teachings.

Referring now to FIG. 14, another exemplary adjustable locking member 240 can include an adjustable loop construct including a fiber or strand 242 and sleeves 244, 246. The strand 242 can be wound into a single loop or coil passing through the sleeves 244, 246, as shown, to create an adjustable closed loop configuration similar to that of the locking member 180 discussed above. First and second ends 248, 250 can exit opposite ends of the sleeve 244. The first end 248 can be a free end that functions as a tensioning member. The second end 250 can be tied in a knot 252 that engages the sleeve 244 to prevent the second end 250 from pulling through the sleeve 244 when pulling on the first end 248 to make adjustments.

Figure 15:
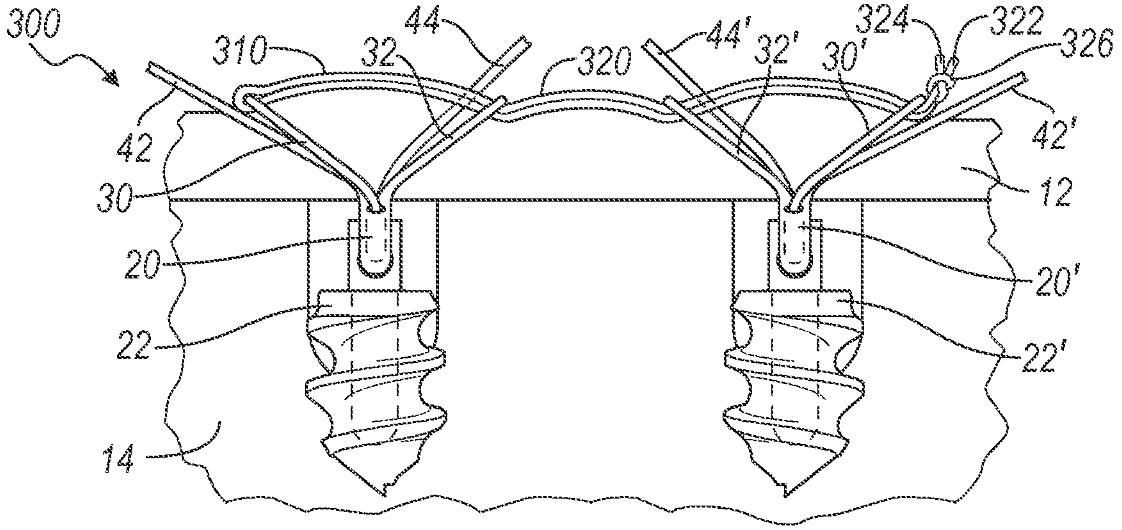
FIG. 15 is a fragmentary side view illustrating an exemplary method for coupling a locking member to a flexible suture construct according to the present teachings.

With particular reference to FIG. 15, another TFD 300 and surgical method for using the TFD 300 for affixing the first tissue 12 to the second tissue 14 is shown. The TFD 300 and the method illustrate alternate features that can be employed to engage a locking member with two or more loops of a suture construct, according to the present teachings. For exemplary purposes, the TFD 300 can include the suture constructs 20, 20' and the suture anchoring members 22, 22'. The TFD 300 can further include a locking member 310. The locking member 310 can incorporate one or more features of the locking members 24, 100, 120, 140, 160, 180, 200, 220, 240 discussed above. According to the example shown in FIG. 15, the locking member 310 can be a fiber or strand 320 having first and second ends 322, 324.

With continued reference to FIG. 15, an exemplary method of using the TFD 300 can include coupling the suture constructs 20, 20' to the second tissue 14 and passing the loops 30, 32, 30', 32' through the first tissue 12 in substantially the same manner as described above for the TFD 10. Next, with the suture constructs 20, 20' in an untensioned state, the first end 322 can be passed through a first end loop, for example, the loop 30', and then successively through the remaining loops 32', 32, 30 in that order. Next, the strand 320 can be wrapped around a second end loop, here, the loop 30, by pulling the first end 322 back towards the adjacent loop 32. Next, the first end 322 can be successively passed back through the loops 32, 32', 30' in that order.

Once the strand 320 is routed through the loops 30, 32, 30', 32' in the foregoing manner, the tensioning strands 42, 44, 42', 44' can be selectively pulled to cinch the loops 30, 32, 30', 32' around the strand 320 and to draw the strand 320 into engagement with the first tissue 12. With the strand 320 engaged, a distance between the loops 30, 30' can be adjusted by manipulating (e.g., pulling) one or both the first and second ends 322, 324. Next, the first and second ends 322, 324 can be secured together using a knot 326 that functions as a loop engaging member that engages the loop 30' and thereby inhibits the loops 30, 30' from separating during subsequent steps.

Next, the tensioning strands 42, 44, 42', 44' can be further selectively pulled to draw the loops 30, 32, 30', 32' and the strand 320 towards the suture anchoring members 22, 22'. Further drawing the loops 30, 32, 30', 32' can draw the first tissue 12 in close proximity with the second tissue 14 in a desired relationship, and subsequently compress the first tissue 12 thereby creating tension in the suture constructs 20, 20'. FIG. 15 illustrates the suture constructs 20, 20' in a tensioned state. With the first and second tissues in the desired relationship, the tensioning strands 42, 44, 42', 44' can be drawn under tension and attached to a selected area of the second tissue 14 in any suitable manner. For example, the tensioning strands 42, 44, 42', 44' can be attached in a manner substantially similar to that described above for the TFD 10.

Figure 16:
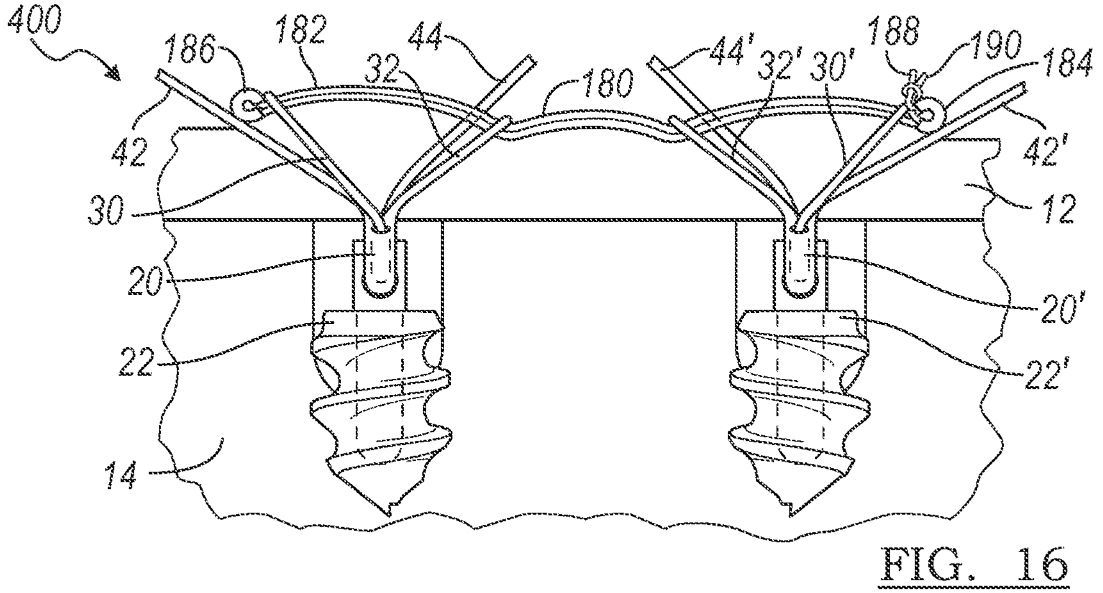
FIG. 16 is a fragmentary side view illustrating another exemplary method for coupling a locking member to a flexible suture construct according to the present teachings.

With particular reference to FIG. 16, another TFD 400 and surgical method for using the TFD 400 for affixing the first tissue 12 to the second tissue 14 will now be described. The TFD 400 and the method illustrate alternate features according to the present teachings that can be employed to engage loop engaging members of an adjustable locking member with two or more loops of a suture construct. For purposes of the example shown in FIG. 16, the locking member 180 shown in FIG. 11 can be employed in the TFD 400. The TFD 400 can include the suture constructs 20, 20' and the suture anchoring members 22, 22'.

With reference to FIG. 11 and FIG. 16, an exemplary method of using the TFD 400 can include coupling the suture constructs 20, 20' to the second tissue 14 and passing the loops 30, 32, 30', 32' through the first tissue 12 in substantially the same manner as described above for the TFD 10. Next, with the TFD 400 in an untensioned state, the locking member 180 can be passed through and positioned within the loops 30, 32, 30', 32' such that ends of the locking member 180 extend past the end loops 30, 30'. More particularly, the locking member 180 can be positioned such that the sleeves 184, 186 are disposed outboard of the end loops 30, 30'.

Once the locking member 180 is routed through the loops 30, 32, 30', 32' in the foregoing manner, the tensioning strands 42, 44, 42', 44' can be selectively pulled to cinch the loops 30, 32, 30', 32' around the locking member 180 and to draw the locking member 180 into engagement with the first tissue 12. With the locking member 180 engaged, the sleeves 184, 186 can be brought into engagement with the loops 30, 30', respectively, by pulling on one or both the ends 188, 190. The sleeves 184, 186 can deform from a first configuration having a first shape (see FIG. 11) to a second configuration having a cinched shape as shown in FIG. 16 that resists pull through. Once the sleeves 184, 186 are engaged, a distance between the loops 30, 30' can be reduced by further pulling on one or both of the ends 188, 190. Next, the first and second ends 188, 190 can be tied together to create the knot 326 that engages the sleeve 184 and thereby fixes the length of the locking member 180 and the distance between the loops 30, 30'.

Next, the tensioning strands 42, 44, 42', 44' can be further selectively pulled to draw the locking member 180 towards the suture anchoring members 22, 22'. Further drawing the loops 30, 32, 30', 32' can draw the first tissue 12 in close proximity with the second tissue 14 in a desired relationship and subsequently compress the first tissue 12, thereby creating tension in the suture constructs 20, 20'. FIG. 16 illustrates the suture constructs 20, 20' in a tensioned state. With the first and second tissues 12, 14 in the desired relationship, the tensioning strands 42, 44, 42', 44' can be drawn under tension and attached to a selected area of the second tissue 14 in any suitable manner. For example, the tensioning strands 42, 44, 42', 44' can be attached in a manner substantially similar to that described above for the TFD 10.

Figure 17:
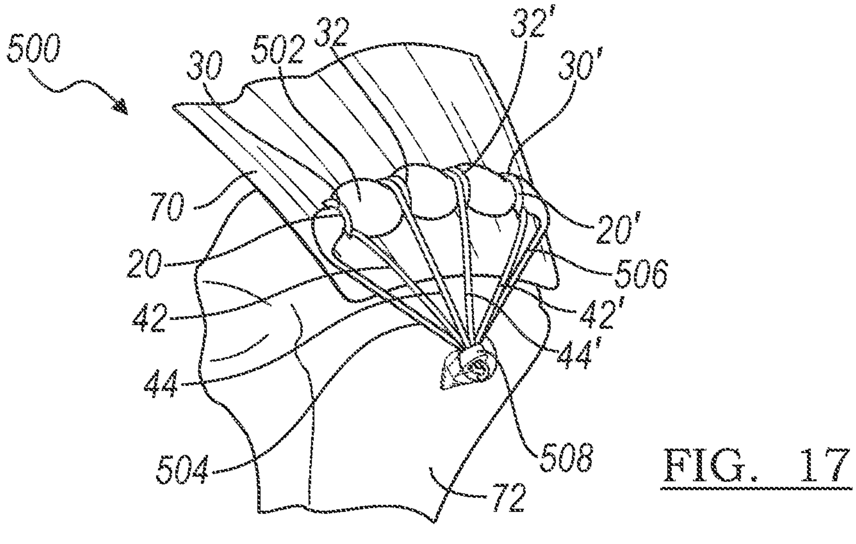
FIG. 17 is a fragmentary environmental perspective view illustrating another exemplary method for affixing a rotator cuff to a humerus using another tissue fixation device according to the present teachings.

With particular reference to FIG. 17, another TFD 500 and surgical method of using the TFD 500 for affixing two tissues according to the present teachings will now be described. The TFD 500 can be used, for example, to affix the rotator cuff 70 to the humerus 72. The TFD 500 and the method illustrate alternate features according to the present teachings including coupling ends of a locking member with a tensioning member of a suture construct. In this way, the locking member can assist the suture construct to resist tension generated in one or both the tissues due to muscle contraction.

For purposes of the example shown in FIG. 17, the TFD 500 can include the self-locking suture constructs 20, 20', the suture anchoring members 22, 22', and a locking member 502. The locking member 502 can be similar to the locking member 24, except that the locking member 502 can have a length sufficient to enable ends 504, 506 to be coupled to the humerus 72 at one or more remote locations. For example, the ends 504, 506 can be coupled at the locations separate from the locations where the locking member 502 is coupled via the suture anchoring members 22, 22'. According to the example shown in FIG. 17, the ends 504, 506 can be coupled to the humerus 72 along with the tensioning strands 42, 44, 42', 44' via a suture anchoring member 508. The ends 504, 506 can be coupled to the suture anchoring member 508 via a knot or other suitable locking device.

With continued reference to FIG. 17, an exemplary method of using the TFD 500 can include coupling the suture constructs 20, 20' to the humerus 72 and passing the loops 30, 32, 30', 32' through the rotator cuff 70 in substantially the same manner as described above for the TFD 10. Next, with the TFD 500 in an untensioned state, the locking member 502 can be passed through and positioned within the loops 30, 32, 30', 32' such that the ends 504, 506 extend past the end loops 30, 30'.

Once the locking member 502 is routed through the loops 30, 32, 30', 32' in the foregoing manner, the tensioning strands 42, 44, 42', 44' can be selectively pulled to cinch the loops 30, 32, 30', 32' around the locking member 502 and to draw the locking member 502 into engagement with the rotator cuff 70. Next, the tensioning strands 42, 44, 42', 44' can be further selectively pulled to draw the locking member 180 towards the suture anchoring members 22, 22'. Further drawing the loops 30, 32, 30', 32' can draw the first tissue 12 in close proximity with the second tissue 14 in a desired relationship and subsequently compress the first tissue 12, thereby creating tension in the suture constructs 20, 20'. FIG. 17 illustrates the suture constructs 20, 20' in a tensioned state. With tension in the suture constructs 20, 20', one or more of the tensioning strands 42, 44, 42', 44' can be cut to remove excess length where the ends of the one or more strands are not to be attached to the humerus 72. Alternately, the tensioning strands 42, 44, 42', 44' can be drawn past an end of the rotator cuff 70 and attached to the humerus 72 as shown. While drawing and/or attaching one or more of the tensioning strands 42, 44, 42', 44', the ends 504, 506 can be drawn past the end of the rotator cuff 70 and attached to the humerus 72.

Figure 18:
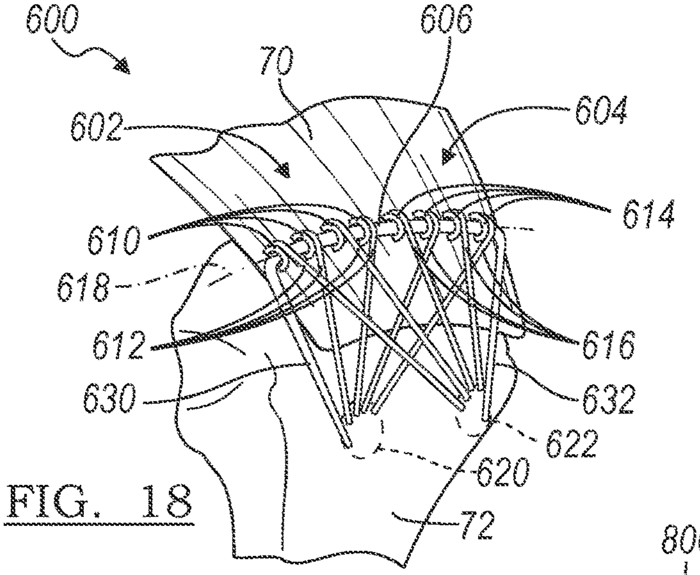
FIG. 18 is a fragmentary environmental perspective view illustrating another exemplary method for affixing a rotator cuff to a humerus using another tissue fixation device according to the present teachings.

With particular reference to FIG. 18 another TFD 600 and surgical method of using the TFD 600 for affixing two tissues according to the present teachings will now be described. The TFD 600 can be used, for example, to affix the rotator cuff 70 to the humerus 72. The TFD 600 and the method illustrate alternate features according to the present teachings including overlapping tensioning members of suture constructs in a criss-cross fashion and securing the tensioning members of each suture construct to the humerus 72 at at least two separate locations. An overlapping structure of the tensioning members can engage and thereby further affix the rotator cuff 70 to the humerus 72. The overlapping structure can further reduce localized stress in one or both the rotator cuff 70 and the humerus 72 by distributing the loads transmitted between the TFD 600 and the rotator cuff 70 and humerus over a larger area and creating a larger area of compression.

According to the example shown in FIG. 18 the TFD 600 can include a first suture construct 602, a second suture construct 604, and a locking member 606. The first and second suture constructs 602, 604 each can include at least two adjustable loops tensioned by corresponding tensioning members. For example, the first suture construct 602 can include four adjustable loops 610 tensioned by four corresponding tensioning strands 612 as shown. Similarly, the second suture construct 604 can include four adjustable loops 614 tensioned by four corresponding tensioning strands 616. The adjustable loops 610, 614 can be created using various suturing techniques and devices. According to the example shown in FIG. 18, the adjustable loops 610, 614 can be created by passing a suture through the rotator cuff 70 using a whip and/or a mattress stitching technique. In various implementations, the adjustable loops 610, 614 can be created from separate sutures attached to the humerus 72 in a manner similar to that discussed below with reference to FIG. 21. The adjustable bops 610, 614 can create a series of loops spaced apart in a substantially linear arrangement along a line or axis 618 as shown. The linear arrangement or axis 618 can extend in a direction substantially transverse to a direction in which the rotator cuff 70 tensions due to muscle contraction.

The tensioning strands 612, 616 can exit the same proximal side of the rotator cuff 70 that the adjustable loops 610, 614 are disposed, and in a substantially linear arrangement in the direction in which the rotator cuff 70 tensions due to muscle contraction. The tensioning strands 612, 614 can exit on either side of the adjustable loops 610, 614. For example, the tensioning strands 610, 614 can each exit in close proximity to the corresponding adjustable loops 610, 614 on a side closest to an end of the rotator cuff 70 as shown. The tensioning strands 612, 616 can be attached to the humerus 72 in at least two selected areas separated in the same direction in which the adjustable loops 610, 614 are arranged.

According to the example shown in FIG. 18, the tensioning strands 612, 616 can be secured at two locations indicated by reference numerals 620, 622. More specifically, at least one of each of the tensioning strands 612 and the tensioning strands 616 can be attached at the first location 620 and at least another one of each of the tensioning strands 612 and the tensioning strands 616 can be attached at the second location 622. For exemplary purposes, the tensioning strands 612, 614 can be attached to the first and second locations 620, 622 in an alternating arrangement as shown. When secured, the tensioning strands 612, 616 secured at the first location 620 can overlap the tensioning strands 612, 616 secured at the second location 622 in a criss-cross fashion. The locking member 606 can extend through each of the loops 610, 614 and can include a first end 630 and a second end 632 that are attached at the first location 620 and the second location 622, respectively.

With continued reference to FIG. 18, an exemplary method of using the TFD 600 will now be described. The method can include creating the loops 610, 614 and tensioning strands 612 and 616 to pass through and exit the rotator cuff 70 and attaching the loops 610, 614 to the humerus 72. The adjustable loops 610 can be attached to the humerus 72 using a first suture anchoring member such as, for example, the suture anchoring member 22 discussed above. Similarly, the adjustable loops 614 can be attached to the humerus 72 using a separate, second suture anchoring member in a similar manner.

Next, with the adjustable loops 610, 614 in an untensioned state, the locking member 606 can be passed through and positioned within the loops 610, 614 such that the ends 630, 632 extend past end loops of the adjustable loops 610, 614. Once the locking member 606 is routed through the loops 610, 614, the tensioning strands 612, 616 can be selectively pulled to cinch the loops 610, 614 around the locking member 606 and to draw the locking member 606 into engagement with the rotator cuff 70. Next, the tensioning strands 612, 616 can be further selectively pulled to draw the locking member 606 towards the humerus 72. Further drawing the loops 30, 32, 30', 32' can draw the rotator cuff 70 in close proximity with the humerus 72 in a desired relationship and subsequently compress the rotator cuff 70 against the humerus 72, thereby creating tension in the loops 610, 614. FIG. 18 illustrates the loops 610, 614 in a tensioned state.

While maintaining the tension in the loops 610, 614, a first pair of the tensioning strands 612 and a first pair of the tensioning strands 616 can be drawn together and attached at the selected location 620. Subsequently, a second pair of the tensioning strands 612 and a second pair of the tensioning strands 616 can be drawn together and attached at the selected location 622. When attached in the foregoing manner, the first and second pairs of the tensioning strands 612, 616 can extend at angles with respect to the axis 618 and overlap in a criss-cross fashion to create an overlapping structure that compresses an end portion of the rotator cuff 70 against the humerus 72. In this way, the overlapping structure can further secure the rotator cuff 70 to the humerus 72.

Figure 19:
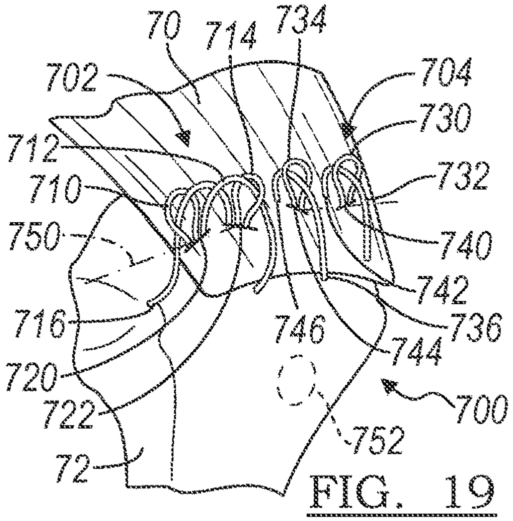
FIG. 19 is a fragmentary environmental perspective view illustrating another exemplary method for affixing a rotator cuff to a humerus using another tissue fixation device according to the present teachings.

With particular reference to FIG. 19, another TFD 700 and surgical method of using the TFD 700 for affixing two tissues according to the present teachings will now be described. The TFD 700 can be used, for example, to affix the rotator cuff 70 to the humerus 72. The TFD 700 and the method illustrate alternate features according to the present teachings including using one or more portions of a suture construct to create a locking member for adjustable loops of the suture construct and securing the portions at a remote location.

According to the example shown in FIG. 19, the TFD 700 can include a first suture construct 702 and a second suture construct 704. The first and second suture constructs 702, 704 can be substantially similar to the suture constructs 20, 20' and can be attached to the humerus 72 in substantially the same way as the suture constructs 20, 20'. The first suture construct 702 can include a first adjustable loop 710 tensioned by a tensioning strand 712 and a second adjustable loop 714 tensioned by a tensioning strand 716. The first adjustable loop 710 and the tensioning strand 712 can pass through a common first aperture 720 formed through the rotator cuff 70 and exit on the same side. The tensioning strand 712 can pass through the second adjustable loop 714. The second adjustable loop 714 and tensioning strand 716 can pass through a common second aperture 722. The tensioning strand 716 can pass through the adjustable loop 710.

The second suture construct 704 can include a third adjustable loop 730 tensioned by a tensioning strand 732 and a fourth adjustable loop 734 tensioned by a tensioning strand 736. The third adjustable loop 730 can pass through a first aperture 740 and the tensioning strand 732 can pass through a separate, second aperture 742 and through the adjustable loop 730. The fourth adjustable loop 734 can pass through a third aperture 744 and the tensioning strand 736 can pass through a separate, fourth aperture 746 and through the fourth adjustable loop 734. The adjustable loops 710, 714, 730, 734 can be spaced apart along a line or axis 750 and the apertures 720, 722, 740, 744 can extend at angles with respect to the axis 750. For example, the apertures 720, 722 can extend at angles of, for example, approximately forty-five degrees (45°) so that the adjustable loops 710, 714 can face each other and to facilitate the passage of the tensioning strands 712, 716. The apertures 740, 744 can extend at angles so that the adjustable loops 730, 734 face towards the apertures 742, 746 and thereby facilitate the passage of the tensioning strands 732, 736. The tensioning strands 712, 716, 732, 736 can be cut to remove excess length and/or attached to a selected area of the humerus 72 at a single, remote location 752 as shown or, alternately, can be secured at two or more remote locations.

With continued reference to FIG. 19, an exemplary method of using the TFD 700 can include attaching the first and second suture constructs 702, 704 to the humerus 72 and passing the adjustable loops 710, 714, 730 through the respective apertures 720, 722 of rotator cuff 70. The method can further include passing the tensioning strands 712, 716, 732 through the respective apertures 720, 722, 734. In various implementations, the tensioning strands 712, 716 can be passed through the apertures 720, 722 at the same time as the respective adjustable loops 710, 714 are passed.

Next, with the first suture construct 702 in an untensioned state, an end of the tensioning strand 712 can be inserted through the second adjustable loop 714 and an end of the tensioning strand 716 can be inserted through the adjustable loop 710. Next, the tensioning strands 712, 714 can be selectively pulled to cinch the adjustable loops 710, 714 around the tensioning strands 712, 714 and engage intermediate portions of the tensioning strands 712, 714 with the rotator cuff 70. Once the tensioning strands 712, 714 are engaged, the tensioning strands 712, 714 can be further selectively pulled to draw the rotator cuff 70 in close proximity to the humerus 72. Once the rotator cuff 70 is positioned against the humerus 72 in a desired relationship, the tensioning strands 712, 714 can be attached to the humerus 72 in tension to retain the relationship.

With the second suture construct 704 in an untensioned state, an end of the tensioning strand 732 can be inserted through the adjustable loop 730 and pulled to cinch the adjustable loop 730 and engage an intermediate portion of the tensioning strand 732 with the rotator cuff 70. Once engaged in the foregoing manner, the tensioning strand 732 can be further pulled to draw the rotator cuff 70 into a desired relationship and subsequently attached in tension to the humerus 72.

Figure 20:
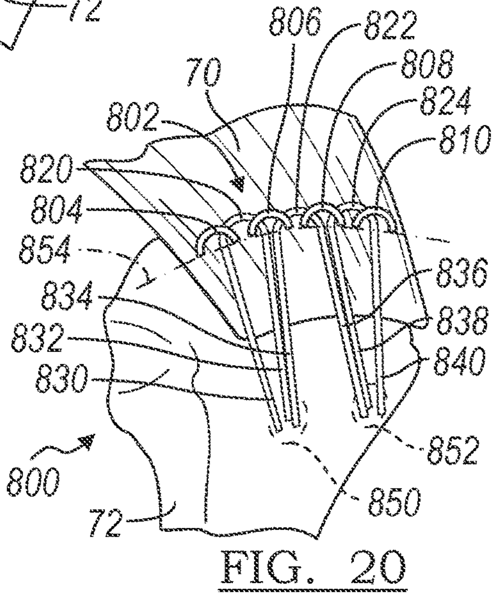
FIG. 20 is a fragmentary environmental perspective view illustrating another exemplary method for affixing a rotator cuff to a humerus using another tissue fixation device according to the present teachings.

With particular reference to FIG. 20, another TFD 800 and surgical method of using the TFD 800 for affixing two tissues according to the present teachings will now be described. The TFD 800 can be used, for example, to affix the rotator cuff 70 to the humerus 72. The TFD 800 can include a suture construct 802 having at least two adjustable loops and at least one locking member that engages the adjustable loops. According to the example shown in FIG. 20, the suture construct 802 can include four adjustable loops 804, 806, 808, 810 and three locking members 820, 822, 824. In various implementations, the adjustable loops 804, 806 and the adjustable loops 808, 810 can be created using the suture construct 20 and the suture construct 20', respectively.

The locking member 820, locking member 822, and locking member 824 can have ends 830, 832, ends 834, 836, and ends 838, 840, respectively. The locking member 820 can extend through and engage the loops 804, 806. The locking member 822 can extend through and engage the loops 806, 808. The locking member 824 can extend through and engage the loops 808, 810. The ends 830, 832, 834 can be attached to a selected area of the humerus 72 at a first location indicated by reference numeral 850, and the ends 836, 838, 840 can be attached at a second location indicated by reference numeral 852.

With continued reference to FIG. 20, an exemplary method of using the TFD 800 can include attaching the loops 804, 806, 808, 810 to the humerus 72 and passing the loops 804, 806, 808, 810 through the rotator cuff 70. The loops 804, 806, 808, 810 can be passed so as to extend along a line or axis 854 and face in a second direction substantially perpendicular to the axis 854. With the loops 804, 806, 808, 810 in an untensioned state, the ends 830, 832, the ends 834, 836, and the ends 838, 840 can be passed through the loops 804, 806, the loops 806, 808, and the loops 808, 810, respectively, in the second direction. When passed in the foregoing manner, portions of the locking members 804, 806, 808, 810 can span the corresponding loops 804, 806, 808, 810. Next, the ends 830, 832, 834, 836, 838, 840 can be pulled to create tension in the loops 804, 806, 808, 810 and to draw the rotator cuff 70 into close proximity with the humerus 72 in a desired relationship. With the rotator cuff 70 and the humerus 72 in the desired relationship, the ends 830, 832, 834, 836, 838, 840 can be attached to the humerus 72 at the respective locations 850, 852 in a tensioned state.

Figure 21:
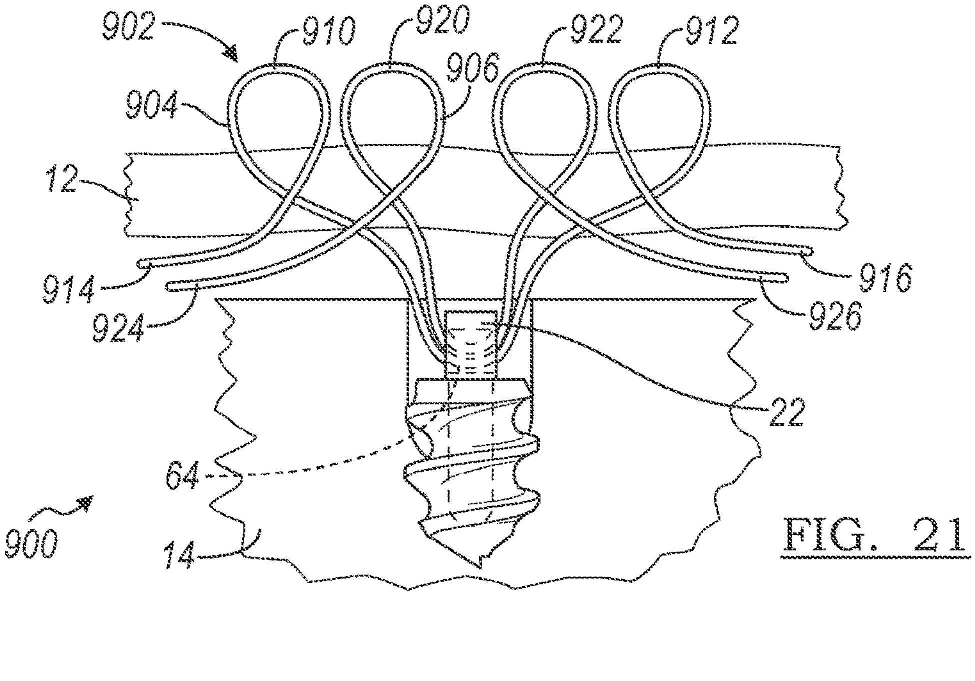
FIG. 21 is an environmental perspective view illustrating another exemplary method for affixing two tissues together using another tissue fixation device according to the present teachings.

With particular reference to FIG. 21, another exemplary TFD 900 and surgical method of using the TFD 900 for affixing the first and second tissues 12, 14 according to the present teachings will now be described. The TFD 900 can be used, for example, to affix the rotator cuff 70 to the humerus 72. The TFD 900 and the method illustrate alternate features according to the present teachings. The alternate features can include engaging a locking member with at least two adjustable loops disposed on one side of a first tissue and drawing the locking member and the first tissue into engagement with a second tissue using tensioning strands disposed between the first and second tissues.

According to the example shown in FIG. 21, the TFD 900 can include a flexible suture construct 902 created by suture strands 904, 906. The suture strand 904 can be passed through the first tissue 12 to create loops 910, 912 that extend from a first side of the first tissue 12 opposite a second side to be engaged with the second tissue 14. The suture strand 904 can be further passed through the first tissue 12 such that ends 914 and 916 text and extend from the first tissue 12 on the second side of the tissue facing the second tissue 14. The suture strand 906 can be passed through the first tissue 12 to create loops 920, 922 that extend from the first side of the first tissue 12 and ends 924, 926 that exit and extend from the second side of the first tissue 12. Each of the loops 910, 912, 920, 922 can be created by passing the respective suture strands 904, 906 through a single aperture or, alternately, through separate apertures in the first tissue 12. Ends of the suture strands 904, 906 can be secured to the second tissue 14 in any desired manner such as, for example, using one or more suture anchors. While two suture strands 904, 906 forming four loops 910, 912, 920, 922 are shown, fewer or more suture strands can be used where fewer or more loops are desired.

With continued reference to FIG. 21, an exemplary method of using the TFD 900 can include positioning a locking member (not shown) within the loops 910, 912, 920, 922 and subsequently engaging the loops 910, 912, 920, 922 with the first tissue 12 via the locking member. The loops 910, 912, 920, 922 can be engaged by pulling on the ends 914, 916, 924, 926 to cinch the loops 910, 912, 920, 922 into engagement with the locking member and to draw the locking member into engagement with the first tissue 12, The locking member can include one or more features of the locking members 24, 100, 120, 140, 160, 180, 200, 220, 240. With the loops 910, 912, 920, 922 engaged, the ends 914, 916, 924, 926 can be selectively pulled to draw the first tissue 12 into close proximity with the second tissue 14 in a desired relationship. The desired relationship can be maintained by maintaining tension in the loops 910, 912, 920, 922. With the first and second tissues 12, 14 in the desired relationship, the ends 914, 916, 924 and 926 can be drawn and attached to the second tissue 14 in tension to retain the relationship.

Figure 22:
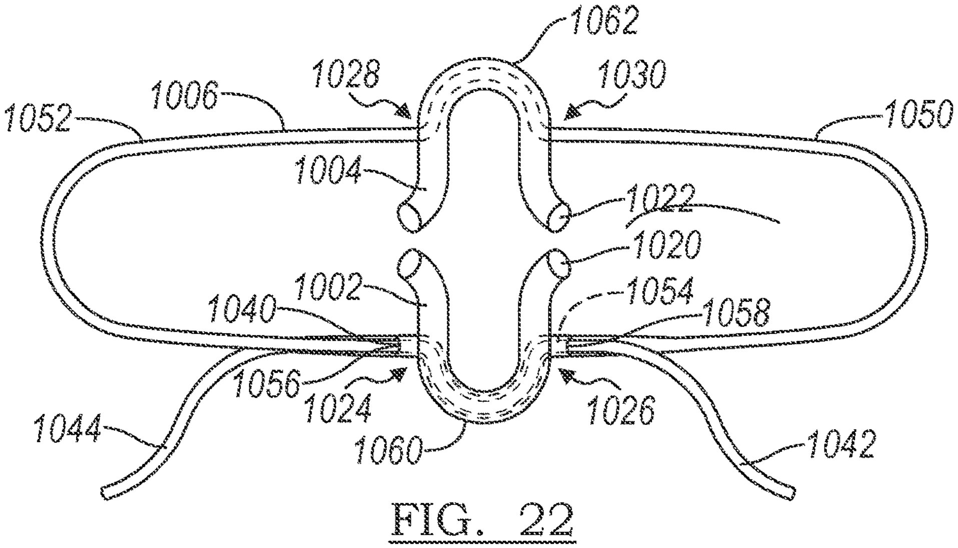
FIG. 22 is a view illustrating a flexible loop construct according to the present teachings.
Figure 23:
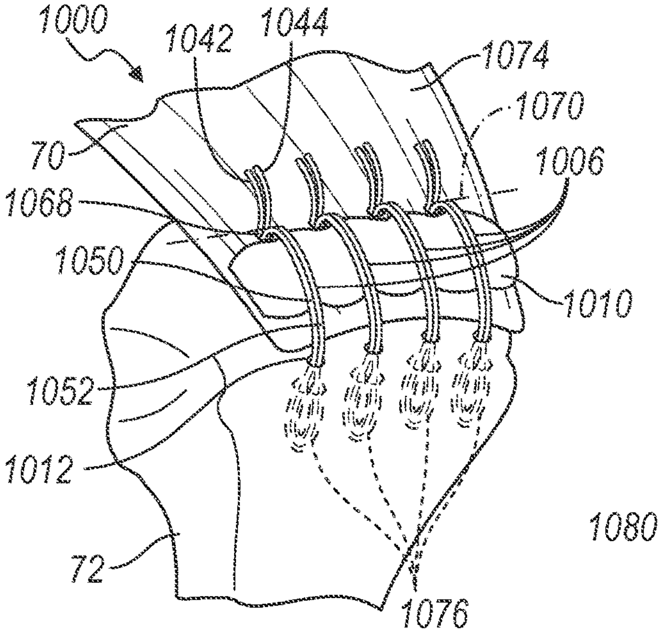
FIGS. 23-24 are fragmentary environmental perspective views Illustrating another exemplary tissue fixation device and method of using the tissue fixation device for affixing a rotator cuff to a humerus.
Figure 24:
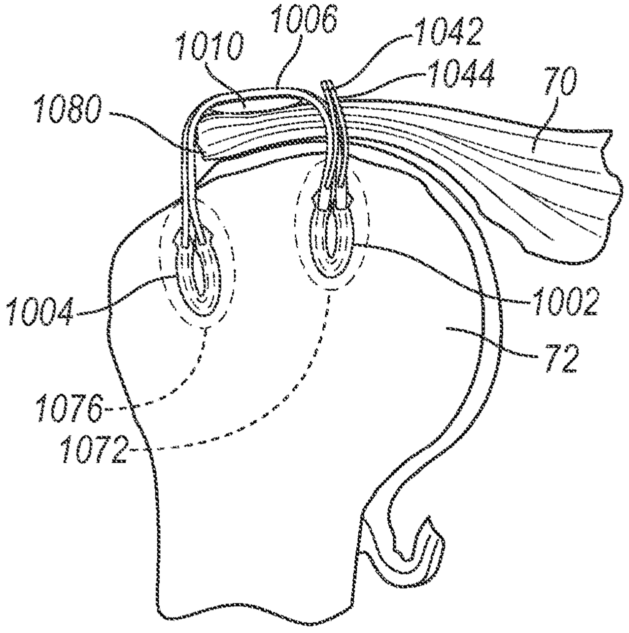

With reference to FIGS. 22-24, another TFD 1000 and surgical method of using the TFD 1000 for affixing the rotator cuff 70 to the humerus 72 according to the present teachings will now be described. The TFD 1000 can Include two or more flexible anchors 1002, 1004, one or more self-locking, flexible suture constructs 1006, and a locking member 1010. For example, the TFD 1000 can include four (4) flexible anchors 1002, four (4) flexible anchors 1004, four (4) flexible suture constructs 1006, and one (1) locking member 1010 as shown. The locking member 1010 can incorporate one or more features of the locking members 24, 100, 120, 140, 160, 180, 200, 220, 240 discussed above.

With particular reference to FIG. 22, the flexible anchors 1002, 1004 can be elongate members having a sleeve or tubular construction. The flexible anchors 1002, 1004 can be configured to attach to the humerus 72 within respective bores 1012 formed in the humerus 72. For example, the flexible anchors 1002, 1004 can deform between a first shape configured to be received within the bores 1012 and a second shape larger than the first shape configured to engage the bores 1012. The flexible anchors 1002, 1004 can include longitudinal passages 1020, 1022 and openings 1024, 1026, 1028, 1030 extending through respective walls. The flexible suture construct 1006 can include a braided body 1040 and tensioning strands 1042, 1044 that form a self-locking adjustable loop including loop sections 1050, 1052. The braided body 1040 can define a longitudinal passage 1054 and openings 1056, 1058 in communication with the longitudinal passage 1054. The tensioning strands 1042, 1044 can extend from opposite ends of the braided body 1040.

The loop sections 1050, 1052 can be formed and coupled to the flexible anchors 1002, 1004 by passing the braided body 1040 and the tensioning strand 1042 through the flexible anchors 1002, 1004 as shown. More specifically, the tensioning strand 1042 and the braided body 1040 can pass through the openings 1024, 1026 and the longitudinal passage 1020 of the flexible anchor 1002. The tensioning strand 1042 can further pass through the openings 1028, 1030 and longitudinal passage 1022 of the flexible anchor 1004 and the openings 1056, 1058 and the longitudinal passage 1054 of the braided body 1040. When coupled, the flexible anchor 1002 and the braided body 1040 can be disposed at a first end 1060 and the flexible anchor 1004 can be disposed at a second end 1062. Further details of the flexible anchors 1002, 1004 and the flexible suture construct 1006 are disclosed in commonly assigned U.S. patent application Ser. No. 12/915,962, the entire disclosure of which is expressly incorporated herein by reference.

With continued reference to FIGS. 22-24 the method of using the TFD 1000 can include selectively adjusting a size of the loop sections 1050, 1052 by pulling on the tensioning strand 1042. The size of the loop sections 1050, 1052 can be adjusted to provide a desired length between the first and second ends 1060, 1062. The first ends 1060 can be passed through apertures 1068 in the rotator cuff 70 along a line or axis 1070 and the flexible suture anchors 1002 can secured within the respective bores 1012 formed in the humerus 72 at proximal locations 1072. The proximal locations 1072 can be located beneath the rotator cuff 70 when the rotator cuff 70 is secured in a desired position. The locking member 1010 can be positioned on an outer surface 1074 of the rotator cuff 70 to extend between the flexible suture constructs 1006, and generally parallel to the axis 1070, The second ends 1062 can be drawn over the locking member 1010, past an end 1080 of the rotator cuff 70, and secured within the respective bores 1012 formed in the humerus 72 at distal locations 1076 adjacent the end 1080. The distal locations 1076 can be spaced apart from the proximal locations 1072 and can be disposed adjacent the end 1080 of the rotator cuff 70 as best seen in FIG. 24. When secured, tension in the flexible suture constructs 1006 can compress the locking member 1010. The tensioning strands 1042, 1044 can be cut to a desired length, for example, flush to the outer surface 1074 of the rotator cuff 70.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of securing a suture anchor system to bone, comprising:

positioning a suture anchor in a hole in a bone; and coupling an adjustable suture construct to the suture anchor after positioning the suture anchor in the hole in the bone, wherein the adjustable suture construct comprises a braided suture with a first free end, and wherein said coupling includes passing the first free end longitudinally through a longitudinal passage in the braided suture and thereby along a passageway inside the suture anchor to form a first self-locking adjustable loop that encircles a portion of the suture anchor with part of the first self-locking adjustable loop left outside the suture anchor and outside the bone, wherein, following said passing, the first free end is also left outside the bone available for pulling for reducing a size of the first self-locking adjustable loop.

2. The method of claim 1 further comprising pulling on the first free end after said passing so as to reduce the size of the first self-locking adjustable loop.

3. The method of claim 1, wherein the suture anchor is threaded.

4. The method of claim 1, wherein the bone is a humerus.

5. The method of claim 1, wherein the braided suture includes a first aperture and a second aperture therein that are each longitudinally spaced apart from the first free end and which are longitudinally spaced apart from each other such that, along the braided suture, the first aperture is situated between the first free end and the second aperture, and wherein said passing includes passing the first free end into the braided suture through the second aperture, longitudinally within the braided suture along said longitudinal passage, and out of the braided suture through the first aperture to form the first self-locking adjustable loop.

6. The method of claim 5, wherein, following said coupling, the first aperture and the second aperture are located outside the suture anchor.

7. The method of claim 5, wherein, following said coupling, the first aperture and the second aperture are located inside the bone.

8. The method of claim 7, wherein, following said coupling, the first aperture and the second aperture are located outside the suture anchor.

9. The method of claim 1, wherein said positioning includes delivering the suture anchor into the hole in the bone in a folded delivery condition, wherein, in the folded delivery condition, the suture anchor includes a folded leading portion that leads the suture anchor into the hole and a first trailing end and a second trailing end that trail the folded leading portion into the hole.

10. The method of claim 9 further comprising converting the suture anchor from the folded delivery condition to a deformed anchoring condition in the hole in the bone.

11. A method of securing a suture anchor system to bone, comprising:

positioning a suture anchor in a hole in a bone; and passing, after said positioning, a first free end of a braided suture longitudinally through a longitudinal passage in the braided suture and thereby along a passageway inside the suture anchor along which the braided suture is extending to form a first self-locking adjustable loop, wherein said passing leaves a segment of the first self-locking adjustable loop outside the suture anchor, and wherein, following said passing, the first free end is left outside the bone available for pulling for reducing a size of the first self-locking adjustable loop, wherein the suture anchor comprises a deformable sleeve construct, and wherein the passageway extends longitudinally within the deformable sleeve construct.

12. The method of claim 11, wherein the bone is a humerus.

13. The method of claim 11 further comprising pulling on the first free end after said passing so as to reduce the size of the first self-locking adjustable loop, wherein said pulling is conducted while at least part of the longitudinal passage in the braided suture is extending longitudinally along the passageway in the deformable sleeve construct.

14. The method of claim 11, wherein the braided suture includes a first aperture and a second aperture therein that are each longitudinally spaced apart from the first free end and which are longitudinally spaced apart from each other such that, along the braided suture, the first aperture is situated between the first free end and the second aperture, and wherein said passing includes passing the first free end into the braided suture through the second aperture, longitudinally within the braided suture along said longitudinal passage, and out of the braided suture through the first aperture to form the first self-locking adjustable loop.

15. The method of claim 14, wherein, following said passing, the first aperture and the second aperture are located outside the deformable sleeve construct.

16. The method of claim 14, wherein, following said passing, the first aperture and the second aperture are located inside the bone.

17. The method of claim 10, wherein, following said passing, the first aperture and the second aperture are located outside the deformable sleeve construct.

18. The method of claim 11, wherein said positioning includes delivering the deformable sleeve construct into the hole in the bone in a folded delivery condition, wherein, in the folded delivery condition, the deformable sleeve construct includes a folded leading portion that leads the deformable sleeve construct into the hole and a first trailing end and a second trailing end that trail the folded leading portion into the hole.

19. The method of claim 18 further comprising converting the deformable sleeve construct from the folded delivery condition to a deformed anchoring condition in the hole in the bone.

20. The method of claim 11, wherein said passing leaves the first self-locking adjustable loop encircling a portion of the deformable sleeve construct to connect the first self-locking adjustable loop to the deformable sleeve construct.

21. The method of claim 11, wherein said passing additionally leaves the segment of the first self-locking adjustable loop outside the bone.

22. A method of securing a suture anchor system to a bone, comprising:

positioning a suture anchor in a hole in a bone with a first portion of a braided suture extending along a passageway inside the suture anchor and with a first free end of the braided suture remaining outside the suture anchor, wherein the first portion of the braided suture extending along the passageway in the suture anchor includes a longitudinal passage therein that extends longitudinally within the first portion; and passing the first free end of the braided suture longitudinally through the longitudinal passage in the first portion after said positioning so as to form a first self-locking adjustable loop connected to the suture anchor, wherein said passing leaves the first self-locking adjustable loop extending partly along the passageway in the suture anchor and partly outside the suture anchor, wherein, following said passing, the first free end is left outside the bone available for pulling for reducing a size of the first self-locking adjustable loop, wherein the suture anchor comprises a deformable suture anchor that is positionable in the hole in the bone in a folded condition.

23. The method of claim 22, wherein the bone is a humerus.

24. The method of claim 22, wherein the braided suture includes a first aperture and a second aperture therein that are each longitudinally spaced apart from the first free end and which are longitudinally spaced apart from each other such that, along the braided suture, the first aperture is situated between the first free end and the second aperture, and wherein said passing includes passing the first free end into the braided suture through the second aperture, longitudinally within the braided suture along said longitudinal passage, and out of the braided suture through the first aperture to form the first self-locking adjustable loop.

25. The method of claim 24, wherein, following said passing, the first aperture and the second aperture are located outside the deformable suture anchor.

26. The method of claim 24, wherein, following said passing, the first aperture and the second aperture are located inside the bone.

27. The method of claim 26, wherein, following said passing, the first aperture and the second aperture are located outside the deformable suture anchor.

28. The method of claim 22, wherein the deformable suture anchor comprises an deformable sleeve construct.

* * * * *